(12) United States Patent
Nam et al.

(10) Patent No.: US 10,934,274 B2
(45) Date of Patent: Mar. 2, 2021

(54) QUINOLINE DERIVATIVES AS TAM RTK INHIBITORS

(71) Applicants: Qurient Co., Ltd., Gyeonggi-do (KR); Lead Discovery Center GmbH, Dortmund (DE)

(72) Inventors: Kiyean Nam, Gyeonggi-do (KR); Jaeseung Kim, Seoul (KR); Seohyun Ahn, Gyeonggi-do (KR); Yeejin Jeon, Gyeonggi-do (KR); Doohyung Lee, Seoul (KR); Dongsik Park, Gyeonggi-do (KR); Young-In Yang, Gyeonggi-do (KR); SaeYeon Lee, Gyeonggi-do (KR); Jeongjun Kim, Seoul (KR); Jiye Ahn, Gyeonggi-do (KR); Hana Kim, Gyeonggi-do (KR); Chun-won Jung, Gyeonggi-do (KR); Carsten Schultz-Fademrecht, Dortmund (DE)

(73) Assignees: QURIENT CO., LTD., Gyeonggi-Do (KR); LEAD DISCOVERY CENTER GMBH, Dortmund (DE)

( * ) Notice: Subject to any disclaimer, the term of this patent is extended or adjusted under 35 U.S.C. 154(b) by 0 days.

(21) Appl. No.: 15/563,123

(22) PCT Filed: Apr. 14, 2016

(86) PCT No.: PCT/EP2016/058284
§ 371 (c)(1),
(2) Date: Sep. 29, 2017

(87) PCT Pub. No.: WO2016/166250
PCT Pub. Date: Oct. 20, 2016

(65) Prior Publication Data
US 2018/0093968 A1 Apr. 5, 2018

Related U.S. Application Data

(60) Provisional application No. 62/147,925, filed on Apr. 15, 2015, provisional application No. 62/147,262, filed on Apr. 14, 2015.

(51) Int. Cl.
*C07D 401/12* (2006.01)
*C07D 401/14* (2006.01)
*C07D 405/14* (2006.01)
*C07D 409/14* (2006.01)
*C07D 413/14* (2006.01)
*C07D 417/14* (2006.01)
*A61P 35/02* (2006.01)
*A61P 35/04* (2006.01)
*A61P 35/00* (2006.01)
*A61K 31/4709* (2006.01)
*A61K 31/497* (2006.01)
*A61K 31/501* (2006.01)
*A61K 31/506* (2006.01)
*A61K 45/06* (2006.01)

(52) U.S. Cl.
CPC ........ *C07D 401/14* (2013.01); *A61K 31/4709* (2013.01); *A61K 31/497* (2013.01); *A61K 31/501* (2013.01); *A61K 31/506* (2013.01); *A61K 45/06* (2013.01); *A61P 35/00* (2018.01); *A61P 35/02* (2018.01); *A61P 35/04* (2018.01); *C07D 401/12* (2013.01); *C07D 405/14* (2013.01); *C07D 409/14* (2013.01); *C07D 413/14* (2013.01); *C07D 417/14* (2013.01)

(58) Field of Classification Search
CPC .. C07D 401/12; C07D 401/14; C07D 405/14; C07D 409/14; C07D 413/14; C07D 417/14
See application file for complete search history.

(56) References Cited

U.S. PATENT DOCUMENTS

| 8,999,982 B2 * | 4/2015 | Schultz-Fademrecht ............... C07D 401/12 514/235.2 |
| 2008/0004273 A1 | 1/2008 | Raeppel et al. |
| 2012/0219522 A1 | 8/2012 | Xi |
| 2014/0018365 A1 * | 1/2014 | Schultz-Fademrecht ............... C07D 401/12 514/235.2 |

FOREIGN PATENT DOCUMENTS

| EA | 13231 B1 | 4/2010 |
| EP | 2423208 A1 | 2/2012 |

(Continued)

OTHER PUBLICATIONS

Paolino, et al., "The E3 ligase Cbl-b and TAM receptors regulate cancer metastasis via natural killer cells," Nature, Mar. 27, 2014, pp. 508-526, vol. 507.

(Continued)

*Primary Examiner* — Rebecca L Anderson
(74) *Attorney, Agent, or Firm* — Saliwanchik, Lloyd & Eisenschenk

(57) ABSTRACT

The present invention relates to novel compounds which are inhibitors of TAM (Axl, Mer and Tyro 3) and/or Met family receptor tyrosine kinases (RTKs). These compounds are suitable for the treatment of disorders associated with, accompanied by, caused by or induced by a receptor of the TAM family, in particular a hyperfunction thereof. The compounds are suitable for the treatment of hyperproliferative disorders, such as cancer, particularly immune-suppressive cancer, refractory cancer and cancer metastases.

16 Claims, 1 Drawing Sheet

(56) References Cited

FOREIGN PATENT DOCUMENTS

| EP | 1881976 B1 | 10/2012 |
|---|---|---|
| RU | 2013135662 A | 4/2015 |
| WO | 2013074633 A1 | 5/2013 |

OTHER PUBLICATIONS

Tang, et al., "Design, synthesis, and structure-activity relationships of novel 6,7-disubstituted-4-phenoxyquinoline derivatives as potential antitumor agents." European J. of Med. Chem., 2013, pp. 77-89, vol. 69.

Zhou, et al., "Discovery and biological evaluation of novel 6,7-disubstituted-4-(2-fluorophenoxy)quinoline derivatives possessing 1,2,3-trazole-4-carboxamide moiety as c-Met kinase inhibitors." Bioorganic & Medicinal Chemistry, 2014, pp. 6438-6452, vol. 22.

Lemke, Greg, "Biology of the TAM Receptors." Cold Spring Harbor perspectives in biology, Nov. 2013, 5(11): a009076, 1-17.

Office Action dated Aug. 7, 2019 by the Russian Patent Office (with English translation) in the corresponding Russian Patent Application No. RU-2017139515/04(068762).

Zhang, Zhenfeng et al. "Activation of the AXL kinase causes resistance to EGFR-targeted therapy in lung cancer," Nature Genetics vol. 44, No. 8, pp. 852-862, Aug. 2012.

Office Action issued by the China National Intellectual Property Administration on Jul. 31, 2020 in the parallel Chinese Patent Application No. 201680022317.2, with an English translation.

* cited by examiner

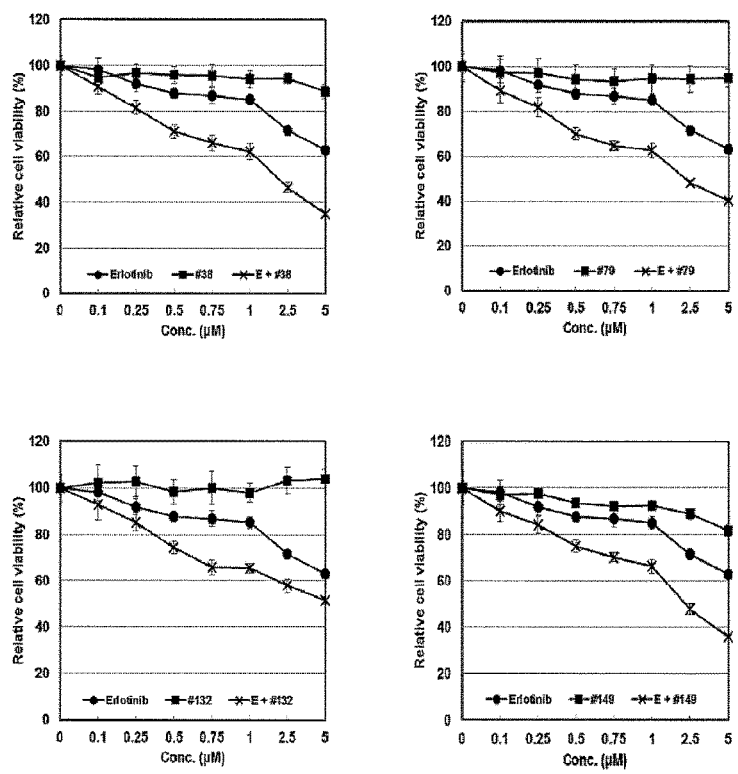
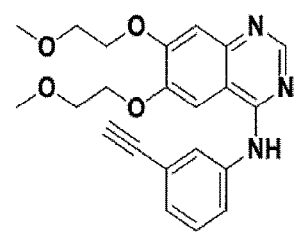
Figure 2. Chemical structure of Erlotinib
Figure 1 Combination effect of compound and erlotinib on inhibition activity in Erlotinib – resistant cell-line

QUINOLINE DERIVATIVES AS TAM RTK INHIBITORS

CROSS REFERENCE TO A RELATED APPLICATION

This application is a National Stage Application of International Application Number PCT/EP2016/058284, filed Apr. 14, 2016; which claims priority to U.S. Provisional Application No. 62/147,262, filed Apr. 14, 2015 and U.S. Provisional Application Ser. No. 62/147,925, filed Apr. 15, 2015.

BACKGROUND OF THE INVENTION

The present invention relates to novel compounds which are inhibitors of TAM (Axl, Mer and Tyro3) family and/or Met receptor tyrosine kinases (RTKs). These compounds are suitable for the treatment of disorders associated with, accompanied by, caused by or induced by a receptor of the TAM family, in particular a hyperfunction thereof. The compounds are suitable for the treatment of hyperproliferative disorders, such as cancer, particularly immune-suppressive cancer, refractory cancer and cancer metastases.

The compounds are also suitable for the treatment of infectious diseases, particularly those caused by viral infection. (Including HIV virus disease, Ebola virus disease and WMN). Activation of TAM protein is known to reduce the innate immune signaling in IFN signal of the dendritic cells (Rothlin et al., 2007). The compounds led to a marked reduction in virus infectivity for HIV-1-derived lentivirus and WMN (Bhattacharyya et al., 2013).

Receptor tyrosine kinases (RTKs) are cell surface receptors that transmit signals from the extracellular environment to control growth, differentiation and survival of cells. Deregulated expression of protein kinases by gene deletion, -mutation or -amplification has been found to be important for tumor initiation and -progression, involving cancer cell proliferation, -survival, -motility and -invasivity as well tumor angiogenesis and chemotherapy resistance. Because of the advanced understanding of their critical role, protein kinases are important targets for novel therapies, especially for cancer (Hananhan et al., 2000; Blume-Jensen et al., 2001).

TAM family RTKs regulate a diverse range of cellular responses, including cell survival, proliferation, migration and adhesion (Hafizi et al., 2006). TAM receptor signalling has been shown to regulate vascular smooth muscle homeostasis, platelet function, thrombus stabilization (Angelillo-Scherrer et al., 2001), and erythropoiesis (Angelillo-Scherrer et al., 2008). Furthermore TAM receptors are implicated in the control of oligodendrocyte cell survival and the regulation of osteoclast function. The TAM receptors play pivotal roles in innate immunity (Lemke et al., 2008) and in inflammation (Sharif et al., 2006; Rothlin et al., 2007). The TAM family promotes the phagocytosis of apoptotic cells and stimulates the differentiation of natural killer cells (Park et al., 2009; Caraux et al., 2006). Axl activation is linked to several signal transduction pathways, including Akt, MAP kinases, NF-kappa B, STAT signal transduction pathways and others (Hafizi et al., 2006).

Axl is a member of the TAM (Tyro-Axl-Mer) receptor tyrosine kinases. This family is characterised by an extracellular domain, consisting of two immunoglobulin-like domains followed by two fibronectin type 3-like domains. The activation of the Axl RTK subfamily occurs by its cognate protein ligand, growth arrest specific 6 (Gas6). The affinity of Gas6 is highest for Axl, followed by Tyro3, and finally Mer, and thereby activates the three proteins to varying degrees. Gas6 is a member of the vitamin K-dependent family and shows a 43% sequence identity to and the same domain organisation as the protein S, a serum protein (Hafizi et al., 2006).

High Axl expression is observed in many human tumors (Shieh et al., 2005; Sun et al., 2004; Green et al., 2006; Ito et al., 1999) and it is associated with tumor stage and -progression in cancer patients (Gjerdrum et al., 2010; Sawabu et al., 2007; Green et al., 2006; Shieh et al., 2005). The kinase activity of Axl is required for erlotinib resistance in EGFR-mutant NSCLC tumor models. Genetic or pharmacologic inhibition of Axl restored sensitivity to erlotinib in these tumor models (Zhang et al., 2012). Accordingly, inhibition of Axl could prevent or overcome EGFR TKI acquired resistance in EGFR-mutant lung cancer patients.

Met is a receptor tyrosine kinase, like Axl, which has been associated with tumor progression in a wide variety of human malignancies, including those involved in proliferation, motility, migration and invasion. The inhibition of Axl and Met activity may overcome resistance therapy in metastatic renal cell carcinoma (Zhou et al., 2015; Burbridge et al., 2013).

It is an object of the present invention to provide compounds and/or pharmaceutically acceptable salts thereof which can be used as pharmaceutically active agents, especially for treatment of cell proliferative diseases like cancer, as well as compositions comprising at least one of those compounds and/or pharmaceutically acceptable salts thereof as pharmaceutically active ingredients.

In a first aspect, the present invention relates to a compound having the general formula I:

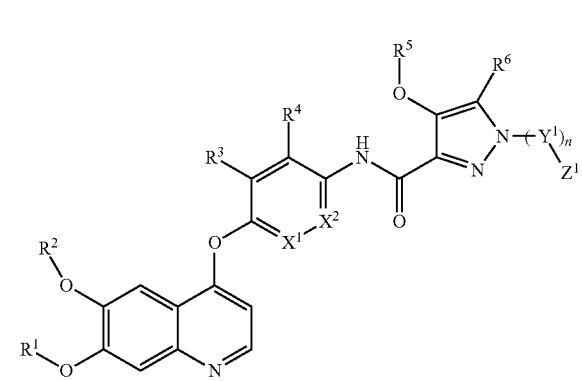

wherein
$X^1$ is, independently at each occurrence, selected from CH and N;
$X^2$ is, independently at each occurrence, selected from CH and N;
$Y^1$ is, independently at each occurrence, selected from $CH_2$, $CH(CH_3)CH_2$, $C(CH_3)_2$, $C(CH_3)_2CH_2$ and $CH_2CH_2$;
n is, independently at each occurrence, selected from 0 and 1;
$R^1$ is, at each occurrence, independently selected from the group consisting of C1-C6 alkyl and C1-C3 haloalkyl;
$R^2$ is, at each occurrence, independently selected from the group consisting of C1-C6 alkyl and C1-C3 haloalkyl, any of which is optionally substituted;

R³ is, at each occurrence, independently selected from the group consisting of hydrogen, halogen, e.g. Cl or F, C1-C3 alkyl, which is optionally substituted, and NHCH(CH₃)CH₃;

R⁴ is, at each occurrence, independently selected from the group consisting of hydrogen, halogen, e.g. Cl or F, NHCH(CH₃)₂, —CH₂OH, C1-C3 alkyl, which is optionally substituted, alkoxy, in particular C₁-C₃ alkoxy, e.g. methoxy, and —CF₃;

R⁵ is, at each occurrence, independently selected from the group consisting of C1-C6 alkyl, C1-C6 alkyl substituted with C1-C6 cycloalkyl, with heterocyclyl or with O—(C1-C6 alkyl); C1-C3 haloalkyl, e.g. CH₂F, CHF₂, CF₃, CH₂CF₃, N,N-dimethylethane-amino, N,N-dimethylpropan-1-amino;

R⁶ is, at each occurrence, independently selected from the group consisting of hydrogen and CH₃;

Z¹ is, at each occurrence, independently selected from the group consisting of hydrogen, hydroxyl, C1-C6 alkyl, C(O)R⁷, C(O)NHR⁷, C(O)OR⁷, CN, C(O)R⁸, C(O)OR⁸, N(R⁷)₂, OR⁸, OCH₃, OCH₂F, OCHF₂, OCF₃ and any structure of the following group A, any structure of which is optionally substituted;

group A

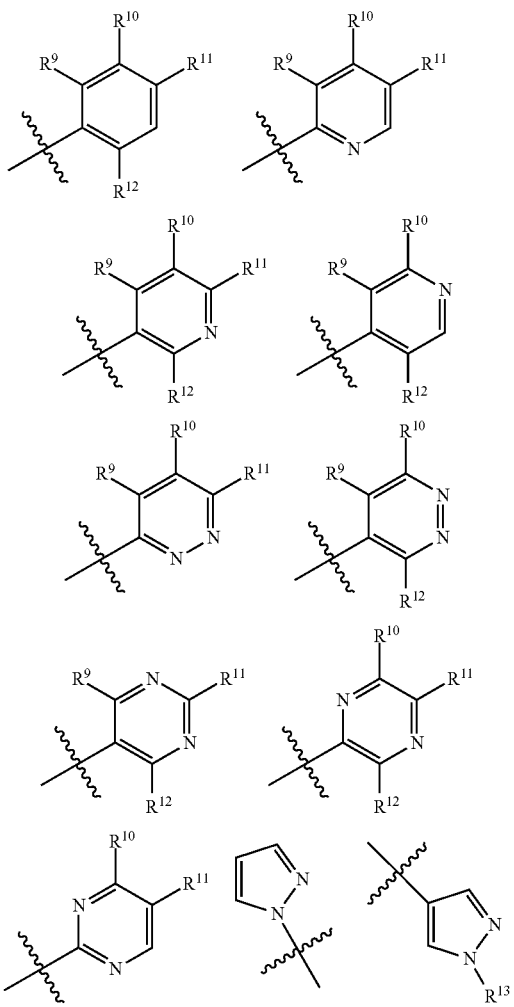

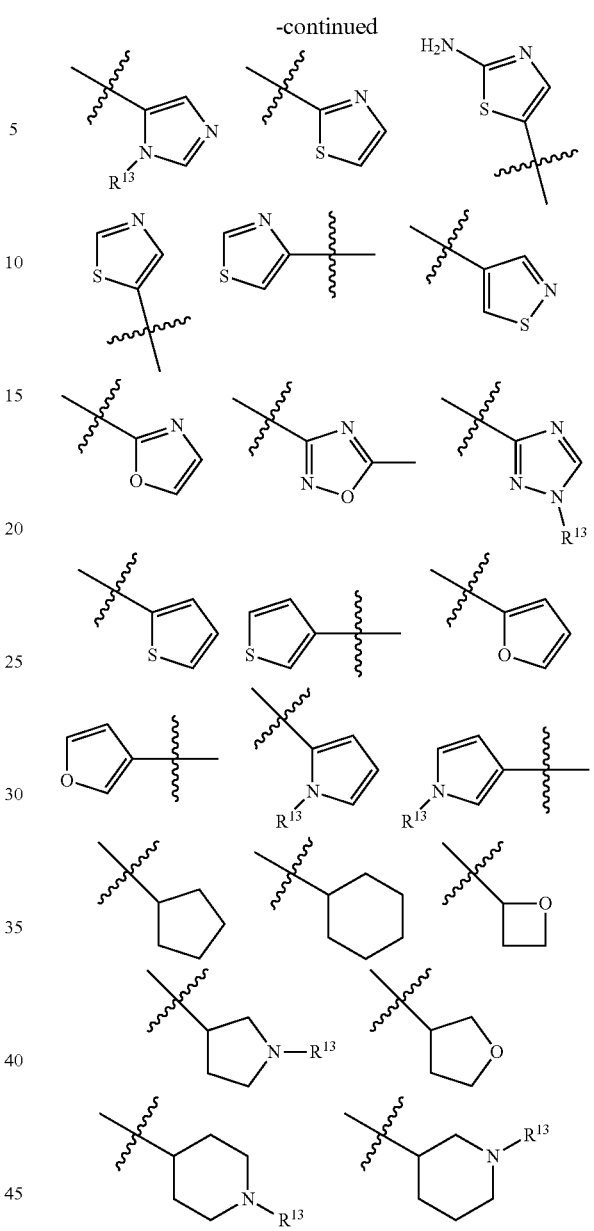

R⁷ is, at each occurrence, independently selected from the group consisting of hydrogen and C1-C6 alkyl, any of which is optionally substituted;

R⁸ is, at each occurrence, independently selected from the group consisting of hydrogen, C1-C6 alkyl, C1-C3 haloalkyl, e.g. CH₂F, CHF₂, CF₃, CH₂CF₃, and phenyl any of which is optionally substituted;

R⁹ is, at each occurrence, independently selected from the group consisting of hydrogen, C1-C6 alkyl, C1-C6 cycloalkyl, C1-C6 alkyl substituted with C1-C6 cycloalkyl; C1-C6 alkenyl, heterocyclyl, C1-C3 haloalkyl, e.g. CH₂F, CHF₂, CF₃, CH₂CF₃, C(O)OR⁷, CH₂C(O)OR⁷, C(O)R⁷, —(CH₂)ₘNR⁷R¹³, —(CH₂)ₘOR⁷, OR⁸, alkoxy, in particular C1-C3 alkoxy, e.g. methoxy, haloalkoxy, e.g. OCF₃, aryloxy, in particular phenoxy, C(CH₃)₂OH, C(CH₃)(OH)CH₂OH, N,N-dimethylethane-amino, F, Cl, NO₂, NH₂, CN, aryl, in particular benzyl or phenyl, benzyl hydroxyl and pyrrolidinyl, any of which is optionally substituted, m being an integer, independently at each occurrence, selected from 0, 1, 2, and 3;

$R^{10}$ is, at each occurrence, independently selected from the group consisting of hydrogen, hydroxyl, halogen, e.g. F, Cl, C1-C6 alkyl, C1-C3 haloalkyl, e.g. $CH_2F$, $CHF_2$, $CF_3$, $CH_2CF_3$, C(O)R', e.g. $CH_2F$, $CHF_2$, $CF_3$, $CH_2NR^7R^{13}$, $CH_2OH$, $C(O)NR^7R^{13}$, $NO_2$, and CN, any of which is optionally substituted;

$R^{11}$ is, at each occurrence, independently selected from the group consisting of hydrogen, hydroxyl, C1-C6 alkyl, C1-C3 haloalkyl, e.g. $CH_2F$, $CHF_2$, $CF_3$, $CH_2CF_3$, C(O)OR$^7$, $C(CH_3)_2(CH_2)_mNR^7R^{13}$, $—(CH_2)_mNR^7R^{13}$, $CH_2OH$, alkoxy, in particular C1-C$_3$ alkoxy, e.g. methoxy, haloalkoxy, e.g. $OCF_3$, halogen, e.g. F, Cl, CN, $NO_2$, $NH_2$, $NH_2—(CH_2)_m$ aryl, $—(CH_2)_m$ heteroaryl, $—NH(C_1-C_6$ alkyl), and $OR^8$, any of which is optionally substituted; m being an integer, independently at each occurrence, selected from 0, 1, 2 and 3;

$R^{12}$ is, at each occurrence, independently selected from the group consisting of hydrogen, halogen, in particular Cl or F, C1-C6 alkyl, C1-C6 alkyl substituted with C1-C6 cycloalkyl; C1-C6 cycloalkyl, heterocycloalkyl any of which is optionally substituted, $—(CH_2)_mNR^7R^{13}$, m being an integer independently at each occurrence selected from 0, 1, 2 and 3;

$R^{13}$ is, at each occurrence, independently selected from the group consisting of hydrogen and C1-C6 alkyl, COMe, $CONH_2$, any of which is optionally substituted;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{10}$ is hydrogen and $R^{12}$ is hydrogen, then $R^{11}$ is not F;

Wherein, if n is 0, $X^1$ is CH, $X^2$ is CH, $R^1$ is methyl, $R^2$ is methyl, $R^3$ is F, $R^4$ is hydrogen, $R^6$ is hydrogen, $Z^1$ is phenyl with substituents $R^9$-$R^{12}$ as depicted in group A, $R^9$ is hydrogen, $R^{10}$ is hydrogen, $R^{11}$ is F and $R^{12}$ is hydrogen, then $R^5$ is not methyl, methylcyclopropyl, N,N-dimethylethane-amino, N,N-dimethylpropan-1-amino or iso-propyl;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen, $Z^1$ is phenyl with substituents $R^9$-$R^{12}$ as depicted in group A, $R^{10}$ is hydrogen, $R^{11}$ is F and $R^{12}$ is hydrogen, then $R^9$ is not methyl or Cl;

Wherein, if n is 0, $X^1$ is CH, $X^2$ is CH, $R^1$ is methyl, $R^2$ is methyl, $R^3$ is hydrogen, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{10}$ is hydrogen and $R^{12}$ is hydrogen, then $R^{11}$ is not F;

Wherein, if n is 0, $X^1$ is CH, $X^2$ is CH, $R^1$ is methyl, $R^2$ is methyl, $R^3$ is hydrogen, $R^4$ is hydrogen, $R^6$ is hydrogen, $Z^1$ is phenyl with substituents $R^9$-$R^{12}$ as depicted in group A, $R^9$ is hydrogen, $R^{10}$ is hydrogen $R^{11}$ is F and $R^{12}$ is hydrogen, then $R^5$ is not iso-propyl or methylcyclopropyl;

Wherein, if n is 0, $X^1$ is CH, $X^2$ is CH, $R^1$ is methyl, $R^2$ is methyl, $R^3$ is hydrogen, $R^4$ is hydrogen, $R^5$ is ethyl, $R^6$ is hydrogen, $Z^1$ is phenyl with substituents $R^9$-$R^{12}$ as depicted in group A, $R^9$ is methyl, $R^{11}$ is hydrogen and $R^{12}$ is hydrogen, then $R^{11}$ is not F, Wherein, if n is 0, $X^1$ is CH, $X^2$ is CH, $R^1$ is methyl, $R^2$ is methyl, $R^3$ is methyl, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{10}$ is hydrogen and $R^{12}$ is hydrogen, then $R^{11}$ is not F;

Wherein, if n is 0, $X^1$ is CH, $X^2$ is CH, $R^1$ is methyl, $R^2$ is methyl, $R^3$ is methyl, $R^4$ is hydrogen, $R^6$ is hydrogen, $Z^1$ is phenyl with substituents $R^9$-$R^{12}$ as depicted in group A, $R^9$ is hydrogen, $R^{10}$ is hydrogen $R^{11}$ is F and $R^{12}$ is hydrogen, then $R^5$ is not iso-propyl or methylcyclopropyl;

Wherein, if n is 0, $X^1$ is CH, $X^2$ is CH, $R^1$ is methyl, $R^2$ is methyl, $R^3$ is methyl, $R^4$ is hydrogen, $R^5$ is ethyl, $R^6$ is hydrogen, $Z^1$ is phenyl with substituents $R^9$-$R^{12}$ as depicted in group A, $R^9$ is methyl, $R^{10}$ is hydrogen and $R^{12}$ is hydrogen, then $R^{11}$ is not F;

Wherein, if n is 0, $X^1$ is CH, $X^2$ is CH, $R^1$ is methyl, $R^2$ is methyl, $R^3$ is Cl, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{10}$ is hydrogen and $R^{12}$ is hydrogen, then $R^{11}$ is not F;

Wherein, if n is 0, $X^1$ is CH, $X^2$ is CH, $R^1$ is methyl, $R^2$ is methyl, $R^3$ is Cl, $R^4$ is hydrogen, $R^6$ is hydrogen, $Z^1$ is phenyl with substituents $R^9$-$R^{12}$ as depicted in group A, $R^9$ is hydrogen, $R^{10}$ is hydrogen, $R^{11}$ is F and $R^{12}$ is hydrogen, then $R^5$ is not iso-propyl or methylcyclopropyl;

Wherein, if n is 0, $X^1$ is CH, $X^2$ is CH, $R^1$ is methyl, $R^2$ is methyl, $R^3$ is Cl, $R^4$ is hydrogen, $R^5$ is ethyl, $R^6$ is hydrogen, $Z^1$ is phenyl with substituents $R^9$-$R^{12}$ as depicted in group A, $R^9$ is methyl, $R^{10}$ is hydrogen and $R^{12}$ is hydrogen, then $R^{11}$ is not F;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen, $Z^1$ is phenyl with substituents $R^9$-$R^{12}$ as depicted in group A, $R^{10}$ is hydrogen, $R^{11}$ is F and $R^{12}$ is hydrogen, then $R^9$ is not N,N-dimethylethane-amino;

Wherein, if n is 0, $X^1$ is CH, $X^2$ is N, $R^1$ is methyl, $R^2$ is methyl, $R^3$ is hydrogen, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{10}$ is hydrogen and $R^{12}$ is hydrogen, then $R^{11}$ is not F;

Wherein, if n is 0, $X^1$ is CH, $X^2$ is N, $R^1$ is methyl, $R^2$ is methyl, $R^3$ is hydrogen, $R^4$ is hydrogen, $R^5$ is ethyl, $R^6$ is hydrogen, $Z^1$ is phenyl with substituents $R^9$-$R^{12}$ as depicted in group A, $R^{10}$ is hydrogen, $R^{11}$ is F, and $R^{12}$ is hydrogen, then $R^9$ is not methyl, Cl, benzyloxy, or hydroxyl;

Wherein, if n is 0, $X^1$ is CH, $X^2$ is N, $R^1$ is methyl, $R^2$ is methyl, $R^3$ is hydrogen, $R^4$ is hydrogen, $R^5$ is ethyl, $R^6$ is hydrogen, $Z^1$ is phenyl with substituents $R^9$-$R^{12}$ as depicted in group A, $R^9$ is methyl, $R^{10}$ is hydrogen and $R^{12}$ is hydrogen, then $R^{11}$ is not methoxy;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{11}$ is hydrogen and $R^{12}$ is hydrogen, then $R^{10}$ is not $NO_2$;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen, $Z^1$ is phenyl with substituents $R^9$-$R^{12}$ as depicted in group A, $R^9$ is methyl, $R^{10}$ is hydrogen and $R^{12}$ is hydrogen, then $R^{11}$ is not methoxy;

Wherein, if n is 0, $X^1$ is CH, $X^2$ is N, $R^1$ is methyl, $R^2$ is methyl, $R^3$ is hydrogen, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{11}$ is hydrogen and $R^2$ is hydrogen, then $R^{11}$ is not $NO_2$;

Wherein, if n is 0, $X^1$ is CH, $X^2$ is CH, $R^1$ is methyl, $R^2$ is methyl, $R^3$ is hydrogen, $R^5$ is ethyl, $R^6$ is hydrogen, $Z^1$ is phenyl with substituents $R^9$-$R^{12}$ as depicted in group A, $R^9$ is methyl, $R^{10}$ is hydrogen, $R^{11}$ is F and $R^{12}$ is hydrogen, then $R^4$ is not methoxy or methyl;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{10}$ is methoxy and $R^{12}$ is hydrogen, then $R^{11}$ is not F;

Wherein, if n is 0, $X^1$ is CH, $X^2$ is N, $R^1$ is methyl, $R^2$ is methyl, $R^3$ is hydrogen, $R^4$ is hydrogen, $R^5$ is ethyl, $R^6$ is hydrogen, $Z^1$ is phenyl with substituents $R^9$-$R^{12}$ as depicted in group A, $R^9$ is hydrogen, $R^{10}$ is methoxy and $R^{12}$ is hydrogen, then $R^{11}$ is not F;

Wherein, if n is 0, $X^1$ is CH, $X^2$ is N, $R^1$ is methyl, $R^2$ is methyl, $R^3$ is hydrogen, $R^4$ is hydrogen, $R^5$ is ethyl, $R^6$ is hydrogen, Z is phenyl with substituents $R^9$-$R^{12}$ as depicted in group A, $R^9$ is hydrogen, $R^{10}$ is hydrogen and $R^{12}$ is hydrogen, then $R^{11}$ is not $NO_2$ or $NH_2$;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen, $R^9$ is hydrogen, $R^{10}$ is hydrogen, $R^{11}$ is hydrogen and $R^{12}$ is hydrogen, then $Z^1$ is not 3-pyridine as depicted in group A;

Wherein, if n is 0, $X^1$ is CH, $X^2$ is CH, $R^1$ is methyl, $R^2$ is methyl, $R^3$ is F, $R^4$ is hydrogen, $R^5$ is ethyl, $R^6$ is hydrogen and $Z^1$ is pyrazole as depicted in group A, then $R^{13}$ is not methyl;

and pharmaceutically acceptable salts thereof.

In one embodiment, one of $X_1$ and $X_2$ is N and the other is not, preferably $X_2$ is N and $X_1$ is CH.

In one embodiment, the present invention relates to a compound having the general formula II:

II wherein $Y^2$ is, independently at each occurrence, selected from $CH_2$ and $CH_2CH_2$;

n is, independently at each occurrence, selected from 0 and 1;

$R^1$ is, at each occurrence, independently selected from the group consisting of C1-C6 alkyl and C1-C3 haloalkyl;

$R^2$ is, at each occurrence, independently selected from the group consisting of C1-C6 alkyl and C1-C3 haloalkyl, any of which is optionally substituted;

$R^5$ is, at each occurrence, independently selected from the group consisting of C1-C6 alkyl, C1-C6 alkyl substituted with C1-C6 cycloalkyl, with heterocyclyl or with O—(C1-C6 alkyl); C1-C3 haloalkyl, e.g. $CH_2F$, $CHF_2$, $CF_3$, $CH_2CF_3$, N,N-dimethylethane-amino, N,N-dimethylpropan-1-amino;

$R^6$ is, at each occurrence, independently selected from the group consisting of hydrogen and $CH_3$;

$Z^2$ is, at each occurrence, independently selected from the group consisting of hydrogen, hydroxyl, C1-C6 alkyl, C(O)$R^7$, C(O)NH$R^7$, CN, C(O)$R^8$, N($R^7$)$_2$, O$R^8$ and any structure of the following group B, any structure of which is optionally substituted;

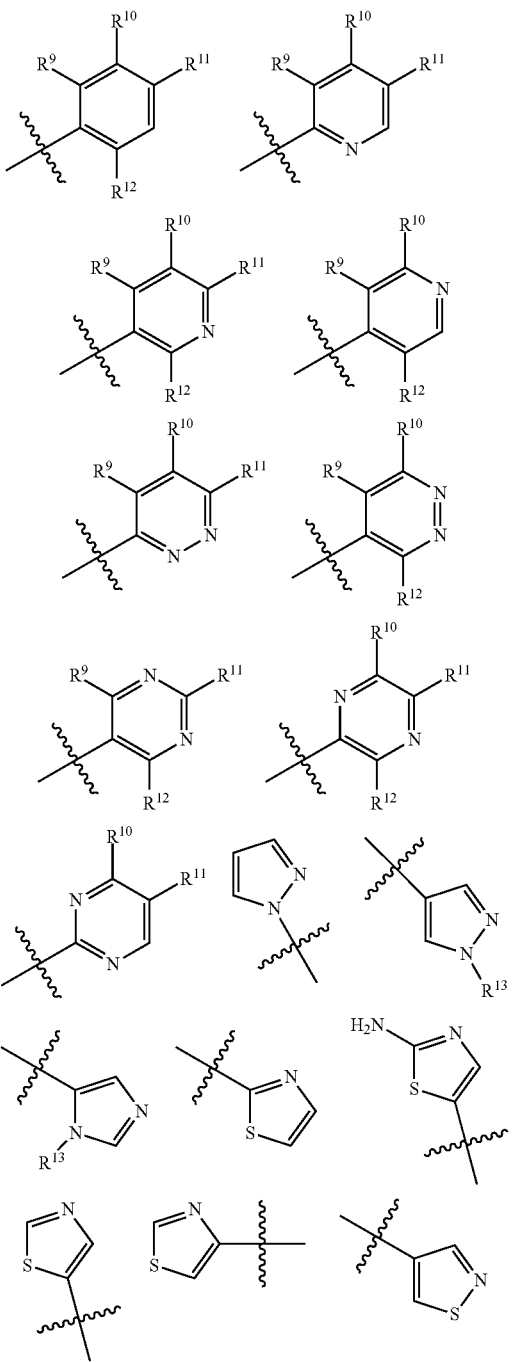

group B

-continued

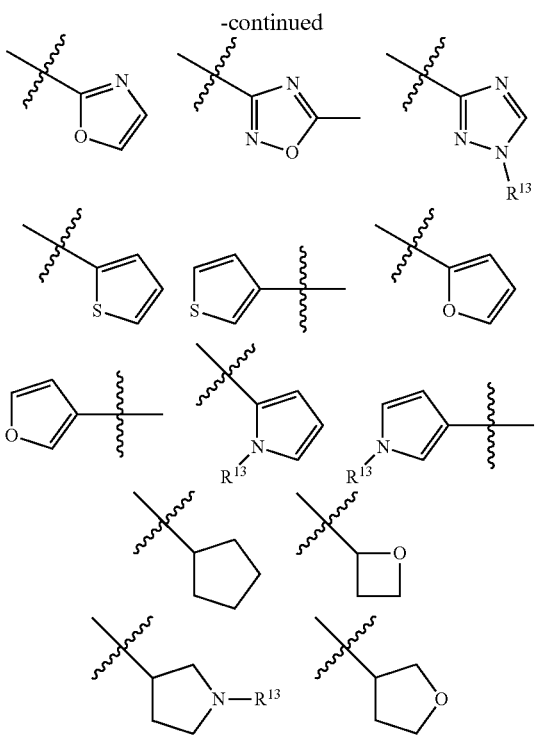

R$^7$ is, at each occurrence, independently selected from the group consisting of hydrogen and C1-C6 alkyl, any of which is optionally substituted;

R$^8$ is, at each occurrence, independently selected from the group consisting of hydrogen, C1-C6 alkyl, C1-C3 haloalkyl, e.g. CH$_2$F, CHF$_2$, CF$_3$, CH$_2$CF$_3$, and phenyl any of which is optionally substituted;

R$^9$ is, at each occurrence, independently selected from the group consisting of hydrogen, C1-C6 alkyl, C1-C6 cycloalkyl, C1-C6 alkyl substituted with C1-C6 cycloalkyl; C1-C6 alkenyl, heterocyclyl, C1-C3 haloalkyl, e.g. CH$_2$F, CHF$_2$, CF$_3$, CH$_2$CF$_3$, C(O)OR$^7$, CH$_2$C(O)OR$^7$, C(O)R$^7$, —(CH$_2$)$_m$NR$^7$R$^{13}$, —(CH$_2$)$_m$OR$^7$, OR$^8$, alkoxy, in particular C1-C3 alkoxy, e.g. methoxy, haloalkoxy, e.g. OCF$_3$, aryloxy, in particular phenoxy, C(CH$_3$)$_2$OH, C(CH$_3$)(OH)CH$_2$OH, N,N-dimethylethane-amino, F, Cl, NO$_2$, NH$_2$, CN, aryl, in particular benzyl or phenyl, benzyl hydroxyl and pyrrolidinyl, any of which is optionally substituted, m being an integer, independently at each occurrence, selected from 0, 1, 2, and 3;

R$^{10}$ is, at each occurrence, independently selected from the group consisting of hydrogen, hydroxyl, halogen, e.g. F, Cl, C1-C6 alkyl, C1-C3 haloalkyl, e.g. CH$_2$F, CHF$_2$, CF$_3$, CH$_2$CF$_3$, C(O)R$^7$, CH$_2$NR$^7$R$^{13}$, CH$_2$OH, C(O)NR$^7$R$^{13}$, NO$_2$ and CN, any of which is optionally substituted;

R$^{11}$ is, at each occurrence, independently selected from the group consisting of hydrogen, hydroxyl, C1-C6 alkyl, C1-C3 haloalkyl, e.g. CH$_2$F, CHF$_2$, CF$_3$, CH$_2$CF$_3$, C(O)OR$^7$, C(CH$_3$)$_2$(CH$_2$)$_m$NR$^7$R$^{13}$, —(CH$_2$)$_m$NR$^7$R$^{13}$, CH$_2$OH, alkoxy, in particular C$_1$-C$_3$ alkoxy, e.g. methoxy, haloalkoxy, e.g. OCF$_3$, halogen, e.g. F, Cl, CN, NO$_2$, NH$_2$, NH$_2$—(CH$_2$)$_m$ aryl, —(CH$_2$)$_m$ heteroaryl, —NH(C$_1$-C$_6$ alkyl), and OR$^8$, any of which is optionally substituted; m being an integer, independently at each occurrence, selected from 0, 1, 2 and 3;

R$^{12}$ is, at each occurrence, independently selected from the group consisting of hydrogen, halogen, in particular Cl or F, C1-C6 alkyl, C1-C6 alkyl substituted with C1-C6 cycloalkyl; C1-C6 cycloalkyl, heterocycloalkyl any of which is optionally substituted, —(CH$_2$)$_m$NR$^7$R$^{13}$, m being an integer independently at each occurrence selected from 0, 1, 2 and 3;

R$^{13}$ is, at each occurrence, independently selected from the group consisting of hydrogen and C1-C6 alkyl, COMe, CONH$_2$, any of which is optionally substituted;

R$^{14}$ and R$^{15}$ are, at each occurrence, independently selected from the group consisting of hydrogen, halogen, e.g. F, Cl, and methyl, which is optionally substituted;

Wherein, if n is 0, R$^1$ is methyl, R$^2$ is methyl, R$^{14}$ is hydrogen, R$^{15}$ is hydrogen, R$^5$ is ethyl, R$^6$ is hydrogen, Z$^2$ is phenyl with substituents R$^9$-R$^{12}$ as depicted in group B, R$^9$ is hydrogen, R$^{11}$ is hydrogen and R$^{12}$ is hydrogen, then R$^{10}$ is not NO$_2$;

Wherein, if n is 0, R$^1$ is methyl, R$^2$ is methyl, R$^{14}$ is hydrogen, R$^{15}$ is hydrogen, R$^5$ is ethyl, R$^6$ is hydrogen, Z$^2$ is phenyl with substituents R$^9$-R$^{12}$ as depicted in group B, R$^9$ is hydrogen, R$^{10}$ is methoxy and R$^{12}$ is hydrogen,
then R$^{11}$ is not F;

Wherein, if n is 0, R$^1$ is methyl, R$^2$ is methyl, R$^{14}$ is hydrogen, R$^{15}$ is hydrogen, R$^5$ is ethyl, R$^6$ is hydrogen, Z$^2$ is phenyl with substituents R$^9$-R$^{12}$ as depicted in group B, R$^9$ is hydrogen, R$^{10}$ is hydrogen and R$^{12}$ is hydrogen,
then R$^{11}$ is not NO$_2$ or NH$_2$;

and pharmaceutically acceptable salts thereof.

In one embodiment, the present invention relates to a compound having the general formula III:

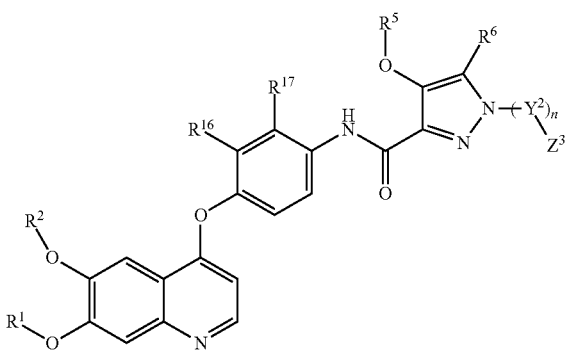

III wherein

Y$^2$ is, independently at each occurrence, selected from CH$_2$ and CH$_2$CH$_2$;

n is, independently, at each occurrence, selected from 0 and 1;

R$^1$ is, at each occurrence, independently selected from the group consisting of C1-C6 alkyl and C1-C3 haloalkyl, R$^2$ is, at each occurrence, independently selected from the group consisting of C1-C6 alkyl and C1-C3 haloalkyl, any of which is optionally substituted;

R$^5$ is, at each occurrence, independently selected from the group consisting of C1-C6 alkyl, C1-C6 alkyl substituted with C1-C6 cycloalkyl, with heterocyclyl or with O—(C1-C6 alkyl); C1-C3 haloalkyl, e.g. CH$_2$F, CHF$_2$, CF$_3$, CH$_2$CF$_3$, N,N-dimethylethane-amino, N,N-dimethylpropan-1-amino;

R$^6$ is, at each occurrence, independently selected from the group consisting of hydrogen and CH$_3$;

$Z^3$ is, at each occurrence, independently selected from any of the structures as depicted in the following group C, any structure of which is optionally substituted;

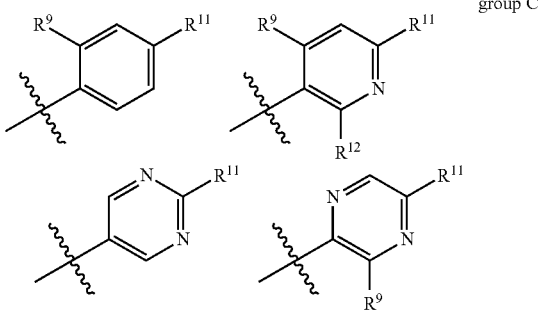

group C $R^7$ is, at each occurrence, independently selected from the group consisting of hydrogen and C1-C6 alkyl, any of which is optionally substituted;

$R^8$ is, at each occurrence, independently selected from the group consisting of hydrogen, C1-C6 alkyl, C1-C3 haloalkyl, e.g. $CH_2F$, $CHF_2$, $CF_3$, $CH_2CF_3$, and phenyl any of which is optionally substituted;

$R^9$ is, at each occurrence, independently selected from the group consisting of hydrogen, C1-C6 alkyl, C1-C6 cycloalkyl, C1-C6 alkyl substituted with C1-C6 cycloalkyl; C1-C6 alkenyl, heterocyclyl, C1-C3 haloalkyl, e.g. $CH_2F$, $CHF_2$, $CF_3$, $CH_2CF_3$, $C(O)OR^7$, $CH_2C(O)OR^7$, $C(O)R^7$, $—(CH_2)_m NR^7R^{13}$, $—(CH_2)_m OR^7$, $OR^8$, alkoxy, in particular C1-C3 alkoxy, e.g. methoxy, haloalkoxy, e.g. $OCF_3$, aryloxy, in particular phenoxy, $C(CH_3)_2OH$, $C(CH_3)(OH)CH_2OH$, N,N-dimethylethane-amino, F, Cl, $NO_2$, $NH_2$, CN, aryl, in particular benzyl or phenyl, benzyl hydroxyl and pyrrolidinyl, any of which is optionally substituted, m being an integer, independently at each occurrence, selected from 0, 1, 2, and 3;

$R^{11}$ is, at each occurrence, independently selected from the group consisting of hydrogen, hydroxyl, C1-C6 alkyl, C1-C3 haloalkyl, e.g. $CH_2F$, $CHF_2$, $CF_3$, $CH_2CF_3$, $C(O)OR^7$, $C(CH_3)_2(CH_2)_m NR^7R^{13}$, $—(CH_2)_m NR^7R^{13}$, $CH_2OH$, alkoxy, in particular $C_1$-$C_3$ alkoxy, e.g. methoxy, haloalkoxy, e.g. $OCF_3$, halogen, e.g. F, Cl, CN, $NO_2$, $NH_2$, $NH_2—(CH_2)_m$ aryl, $—(CH_2)_m$ heteroaryl, $—NH(C_1$-$C_6$ alkyl), and $OR^8$, any of which is optionally substituted; m being an integer, independently at each occurrence, selected from 0, 1, 2 and 3;

$R^{12}$ is, at each occurrence, independently selected from the group consisting of hydrogen, halogen, in particular Cl or F, C1-C6 alkyl, C1-C6 alkyl substituted with C1-C6 cycloalkyl; C1-C6 cycloalkyl, heterocycloalkyl any of which is optionally substituted, $—(CH_2)_m NR^7R^{13}$, m being an integer independently at each occurrence selected from 0, 1, 2 and 3;

$R^{13}$ is, at each occurrence, independently selected from the group consisting of hydrogen and C1-C6 alkyl, COMe, $CONH_2$, any of which is optionally substituted;

$R^{16}$ is, at each occurrence, independently selected from the group consisting of hydrogen, halogen, e.g. F, Cl, and methyl;

$R^{17}$ is, at each occurrence, independently selected from the group consisting of hydrogen, halogen, e.g. F, Cl, $NHCH(CH_3)_2$, $CF_3$, $—CH_2OH$, alkoxy, in particular $C_1$-$C_3$ alkoxy, e.g. methoxy, and methyl;

Wherein, if n is 0, $R^1$ is methyl, $R^2$ is methyl, $R^{16}$ is F, $R^{17}$ is hydrogen, $R^5$ is ethyl, $R^6$ is hydrogen, $Z^3$ is phenyl with substituents $R^9$ and $R^{11}$ as depicted in group C, and $R^9$ is hydrogen,
then $R^{11}$ is not F;

Wherein, if n is 0, $R^2$ is methyl, $R^2$ is methyl, $R^{16}$ is F, $R^{17}$ is hydrogen, $R^6$ is hydrogen, $Z^3$ is phenyl with substituents $R^9$ and $R^{11}$ as depicted in group C, $R^9$ is hydrogen, and $R^{11}$ is F,
then $R^5$ is not methyl, methylcyclopropyl, N,N-dimethylethane-amino, N,N-dimethylpropan-1-amino or i-propyl;

Wherein, if n is 0, $R^1$ is methyl, $R^2$ is methyl, $R^{16}$ is F, $R^{17}$ is hydrogen, $R^5$ is ethyl, $R^6$ is hydrogen, $Z^3$ is phenyl with substituents $R^9$ and $R^{11}$ as depicted in group C, and $R^{11}$ is F,
then $R^9$ is not methyl or Cl;

Wherein, if n is 0, $R^1$ is methyl, $R^2$ is methyl, $R^{16}$ is hydrogen, $R^{17}$ is hydrogen, $R^5$ is ethyl, $R^6$ is hydrogen, $Z^3$ is phenyl with substituents $R^9$ and $R^{11}$ as depicted in group C and $R^9$ is hydrogen,
then $R^{11}$ is not F;

Wherein, if n is 0, $R^1$ is methyl, $R^2$ is methyl, $R^{16}$ is hydrogen, $R^{17}$ is hydrogen, $R^6$ is hydrogen, $Z^3$ is phenyl with substituents $R^9$ and $R^{11}$ as depicted in group C, $R^9$ is hydrogen and $R^{11}$ is F,
then $R^5$ is not iso-propyl or methylecyclopropyl;

Wherein, if n is 0, $R^1$ is methyl, $R^2$ is methyl, $R^{16}$ is hydrogen, $R^{17}$ is hydrogen, $R^5$ is ethyl, $R^6$ is hydrogen, $Z^3$ is phenyl with substituents $R^9$ and $R^{11}$ as depicted in group C, and $R^9$ is methyl,
then $R^{11}$ is not F;

Wherein, if n is 0, $R^1$ is methyl, $R^2$ is methyl, $R^{16}$ is methyl, $R^{17}$ is hydrogen, $R^5$ is ethyl, $R^6$ is hydrogen, $Z^3$ is phenyl with substituents $R^9$ and $R^{11}$ as depicted in group C, and $R^9$ is hydrogen,
then $R^{11}$ is not F;

Wherein, if n is 0, $R^1$ is methyl, $R^2$ is methyl, $R^{16}$ is methyl, $R^{17}$ is hydrogen, $R^6$ is hydrogen, $Z^3$ is phenyl with substituents $R^9$ and $R^{11}$ as depicted in group C, $R^9$ is hydrogen, and $R^{11}$ is F,
then $R^5$ is not iso-propyl or methylcyclopropyl;

Wherein, if n is 0, $R^2$ is methyl, $R^2$ is methyl, $R^{16}$ is methyl, $R^{17}$ is hydrogen, $R^5$ is ethyl, $R^6$ is hydrogen, $Z^3$ is phenyl with substituents $R^9$ and $R^{11}$ as depicted in group C, and $R^9$ is methyl, then $R^{11}$ is not F;

Wherein, if n is 0, $R^2$ is methyl, $R^2$ is methyl, $R^{16}$ is Cl, $R^{17}$ is hydrogen, $R^5$ is ethyl, $R^6$ is hydrogen, $Z^3$ is phenyl with substituents $R^9$ and $R^{11}$ as depicted in group C, and $R^9$ is hydrogen,
then $R^{11}$ is not F;

Wherein, if n is 0, $R^1$ is methyl, $R^2$ is methyl, $R^{16}$ is Cl, $R^{17}$ is hydrogen, $R^6$ is hydrogen, $Z^3$ is phenyl with substituents $R^9$ and $R^{11}$ as depicted in group C, $R^9$ is hydrogen, and $R^{11}$ is F,
then $R^5$ is not iso-propyl or methylcyclopropyl;

Wherein, if n is 0, $R^1$ is methyl, $R^2$ is methyl, $R^{16}$ is Cl, $R^{17}$ is hydrogen, $R^5$ is ethyl, $R^6$ is hydrogen, $Z^3$ is phenyl with substituents $R^9$ and $R^{11}$ as depicted in group C, and $R^9$ is methyl,
then $R^{11}$ is not F;

Wherein, if n is 0, $R^1$ is methyl, $R^2$ is methyl, $R^{16}$ is F, $R^{17}$ is hydrogen, $R^5$ is ethyl, $R^6$ is hydrogen, $Z^3$ is phenyl with substituents $R^9$ and $R^{11}$ as depicted in group C, and $R^{11}$ is F,
then $R^9$ is not N,N-dimethylethane-amino;

Wherein, if n is 0, $R^1$ is methyl, $R^2$ is methyl, $R^{16}$ is F, $R^{17}$ is hydrogen, $R^5$ is ethyl, $R^6$ is hydrogen, $Z^3$ is phenyl with substituents $R^9$ and $R^{11}$ as depicted in group C, and $R^9$ is methyl, then $R^{11}$ is not methoxy;

Wherein, if n is 0, $R^1$ is methyl, $R^2$ is methyl, $R^{16}$ is hydrogen, $R^5$ is ethyl, $R^6$ is hydrogen, $Z^3$ is phenyl with substituents $R^9$ and $R^{11}$ as depicted in group C, $R^9$ is methyl, and $R^{11}$ is F, then $R^{17}$ is not methoxy or methyl;

Wherein, if n is 0, $R^1$ is methyl, $R^2$ is methyl, $R^{16}$ is F, $R^{17}$ is hydrogen, $R^5$ is ethyl, $R^6$ is hydrogen, $R^9$ is hydrogen, $R^{11}$ is hydrogen and $R^{12}$ is hydrogen, then $Z^3$ is not 3-pyridine as depicted in group C;

and pharmaceutically acceptable salts thereof.

In one embodiment, the present invention relates to a compound having the general formula IV:

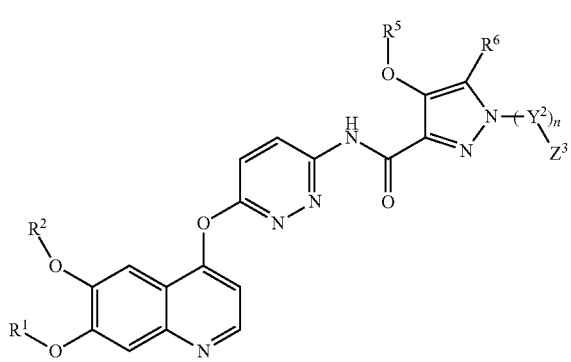

IV wherein $Y^2$ is, independently at each occurrence, selected from $CH_2$ and $CH_2CH_2$;

n is, independently at each occurrence, selected from 0 and 1;

$R^1$ is, at each occurrence, independently selected from the group consisting of C1-C6 alkyl and C1-C3 haloalkyl;

$R^2$ is, at each occurrence, independently selected from the group consisting of C1-C6 alkyl and C1-C3 haloalkyl, any of which is optionally substituted;

$R^5$ is, at each occurrence, independently selected from the group consisting of C1-C6 alkyl, C1-C6 alkyl substituted with C1-C6 cycloalkyl, with heterocyclyl or with O—(C1-C6 alkyl); C1-C3 haloalkyl, e.g. $CH_2F$, $CHF_2$, $CF_3$, $CH_2CF_3$, N,N-dimethylethane-amino, N,N-dimethylpropan-1-amino;

$R^6$ is, at each occurrence, independently selected from the group consisting of hydrogen and $CH_3$;

$Z^3$ is, at each occurrence, independently selected from any of the structures as depicted in the following group C, any structure of which is optionally substituted;

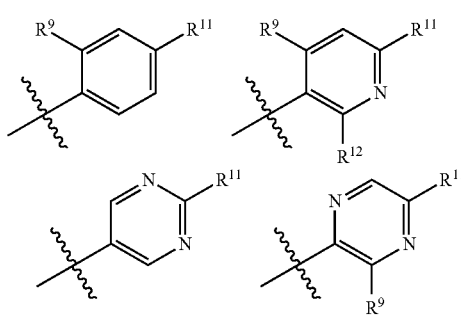

group C $R^7$ is, at each occurrence, independently selected from the group consisting of hydrogen and C1-C6 alkyl, any of which is optionally substituted;

$R^8$ is, at each occurrence, independently selected from the group consisting of hydrogen, C1-C6 alkyl, C1-C3 haloalkyl, e.g. $CH_2F$, $CHF_2$, $CF_3$, $CH_2CF_3$, and phenyl any of which is optionally substituted;

$R^9$ is, at each occurrence, independently selected from the group consisting of hydrogen, C1-C6 alkyl, C1-C6 cycloalkyl, C1-C6 alkyl substituted with C1-C6 cycloalkyl; C1-C6 alkenyl, heterocyclyl, C1-C3 haloalkyl, e.g. $CH_2F$, $CHF_2$, $CF_3$, $CH_2CF_3$, $C(O)OR^7$, $CH_2C(O)OR^7$, $C(O)R^7$, —$(CH_2)_m$$NR^7R^{13}$, —$(CH_2)_mOR^7$, $OR^8$, alkoxy, in particular C1-C3 alkoxy, e.g. methoxy, haloalkoxy, e.g. $OCF_3$, aryloxy, in particular phenoxy, $C(CH_3)_2OH$, $C(CH_3)(OH)CH_2OH$, N,N-dimethylethane-amino, F, Cl, $NO_2$, $NH_2$, CN, aryl, in particular benzyl or phenyl, benzyl hydroxyl and pyrrolidinyl, any of which is optionally substituted, m being an integer, independently at each occurrence, selected from 0, 1, 2, and 3;

$R^{11}$ is, at each occurrence, independently selected from the group consisting of hydrogen, hydroxyl, C1-C6 alkyl, C1-C3 haloalkyl, e.g. $CH_2F$, $CHF_2$, $CF_3$, $CH_2CF_3$, $C(O)OR^7$, $C(CH_3)_2(CH_2)_mNR^7R^{13}$, —$(CH_2)_mNR^7R^{13}$, $CH_2OH$, alkoxy, in particular $C_1$-$C_3$ alkoxy, e.g. methoxy, haloalkoxy, e.g. $OCF_3$, halogen, e.g. F, Cl, CN, $NO_2$, $NH_2$, $NH_2$—$(CH_2)_m$ aryl, —$(CH_2)_m$ heteroaryl, —$NH(C_1$-$C_6$ alkyl), and $OR^8$, any of which is optionally substituted; m being an integer, independently at each occurrence, selected from 0, 1, 2 and 3;

$R^{12}$ is, at each occurrence, independently selected from the group consisting of hydrogen, halogen, in particular Cl or F, C1-C6 alkyl, C1-C6 alkyl substituted with C1-C6 cycloalkyl, C1-C6 cycloalkyl, heterocycloalkyl any of which is optionally substituted, —$(CH_2)_mNR^7R^{13}$, m being an integer independently at each occurrence selected from 0, 1, 2 and 3;

$R^{13}$ is, at each occurrence, independently selected from the group consisting of hydrogen and C1-C6 alkyl, COMe, $CONH_2$, any of which is optionally substituted; and pharmaceutically acceptable salts thereof.

In a further aspect, the present invention also relates to a compound having the general formula V:

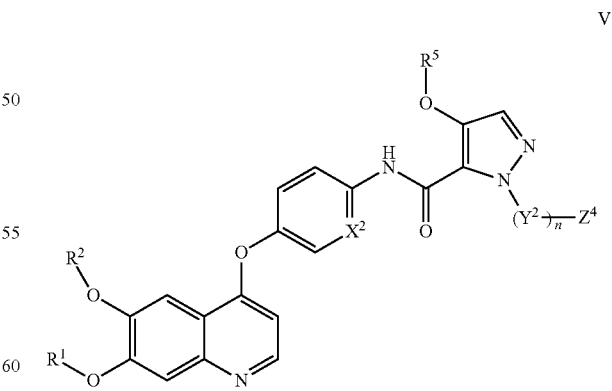

V wherein $X^2$ is, independently at each occurrence, selected from CF and N;

$Y^2$ is, independently at each occurrence, selected from $CH_2$ and $CH_2CH_2$;

n is, independently at each occurrence, selected from 0 and 1;

$R^1$ is, at each occurrence, independently selected from the group consisting of C1-C6 alkyl and C1-C3 haloalkyl;

$R^2$ is, at each occurrence, independently selected from the group consisting of C1-C6 alkyl and C1-C3 haloalkyl, any of which is optionally substituted;

$R^5$ is, at each occurrence, independently selected from the group consisting of C1-C6 alkyl, C1-C6 alkyl substituted with C1-C6 cycloalkyl, with heterocyclyl or with O—(C1-C6 alkyl); C1-C3 haloalkyl, e.g. $CH_2F$, $CHF_2$, $CF_3$, $CH_2CF_3$, N,N-dimethylethane-amino, N,N-dimethylpropan-1-amino;

$Z^4$ is, at each occurrence, independently selected from the group consisting of hydrogen, hydroxyl, $C_1$-$C_6$ alkyl, in particular methyl, ethyl, —$N(C1$-$C_6$ alkyl$)_2$, in particular $N(CH_3)_2$, alkoxy, in particular $C_1$-$C_3$ alkoxy and haloalkoxy, e.g. $OCH_3$, $OCH_2F$, $OCHF_2$, $OCF_3$ and any structure of the following group D, any structure of which is optionally substituted;

group D $R^{18}$ is, at each occurrence, independently selected from the group consisting of hydrogen, $C_1$-$C_6$ alkyl, in particular methyl and ethyl;

$R^{19}$ is, at each occurrence, independently selected from the group consisting of hydrogen, $C_1$-$C_6$ alkyl, in particular methyl, and $C_1$-$C_3$ haloalkyl, e.g. $CH_2F$, $CHF_2$, $CF_3$, $CH_2CF_3$;

$R^{20}$ is, at each occurrence, independently selected from the group consisting of hydrogen, $C_1$-$C_6$ alkyl, in particular methyl and $CH_2N(CH_3)_2$;

$R^{21}$ is, at each occurrence, independently selected from the group consisting of hydrogen, halogen, e.g. Cl or F, $C_1$-$C_6$ alkyl, in particular methyl, $CH(CH_3)_2$, $C(CH_3)_3$, $C_1$-$C_3$ haloalkyl, e.g. $CH_2F$, $CHF_2$, $CF_3$, $CH_2CF_3$, $NR^{18}R^{19}$, in particular $NH_2$, and CN; and pharmaceutically acceptable salts thereof.

In a further aspect, the present invention also relates to a compound having the general formula VI:

VI wherein $X^3$ is, independently at each occurrence, selected from CH, CF and N;

$Y^2$ is, independently at each occurrence, selected from $CH_2$ and $CH_2CH_2$;

n is, independently at each occurrence, selected from 0 and 1;

$R^1$ is, at each occurrence, independently selected from the group consisting of C1-C6 alkyl and C1-C3 haloalkyl;

$R^2$ is, at each occurrence, independently selected from the group consisting of C1-C6 alkyl and C1-C3 haloalkyl, any of which is optionally substituted;

$R^{22}$ is, at each occurrence, independently selected from the group consisting of hydrogen and halogen, in particular F and Cl;

W is, at each occurrence, independently selected from any structure as depicted in the following group E, any of which is optionally substituted;

group E

-continued

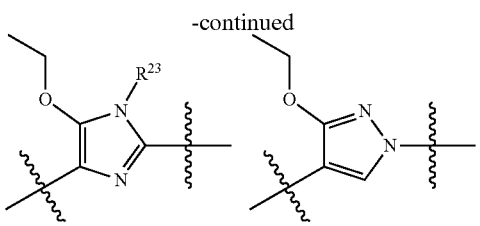

R$^{23}$ is, at each occurrence, independently selected from the group consisting of hydrogen and C1-C6 alkyl, any of which is optionally substituted;

Z$^5$ is, at each occurrence, independently selected from any structure as depicted in the following group F, any structure of which is optionally substituted;

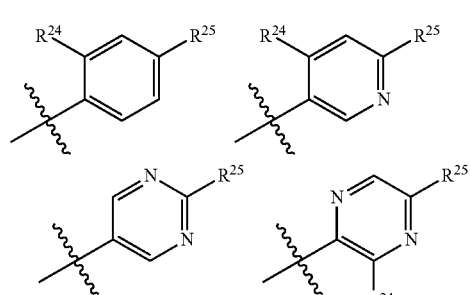

group F

R$^{24}$ and R$^{25}$ are, at each occurrence, independently selected from the group consisting of hydrogen, halogen, C1-C6 alkyl, C1-C3 haloalkyl, e.g. CH$_2$F, CHF$_2$, CF$_3$, CH$_2$CF$_3$, NH$_2$, CN, CH$_2$OH, alkoxy, in particular C$_1$-C$_3$ alkoxy, e.g. OCH$_3$ and OCF$_3$, any of which is optionally substituted;

and pharmaceutically acceptable salts thereof.

In a further aspect, the present invention also relates to a compound having the general formula VII:

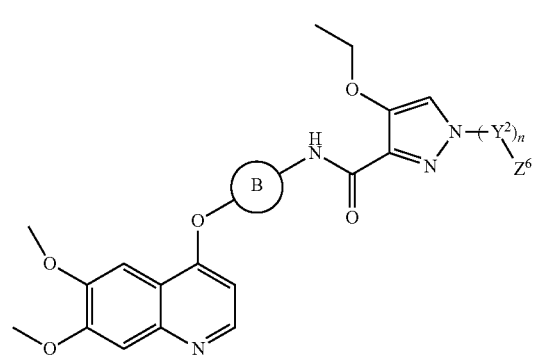

VII wherein

Y$^2$ is, independently at each occurrence, selected from CH$_2$ and CH$_2$CH$_2$;

n is, independently at each occurrence, selected from 0 and 1;

B is, at each occurrence, independently selected from any structure of the following group G, any structure of which is optionally substituted;

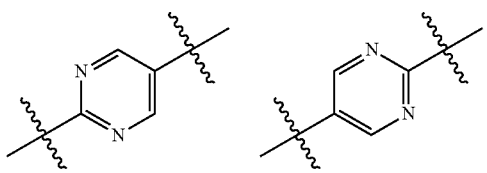

group G

Z$^6$ is, at each occurrence, independently selected from any structure of the following group H, any structure of which is optionally substituted;

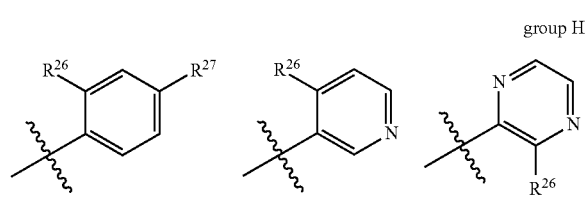

group H

R$^{26}$ is, at each occurrence, independently selected from the group consisting of hydrogen, halogen, in particular F, Cl, C$_1$-C$_6$ alkyl, in particular CH$_3$, any of which is optionally substituted;

R$^{27}$ is, at each occurrence, independently selected from the group consisting of hydrogen and halogen, in particular F;

and pharmaceutically acceptable salts thereof.

In one embodiment, the compound according to the present invention is a compound selected from compounds 1-280, as listed further below in any of tables 1-4, particularly in table 4.

In a further aspect, the present invention also relates to a compound according to the present invention for use as a pharmaceutically active agent.

In one aspect, the compounds according to the present invention are for use as an inhibitor of a TAM family receptor tyrosine kinase and/or a Met receptor tyrosine kinase.

In one aspect, the compounds according to the present invention are for use in the treatment of a disorder associated with, accompanied by, caused by and/or induced by TAM family receptor tyrosine kinase and/or Met receptor tyrosine kinase, preferably a hyperfunction of said TAM family receptor tyrosine kinase and/or of said Met receptor tyrosine kinase.

In one embodiment, the TAM family receptor tyrosine kinase induced disorder is selected from hyperproliferative disorders.

In one embodiment, the hyperproliferative disorders are selected from the group comprising cancer, in particular immune-suppressive cancer and primary tumor metastases.

In one embodiment, the hyperproliferative disorders are selected refractory cancers.

In one embodiment, the hyperproliferative disorder is selected from adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome, colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear tumors, nose tumors and throat tumors, hematologic neoplasias, hairy cell leukemia, urethral cancer, skin cancer, skin testis cancer, brain tumors, brain metastases, testicle cancer, hypophysis tumor, carcinoids, Kaposi's sarcoma, laryngeal cancer, germ cell tumor, bone cancer, colorectal carcinoma, head and neck tumors, colon carcinoma, craniopharyngiomas, oral cancer, cancer of the central nervous system, liver cancer, liver metastases, leukemia, eyelid tumor, lung cancer, lymph node cancer, lymphomas, stomach cancer, malignant melanoma, malignant neoplasia, malignant tumors of the gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinaliomas, T-cell lymphoma, thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

In one embodiment, the TAM family receptor tyrosine kinase induced disorder is selected from the group comprising infectious diseases.

In one embodiment, said use is in combination with another anti-cancer agent, preferably an inhibitor of a growth factor receptor, more preferably an inhibitor of an epidermal growth factor receptor (EGFR) or of a vascular endothelial growth factor receptor (VEGFR), e.g. erlotinib, afatinib, cetuximab, panitumumab, lenvatinib, motesanib, regorafenib, and pazopanib.

In a further aspect, the present invention also relates to a pharmaceutical composition comprising at least one compound according to any of claims 1-8, together with at least one pharmaceutically acceptable carrier, excipient and/or diluent.

In one embodiment, the pharmaceutical composition according to the present invention further comprises another anti-cancer agent, preferably an inhibitor of a growth factor receptor, more preferably an inhibitor of an epidermal growth factor receptor (EGFR) or of a vascular endothelial growth factor receptor (VEGFR), e.g. erlotinib, afatinib, cetuximab, panitumumab, lenvatinib, motesanib, regorafenib, and pazopanib.

The present invention also relates to the use of a compound as defined above for the manufacture of a medicament for the treatment of a disease associated with, accompanied by, caused by and/or induced by TAM family RTKs. The present invention also relates to a method of treatment of a disease associated with, accompanied by, caused by and/or induced by TAM family RTKs, said method comprising the administration of a compound according to the present invention to a patient in need thereof. In one embodiment, the disease associated with, accompanied by, caused by and/or induced by TAM family RTKs is a disease selected from hyperproliferative disorders and infectious diseases.

The compounds of the present invention are efficient inhibitors of TAM family RTKs and thus, are suitable for the treatment of disorders associated with, accompanied by, caused by and/or induced by TAM family RTKs, in particular their hyperfunction, and thereby having an effect on one or several of cell survival, proliferation, autophagy, vascular smooth muscle homeostasis, migration, adhesion, angiogenesis, platelet aggregation, thrombus stabilization, erythropoiesis, oligodendrocyte cell survival, osteoclast function, innate immunity, inflammation, phagocytosis of apoptotic cells and/or natural killer cell differentiation.

The compounds of the invention are capable of inhibiting cell proliferation and thus, are suitable for the treatment and/or prevention of TAM receptor tyrosine kinase induced hyperproliferative disorders, particularly selected from the group comprising cancer, especially immune-suppressive cancer and refractory cancer, and primary tumor metastases. In a preferred embodiment of the invention, the TAM receptor tyrosine kinase induced disorders are associated with TAM receptor tyrosine kinase receptor overexpression and/or hyperactivity, e.g. an increased degree of autophosphorylation compared to normal tissue. The disorders may be selected from breast cancer, colon cancer, prostate cancer, lung cancer, gastric cancer, ovarian cancer, endometrial cancer, renal cancer, hepatocellular cancer, thyroid cancer, uterine cancer, esophagus cancer, squamous cell cancer, leukemia, osteosarcoma, melanoma, glioblastoma and neuroblastoma. In an especially preferred embodiment, the disorders are selected from breast cancer, glioblastoma, renal cancer, non-small cell lung cancer (NSCLC), and melanoma.

Examples for disorders associated with, accompanied by, caused by and/or induced by TAM hyperfunction are acute lymphoblastic leukemia, acute myeloid leukemia, adrenocortical carcinoma, aids-related cancers, aids-related lymphoma, anal cancer, appendix cancer, astrocytomas, atypical teratoid/rhabdoid tumor, basal cell carcinoma, bile duct cancer, bladder cancer, bone cancer, osteosarcoma and malignant fibrous histiocytoma, brain stem glioma, brain tumor, central nervous system atypical teratoid/rhabdoid tumor, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma, brain and spinal cord tumors, breast cancer, bronchial tumors, burkitt lymphoma, carcinoid tumor, gastrointestinal cancer, central nervous system (CNS) lymphoma, cervical cancer, chordoma, chronic lymphocytic leukemia, chronic myelogenous leukemia, chronic myeloproliferative disorders, colon cancer, colorectal cancer, craniopharyngioma, cutaneous t-cell lymphoma, mycosis fungoides, sezary syndrome, endometrial cancer, ependymoblastoma, ependymoma, esophageal cancer, esthesioneuroblastoma, ewing sarcoma family of tumors, extracranial germ cell tumor, extragonadal germ cell tumor, extrahepatic bile duct cancer, intraocular melanoma, retinoblastoma, gallbladder cancer, gastric (stomach) cancer, gastrointestinal carcinoid tumor, gastrointestinal stromal tumor (gist), gastrointestinal stromal cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular (liver) cancer, histiocytosis, hodgkin lymphoma, hypopharyngeal cancer, intraocular melanoma, islet cell tumors (endocrine pancreas), kaposi sarcoma, renal cell cancer, kidney cancer, langerhans cell histiocytosis, laryngeal cancer, acute lymphoblastic leukemia, acute myeloid leukemia, chronic lymphocytic leukemia, chronic myelogenous leukemia, leukemia, lip and oral cavity cancer, liver cancer, lung cancer, non-small cell lung cancer, small cell lung cancer, aids-related lymphoma, burkitt lymphoma, (cutaneous t-cell lymphoma, hodgkin lymphoma, non-hodgkin lymphoma, primary central nervous system lymphoma, macroglobulinemia, malignant fibrous histiocytoma of bone and osteosarcoma, medulloblastoma, medulloepithelioma, melanoma, melanoma intraocular (eye), merkel cell carcinoma, mesothelioma, metastatic squamous neck cancer with occult primary, mouth cancer, multiple endocrine neoplasia syndromes, multiple myeloma/plasma cell neoplasm, myelodysplastic syndromes, myelodysplastic/myeloproliferative neoplasms, myelogenous leukemia, myeloid leukemia, myeloma (multiple), myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineoblastoma and supratentorial primitive neuroectodermal tumors, pituitary tumor, plasma, cell neoplasm/multiple myeloma, pleuropulmonary blastoma, pregnancy and breast cancer, prostate cancer, rectal cancer, renal cell (kidney) cancer, transitional cell cancer, respiratory tract cancer, retinoblastoma, rhabdomyosarcoma, salivary gland cancer, sarcoma, ewing sarcoma, kaposi sarcoma, uterine sarcoma, nonmelanoma skin cancer, melanoma skin cancer, skin carcinoma, small cell lung cancer, small intestine cancer, soft tissue sarcoma, squamous cell carcinoma, squamous neck cancer, stomach (gastric) cancer, supratentorial primitive neuroectodermal tumors, t-cell lymphoma, testicular cancer, throat cancer, thymoma and thymic carcinoma, thyroid cancer, transitional cell cancer of the renal pelvis and ureter, trophoblastic tumor, gestational cancer, ureter and renal pelvis cancer, transitional cell cancer, urethral cancer, uterine cancer, endometrial cancer, uterine sarcoma, vaginal cancer, vulvar cancer, Waldenstrom macroglobulinemia and Wilms tumor.

The compounds of the present invention are efficient inhibitors of TAM family and/or Met RTKs. The inventive compounds are suitable for the use as a pharmaceutically active agent. The inventive compounds are suitable for the treatment of disorders associated with, accompanied by, caused by and/or induced by TAM family RTKs, in particular a hyperfunction thereof. The inventive compounds are thus suitable for the treatment of TAM receptor tyrosine kinase induced disorders.

The inventive compounds are also useful in the manufacture of a medicament or of a pharmaceutical composition for the treatment of disorders associated with, accompanied by, caused by and/or induced by TAM family receptor tyrosine kinases, in particular a hyperfunction thereof. The inventive compounds are further used in the manufacture of a medicament or of a pharmaceutical composition for the treatment and/or prevention of TAM receptor tyrosine induced disorders.

The term "optionally substituted" as used herein is meant to indicate that a hydrogen atom where present and attached to a member atom within a group, or several such hydrogen atoms, may be replaced by a suitable group, such as halogen including fluorine, chlorine, $C_1$-$C_3$ alkyl, $C_1$-$C_3$ haloalkyl, e.g. $CH_2F$, $CHF_2$, $CF_3$, $CH_2CF_3$, methylhydroxyl, hydroxyl, COOMe, C(O)H, COOH, alkoxy, in particular C1-C3 alkoxy, e.g. OMe, or $OCF_3$; In one embodiment, the present invention also relates to pharmaceutically acceptable salts of the compounds according to the present invention.

The present invention also relates to combinations of compounds in accordance with the present invention as well as to combinations of a compound in accordance with the present invention together with another anti-cancer agent. As will be shown further below, the combination of a compound in accordance with the present invention with another anti-cancer agent has a synergistic effect. For example combinations with other anti-cancer agents may restore sensitivity of cell lines which have become resistant to other anti-cancer agents. As examples of agents with which the compounds according to the present invention may be combined, inhibitors of growth factor receptors should be mentioned, in particular inhibitors of epidermal growth factor receptor (EGFR inhibitors) or of vascular endothelial growth factor receptor (VEGFR inhibitors) should be mentioned. Typical examples of such growth factor receptor inhibitors are erlotinib, afatinib, cetuximab, panitumumab, lenvatinib, motesanib, regorafenib, and pazopanib. Other combinations may also or instead include several compounds in accordance with the present invention together. These are also envisaged and encompassed by combinations in accordance with the present invention.

The term "alkyl" refers to a monovalent straight, branched or cyclic chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, cyclic propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as —$CHF_2$, —$CF_3$, —$CH_2$—$CH_2$—F, —$CH_2$—$CF_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or thioalkyl group (e.g., —$SCH_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), alkyl amine (e.g., —$CH_2NHCH_3$, —$CH_2N(CH_3)_2$, etc.), or thioalkyl ether (e.g., —$CH_2$—S—$CH_3$).

The term "halogen" refers to fluorine, chlorine, bromine, or iodine.

The term "phenyl" as used herein is meant to indicate an optionally substituted or non-substituted phenyl group.

The term "benzyl" as used herein is meant to indicate an optionally substituted or non-substituted benzyl group.

The term "heteroaryl" refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally S(O) or $S(O)_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl.

The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to S(O) or $S(O)_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

Pharmaceutical Compositions

Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like.

Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Administration and Formulation

The production of medicaments containing the compounds of the invention, its active metabolites or isomers and salts according to the invention and their application can be performed according to well-known pharmaceutical methods.

While the compounds of the invention, useable according to the invention for use in therapy, may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds of the invention may be anhydrous or solvated.

In a preferred embodiment, the invention provides medicaments comprising a compound useable according to the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds useable according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compounds useable according to the invention can be administered in a wide variety of oral and parenteral dosage forms. It will be obvious to those skilled in the art that the following dosage forms may comprise, as the active component, either a compound(s) useable according to the invention or a pharmaceutically acceptable salt of a compound(s) useable according to the invention.

For preparing a medicament from a compound useable according to the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The chemical compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

For administration, the compounds of the present invention may, in one embodiment, be administered in a formulation containing 0,001% to 70% per weight of the compound, preferably between 0.01% to 70% per weight of the compound, even more preferred between 0.1% and 70% per weight of the compound. In one embodiment, a suitable amount of compound administered is in the range of from 0.01 mg/kg body weight to 1 g/kg body weight.

Compositions suitable for administration also include lozenges comprising the active agent in a flavoured base, usually sucrose and acacia or tragacanth; pastilles comprising the active ingredient in an inert base such as gelatin and glycerol or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

The invention is further illustrated by the following figures, tables and Examples which are given to illustrate the invention, not to limit it.

FIGURES AND TABLES

Reference is now made to the figures and tables, wherein
FIG. 1. Combination effect of compound and erlotinib on inhibition activity in Erlotinib—resistant cell-line
FIG. 2. Chemical structure of Erlotinib
Table 1 shows activity data in Axl, Mer and TYRO3 binding assay for selected compounds of the invention. Inhibition is indicated as Kd with the following key: A=Kd less than 0.1 uM; B=Kd greater than 0.1 uM, but less than 1.0 uM; C=Kd greater than 1.0 uM.

Table 2 shows activity data in Met binding assay for selected compounds of the invention. Inhibition is indicated as Kd with the following key: A=Kd less than 0.1 uM; B=Kd greater than 0.1 uM, but less than 1.0 uM; C=Kd greater than 1.0 uM.

Table 3 shows activity data in cellular Axl phosphorylation assay for selected compounds of the invention. Inhibition is indicated as $IC_{50}$ with the following key: A=$IC_{50}$ less than 0.1 uM; B=$IC_{50}$ greater than 0.1 uM, but less than 1.0 uM; C=$IC_{50}$ greater than 1.0 uM.

Table 4. Summarizes compounds 1-280 in terms of their structures and corresponding characteristics.

EXAMPLES

The invention is now further described by reference to the following examples which are intended to illustrate, not to limit the scope of the invention.

Example 1 Kinase Binding Assay for Axl, Mer, TYRO3 and Met

Binding Assay Principle

LanthaScreen® Eu Kinase Binding assays were conducted at Life Technologies using the manufacturer's specifications for each kinase indicated.

Briefly, the principle behind this assay is based upon the binding and displacement of an Alexa Fluor 647-labeled tracer to the kinase of interest. Binding of the tracer to the kinase is detected using an EU-labeled anti-tag antibody. Simultaneous binding of both the tracer and antibody to the kinase gives rise to a FRET-signal. Binding of an inhibitor to the kinase competes for binding with the tracer, resulting in a loss of FRET-signal.

Binding Assay Protocol for AXL, Mer, Tyro3 and Met

A given compound was diluted in DMSO to make a stock compound solution. The stock compound solution was serially diluted over eight steps in DMSO. Each diluted compound solution in DMSO was diluted in kinase buffer. Afterwards four kinds of working solution were prepared. First, Tracer-Working solution consists of Tracer 236 and Kinase Buffer. Second, Axl, Mer, Tyro3 or Met/anti-GST-AB-Working solution contained one of the kinases Axl, Mer, Tyro3, Met or anti-GST-AB (=anti glutathione-S-transferase antibody) in Kinase Buffer. Third, anti-GST-AB-Working solution was made with anti-GST-AB and Kinase Buffer. Last, in the DMSO-Working solution DMSO was added to Kinase Buffer to a final concentration to 3%. Each of the four kinds of working solutions were separately added to the assay plate and then incubated for 1 h at room temperature. After incubation, the assay plate was measured with respect to the FRET-Signal with the EnVision (Perkin Elmer) using the program LanthaHTRF-Assay. Data evaluation was done in the Quattro Workflow software. Kd (the equilibrium dissociation constant) values were calculated relative to vehicle (DMSO) control wells.

Table 1 summarises the results obtained for AXL, Mer and Tyro3-kinases binding assays; table 2 summarises the results obtained for the Met kinase binding assay.

Example 2: Cellular Axl Phosphorylation Assay

Cell AXL Inhibition Assay Principle

The assay is based on the measurement of the relative amounts of Total-Axl and Phosphorylated-Axl in whole cell lysates of transiently transfected HEK293T cells. This assay is based on application of the Mesoscale western blot and subsequent electro-chemiluminescence detection. Overexpression of Axl-RTK (Receptor tyrosine kinase) by transfection leads to an increase in Axl-trans-autophosphorylation events. Upon compound treatment, the correlation of the measured values of Phosphorylated-Axl and Total Axl indicate the potential of the tested compound to inhibit Axl-phosphorylation at the given compound concentration.

Cell AXL Inhibition Assay Protocol

HEK293T (CRL-3216™) were obtained from the American Type Culture Collection (ATCC, Netherlands). HEK293T cells ($2.5 \times 10^4$/well) were plated in a 96 well plate and cells were transfected with pcDNA_DEST_40 Axl or pcDNA_DEST_40 by Superfact reagent (Qiagen. Co. Ltd.). After overnight, the transfection reagent of each well was removed from cells and replaced by fresh prewarmed medium. On the following day, cells were treated with the respective test compound which was diluted by the same method, as in the Axl binding assay using DMSO, for 1 hour After incubation with the test compounds, cells in the well of the plate were lysed using Tris lysis buffer. The lysate was transferred to two plates (total-Axl and phosphor-Axl) Mesoscale high bind plates and incubated for two hours at room temperature. Afterwards the lysates were removed from the plates and the plates were blocked using Blocking buffer. Subsequently Total-Axl antibody (H-124, Santa Cruz) was transferred to one Mesoscale high bind plate, and Phospho-Axl antibody (AF2228, R&D) to the other plate. After 1 h incubation, Sulpho-Tag antibody (goat anti-rabbit, Mesoscale) was added and again incubated for 1 hour. For the measurement, 2×MSD read buffer was added to each well and the plates were analyzed with a Mesoscale Sector Imager 2400. $IC_{50}$ (half the maximal inhibitory concentration) was determined relative to between the vehicle (DMSO) control group and minimum control group as transfection of the control vector (pcDNA_DEST_40).

The results after this assay are shown in table 3 for selected compounds.

Example 3: Erlotinib-Resistant Cells (HCC827/ER Sublines) are Resistant to Erlotinib, but not to TAM Inhibitors Treatment as Measured by WST-1 Cell Viability Assay Establishment of Erlotinib-Resistant Cell Lines Erlotinib-resistant sub-cell lines were established referring to published paper (Rho et al., 2014)). Erlotinib-resistant HCC827 cells were generated from HCC827 NSCLC cells, which harbor an activating EGFR mutation (EGFR L858R). HCC827 (CRL-2868™) were obtained from the American Type Culture Collection (ATCC, Netherlands). Erlotinib-resistant HCC827 was isolated by exposure to gradually increasing doses of Erlotinib. Briefly, HCC827 cells were treated with 10 nM (the approximate IC50 dose) of Erlotinib for 72 hours in RPMI-1640 medium containing 10% FBS. The killed cells were discarded and the remaining cells were cultured in a drug-free medium up to 80% confluence. Subsequently, cells were continuously exposed to increasing drug doses of up to 10 μM over a period of 8 months. The established resistant cell lines were maintained in a medium containing 1 μM Erlotinib.

For all in vitro studies, resistant cells were maintained in an erlotinib-free medium for at least 2 weeks prior to experimentation to eliminate the effects of the drugs. Erlotinib-resistant cells are referred to as HCC827/ER.

Cell Viability Assays

Efficacy of the restoration of Erlotinib was determined via a WST-1 cell viability assay. HCC827/ER cells were seeded in a 96-well plate with their respective media containing 10% FBS at 5000 cells/well. After seeding, the HCC827/ER cells were incubated for approximately 24 hours. The HCC827/ER cells were then exposed to compounds in the serum depletion media (FBS 1%); the HCC827/ER cells were either treated with ten two-fold serial dilutions of compounds (the final concentration of the compounds ranged from 10 to 0.16μ M), of erlotinib or of the compounds combined with Erlotinib at a constant 1:1 ratio as indicated The HCC827/ER cells were incubated with the compounds for 3 days. The viability of the HCC827/ER cells was determined by adding WST-1 reagent according to Manufacturer's instructions (DoGenbio co., Ltd) and incubating for four hours. The plates were then read using an absorbance of 440 nm on Tecan Microplate reader (Infinite M200 pro, TECAN). The HCC827/ER cells' viability were calculated relative to vehicle (DMSO) control wells. FIG. 1 shows the results of the cell viability assay using erlotinib alone, selected representative compound alone (compounds no. 38, 79, 132 and 149), and a combination of erlotinib with the selected compound (such combination indicated by "+" followed by the selected compound's number). The respective combination have a synergistic effect on the inhibitory effect on erlotinib-resistant cell lines.

Example 4: Derivatization of the Dimethoxyquinoline General Scaffold

The presented compounds underwent derivatization according to the methods outlined below (Schemes 1-13). Resulting derivatives were examined for kinase binding and Axl celluar activity (Axl, Mer, TYRO3, cMet and Axl cell) using the assays described above (Example 1-3) and the results are summarized in Table 1-3. The synthesized compounds 1-280 are shown in Table 4.

Scheme 1-General Synthetic route I; amide coupling

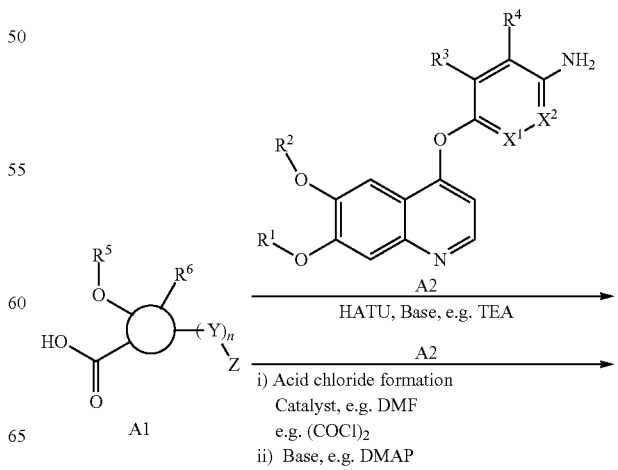

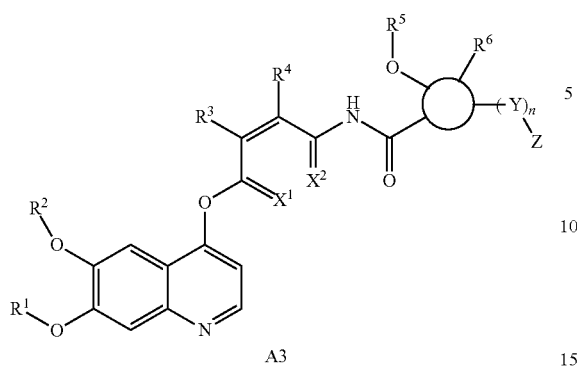

A3

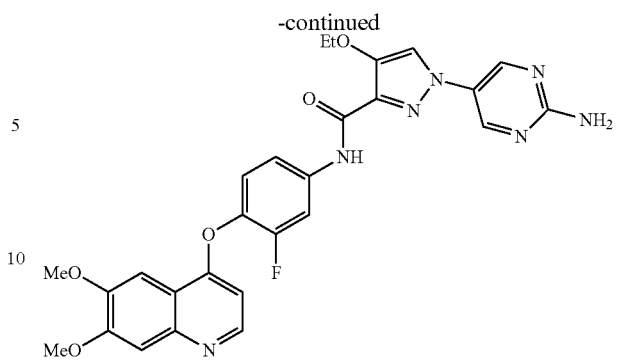

A method to prepare compounds of A3 is shown in Scheme 1. Carboxylic acids can be directly coupled with anilines A2 under standard procedures, such as HATU (O-(7-Azabenzotriazol-1-yl)-N,N,N',N'-tetramethyluronium hexafluorophosphate) to give A3 compounds. Alternatively, the reaction of acid chloride (e.g. thiazole and oxazole derivatives) and aniline is carried out in the presence of a base like pyridine and optionally in an inert solvent like DCM (dichloromethane). The acid chlorides can be prepared from commercially available carboxylic acids via standard procedures, using thionyl chloride or oxalyl chloride as reagents.

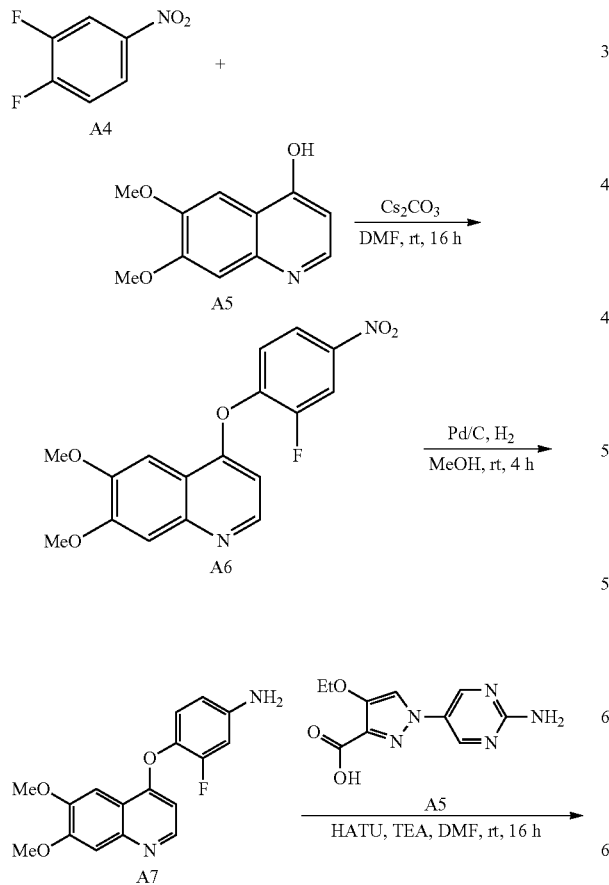

General Procedure for Synthesis of A6

To a mixture of compound A5 (12.0 g, 58.5 mmol) in DMF (150 mL) was added compound A4, 4-difluoronitrobenzene (9.77 g, 61.4 mmol) and $Cs_2CO_3$ (22.9 g, 70.2 mmol), the reaction mixture was stirred at 25° C. for 16 hours. TLC showed the reaction was completed. The mixture was quenched with water (250 mL), then filtered, the filter cake was combined with above batch, purified by silica gel column (EtOAc/DCM=1/3 to 1/1) to give 9.60 g (yield: 40.9%) of compound A6 as a yellow solid.

General Procedure for Synthesis of A7

To a mixture of compound A6 (1.00 g, 2.90 mmol) in MeOH (20 mL) was added Pd/C (800 mg) under $N_2$ atmosphere, the reaction mixture was purged in $H_2$ atmosphere for 3 times, then stirred at 25° C. under $H_2$ balloon (15 psi) for 4 hours. LCMS showed the reaction was completed. The mixture was filtered, the filtrate was concentrated under reduced pressure to give 840 mg (yield: 92.2%) of compound A7 as a white solid.

General Procedure for Synthesis of 141

To a mixture of compound A5 (90 mg, 0.361 mmol) in DMF (20 mL) was added HATU (412 mg, 1.08 mmol) and TEA (110 mg, 1.08 mmol), the reaction mixture was stirred at 25° C. for 0.5 hour, then compound A7 (150 mg, 0.477 mmol) was added. The reaction mixture was stirred at 25° C. for 15.5 hours. The mixture was diluted with water (20 mL) and extracted with EtOAc (20 mL×3). The combined extracts were washed with brine (30 mL×2), dried over anhydrous $Na_2SO_4$ and concentrated under reduced pressure to give a residue. The residue was purified by prep-HPLC (0.01% $NH_3.H_2O$). Most of $CH_3CN$ was removed by evaporation under reduced pressure, and the remaining solvent was removed by lyophilization to afford 24.8 mg (yield: 12.6%) of compound 141 as a pale white powder.

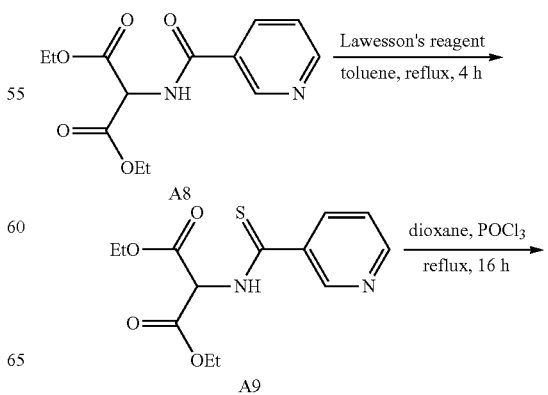

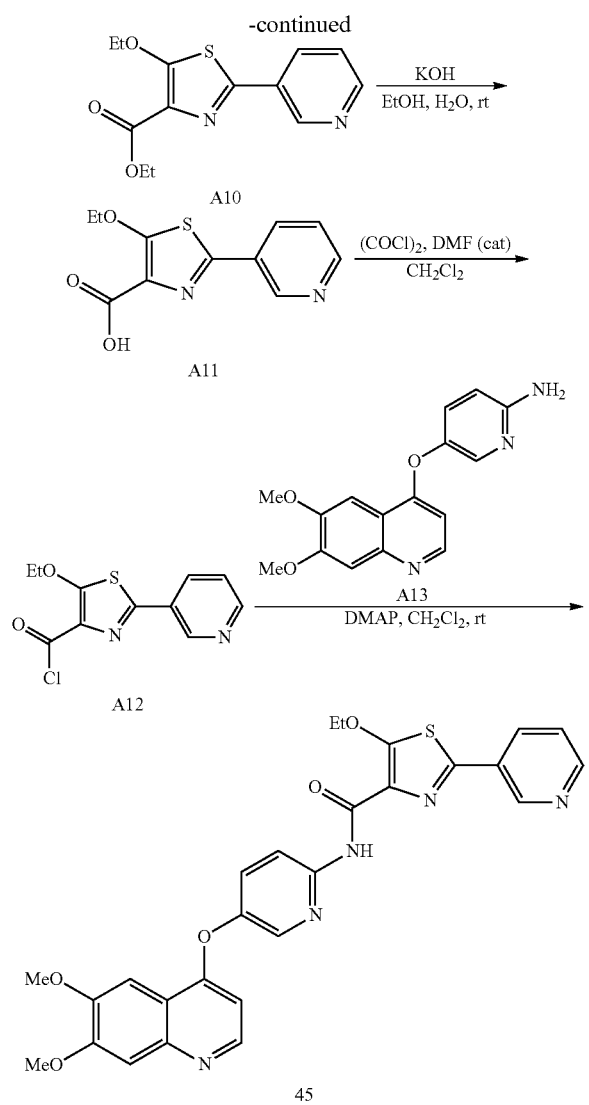

1 N HCl to pH=6. The mixture was filtered, the filter cake was collected and dried over high vacuum to give compound A11 (650 mg, yield: 90%) as a white solid.

General Procedure for Synthesis of 45

To a mixture of compound A11 (500 mg, 1.79 mmol) in $CH_2Cl_2$ (10 mL) was added $(COCl)_2$ (2.27 g, 17.9 mmol) and a drop of DMF. The mixture was stirred at 15° C. for 1 hour. The solvent and excessive $(COCl)_2$ was removed to give crude compound A12, which was dissolved in anhydrous $CH_2Cl_2$ (5 mL).

To a mixture of compound A13 (356 mg, 1.19 mmol) and DMAP (655 mg, 5.37 mmol) in $CH_2Cl_2$ (20 mL) was added the solution of compound 5 in $CH_2Cl_2$. The mixture was stirred at 15° C. for 16 hours. $CH_2Cl_2$ (200 mL) and $H_2O$ (100 mL) was added to the mixture. The organic phase was separated and the aqueous phase was extracted with $CH_2Cl_2$ (100 mL). The combined organic phase was washed with brine (100 mL), $H_2O$ (100 mL), dried over anhydrous $Na_2SO_4$ and concentrated to give crude product. The crude product was purified by prep-TLC ($CH_2Cl_2$/MeOH=20/1) and further washed with $CH_3CN$ (5 mL) to give 45 (36 mg, two steps yield: 7%).

Scheme 4-General synthesis for compound 44

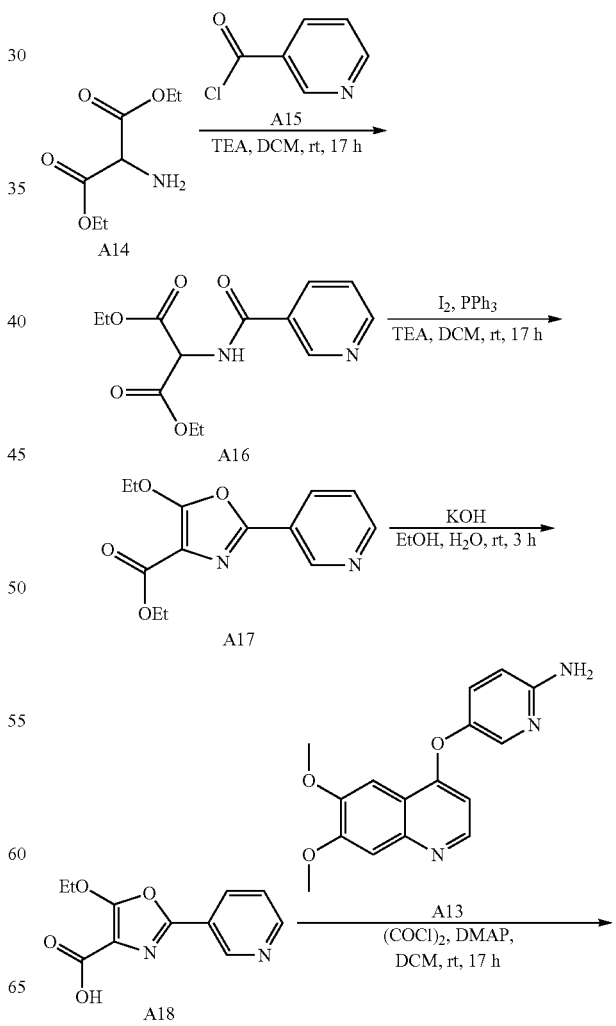

General Procedure for Synthesis of A9

To a mixture of compound A8 (4.50 g, 16.0 mmol) and Lawesson's reagent (6.49 g, 16.0 mmol) in Toluene (100 mL) was stirred reflux for 4 hours. After cooling to room temperature, most toluene was removed under reduced pressure to give crude product.

General Procedure for Synthesis of A10

To a mixture of compound A9 (1.20 g, 4.05 mmol) and $POCl_3$ (2.50 g, 16.2 mmol) in 1,4-dioxane (20 mL) was stirred at reflux for 16 hours. After cooling to room temperature, most of solvent was removed under reduced pressure to give crude product, to which $H_2O$ (100 mL) and EtOAc (100 mL) was added. The organic phase was separated and the aqueous phase was extracted with EtOAc (100 mL×2). The combined organic phase was washed with brine (100 mL), $H_2O$ (100 mL), dried over anhydrous $Na_2SO_4$ and concentrated under reduced pressure to give crude product, which was purified by silica gel column (eluted with PE/EtOAc: 100/1 to 100/8) to give compound A10 (800 mg, yield: 71%) as an off-white solid.

General Procedure for Synthesis A11

To a solution of compound A10 (800 mg, 2.87 mmol) and KOH (482 mg, 8.61 mmol) in EtOH/$H_2O$ (5 mL/5 mL) was stirred at 15° C. for 16 hours. The mixture was acidified with

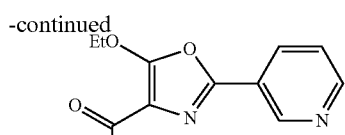

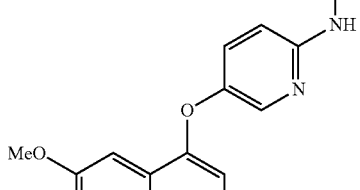

44

General Procedure for Synthesis of A16

To a mixture of diethyl aminomalonate HCl salt (12.0 g, 56.7 mmol) and TEA (22.7 g, 225 mmol) in anhydrous DCM (300 mL) was added nicotinoyl chloride HCl salt (10.0 g, 56.2 mmol), the resulting mixture was stirred at 25° C. for 17 hours. The mixture was filtered, the filtrate was concentrated under reduced pressure to give a residue, which was purified by silica gel column (eluted with EtOAc/PE=1/1) to afford 15.0 g (yield: 94%) of compound A16 as a white solid.

General Procedure for Synthesis of A17

To a mixture of compound A16 (3.00 g, 10.7 mmol) and TEA (3.88 g, 38.4 mmol) in anhydrous DCM (30 mL) was added a mixture of $I_2$ (3.26 g, 12.8 mmol) and $PPh_3$ (3.36 g, 12.8 mmol) in DCM (30 mL), the resulting mixture was stirred at 25° C. under $N_2$ for 17 hours. The reaction was quenched with water (30 mL), extracted with DCM (50 mL×3), the combined organic layer was washed with brine (100 mL), dried over anhydrous $Na_2SO_4$ and concentrated under reduced pressure to give a residue, which was purified by silica gel column (eluted with EtOAc/PE=1/3) to afford 3.00 g (70% of compound A17 and 30% of $PPh_3O$ from H NMR) of compound A17 as a white solid.

General Procedure for Synthesis of A18

To a mixture of compound A17 (2.50 g, HNMR purity: 70%) in EtOH (20 mL) was added a solution of KOH (1.06 g, 19.0 mmol) in water (20 mL), the resulting mixture was stirred at 25° C. for 3 hours. The mixture was extracted with DCM (20 mL), the aqueous phase was adjusted to pH=6 with aqueous HCl (3M), filtered, the filter cake was dried over high vacuum to afford 800 mg (2 steps yield: 32%) of compound A18 as a white solid.

General Procedure for Synthesis of 44

To a mixture of compound A18 (400 mg, 1.69 mmol) in anhydrous DCM (15 mL) was added $(COCl)_2$ (1.08 g, 8.56 mmol), the resulting mixture was stirred at 25° C. for 3 hours, then DCM and excessive $(COCl)_2$ was removed under reduced pressure to give acyl chloride as a white solid. The solid was suspended in anhydrous toluene (5 mL) and concentrated under reduced pressure to remove residual $(COCl)_2$ twice. Then the solid was added into a mixture of compound A13 (1.05 g, 3.41 mmol) and DMAP (2.08 g, 16.8 mmol) in anhydrous DCM (15 mL), the resulting mixture was stirred at 25° C. under $N_2$ for 17 hours. The reaction was quenched with water (50 mL), extracted with DCM (50 mL×3), the combined organic layer was washed with brine (100 mL), dried over anhydrous $Na_2SO_4$ and concentrated under reduced pressure to give a residue. The residue was purified by prep-HPLC (0.01% $NH_3.H_2O$). Most of $CH_3CN$ was removed by evaporation under reduced pressure, and the remaining solvent was removed by lyophilization to afford 56 mg (yield: 6.4%) of 44 as a white powder (amorphous).

Scheme 5-General synthesis for compound 203

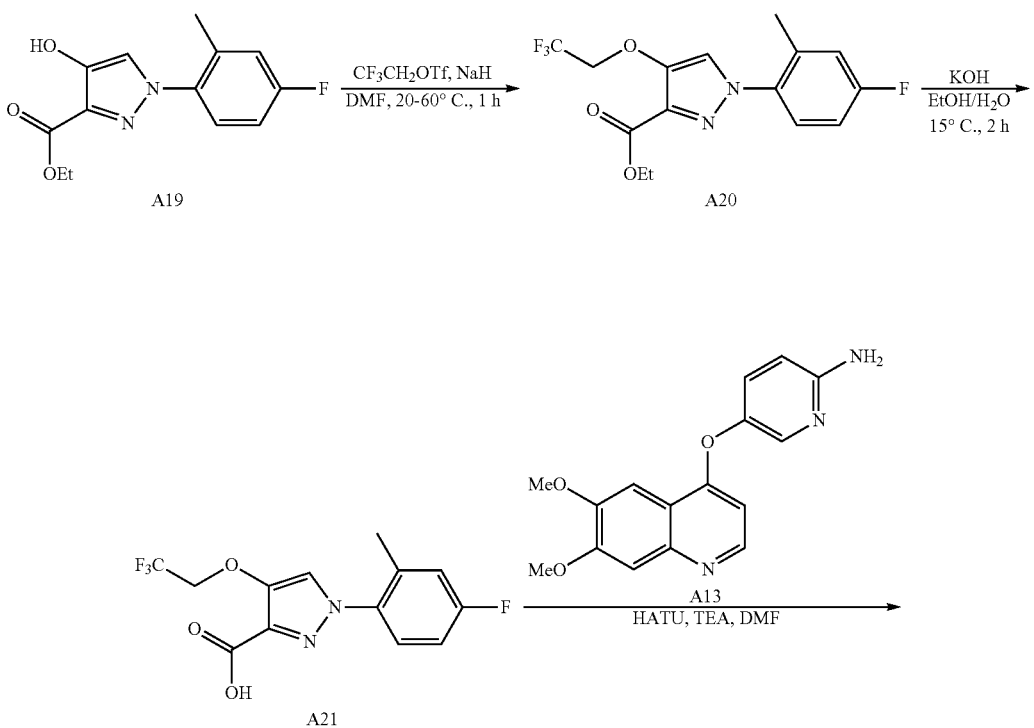

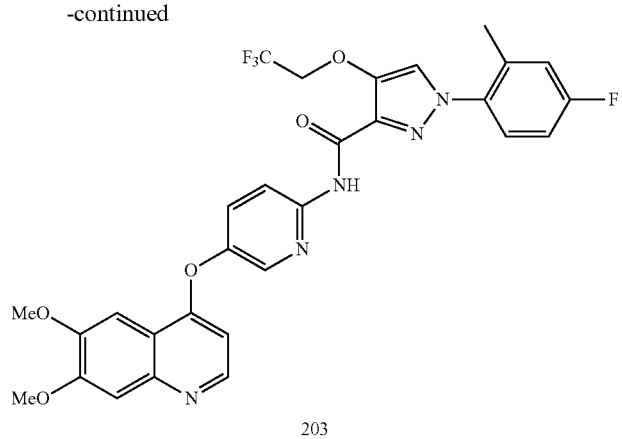

203

General Procedure for Synthesis of A20

To a solution of compound A19 (1.00 g, 3.78 mmol) in anhydrous DMF (10 mL) was added NaH (302 mg, 7.56 mmol, 60% dispersion in mineral oil), the mixture was stirred at 20° C. for 20 minutes, then 2,2,2-trifluoroethyl trifluoromethanesulfonate (1.75 g, 7.56 mmol) was added to the mixture and the reaction mixture was warmed to 60° C. for 40 minute. The mixture was a black brown solution. LCMS showed the reaction was completed. The mixture was cooled to room temperature, quenched with saturated aqueous $NH_4Cl$ (5 mL), diluted with water (20 mL), extracted with EtOAc (30 mL×3). The combined extracts was washed with brine (80 m L×2), dried over anhydrous $Na_2SO_4$ and filtered, then concentrated under reduced pressure to give 1.05 g of compound A20 (yield: 80.2%) as a black brown powder.

General Procedure for Synthesis of A21

To a solution of compound A20 (1.05 g, 3.03 mmol) in EtOH (10 mL) was added KOH (340 mg, 6.06 mmol) in $H_2O$ (10 mL). The mixture was stirred at 20° C. for 2 hours. TLC showed the reaction was completed ($SiO_2$, PE:EtOAc=1:1). The mixture was a black brown solution. The mixture was concentrated under reduced pressure to remove EtOH. The aqueous phase was diluted with water (20 mL), acidized with HCl (3 M, 3 mL) to pH=5-6, white powder precipitated out from the mixture. The mixture was filtered, the filter cake was dried over high vacuum to give 910 mg of compound A21 (yield: 94.38%) as a white powder.

General Procedure for Synthesis of 203

To a solution of compound A13 (200 mg, 0.673 mmol) and compound A21 (257 mg, 0.807 mmol) in anhydrous DMF (10 mL) was added HATU (384 mg, 1.01 mmol) and TEA (204 mg, 2.02 mmol) under $N_2$ atmosphere, the reaction mixture was stirred at 60° C. under $N_2$ atmosphere for 16 hours. LCMS showed the reaction was completed. The mixture was cooled to room temperature, diluted with water (10 mL) and extracted with EtOAc (15 mL×3). The combined extracts was washed with brine (30 mL×3), dried over anhydrous $Na_2SO_4$ and filtered, then concentrated under reduced pressure to afford 400 mg of crude residue. The crude residue was purified by prep-HPLC (0.01% $NH_3H_2O$). The collected fractions were combined and the resulting mixture was concentrated under reduced pressure to remove most of $CH_3CN$. The resulting mixture was lyophilized to afford 172.0 mg of 203 (yield: 42.15%) as a white powder.

Scheme 6 - General synthesis for compound 240

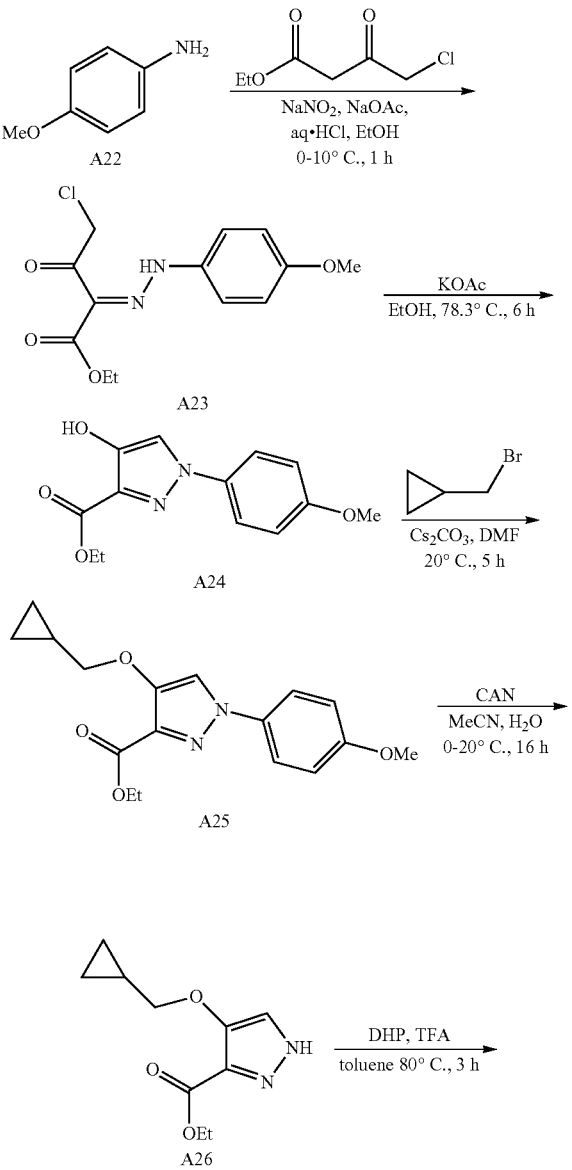

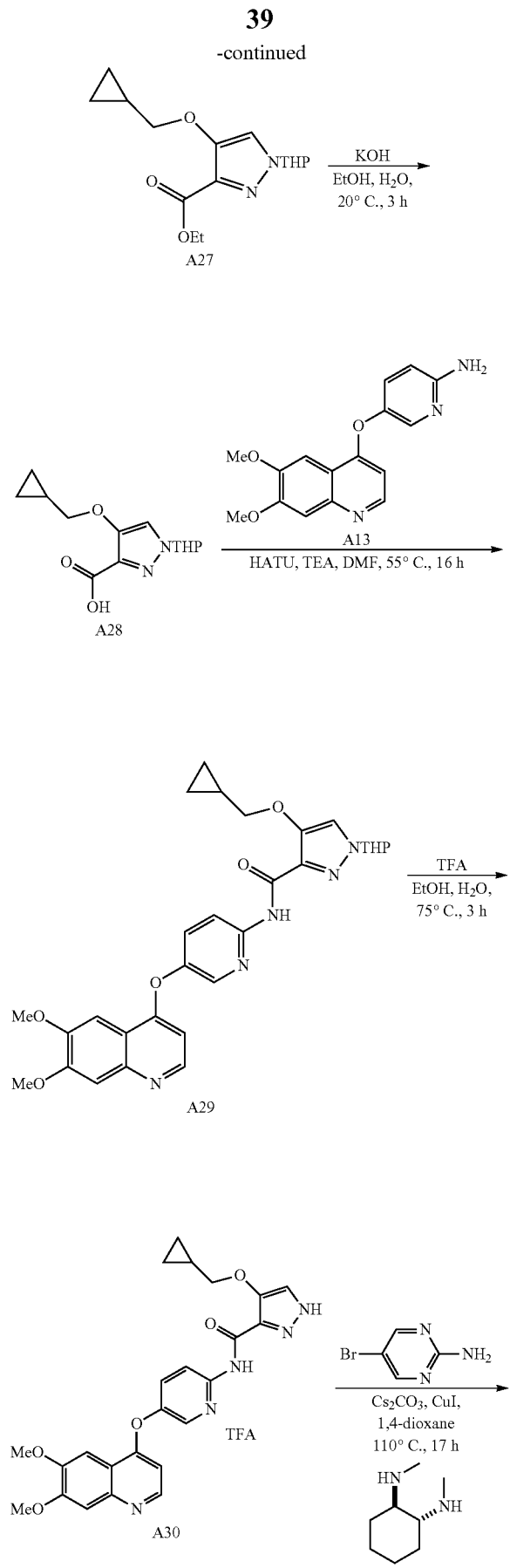

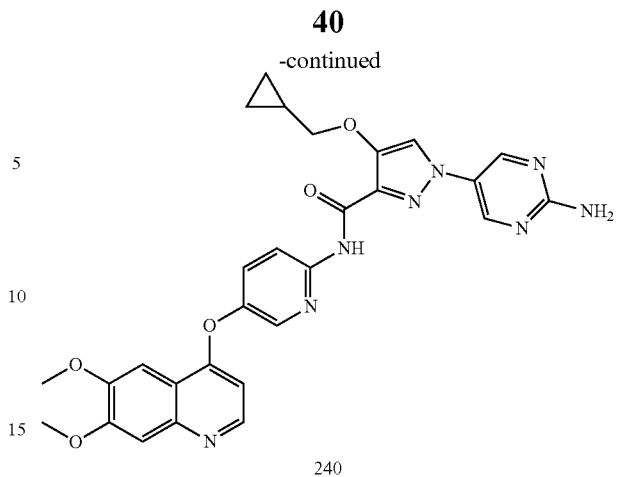

240

General Procedure for Synthesis of A23

To a HCl (3 M, 180 mL) was added compound A22 (20.0 g, 53.1 mmol) slowly at 10° C., then the mixture was cooled to 0° C., and a solution of NaNO$_2$ (11.8 g, 55.8 mmol) in water (50 mL) was added, the mixture turn to a brown solution (solution A). To a mixture of ethyl 4-chloro-3-oxo-butanoate (28.2 g, 170 mmol) and NaOAc (66.1 g, 812 mmol) in H$_2$O (2000 mL)/EtOH (500 mL) was dropwise added solution A at 0-5° C. Then the mixture was stirred at 10° C. for 1 hour. Yellow powder precipitated out from the reaction mixture. This phenomenon indicated that the reaction worked, and LCMS showed 80% desired MS value. The mixture was filtrated, the filter cake was washed with water (500 mL) and dried over high vacuum to give 35.0 g of compound A23 (yield: 72.2%) as a yellow powder.

General Procedure for Synthesis of A24

To a solution of compound A23 (35.0 g, 117.17 mmol) in absolute EtOH (300 mL) was added KOAc (23.0 g, 234 mmol). The mixture was heated to reflux at 78.3° C. for 6 hours. The reaction mixture was a yellow solution. LCMS showed 86.7% desired MS value. The mixture was cooled to room temperature, Most EtOH was removed under reduced pressure, the residue was partitioned between EtOAc (800 mL) and H$_2$O (800 mL). The aqueous was extracted with EtOAc (800 mL). The combined organic extract was washed with brine (900 mL×2), dried over anhydrous Na$_2$SO$_4$, filtered and concentrated under reduced pressure to give 27.0 g of compound A24 (yield: 87.9%) as a yellow powder.

General Procedure for Synthesis of A25

To a solution of compound A24 (20.0 g, 76.26 mmol) and Cs$_2$CO$_3$ (49.7 g, 153 mmol) in anhydrous DMF (400 mL) was added bromomethylcyclopropane (20.6 g, 152 mmol), the mixture was stirred at 20° C. for 5 hours and 73.9% of desired MS value was observed. The mixture was partitioned between EtOAc (1000 mL) and H$_2$O (1000 mL). The aqueous was extracted with EtOAc (1000 mL). The combined organic extract was washed with brine (2000 mL×2), dried over anhydrous Na$_2$SO$_4$, filtered and concentrated under reduced pressure to give 23.0 g of compound A25 (yield: 95.34%) as a yellow powder.

General Procedure for Synthesis of A26

To a solution of A25 (10.0 g, 31.6 mmol) in MeCN (100 mL) was dropwise added H$_2$O (200 mL) of CAN (52.0 g, 94.8 mmol) at 0-5° C. The reaction mixture was stirred at 20° C. for 16 hours. LCMS showed A25 consumed completely and 21.3% desired MS value. The reaction mixture was diluted with water (200 mL). The mixture was extracted with EtOAc (500 mL×2). The combined organic extracts were washed with saturated aqueous NaHCO$_3$ solution to pH=7-8 and dried over Na₂SO₄ and filtered, then concentrated under reduced pressure to afford a crude residue as a yellow powder. The crude residue was purified by Combi flash (EtOAc/PE=0:1 to 1:6 to 1:2) to give A26 (1.30 g, yield: 19.6%) as a yellow powder.

General Procedure for Synthesis of A27

To a solution of A26 (1.30 g, 6.18 mmol) in absolute toluene (20 mL) was added DHP (572 mg, 6.80 mmol) and TFA (705 mg, 6.18 mmol). The mixture was heated to reflux at 80° C. for 3 hours to form a red mixture. TLC (eluent: PE/EtOAc=3:1) indicated A26 was consumed completely and one new spot formed. The mixture was partitioned between EtOAc (80 mL) and H₂O (80 mL). The aqueous was extracted with EtOAc (80 mL). The combined organic extract was washed with brine (150 mL×2), dried over anhydrous Na₂SO₄, filtered and concentrated under reduced pressure to give compound A27 (1.50 g, yield: 82.5%) as a black brown oil.

General Procedure for Synthesis of A28

To a solution of A27 (1.50 g, 5.10 mmol) in EtOH (20 mL) was added KOH (572 mg, 10.2 mmol) in H₂O (20 mL). The mixture was stirred at 20° C. for 3 hours to form a black mixture.

LCMS showed A27 consumed completely and 62.0% desired MS value. The mixture was concentrated under reduced pressure to remove EtOH. The aqueous phase was diluted with water (30 mL), acidized with HCl (3 M) to pH=5-6. The mixture was partitioned between dichloromethane (50 mL) and H₂O (10 mL). The aqueous was extracted with dichloromethane (50 mL). The combined organic extract dried over anhydrous Na₂SO₄, filtered and concentrated under reduced pressure to give compound A28 (1.00 g, yield: 73.7%) as a black brown oil.

General Procedure for Synthesis of A29

To a solution of compound A28 (800 mg, 3.00 mmol) and compound A13 (758 mg, 2.55 mmol) in anhydrous DMF (20 mL) was added HATU (1.43 g, 3.75 mmol) and TEA (501 mg, 4.95 mmol) under N₂ atmosphere. The mixture was stirred at 55° C. under N₂ atmosphere for 16 hours. LCMS showed compound A28 consumed completely and 61.9% desired MS value. The mixture diluted with water (400 mL), white powder precipitated out from the mixture. The mixture was filtered, the filter cake was dried over high vacuum to give A29 (800 mg, yield: 48.9%) as a white solid, which was used for next step.

General Procedure for Synthesis of A30

To a solution of compound A29 (1.00 g, 1.83 mmol) in absolute EtOH (8 mL) and H₂O (4 mL) was added TFA (271 mg, 2.38 mmol). The mixture was heated to reflux at 75° C. for 3 hours to form a red mixture. LCMS showed the reaction was complete. 87.6% of desired MS value was observed. The reaction mixture was concentrated under reduced pressure to remove EtOH (8 mL). The residue was diluted with dichlororomethane (5 mL) and filtered, the filter cake was dried over high vacuum to give A30 (434 mg, yield: 41.2%, TFA salt) as a white solid.

General Procedure for Synthesis of 240

To a mixture of compound A30 (384 mg, 0.832 mmol) and an amino-pyrimidine (289 mg, 1.66 mmol) in dioxane (10 mL) was added Cs₂CO₃ (678 mg, 2.08 mmol), CuI (48 mg, 0.25 mmol) and trans-N1,N2-dimethylcyclohexane-1,2-diamine (36 mg, 0.25 nmol) under N₂ atmosphere. The mixture was stirred at 110° C. under N₂ atmosphere for 17 hours in a 40 mL sealed tube to form a brown mixture. LCMS showed 40.3% desired MS value. The mixture was partitioned between DCM (50 mL) and NH3-H2O (10%, 50 mL). The aqueous was extracted with DCM (50 mL). The combined organic extract was washed with water (100 mL×2), dried over anhydrous Na₂SO₄, filtered and concentrated under reduced pressure to give a residue. The residue was purified by prep-HPLC (0.01% NH₄HCO₃). Most of MeCN was removed under reduced pressure. The remaining solvent was removed by lyophilization to give impure 240. Impure 240 was further purified by Combi flash (dichloromethane/MeOH=1/0 to 20/1) to give 240 (19 mg, yield: 4.12%, LCMS: 98.5%) as a white powder.

Scheme 7-General Synthetic route II; coupling reaction of pyrazole with aryl or alkyl halide

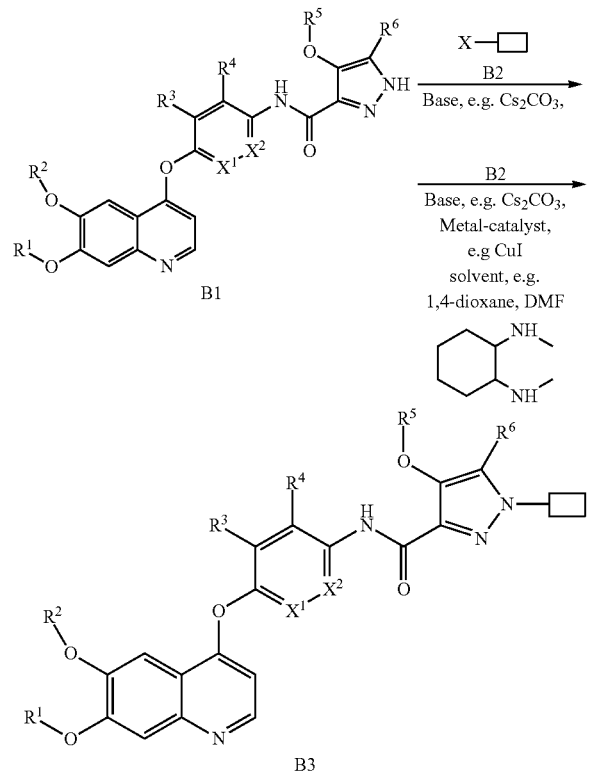

A method to prepare compounds of B3 is shown in Scheme 7. The halogen derivative B2 can be used in a base like Cs₂CO₃ (cesium carbonate) or metal-catalyzed cross-couplings, for instance under Sonogashira conditions using an alkyne, copper iodide in the presence of a base like Cs₂CO₃ (cesium carbonate).

Scheme 8-General synthesis for compound 38

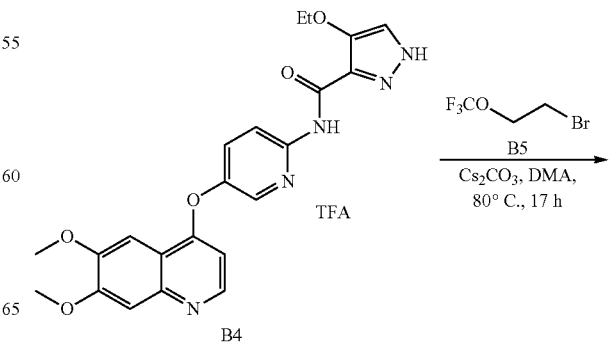

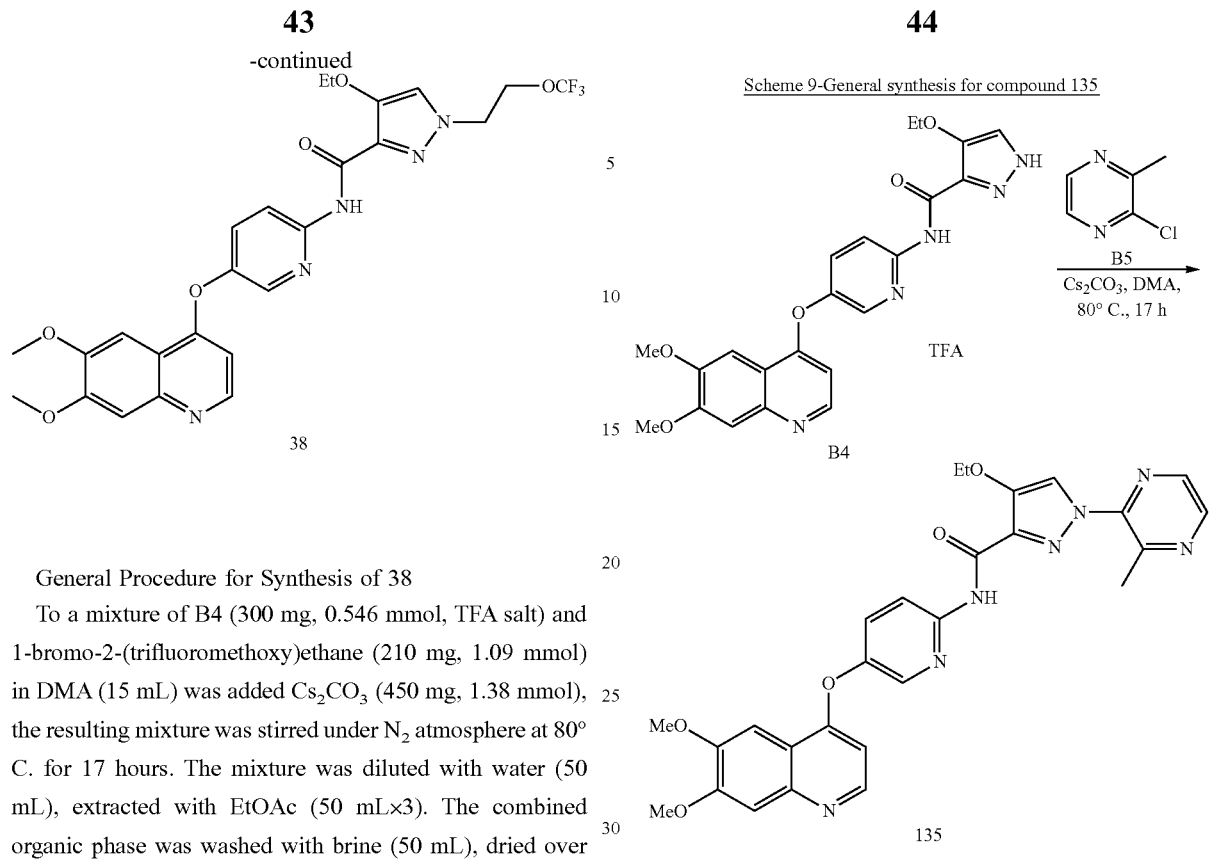

General Procedure for Synthesis of 38

To a mixture of B4 (300 mg, 0.546 mmol, TFA salt) and 1-bromo-2-(trifluoromethoxy)ethane (210 mg, 1.09 mmol) in DMA (15 mL) was added $Cs_2CO_3$ (450 mg, 1.38 mmol), the resulting mixture was stirred under $N_2$ atmosphere at 80° C. for 17 hours. The mixture was diluted with water (50 mL), extracted with EtOAc (50 mL×3). The combined organic phase was washed with brine (50 mL), dried over $Na_2SO_4$ and concentrated under reduced pressure to give a residue, which was purified by prep-HPLC (0.1% $NH_3.H_2O$). Most of $CH_3CN$ was removed by evaporation under reduced pressure, and the remaining solvent was removed by lyophilization to afford 46 mg (yield: 15%) of 38 as a white powder, HNMR and NOE spectra confirmed the structure.

General Procedure for Synthesis of 135

To a mixture of B4 (200 mg, 0.336 mmol, TFA salt) and 2-chloro-3-methylpyrazine (94 mg, 0.73 mmol) in DMA (5.00 mL) was added $Cs_2CO_3$ (237 mg, 0.728 mmol), the mixture was stirred at 80° C. for 17 hours. The mixture was poured into water (50 mL), filtered, the filter cake was washed with MeCN (10 mL×3) to afford 62 mg (yield: 32.3%) of 135 as a white powder.

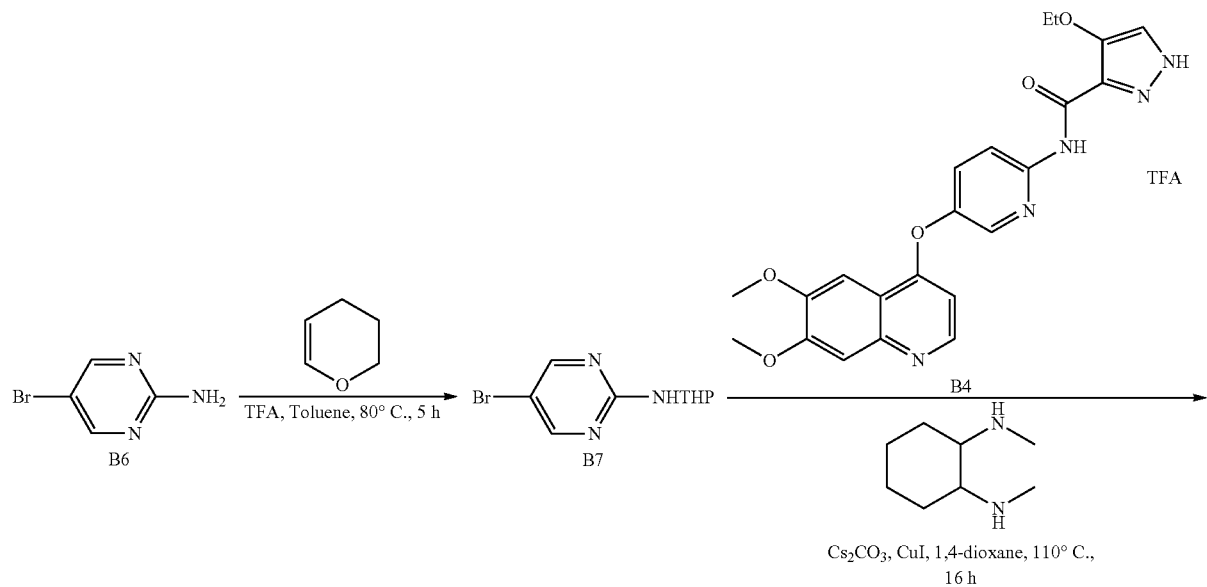

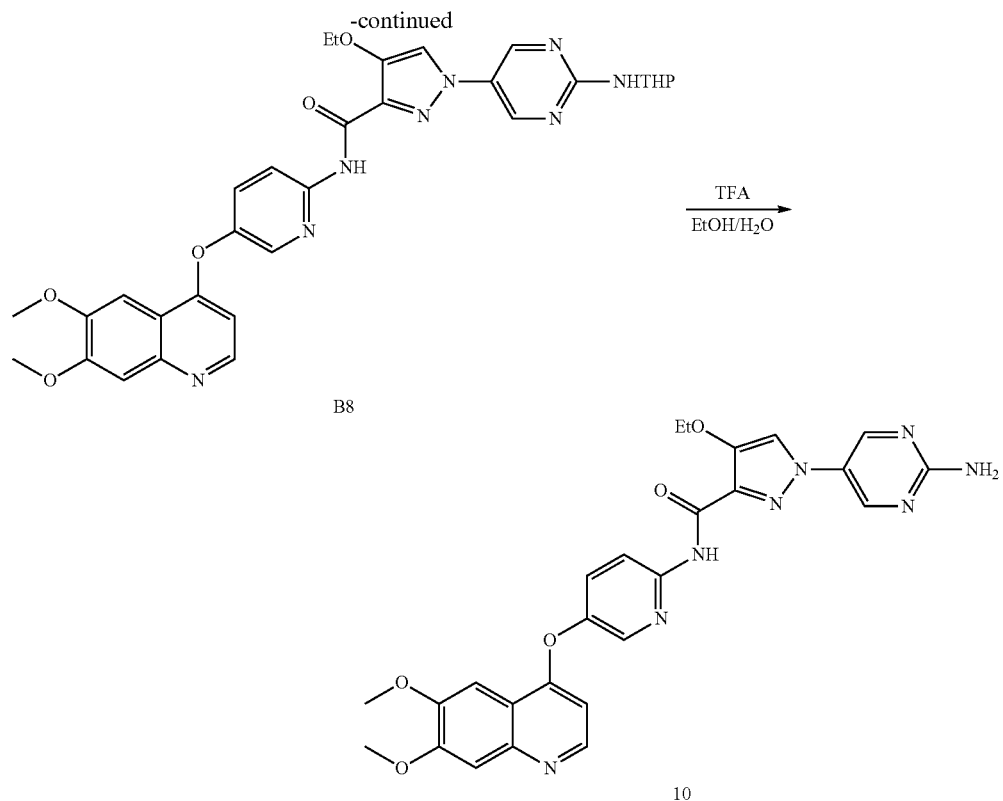

General Procedure for Synthesis of B7

To a mixture of B6 (500 mg, 2.87 mmol) and TFA (56 mg, 0.58 mmol) in anhydrous Toluene (10 mL) was added DHP (266 mg, 3.16 mmol) at 80° C. The mixture was stirred at 80° C. for 12 hours. Most toluene was removed under reduced pressure. The residue was diluted with DCM (50 mL) and washed with water (50 mL×3). The organic extract was dried over anhydrous $Na_2SO_4$ and concentrated under reduced pressure to give compound B7 (600 mg, yield: 81.0%) as a pale-yellow powder.

General Procedure for Synthesis of B8

A mixture of B7 (593 mg, 2.30 mmol), compound B4 (500 mg, TFA salt, 0.939 mmol), $Cs_2CO_3$ (749 mg, 2.30 mmol), (1R,2R)—$N_1,N_2$-dimethylcyclohexane-1,2-diamine (50 mg, 0.35 mmol) and CuI (67 mg, 0.35 mmol) in 1,4-dioxane (20 mL) was stirred at 110° C. under $N_2$ atmosphere for 16 hours. Most 1,4-dioxane was removed under reduced pressure. The residue was diluted with DCM (100 mL) and washed with water (100 mL×3). The organic phase was dried over anhydrous $Na_2SO_4$ and concentrated under reduced pressure. The residue was purified by silica gel column (eluent: EtOAc/DCM=5/1) to give impure compound B8 (LCMS: 25%) as a pale-yellow powder.

General Procedure for Synthesis of 10

A mixture of compound B8 (600 mg, crude product) and TFA (194 mg, 2.00 mmol) in EtOH (10 mL) and $H_2O$ (5 mL) was stirred at 80° C. for 5 hours. Most solvent was removed under reduced pressure. The residue was purified by basic prep-HPLC (0.01% $NH_3 \cdot H_2O$). Most $CH_3CN$ was removed by evaporation under reduced pressure, and the remaining solvent was removed by lyophilization to give 10 (23 mg, 2-step overall yield: 4.6%) as a white amorphous.

Scheme 11-General synthesis for compound 12

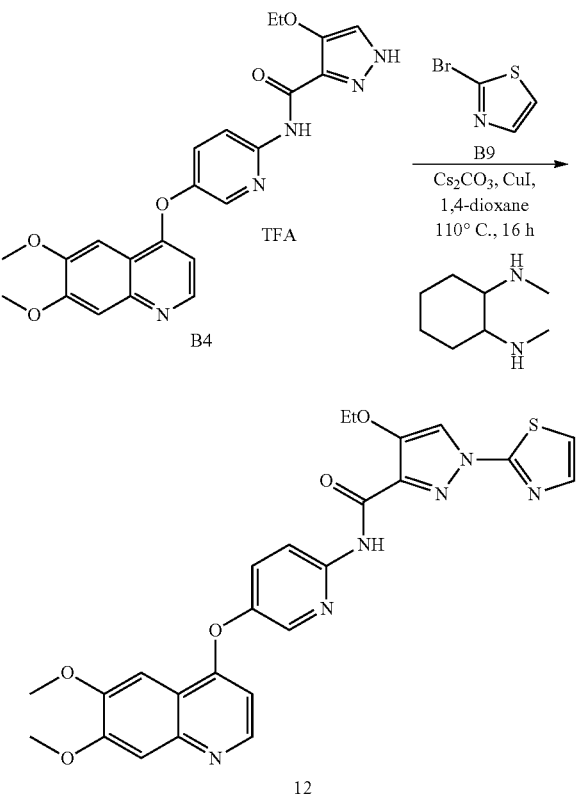

General Procedure for Synthesis of 12

A mixture of compound B4 (200 mg, TFA salt, 0.376 mmol), B9 (150 mg, 0.914 mmol), Cs$_2$CO$_3$ (300 mg, 0.920 mmol), (1R,2R)—N$_1$,N$_2$-dimethylcyclohexane-1,2-diamine (20 mg, 0.14 mmol) and CuI (27 mg, 0.14 mmol) in 1,4-dioxane (15 mL) was stirred at 110° C. under N$_2$ atmosphere for 16 hours. Most of 1,4-dioxane was removed under reduced pressure. The residue was diluted with DCM (100 mL) and washed with 10% NH$_3$.H$_2$O (100 mL×3). The organic phase was dried over anhydrous Na$_2$SO$_4$ and concentrated under reduced pressure. The residue was purified by basic prep-HPLC (0.01% NH$_3$.H$_2$O). Most of CH$_3$CN was removed by evaporation under reduced pressure, and the remaining solvent was removed by lyophilization to give 12 (48 mg, yield: 24.6%) as a white amorphous.

Scheme 12-General Synthetic route III; coupling reaction of amide with aryl halide

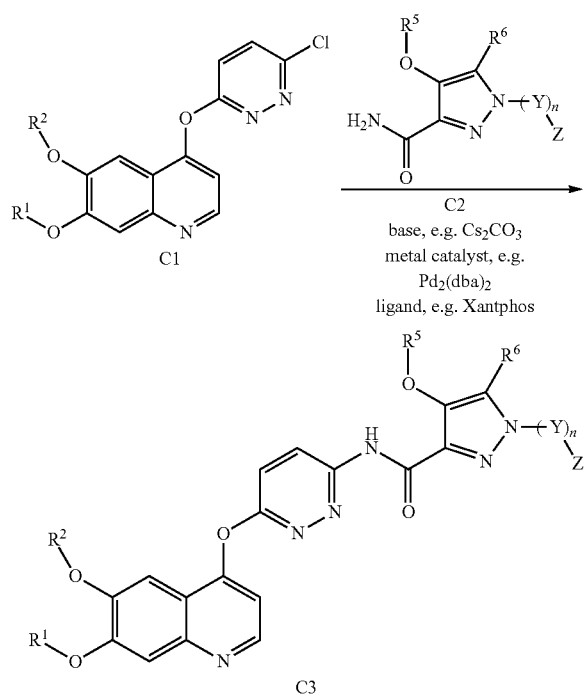

A method to prepare compounds of C3 is shown in Scheme 12. The carboxamide derivative C2 can be used in a base like Cs$_2$CO$_3$ (cesium carbonate), a Ligand like Xantphos and metal-catalyzed cross-couplings, for instance under Sonogashira conditions using an alkyne, copper iodide.

Scheme 13-General synthesis for compound 97

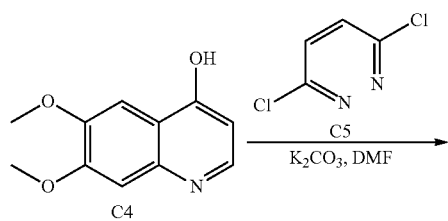

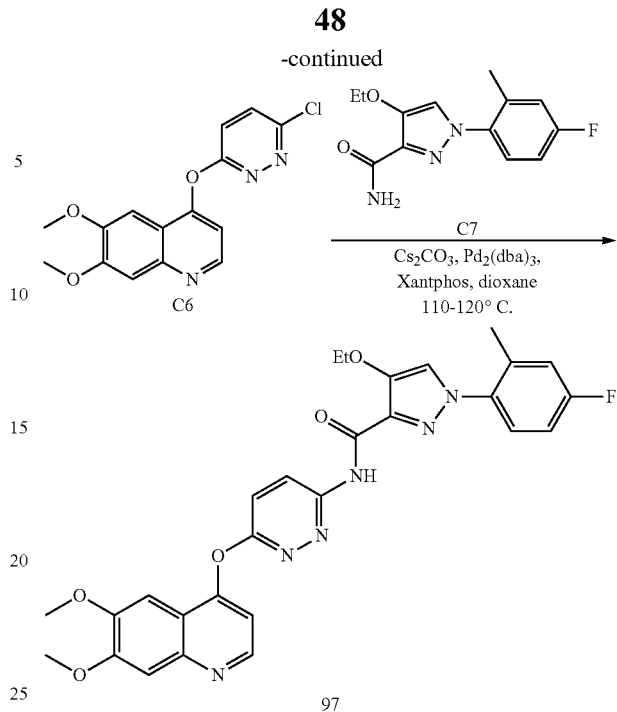

General Procedure for Synthesis of C6

A mixture of compound C4 (1.00 g, 4.87 mmol), C5 (871 mg, 5.84 mmol) and K$_2$CO$_3$ (1.35 g, 9.74 mmol) in DMF (20 mL) was stirred at 120° C. under N$_2$ atmosphere for 16 hours. LCMS observed the reaction was completed. After cooling to room temperature, the reaction mixture was diluted with EtOAc (80 mL), then washed with brine (100 mL×3), dried over anhydrous Na$_2$SO$_4$, filtered and concentrated under reduced pressure. The residue was purified by Combi Flash (PE/EtOAc=1/1 to 0/1) to afford 180 mg (yield: 11.6%) of compound C6 as a yellow powder.

General Procedure for Synthesis of 97

To a mixture of compound C6 (180 mg, 0.567 mmol), compound C7 (149 mg, 0.567 mmol), Cs$_2$CO$_3$ (554 mg, 1.70 mmol) in anhydrous dioxane (5 mL) was added Pd$_2$(dba)$_3$ (52 mg, 0.057 mmol) and Xantphos (33 mg, 0.057 mmol). The suspension was degassed under vacuum and purged with N$_2$ atmosphere several times. The reaction mixture was stirred under N$_2$ atmosphere at 110-120° C. for 16 hours. Crude LCMS showed the reaction was completed. After cooling to room temperature, the reaction mixture was diluted with DCM (30 mL), then filtered and the filter cake was washed with DCM (5 mL×2). The filtrate was concentrated under reduced pressure. The residue was purified by prep-HPLC (0.01% NH$_3$H$_2$O as additive). The collected fractions were combined and the resulting mixture was concentrated under reduced pressure to remove most of CH$_3$CN. The resulting mixture was lyophilized to afford 14 mg (yield: 4.5%) of 97 as a white powder.

REFERENCES

Angelillo-Scherrer A, de Frutos P, Aparicio C, Melis E, Savi P, Lupu F, Arnout J, Dewerchin M, Hoylaerts M, Herbert J, Collen D, Dahlbäck B, Carmeliet P. Deficiency or inhibition of Gas6 causes platelet dysfunction and protects mice against thrombosis. *Nat Med.* 2001 February; 7(2):215-21.

Angelillo-Scherrer A.; Role of Gas6 in erythropoiesis and anemia in mice. *J Clin Invest.* 2008 Feb. 1; 118(2): 583-596.

Bhattacharyya et al., Enveloped Viruses Disable Innate Immune Responses in Dendritic Cells by Direct Activation of TAM Receptors, *Cell Host Microbe.* 2013 Aug. 14; 14(2): 136-147.

Blume-Jensen P, Hunter T., Oncogenic kinase signalling. *Nature,* 2001 May 17; 411(6835):355-65.

Burbrige et al, S49076 is a novel kinase inhibitor of MET, AXL, and FGFR with strong preclinical activity alone and in association with bevacizumab. *Mol Cancer Ther.* 2013 September; 12(9):1749-62

Caraux, Q. Lu, N. Fernandez, S. Riou, J. P. Di Santo, D. H. Raulet, G. Lemke, C. Roth. Natural killer cell differentiation driven by Tyro3 receptor tyrosine kinases. *Nat. Immunol.,* 7 (2006), pp. 747-754

Gjerdrum et al., Axl is an essential epithelial-to-mesenchymal transition-induced regulator of breast cancer metastasis and patient survival. *PNAS,* 2010, 107 (3), 1124-1129

Green et al., *BR. J CANCER* vol. 94, 2006, page 1446

Hanahan D[1], Weinberg R A. The hallmarks od cancer. *Cell.* 2000, Jan. 7; 100(1):57-70.

Hafizi S., Dahlback B. Gas6 and protein S. Vitamin K-dependent ligands for the Axl receptor tyrosine kinase subfamily. *FEBS J.* 2006 December; 273(23):5231-44.

Hafizi S., Dahlback B. Signalling and functional diversity within the Axl subfamily of receptor tyrosine kinases. *Cytokine Growth Factor Rev.* 2006 August; 17(4):295-304. Epub 2006 Jun. 5.

Ito et al., *THYROID.* vol. 9, 1999, page 563

Jin Kyung Rho, Yun Jung Choi, Seon Ye Kim, et al., MET and AXL Inhibitor NPS-1034 Exerts Efficacy against Lung Cancer Cells Resistant to EGFR Kinase Inhibitors Because of MET or AXL Activation. *Cancer Res.* 2014 Jan. 1; 74(1):253-62.

Lemke & Carla V. Rothlin, Immunobiology of the TAM receptors. *Nature Reviews Immunology* 8, 327-336, 2008

Park et al., *BLOOD* vol. 113, 2009, page 2470

Rothlin C V, Ghosh S, Zuniga E I, Oldstone M B, Lemke G. TAM receptors are pleiotropic inhibitors of the innate immune response. Cell. 2007; 131:1124-1136)

Sharif et al., *EXP. MCD.* Vol. 203, 2006, page 1891

Shieh et al., *NEOPLASIA* vol. 7, 2005, page 1058

Sun et al., *ONCOLOGY* vol. 66, 2004, page 450

Sawabu et al., *MOL CARCINOG* vol. 46, 2007, page 155

Zhang et al., Activation of the AXL kinase causes resistance to EGFR-targeted therapy in lung cancer. *Nature Genetics,* 2012; 44(8):852-860.

Zhou et al., Targeting MET and AXL overcomes resistance to sunitinib therapy in renal cell carcinoma. *Oncogene.* 2015 September The invention is now further exemplarily described by tables 1-4 which show activity data of selected compounds in binding assays of example 1 (tables 1 and 2), in a phosphorylation assay of example 2 (table 3), and the structure of compounds 1-280 including $^1$H-NMR-data (table 4).

TABLE 1

Axl, Mer and TYRO3 kinase binding activity

| # cpds | Axl | Mer | TYRO3 |
|---|---|---|---|
| 1 | A | A | B |
| 2 | A | A | A |
| 3 | A | A | A |
| 4 | A | A | B |
| 5 | A | A | A |
| 6 | A | A | A |
| 7 | C | A | C |
| 8 | A | A | B |
| 9 | C | A | C |
| 10 | A | A | A |
| 11 | A | A | B |
| 12 | A | A | A |
| 13 | A | A | A |
| 14 | A | A | A |
| 15 | C | B | C |
| 16 | A | A | B |
| 17 | A | A | A |
| 18 | A | A | A |
| 19 | A | A | A |
| 20 | A | B | B |
| 21 | A | B | B |
| 22 | B | A | A |
| 23 | A | A | A |
| 24 | B | A | C |
| 25 | B | C | C |
| 26 | A | A | B |
| 27 | A | A | A |
| 28 | B | B | C |
| 29 | B | A | B |
| 30 | C | B | C |
| 31 | A | A | C |
| 32 | A | A | A |
| 33 | A | A | A |
| 34 | A | A | A |
| 35 | B | A | C |
| 36 | A | A | A |
| 37 | A | A | B |
| 38 | A | A | B |
| 39 | A | A | A |
| 40 | A | A | C |
| 41 | A | A | B |
| 42 | B | A | C |
| 43 | C | C | C |
| 44 | A | A | C |
| 45 | A | A | A |
| 46 | C | C | C |
| 47 | B | B | C |
| 48 | A | A | A |
| 49 | B | A | B |
| 50 | B | C | C |
| 51 | B | B | C |
| 52 | C | C | C |
| 53 | C | C | C |
| 54 | C | C | C |
| 55 | A | B | A |
| 56 | A | A | A |
| 57 | A | A | A |
| 58 | A | B | B |
| 59 | A | A | A |
| 60 | C | C | C |
| 61 | A | A | A |
| 62 | B | A | C |
| 63 | B | B | B |
| 64 | A | A | A |
| 65 | A | A | A |
| 66 | A | A | B |
| 67 | B | A | B |
| 68 | A | A | C |
| 69 | C | B | C |
| 70 | B | A | B |
| 71 | C | B | C |
| 72 | C | B | C |
| 73 | A | A | B |
| 74 | B | A | B |
| 75 | B | B | C |
| 76 | A | A | A |
| 77 | B | A | B |
| 78 | C | B | C |
| 79 | A | A | A |
| 80 | A | A | B |
| 81 | A | A | B |

TABLE 1-continued

Axl, Mer and TYRO3 kinase binding activity

| # cpds | Axl | Mer | TYRO3 |
|---|---|---|---|
| 82 | A | A | A |
| 83 | A | A | B |
| 84 | B | A | C |
| 85 | A | A | B |
| 86 | A | A | B |
| 87 | A | A | A |
| 88 | C | B | C |
| 89 | A | A | A |
| 90 | A | A | B |
| 91 | B | B | B |
| 92 | A | A | A |
| 93 | A | A | B |
| 94 | B | A | B |
| 95 | B | A | B |
| 96 | A | A | C |
| 97 | A | A | C |
| 98 | C | C | C |
| 99 | A | A | B |
| 100 | A | A | B |
| 101 | A | A | B |
| 102 | A | B | B |
| 103 | B | B | B |
| 104 | A | A | A |
| 105 | A | A | B |
| 106 | A | A | B |
| 107 | A | A | A |
| 108 | A | A | A |
| 109 | B | C | C |
| 110 | A | B | B |
| 111 | A | A | A |
| 112 | A | A | A |
| 113 | A | A | B |
| 114 | A | A | C |
| 115 | A | A | C |
| 116 | A | A | C |
| 117 | A | A | B |
| 118 | B | A | B |
| 119 | B | B | B |
| 120 | A | A | C |
| 121 | B | A | C |
| 122 | C | C | C |
| 123 | B | B | C |
| 124 | A | A | A |
| 125 | A | A | A |
| 126 | A | A | C |
| 127 | A | A | C |
| 128 | A | A | A |
| 129 | A | A | C |
| 130 | A | A | B |
| 131 | B | B | C |
| 132 | A | A | A |
| 133 | A | A | A |
| 134 | B | A | C |
| 135 | A | A | A |
| 136 | A | A | A |
| 137 | A | A | B |
| 138 | B | A | B |
| 139 | A | A | B |
| 140 | A | A | B |
| 141 | A | A | A |
| 142 | B | A | B |
| 143 | A | A | A |
| 144 | A | A | B |
| 145 | C | C | C |
| 146 | A | A | A |
| 147 | A | A | A |
| 148 | A | A | C |
| 149 | A | A | A |
| 150 | A | A | A |
| 151 | A | A | A |
| 152 | C | A | C |
| 153 | A | A | A |
| 154 | A | A | C |
| 155 | A | A | B |
| 156 | A | A | A |
| 157 | A | A | C |
| 158 | B | C | C |
| 159 | C | C | C |
| 160 | A | A | C |
| 161 | A | A | A |
| 162 | A | A | B |
| 163 | A | A | C |
| 164 | B | A | C |
| 165 | A | A | B |
| 166 | A | A | A |
| 167 | A | A | A |
| 168 | A | A | A |
| 169 | A | A | C |
| 170 | A | A | A |
| 171 | A | A | B |
| 172 | A | A | A |
| 173 | A | A | A |
| 174 | A | A | A |
| 175 | A | A | A |
| 176 | A | A | B |
| 177 | A | A | A |
| 178 | A | A | A |
| 179 | A | A | A |
| 180 | B | B | C |
| 181 | A | A | A |
| 182 | A | A | A |
| 183 | A | A | A |
| 184 | A | A | A |
| 185 | A | A | A |
| 186 | B | A | B |
| 187 | A | A | A |
| 188 | A | A | A |
| 189 | A | A | A |
| 190 | A | A | A |
| 191 | A | A | A |
| 192 | A | A | B |
| 193 | A | A | A |
| 194 | A | A | A |
| 195 | A | A | A |
| 196 | A | A | A |
| 197 | A | A | A |
| 198 | A | A | A |
| 199 | A | A | C |
| 200 | A | A | A |
| 201 | C | B | C |
| 202 | 1A | A | A |
| 203 | A | A | A |
| 204 | C | B | C |
| 205 | A | A | A |
| 206 | A | A | C |
| 207 | A | A | A |
| 208 | A | A | B |
| 209 | A | A | A |
| 210 | A | A | B |
| 211 | B | B | B |
| 212 | B | B | B |
| 213 | C | B | C |
| 214 | B | B | B |
| 215 | A | A | A |
| 216 | B | B | C |
| 217 | C | B | C |
| 218 | B | B | B |
| 219 | B | B | B |
| 220 | C | C | C |
| 221 | C | C | C |
| 222 | B | B | C |
| 223 | C | B | C |
| 224 | A | A | B |
| 225 | A | A | B |
| 226 | A | A | B |
| 227 | A | A | A |
| 228 | C | B | C |
| 229 | A | A | A |
| 230 | A | A | C |
| 231 | A | A | A |
| 232 | B | B | C |
| 233 | A | A | A |

TABLE 1-continued

Axl, Mer and TYRO3 kinase binding activity

| # cpds | Axl | Mer | TYRO3 |
|---|---|---|---|
| 234 | A | A | A |
| 235 | A | A | A |
| 236 | A | A | A |
| 237 | A | A | A |
| 238 | C | B | C |
| 239 | A | B | A |
| 240 | A | A | A |
| 241 | A | A | C |
| 242 | C | C | C |
| 243 | A | A | A |
| 244 | A | A | A |
| 245 | C | B | C |
| 246 | A | A | A |
| 247 | A | A | A |
| 248 | A | A | A |
| 249 | A | A | A |
| 250 | A | A | B |
| 251 | A | A | A |
| 252 | A | A | A |
| 253 | A | A | A |
| 254 | A | A | C |
| 255 | A | A | A |
| 256 | B | B | C |
| 257 | A | A | A |
| 258 | A | A | A |
| 259 | A | A | A |
| 260 | A | A | A |
| 261 | A | A | A |
| 262 | A | A | A |
| 263 | A | A | A |
| 264 | A | A | A |
| 265 | B | C | C |
| 266 | A | A | A |
| 267 | A | A | A |
| 268 | A | A | A |
| 269 | A | A | A |
| 270 | B | B | B |
| 271 | A | A | A |
| 272 | B | A | B |
| 273 | A | A | B |
| 274 | A | A | A |
| 275 | B | B | B |
| 276 | A | A | B |
| 277 | C | B | A |
| 278 | A | A | B |
| 279 | A | A | A |
| 280 | A | A | A |

Activity range: A indicates <0.1 uM, B indicates 0.1 ≤ Kd < 1 uM, C indicates ≥1 uM

TABLE 2

Met kinase binding activity

| # cpds | cMet |
|---|---|
| 1 | A |
| 2 | A |
| 3 | A |
| 4 | A |
| 5 | A |
| 6 | B |
| 7 | A |
| 8 | A |
| 9 | A |
| 10 | A |
| 11 | B |
| 12 | B |
| 13 | A |
| 14 | A |
| 15 | B |
| 16 | B |
| 17 | A |
| 18 | B |
| 19 | A |
| 20 | B |
| 21 | B |
| 22 | B |
| 23 | A |
| 24 | B |
| 25 | C |
| 26 | A |
| 27 | B |
| 28 | B |
| 29 | B |
| 30 | B |
| 31 | B |
| 32 | B |
| 33 | A |
| 34 | A |
| 35 | C |
| 36 | A |
| 37 | B |
| 38 | A |
| 39 | A |
| 40 | A |
| 41 | B |
| 42 | B |
| 43 | C |
| 44 | A |
| 45 | A |
| 46 | C |
| 47 | C |
| 48 | B |
| 49 | B |
| 50 | C |
| 51 | B |
| 52 | C |
| 53 | C |
| 54 | C |
| 55 | B |
| 56 | A |
| 57 | A |
| 58 | B |
| 59 | A |
| 60 | C |
| 61 | A |
| 62 | C |
| 63 | B |
| 64 | A |
| 65 | A |
| 66 | B |
| 67 | B |
| 68 | B |
| 69 | B |
| 70 | B |
| 71 | B |
| 72 | B |
| 73 | B |
| 74 | B |
| 75 | B |
| 76 | B |
| 77 | B |
| 78 | B |
| 79 | A |
| 80 | B |
| 81 | B |
| 82 | A |
| 83 | A |
| 84 | A |
| 85 | A |
| 86 | A |
| 87 | A |
| 88 | B |
| 89 | A |
| 90 | B |
| 91 | C |
| 92 | A |
| 93 | A |
| 94 | B |

TABLE 2-continued

Met kinase binding activity

| # cpds | cMet |
|---|---|
| 95 | A |
| 96 | C |
| 97 | C |
| 98 | C |
| 99 | C |
| 100 | B |
| 101 | A |
| 102 | C |
| 103 | B |
| 104 | A |
| 105 | A |
| 106 | A |
| 107 | A |
| 108 | C |
| 109 | B |
| 110 | A |
| 111 | A |
| 112 | A |
| 113 | B |
| 114 | A |
| 115 | A |
| 116 | B |
| 117 | A |
| 118 | B |
| 119 | B |
| 120 | B |
| 121 | B |
| 122 | C |
| 123 | B |
| 124 | A |
| 125 | A |
| 126 | A |
| 127 | A |
| 128 | A |
| 129 | A |
| 130 | A |
| 131 | B |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | B |
| 145 | C |
| 146 | A |
| 147 | A |
| 148 | A |
| 149 | A |
| 150 | A |
| 151 | A |
| 152 | C |
| 153 | A |
| 154 | C |
| 155 | A |
| 156 | A |
| 157 | A |
| 158 | C |
| 159 | C |
| 160 | A |
| 161 | A |
| 162 | A |
| 163 | A |
| 164 | B |
| 165 | A |
| 166 | A |
| 167 | A |
| 168 | A |
| 169 | C |
| 170 | A |
| 171 | A |
| 172 | A |
| 173 | A |
| 174 | A |
| 175 | A |
| 176 | A |
| 177 | A |
| 178 | A |
| 179 | A |
| 180 | C |
| 181 | A |
| 182 | A |
| 183 | A |
| 184 | A |
| 185 | A |
| 186 | B |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | C |
| 200 | A |
| 201 | B |
| 202 | A |
| 203 | A |
| 204 | B |
| 205 | A |
| 206 | C |
| 207 | A |
| 208 | A |
| 209 | A |
| 210 | A |
| 211 | B |
| 212 | B |
| 213 | C |
| 214 | B |
| 215 | A |
| 216 | B |
| 217 | B |
| 218 | B |
| 219 | B |
| 220 | C |
| 221 | C |
| 222 | C |
| 223 | C |
| 224 | B |
| 225 | B |
| 226 | A |
| 227 | A |
| 228 | B |

TABLE 2-continued

Met kinase binding activity

| # cpds | cMet |
|---|---|
| 229 | A |
| 230 | C |
| 231 | B |
| 232 | C |
| 233 | C |
| 234 | B |
| 235 | B |
| 236 | A |
| 237 | A |
| 238 | C |
| 239 | B |
| 240 | A |
| 241 | C |
| 242 | C |
| 243 | A |
| 244 | A |
| 245 | C |
| 246 | C |
| 247 | A |
| 248 | A |
| 249 | A |
| 250 | C |
| 251 | A |
| 252 | C |
| 253 | A |
| 254 | C |
| 255 | A |
| 256 | C |
| 257 | A |
| 258 | A |
| 259 | A |
| 260 | A |
| 261 | A |
| 262 | A |
| 263 | A |
| 264 | A |
| 265 | C |
| 266 | A |
| 267 | A |
| 268 | A |
| 269 | B |
| 270 | B |
| 271 | A |
| 272 | B |
| 273 | B |
| 274 | A |
| 275 | B |
| 276 | A |
| 277 | C |
| 278 | B |
| 279 | A |
| 280 | A |

Activity range:
A indicates <0.1 uM,
B indicates $0.1 \leq Kd < 1$ uM,
C indicates $\geq 1$ uM

TABLE 3

Cellular Axl phosphorylation assay

| # cpds | Axl cellular (IC$_{50}$, uM) | # cpds | Axl cellular (IC$_{50}$, uM) | # cpds | Axl cellular (IC$_{50}$, uM) |
|---|---|---|---|---|---|
| 1 | A | 41 | A | 101 | A |
| 3 | A | 43 | C | 102 | A |
| 4 | A | 44 | A | 99 | A |
| 5 | A | 45 | A | 104 | A |
| 6 | A | 48 | A | 105 | A |
| 7 | C | 55 | A | 106 | A |
| 8 | A | 56 | A | 107 | A |
| 10 | A | 57 | A | 108 | A |
| 11 | A | 58 | A | 110 | A |
| 12 | A | 59 | A | 111 | A |
| 13 | A | 61 | A | 112 | A |
| 14 | A | 64 | A | 113 | A |
| 16 | B | 65 | A | 114 | A |
| 17 | A | 66 | A | 115 | A |
| 18 | A | 68 | A | 116 | A |
| 19 | A | 73 | A | 117 | A |
| 20 | A | 76 | A | 120 | A |
| 21 | A | 79 | A | 124 | A |
| 23 | A | 80 | A | 125 | A |
| 26 | A | 81 | A | 126 | A |
| 27 | A | 82 | A | 127 | A |
| 29 | B | 85 | A | 128 | A |
| 30 | A | 86 | A | 129 | A |
| 31 | A | 87 | A | 130 | A |
| 32 | A | 89 | A | 132 | A |
| 33 | A | 90 | A | 133 | A |
| 34 | A | 92 | A | 141 | A |
| 36 | A | 93 | A | 148 | A |
| 37 | B | 96 | A | 149 | A |
| 38 | A | 97 | A | 151 | A |
| 39 | A | 99 | A | 160 | A |
| 40 | B | 100 | A | 161 | A |
| 162 | A | 202 | A | 246 | A |
| 165 | A | 203 | A | 247 | A |
| 167 | A | 205 | A | 248 | A |
| 168 | A | 206 | A | 249 | A |
| 169 | A | 207 | A | 251 | A |
| 170 | A | 208 | A | 252 | A |
| 177 | A | 209 | A | 253 | A |
| 179 | A | 210 | A | 254 | A |
| 181 | A | 211 | A | 255 | A |
| 182 | A | 212 | A | 257 | A |
| 183 | A | 213 | B | 258 | A |
| 184 | A | 215 | A | 259 | A |
| 185 | A | 224 | A | 260 | A |
| 186 | A | 225 | B | 261 | A |
| 187 | A | 226 | A | 262 | A |
| 188 | A | 227 | A | 263 | A |
| 189 | A | 229 | A | 264 | A |
| 190 | A | 230 | A | 265 | C |
| 191 | A | 231 | A | 266 | A |
| 192 | A | 233 | A | 267 | A |
| 193 | A | 234 | A | 268 | A |
| 194 | A | 236 | A | 269 | A |
| 195 | A | 237 | A | 270 | A |
| 196 | A | 239 | A | 271 | A |
| 197 | A | 240 | A | 272 | A |
| 198 | A | 241 | A | 273 | A |
| 199 | A | 242 | B | 274 | A |
| 200 | A | 243 | A | | |
| 201 | B | 244 | A | | |

Activity range:
A indicates <0.1 uM,
B indicates $0.1 \leq IC50 < 1$ uM,
C indicates $\geq 1$ uM

TABLE 4

Summarizes compounds 1-280 in terms of their structures and corresponding characteristics.

| # cpd | Structure | Characterization Data |
|---|---|---|
| 1 | 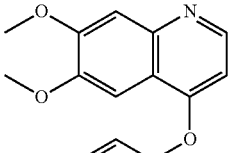 | white powder; ¹H-NMR (CDCl3, 400 MHz): δ 9.65 (1H, brs), 8.59 (1H, d, J = 8.8 Hz), 8.52 (1H, d, J = 5.2 Hz), 8.27 (1H, d, J = 2.4 Hz), 7.63-7.67 (2H, m), 7.56-7.61 (3H, m), 7.45 (1H, s), 6.97-7.01 (2H, m), 6.48 (1H, d, J = 5.2 Hz), 4.19 (2H, q, J = 7.2 Hz), 4.07 (3H, s), 4.06 (3H, s), 3.87 (3H, s), 1.57 (3H, t, J = 7.2 Hz); LCMS: 100%, MS (ESI): m/z 542.1 [M + H]+. |
| 2 | 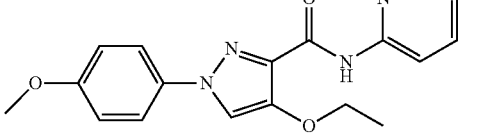 | white powder; ¹H-NMR (CDCl3, 400 MHz): δ 9.52 (1H, brs), 9.20-9.23 (3H, m), 8.57 (1H, d, J = 9.2 Hz), 8.52 (1H, d, J = 5.2 Hz), 8.29 (1H, d, J = 3.2 Hz), 7.72 (1H, s), 7.64 (1H, dd, J = 9.2 Hz, J = 2.8 Hz), 7.56 (1H, s), 7.45 (1H, s), 6.48 (1H, d, J = 5.6 Hz), 4.24 (2H, q, J = 6.8 Hz), 4.07 (6H, s), 1.61 (3H, t, J = 6.8 Hz); LCMS: 97.5%, MS (ESI): m/z 514.2 [M + H]+. |
| 3 | 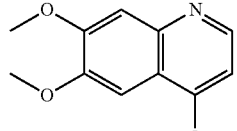 | white powder; ¹H-NMR (CDCl3, 400 MHz): δ 9.54 (1H, brs), 8.56 (1H, d, J = 9.2 Hz), 8.51 (1H, d, J = 5.2 Hz), 8.24 (1H, d, J = 2.8 Hz), 7.56-7.58 (2H, m), 7.45 (1H, s), 7.17 (1H, s), 6.46 (1H, d, J = 5.2 Hz), 4.60-4.67 (1H, m), 4.06-4.12 (8H, m), 2.14-2.22 (2H, m), 2.00-2.09 (2H, m), 1.84-1.93 (2H, m), 1.70-1.75 (2H, m), 1.52 (3H, t, J = 6.8 Hz); LCMS: 96.6%, MS (ESI): m/z 504.2 [M + H]+. |
| 4 | 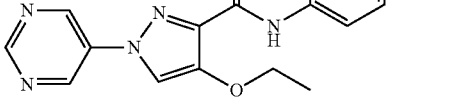 | white amorphous; ¹H-NMR (DMSO-d6, 400 MHz): δ 10.02 (1H, brs), 8.58 (1H, s), 8.48-8.55 (2H, m), 8.43 (1H, d, J = 3.2 Hz), 8.38 (1H, d, J = 9.2 Hz), 8.13 (1H, d, J = 7.6 Hz), 8.00-8.10 (1H, m), 7.90 (1H, dd, J = 9.2, 3.2 Hz), 7.55 (1H, s), 7.40-7.47 (2H, m), 6.57 (1H, d, J = 4.2 Hz), 4.24 (2H, q, J = 7.2 Hz), 3.90-4.05 (6H, m), 1.43 (1H, t, J = 7.2 Hz); LCMS: 100%, MS (ESI): m/z 513.2 [M + H]+. |
| 5 | 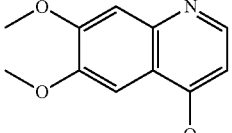 | white powder; amorphous; ¹H-NMR (DMSO-d6, 400 MHz): δ 10.14 (1H, brs), 9.26 (1H, dd, J = 4.8, 1.2 Hz), 8.81 (1H, s), 8.50 (1H, d, J = 5.2 Hz), 8.42-8.49 (2H, m), 8.37 (1H, d, J = 8.8 Hz), 7.96 (1H, dd, J = 8.8, 4.8 Hz), 7.89 (1H, dd, J = 9.2, 2.8 Hz), 7.54 (1H, s), 7.42 (1H, s), 6.57 (1H, d, J = 4.2 Hz), 4.26 (2H, q, J = 7.2 Hz), 3.90-4.05 (6H, m), 1.43 (1H, t, J = 7.2 Hz); LCMS: 98.7%, MS (ESI): m/z 514.0 [M + H]+. |

TABLE 4-continued

Summarizes compounds 1-280 in terms of their structures and corresponding characteristics.

| # cpd | Structure | Characterization Data |
|---|---|---|
| 6 | 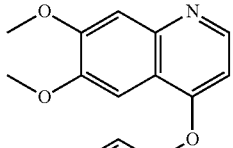 | yellow powder; amorphous; $^1$H-NMR (DMSO-d6, 400 MHz): δ 9.79 (1H, brs), 8.50 (1H, d, J = 5.2 Hz), 8.40-8.42 (2H, m), 8.35-8.39 (2H, m), 7.85-7.95 (2H, m), 7.55 (1H, s), 7.42 (1H, s), 6.55-6.65 (2H, m), 6.27 (2H, brs), 4.18 (2H, q, J = 6.8 Hz), 3.90-4.05 (6H, m), 1.43 (3H, t, J = 6.8 Hz); LCMS: 98.7%, MS (ESI): m/z 528.5 [M + H]+. |
| 7 | 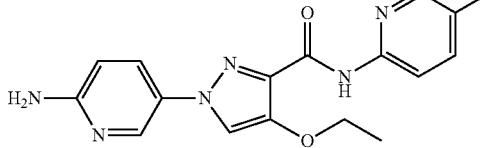 | white powder; $^1$H-NMR (DMSO-d6, 400 MHz): δ 11.70 (1H, brs), 10.04 (1H, brs), 8.61 (1H, s), 8.48 (1H, d, J = 5.6 Hz), 8.41 (1H, d, J = 3.2 Hz), 8.33 (1H, d, J = 8.8 Hz), 7.86 (1H, dd, J = 9.2, 3.2 Hz), 7.45-7.60 (2H, m), 7.40 (1H, s), 6.93 (1H, dd, J = 7.6, 2.4 Hz), 6.84 (1H, d, J = 2.0 Hz), 6.55 (1H, d, J = 5.2 Hz), 4.13 (2H, q, J = 6.8 Hz), 3.94 (3H, s), 3.93 (3H, s), 1.40 (3H, t, J = 6.8 Hz); LCMS: 100%, MS (ESI): m/z 529.0 [M + H]+. |
| 8 | 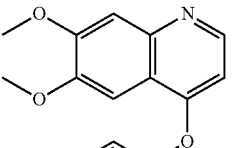 | white amorphous; $^1$H-NMR (DMSO-d6, 400 MHz, t = 80° C.): δ 9.58 (1H, brs), 8.52 (1H, d, J = 5.2 Hz), 8.30-8.38 (2H, m), 8.03-8.18 (3H, m), 7.81 (1H, dd, J = 8.8 Hz, 2.4 Hz), 7.56 (1H, s), 7.43 (1H, s), 6.61 (1H, d, J = 5.2 Hz), 4.19 (2H, q, J = 7.2 Hz), 3.97 (3H, s), 3.96 (3H, s), 1.44 (3H, t, J = 7.2 Hz); LCMS: 97.2%, MS (ESI): m/z 502.1 [M + H]+. |
| 9 | 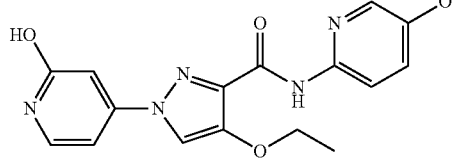 | white powder; $^1$H-NMR (DMSO-d6, 400 MHz): δ 9.88 (1H, brs), 8.50 (1H, d, J = 5.2 Hz), 8.41 (1H, d, J = 2.8 Hz), 8.38 (1H, s), 8.35 (1H, d, J = 9.2 Hz), 8.05-8.10 (2H, m), 7.87 (1H, dd, J = 8.8, 2.8 Hz), 7.54 (1H, s), 7.41 (1H, s), 6.51-6.57 (2H, m), 4.14 (2H, q, J = 7.2 Hz), 3.95 (3H, s), 3.94 (3H, s), 1.42 (3H, t, J = 7.2 Hz); LCMS: 99.4%, MS (ESI): m/z 529.1 [M + H]+. |
| 10 | 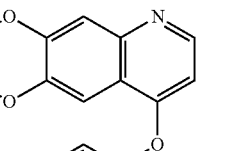 | white amorphous; $^1$H-NMR (DMSO-d6, 400 MHz): δ 9.88 (1H, brs), 8.77 (2H, s), 8.50 (1H, d, J = 5.2 Hz), 8.41-8.43 (2H, m), 8.36 (1H, d, J = 9.2 Hz), 7.88 (1H, dd, J = 8.8 Hz, J = 2.8 Hz), 7.54 (1H, s), 7.42 (1H, s), 7.05 (2H, s), 6.56 (1H, d, J = 5.2 Hz), 4.16 (2H, q, J = 6.8 Hz), 3.95 (3H, s), 3.94 (3H, s), 1.43 (3H, t, J = 6.8 Hz); LCMS: 100%, MS (ESI): m/z 529.0 [M + H]+. |

TABLE 4-continued

Summarizes compounds 1-280 in terms of their structures and corresponding characteristics.

| # cpd | Structure | Characterization Data |
|---|---|---|
| 11 | 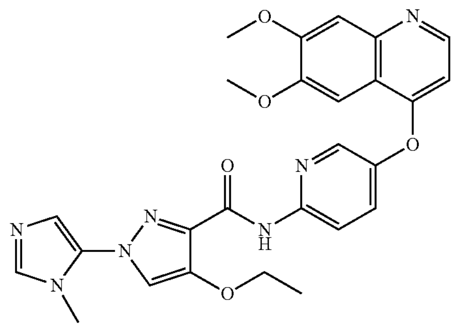 [SMILES: CCOc1cn(-c2cncn2C)nc1C(=O)Nc1ccc(Oc2ccnc3cc(OC)c(OC)cc23)cn1] | white amorphous; $^1$H-NMR (DMSO-d6, 400 MHz): δ 9.85 (1H, brs), 8.50 (1H, d, J = 5.2 Hz), 8.42 (1H, d, J = 2.8 Hz), 8.35 (1H, d, J = 8.8 Hz), 8.17 (1H, s), 7.88 (1H, dd, J = 8.8 Hz, 2.8 Hz), 7.76 (1H, s), 7.54 (1H, s), 7.42 (1H, s), 7.20 (1H, s), 6.55 (1H, d, J = 5.2 Hz), 4.15 (2H, q, J = 6.8 Hz), 3.95 (3H, s), 3.94 (3H, s), 3.61 (3H, s), 1.42 (3H, t, J = 6.8 Hz); LCMS: 100%, MS (ESI): m/z 516.0 [M + H]. |
| 12 | 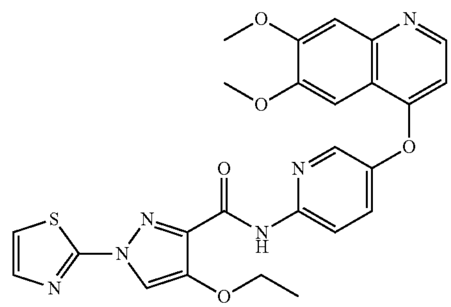 [SMILES: CCOc1cn(-c2nccs2)nc1C(=O)Nc1ccc(Oc2ccnc3cc(OC)c(OC)cc23)cn1] | white amorphous; $^1$H-NMR (DMSO-d6, 400 MHz): δ 9.96 (1H, brs), 8.55 (1H, s), 8.50 (1H, d, J = 5.2 Hz), 8.44 (1H, d, J = 3.2 Hz), 8.36 (1H, d, J = 8.8 Hz), 7.90 (1H, dd, J = 8.8 Hz, 2.8 Hz), 7.71 (1H, d, J = 3.2 Hz), 7.65 (1H, d, J = 3.6 Hz), 7.54 (1H, s), 7.42 (1H, s), 6.55 (1H, d, J = 5.2 Hz), 4.25 (2H, q, J = 6.8 Hz), 3.96 (3H, s), 3.95 (3H, s), 1.43 (3H, t, J = 6.8 Hz); LCMS: 100%, MS (ESI): m/z 518.9 [M + H]+. |
| 13 | 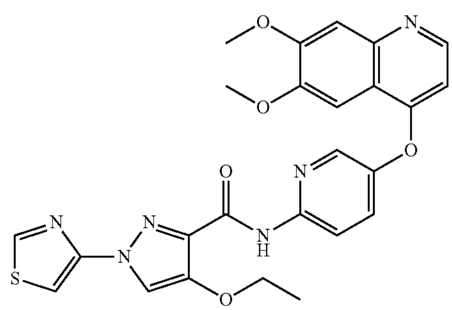 [SMILES: CCOc1cn(-c2cscn2)nc1C(=O)Nc1ccc(Oc2ccnc3cc(OC)c(OC)cc23)cn1] | white amorphous; $^1$H-NMR (DMSO-d6, 400 MHz): δ 9.86 (1H, brs), 9.23 (1H, d, J = 2.0 Hz), 8.50 (1H, d, J = 5.2 Hz), 8.43 (1H, d, J = 3.2 Hz), 8.41 (1H, s), 8.38 (1H, d, J = 9.2 Hz), 7.98 (1H, d, J = 2.0 Hz), 7.89 (1H, dd, J = 8.8 Hz, 2.8 Hz), 7.54 (1H, s), 7.42 (1H, s), 6.56 (1H, d, J = 5.2 Hz), 4.23 (2H, q, J = 6.8 Hz), 3.96 (3H, s), 3.95 (3H, s), 1.43 (3H, t, J = 6.8 Hz); LCMS: 100%, MS (ESI): m/z 518.9 [M + H]+. |
| 14 | 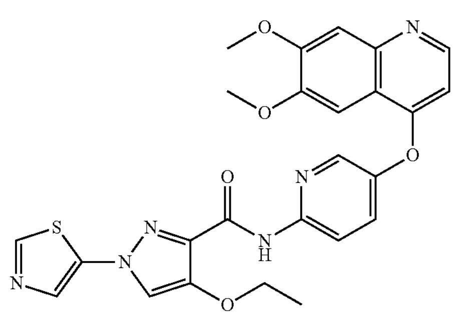 [SMILES: CCOc1cn(-c2cncs2)nc1C(=O)Nc1ccc(Oc2ccnc3cc(OC)c(OC)cc23)cn1] | white amorphous; $^1$H-NMR (DMSO-d6, 400 MHz): δ 9.81 (1H, brs), 8.95 (1H, s), 8.59 (1H, s), 8.50 (1H, d, J = 5.2 Hz), 8.42 (1H, d, J = 2.8 Hz), 8.35 (1H, d, J = 9.2 Hz), 8.27 (1H, s), 7.89 (1H, dd, J = 8.8 Hz, 2.8 Hz), 7.54 (1H, s), 7.42 (1H, s), 6.56 (1H, d, J = 5.2 Hz), 4.20 (2H, q, J = 7.2 Hz), 3.95 (3H, s), 3.94 (3H, s), 1.45 (3H, t, J = 7.2 Hz); LCMS: 100%, MS (ESI): m/z 518.9 [M + H]+. |

TABLE 4-continued

Summarizes compounds 1-280 in terms of their structures and corresponding characteristics.

| # cpd | Structure | Characterization Data |
|---|---|---|
| 15 | 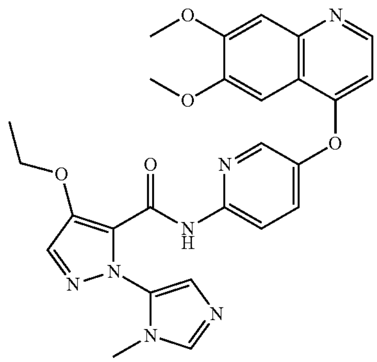 [SMILES: CCOc1cnn(-c2cncn2C)c1C(=O)Nc1ccc(Oc2ccnc3cc(OC)c(OC)cc23)cn1] | white amorphous; $^1$H-NMR (DMSO-d6, 400 MHz): δ 9.79 (1H, brs), 8.52 (1H, d, J = 5.2 Hz), 8.43 (1H, d, J = 2.8 Hz), 8.18 (1H, d, J = 8.8 Hz), 8.08 (1H, s), 7.84 (1H, s), 7.80 (1H, dd, J = 8.8 Hz, 2.8 Hz), 7.54 (1H, s), 7.42 (1H, s), 7.12 (1H, s), 6.56 (1H, d, J = 5.6 Hz), 4.38 (2H, q, J = 6.8 Hz), 3.95 (3H, s), 3.94 (3H, s), 3.35 (3H, s, overlapped with H2O peak), 1.47 (3H, t, J = 6.8 Hz); LCMS: 100%, MS (ESI): m/z 516.1 [M + H]+. |
| 16 | 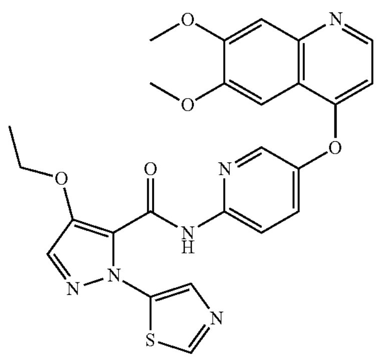 [SMILES: CCOc1cnn(-c2cncs2)c1C(=O)Nc1ccc(Oc2ccnc3cc(OC)c(OC)cc23)cn1] | white amorphous; $^1$H-NMR (DMSO-d6, 400 MHz): δ 10.06 (1H, brs), 9.08 (1H, s), 8.49 (1H, d, J = 5.2 Hz), 8.42 (1H, d, J = 2.8 Hz), 8.22 (1H, d, J = 9.2 Hz), 8.03-8.05 (2H, m), 7.82 (1H, dd, J = 8.8 Hz, 2.8 Hz), 7.53 (1H, s), 7.41 (1H, s), 6.54 (1H, d, J = 5.6 Hz), 4.34 (2H, q, J = 7.2 Hz), 3.95 (3H, s), 3.94 (3H, s), 1.44 (3H, t, J = 7.2 Hz); LCMS: 100%, MS (ESI): m/z 519.1 [M + H]+. |
| 17 | 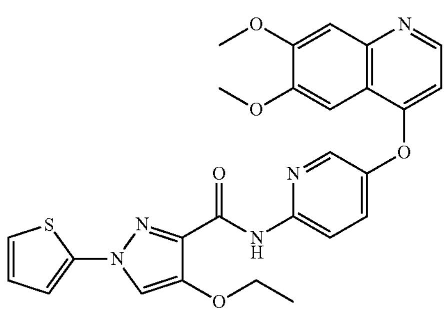 [SMILES: CCOc1cn(-c2cccs2)nc1C(=O)Nc1ccc(Oc2ccnc3cc(OC)c(OC)cc23)cn1] | white amorphous; $^1$H-NMR (DMSO-d6, 400 MHz): δ 9.73 (1H, brs), 8.52 (1H, s), 8.49 (1H, d, J = 5.6 Hz), 8.41 (1H, d, J = 2.8 Hz), 8.35 (1H, d, J = 8.8 Hz), 7.88 (1H, dd, J = 8.8, 2.8 Hz), 7.54 (1H, s), 7.39-7.43 (2H, m), 7.36-7.39 (1H, m), 7.07 (1H, dd, J = 5.6, 4.0 Hz), 6.55 (1H, d, J = 5.2 Hz), 4.19 (2H, q, J = 7.2 Hz), 3.95 (3H, s), 3.94 (3H, s), 1.44 (3H, t, J = 7.2 Hz); LCMS: 100%, MS (ESI): m/z 518.0 [M + H]+. |
| 18 | 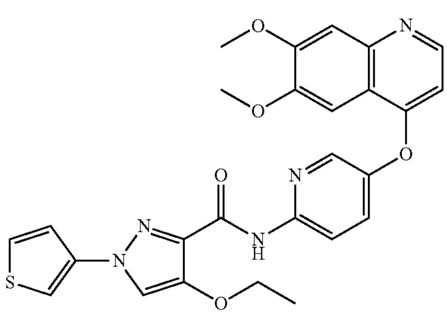 [SMILES: CCOc1cn(-c2ccsc2)nc1C(=O)Nc1ccc(Oc2ccnc3cc(OC)c(OC)cc23)cn1] | white amorphous; $^1$H-NMR (DMSO-d6, 400 MHz): δ 9.81 (1H, brs), 8.50 (1H, d, J = 5.2 Hz), 8.47 (1H, s), 8.42 (1H, d, J = 3.2 Hz), 8.37 (1H, d, J = 9.2 Hz), 7.85-7.91 (2H, m), 7.74 (1H, dd, J = 5.2, 3.2 Hz), 7.65 (1H, dd, J = 5.2, 1.2 Hz), 7.54 (1H, s), 7.41 (1H, s), 6.56 (1H, d, J = 5.2 Hz), 4.18 (2H, q, J = 6.8 Hz), 3.95 (3H, s), 3.94 (3H, s), 1.44 (3H, t, J = 6.8 Hz); LCMS: 100%, MS (ESI): m/z 518.0 [M + H]+. |

TABLE 4-continued

Summarizes compounds 1-280 in terms of their structures and corresponding characteristics.

| # cpd | Structure | Characterization Data |
|---|---|---|
| 19 | 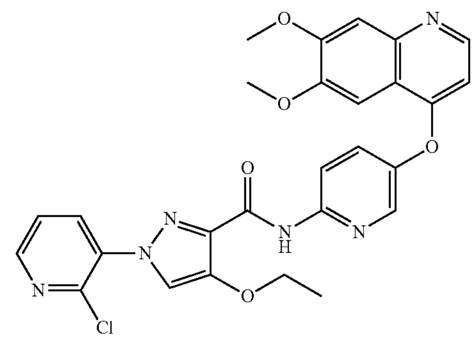 [SMILES: CCOc1cn(-c2cccnc2Cl)nc1C(=O)Nc1ccc(Oc2ccnc3cc(OC)c(OC)cc23)cn1] | white powder; ¹H-NMR (DMSO-d6, 400 MHz): δ 9.84 (1H, brs), 8.58 (1H, d, J = 4.4 Hz), 8.49 (1H, d, J = 5.2 Hz), 8.41 (1H, d, J = 3.2 Hz), 8.34 (1H, d, J = 9.2 Hz), 8.31 (1H, s), 8.24 (1H, dd, J = 7.6, 1.2 Hz), 7.87 (1H, dd, J = 9.2, 2.8 Hz), 7.68 (1H, dd, J = 8.0, 4.8 Hz), 7.53 (1H, s), 7.40 (1H, s), 6.55 (1H, d, J = 4.2 Hz), 4.16 (2H, q, J = 7.2 Hz), 3.94 (3H, s), 3.93 (3H, s), 1.42 (3H, t, J = 6.8 Hz); LCMS: 97.9%, MS (ESI): m/z 546.9 [M + H]+. |
| 20 | 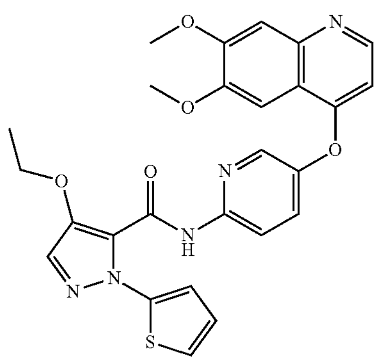 [SMILES: CCOc1cnn(-c2cccs2)c1C(=O)Nc1ccc(Oc2ccnc3cc(OC)c(OC)cc23)cn1] | white amorphous; ¹H-NMR (DMSO-d6, 400 MHz): δ 10.22 (1H, brs), 8.49 (1H, d, J = 5.2 Hz), 8.42 (1H, d, J = 2.8 Hz), 8.22 (1H, d, J = 8.8 Hz), 7.93 (1H, s), 7.82 (1H, dd, J = 8.8, 2.8 Hz), 7.53 (1H, s), 7.49 (1H, dd, J = 5.6, 1.6 Hz), 7.41 (1H, s), 7.18 (1H, dd, J = 4.0, 1.2 Hz), 7.02 (1H, dd, J = 5.6, 4.0 Hz), 6.55 (1H, d, J = 5.2 Hz), 4.30 (2H, q, J = 6.8 Hz), 3.95 (3H, s), 3.94 (3H, s), 1.42 (3H, t, J = 6.8 Hz); LCMS: 100%, MS (ESI): m/z 518.0 [M + H]+. |
| 21 | 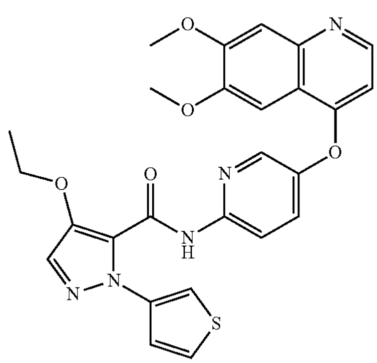 [SMILES: CCOc1cnn(-c2ccsc2)c1C(=O)Nc1ccc(Oc2ccnc3cc(OC)c(OC)cc23)cn1] | white amorphous; ¹H-NMR (DMSO-d6, 400 MHz): δ 10.08 (1H, brs), 8.49 (1H, d, J = 5.2 Hz), 8.41 (1H, d, J = 3.2 Hz), 8.23 (1H, d, J = 9.2 Hz), 7.87 (1H, s), 7.82 (1H, dd, J = 8.8, 2.8 Hz), 7.63-7.66 (1H, m), 7.59 (1H, dd, J = 5.2, 3.2 Hz), 7.53 (1H, s), 7.41 (1H, s), 7.23-7.26 (1H, m), 6.54 (1H, d, J = 5.2 Hz), 4.30 (2H, q, J = 6.8 Hz), 3.95 (3H, s), 3.94 (3H, s), 1.43 (3H, t, J = 6.8 Hz); LCMS: 100%, MS (ESI): m/z 518.0 [M + H]+. |
| 22 | 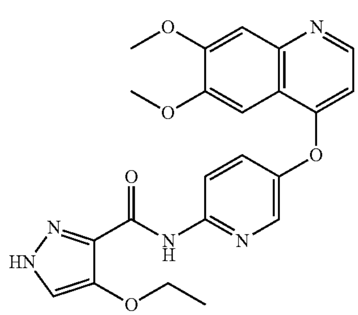 [SMILES: CCOc1c[nH]nc1C(=O)Nc1ccc(Oc2ccnc3cc(OC)c(OC)cc23)cn1] | white powder; ¹H-NMR (DMSO-d6, 400 MHz): δ 13.70 (0.4H, brs), 13.25 (0.6H, brs), 9.63 (0.6H, brs), 9.42 (0.4H, brs), 8.49 (1H, d, J = 5.2 Hz), 8.33-8.44 (2H, m), 7.84-7.91 (1H, m), 7.78 (0.6H, s), 7.64 (0.4H, s), 7.54 (1H, s), 7.42 (1H, s), 6.55 (1H, d, J = 5.2 Hz), 4.27 (0.8H, q, J = 6.8 Hz), 4.09 (1.2H, q, J = 6.8 Hz), 3.95 (3H, s), 3.94 (3H, s), 1.34-1.46 (3H, m); LCMS: 100%, MS (ESI): m/z 436.0 [M + H]+. It is a mixture of tautomer from H NMR. |

TABLE 4-continued

Summarizes compounds 1-280 in terms of their structures and corresponding characteristics.

| # cpd | Structure | Characterization Data |
|---|---|---|
| 23 | 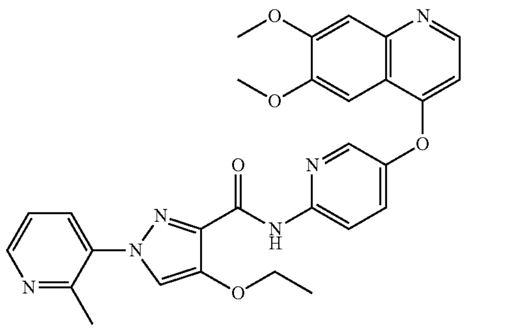 [SMILES: CCOc1cn(-c2cccnc2C)nc1C(=O)Nc1ccc(Oc2ccnc3cc(OC)c(OC)cc23)cn1] | white powder; ¹H-NMR (DMSO-d6, 400 MHz): δ 9.79 (1H, brs), 8.60 (1H, d, J = 4.8 Hz), 8.50 (1H, d, J = 5.6 Hz), 8.41 (1H, d, J = 2.8 Hz), 8.36 (1H, d, J = 9.2 Hz), 8.25 (1H, s), 7.94 (1H, d, J = 6.8 Hz0, 7.88 (1H, dd, J = 8.8 Hz, 2.8 Hz), 7.54 (1H, s), 7.47 (1H, dd, J = 8.4 Hz, 5.2 Hz), 7.42 (1H, s), 6.56 (1H, d, J = 4.8 Hz), 4.18 (2H, q, J = 7.2 Hz), 3.96 (3H, s), 3.95 (3H, s), 2.50 (3H, s, overlapped with DMSO), 1.44 (3H, t, J = 7.2 Hz); LCMS: 97.8%, MS (ESI): m/z 527.0 [M + H]+. |
| 24 | 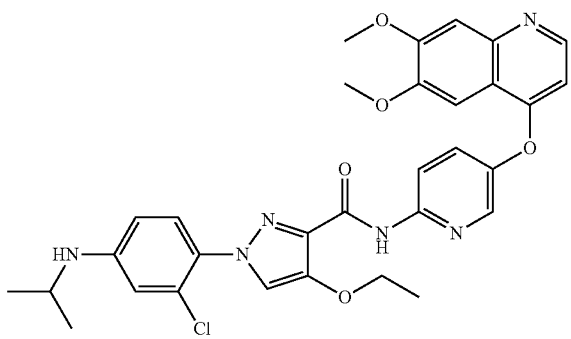 [SMILES: CCOc1cn(-c2ccc(NC(C)C)cc2Cl)nc1C(=O)Nc1ccc(Oc2ccnc3cc(OC)c(OC)cc23)cn1] | white powder; ¹H-NMR (DMSO-d6, 400 MHz): δ 9.66 (1H, brs), 8.48 (1H, d, J = 5.2 Hz), 8.38 (1H, d, J = 2.8 Hz), 8.41 (1H, d, J = 8.8 Hz), 7.99 (1H, s), 7.85 (1H, dd, J = 8.8, 2.4 Hz), 7.52 (1H, s), 7.40 (1H, s), 7.29 (1H, d, J = 8.8 Hz), 6.71 (1H, s), 6.61 (1H, d, J = 8.8 Hz), 6.54 (1H, d, J = 5.2 Hz), 6.18 (1H, d, J = 8.0 Hz), 4.12 (2H, q, J = 6.8 Hz), 3.94 (3H, s), 3.95 (3H, s), 3.50-3.65 (1H, m), 1.39 (3H, t, J = 7.2 Hz), 1.14 (6H, d, J = 6.4 Hz); LCMS: 99.5%, MS (ESI): m/z 603.1 [M + H]+. |
| 25 | 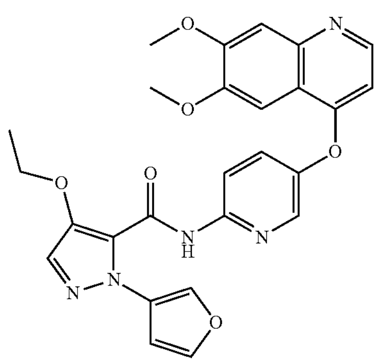 [SMILES: CCOc1cnn(-c2ccoc2)c1C(=O)Nc1ccc(Oc2ccnc3cc(OC)c(OC)cc23)cn1] | white powder; ¹H-NMR (DMSO-d6, 400 MHz): δ 10.04 (1H, brs), 8.50 (1H, d, J = 5.2 Hz), 8.42 (1H, d, J = 2.8 Hz), 8.26 (1H, d, J = 9.2 Hz), 8.07 (1H, s), 7.89 (1H, s), 7.84 (1H, dd, J = 9.2, 3.2 Hz), 7.70-7.75 (1H, m), 7.54 (1H, s), 7.42 (1H, s), 6.78 (1H, d, J = 1.6 Hz), 6.56 (1H, d, J = 5.2 Hz), 4.30 (2H, q, J = 6.8 Hz), 3.95 (3H, s), 3.94 (3H, s), 1.42 (3H, t, J = 6.8 Hz); LCMS: 99.4%, MS (ESI): m/z 502.1 [M + H]+. |
| 26 | 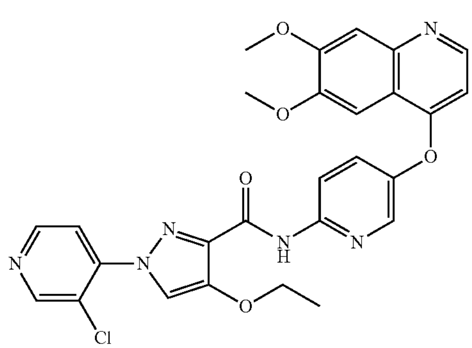 [SMILES: CCOc1cn(-c2ccncc2Cl)nc1C(=O)Nc1ccc(Oc2ccnc3cc(OC)c(OC)cc23)cn1] | white powder; amorphous; ¹H-NMR (DMSO-d6, 400 MHz): δ 10.07 (1H, brs), 8.50 (1H, d, J = 5.2 Hz), 8.46 (1H, s), 8.43 (1H, d, J = 2.8 Hz), 8.36 (1H, d, J = 8.8 Hz), 8.05-8.13 (2H, m), 7.88 (1H, dd, J = 9.2 Hz, 2.8 Hz), 7.52-7.57 (2H, m), 7.42 (1H, s), 6.57 (1H, d, J = 5.2 Hz), 4.25 (2H, q, J = 7.2 Hz), 3.96 (3H, s), 3.95 (3H, s), 1.42 (3H, t, J = 7.2 Hz); LCMS: 100%, MS (ESI): m/z 546.9 [M + H]+. |

TABLE 4-continued

Summarizes compounds 1-280 in terms of their structures and corresponding characteristics.

| # cpd | Structure | Characterization Data |
|---|---|---|
| 27 | 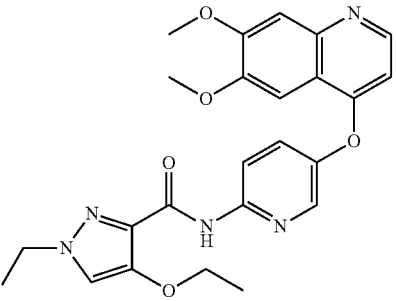 [SMILES: CCOc1cn(CC)nc1C(=O)Nc1ccc(Oc2ccnc3cc(OC)c(OC)cc23)cn1] | white powder; amorphous; $^1$H-NMR (CDCl3, 400 MHz): δ 9.48 (1H, brs), 8.56 (1H, d, J = 8.8 Hz), 8.51 (1H, d, J = 5.2 Hz), 8.25 (1H, d, J = 2.8 Hz), 7.54-7.61 (2H, m), 7.44 (1H, s), 7.16 (1H, s), 6.46 (1H, d, J = 5.2 Hz), 4.18 (2H, q, J = 7.6 Hz), 4.11 (2H, q, J = 6.8 Hz), 4.07 (3H, s), 4.06 (3H, s), 1.50-1.56 (6H, m); LCMS: 100%, MS (ESI): m/z 464.0 [M + H]+. |
| 28 | 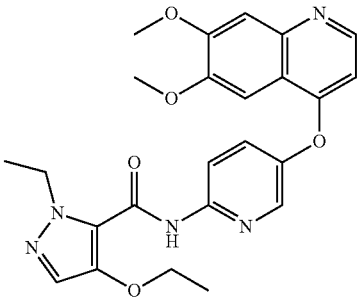 [SMILES: CCOc1cnn(CC)c1C(=O)Nc1ccc(Oc2ccnc3cc(OC)c(OC)cc23)cn1] | white powder; amorphous; $^1$H-NMR (CDCl3, 400 MHz): δ 9.76 (1H, brs), 8.51 (1H, d, J = 5.2 Hz), 8.44 (1H, d, J = 9.2 Hz), 8.26 (1H, d, J = 2.8 Hz), 7.54-7.60 (2H, m), 7.43 (1H, s), 7.31 (1H, s), 6.45 (1H, d, J = 5.2 Hz), 4.67 (2H, q, J = 7.2 Hz), 4.27 (2H, q, J = 6.8 Hz), 4.06 (3H, s), 4.05 (3H, s), 1.57 (3H, t, J = 6.8 Hz), 1.46 (3H, t, J = 7.2 Hz); LCMS: 100%, MS (ESI): m/z 464.0 [M + H]+. |
| 29 | 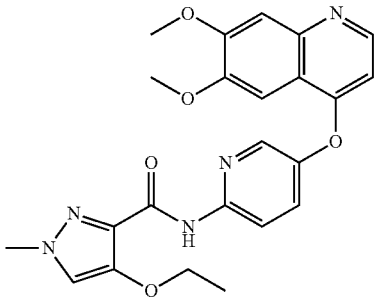 [SMILES: CCOc1cn(C)nc1C(=O)Nc1ccc(Oc2ccnc3cc(OC)c(OC)cc23)cn1] | white powder; amorphous; $^1$H-NMR (CDCl3, 400 MHz): δ 9.46 (1H, brs), 8.56 (1H, d, J = 8.8 Hz), 8.51 (1H, d, J = 5.2 Hz), 8.24 (1H, d, J = 2.8 Hz), 7.55-7.61 (2H, m), 7.43 (1H, s), 7.13 (1H, s), 6.46 (1H, d, J = 5.2 Hz), 4.11 (2H, q, J = 6.8 Hz), 4.07 (3H, s), 4.06 (3H, s), 3.93 (3H, s), 1.53 (3H, t, J = 6.8 Hz); LCMS: 100%, MS (ESI): m/z 449.9 [M + H]+. |
| 30 | 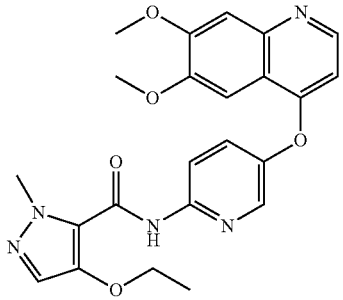 [SMILES: CCOc1cnn(C)c1C(=O)Nc1ccc(Oc2ccnc3cc(OC)c(OC)cc23)cn1] | white powder; $^1$H-NMR (CDCl3, 400 MHz): δ 9.70 (1H, brs), 8.51 (1H, d, J = 5.2 Hz), 8.43 (1H, d, J = 8.8 Hz), 8.27 (1H, d, J = 2.4 Hz), 7.54-7.61 (2H, m), 7.44 (1H, s), 7.30 (1H, s), 6.45 (1H, d, J = 5.2 Hz), 4.27 (2H, q, J = 6.8 Hz), 4.23 (3H, s), 4.07 (3H, s), 4.06 (3H, s), 1.57 (3H, t, J = 6.8 Hz); LCMS: 100%, MS (ESI): m/z 450.0 [M + H]+. |

TABLE 4-continued

Summarizes compounds 1-280 in terms of their structures and corresponding characteristics.

| # cpd | Structure | Characterization Data |
|---|---|---|
| 31 | 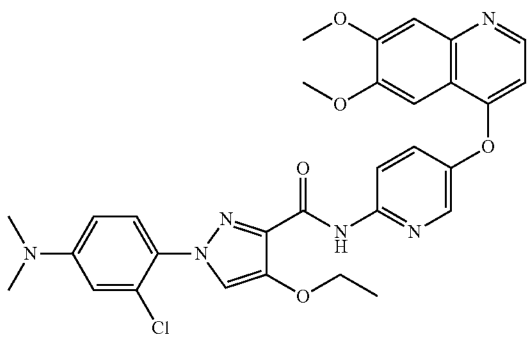 [SMILES: CCOc1cn(-c2ccc(N(C)C)cc2Cl)nc1C(=O)Nc1ccc(Oc2ccnc3cc(OC)c(OC)cc23)cn1] | white powder; amorphous; ¹H-NMR (DMSO-d6, 400 MHz): δ 9.69 (1H, brs), 8.50 (1H, d, J = 5.2 Hz), 8.40 (1H, d, J = 3.2 Hz), 8.35 (1H, d, J = 8.8 Hz), 8.03 (1H, s), 7.87 (1H, dd, J = 9.2, 2.8 Hz), 7.54 (1H, s), 7.35-7.45 (2H, m), 6.85 (1H, d, J = 2.8 Hz), 6.77 (1H, dd, J = 9.2, 2.8 Hz), 6.57 (1H, d, J = 5.2 Hz), 4.14 (2H, q, J = 7.2 Hz), 3.90-4.00 (6H, m), 2.98 (6H, s), 1.40 (3H, t, J = 6.8 Hz); LCMS: 97.5%, MS (ESI): m/z 588.9 [M + H]+. |
| 32 | 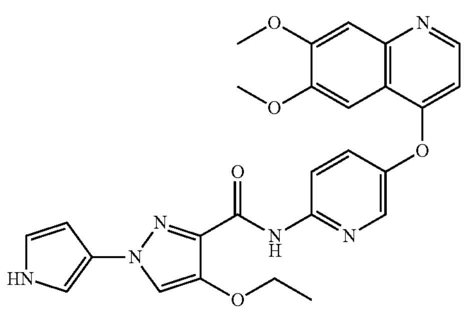 [SMILES: CCOc1cn(-c2cc[nH]c2)nc1C(=O)Nc1ccc(Oc2ccnc3cc(OC)c(OC)cc23)cn1] | white amorphous; ¹H-NMR (DMSO-d6, 400 MHz): δ 11.09 (1H, brs), 9.64 (1H, brs), 8.51 (1H, d, J = 5.2 Hz), 8.41 (1H, d, J = 2.8 Hz), 8.38 (1H, d, J = 9.2 Hz), 8.20 (1H, s), 7.88 (1H, dd, J = 9.2, 2.8 Hz), 7.55 (1H, s), 7.42 (1H, s), 7.24-7.27 (1H, m), 6.79-6.83 (1H, m), 6.57 (1H, d, J = 5.2 Hz), 6.46-6.50 (1H, m), 4.16 (2H, q, J = 6.8 Hz), 3.96 (3H, s), 3.95 (3H, s), 1.43 (3H, t, J = 6.8 Hz); LCMS: 92.4%, MS (ESI): m/z 501.0 [M + H]+. |
| 33 | 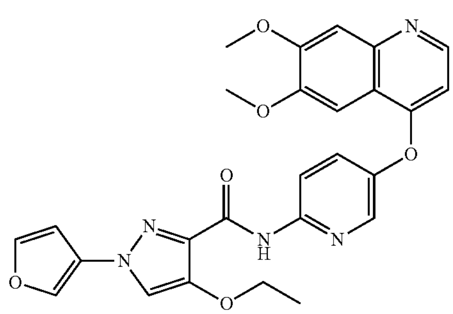 [SMILES: CCOc1cn(-c2ccoc2)nc1C(=O)Nc1ccc(Oc2ccnc3cc(OC)c(OC)cc23)cn1] | white amorphous; ¹H-NMR (DMSO-d6, 400 MHz): δ 9.75 (1H, brs), 8.50 (1H, d, J = 5.2 Hz), 8.42 (1H, d, J = 2.8 Hz), 8.36 (1H, d, J = 9.2 Hz), 8.33 (1H, s), 8.30 (1H, s), 7.88 (1H, dd, J = 9.2, 2.8 Hz), 7.82 (1H, t, J = 2.0 Hz), 7.54 (1H, s), 7.42 (1H, s), 7.03 (1H, d, J = 1.2 Hz), 6.56 (1H, d, J = 5.2 Hz), 4.17 (2H, q, J = 6.8 Hz), 3.96 (3H, s), 3.95 (3H, s), 1.44 (3H, t, J = 6.8 Hz); LCMS: 97.5%, MS (ESI): m/z 502.0 [M + H]+. |
| 34 | 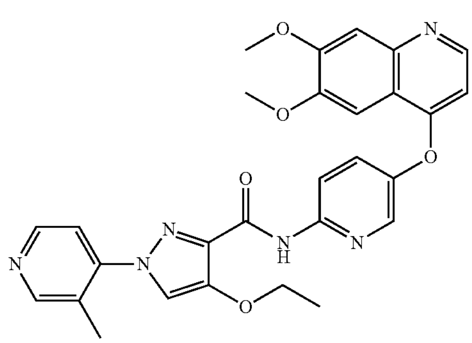 [SMILES: CCOc1cn(-c2ccncc2C)nc1C(=O)Nc1ccc(Oc2ccnc3cc(OC)c(OC)cc23)cn1] | white powder; ¹H-NMR (DMSO-d6, 400 MHz): δ 9.87 (1H, brs), 8.66 (1H, s), 8.59 (1H, d, J = 5.2 Hz), 8.50 (1H, d, J = 5.2 Hz), 8.42 (qH, d, J = 2.8 Hz), 8.30-8.40 (2H, m), 7.89 (1H, dd, J = 8.8, 2.8 Hz), 7.63 (1H, d, J = 5.2 Hz), 7.55 (1H, s), 7.42 (1H, s), 6.56 (1H, d, J = 5.2 Hz), 4.19 (2H, q, J = 6.8 Hz), 3.96 (s, 3H), 3.95 (3H, s), 2.47 (3H, s), 1.43 (3H, t, J = 6.8 Hz); LCMS: 97.6%, MS (ESI): m/z 527.1 [M + H]+. |

TABLE 4-continued

Summarizes compounds 1-280 in terms of their structures and corresponding characteristics.

| # cpd | Structure | Characterization Data |
|---|---|---|
| 35 | 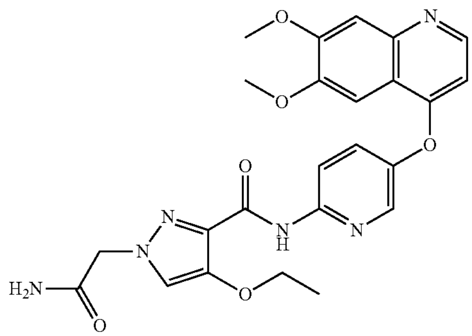 [SMILES: CCOc1cn(CC(N)=O)nc1C(=O)Nc1ccc(Oc2ccnc3cc(OC)c(OC)cc23)cn1] | white powder; ¹H-NMR (DMSO-d6, 400 MHz): δ 9.59 (1H, brs), 8.48 (1H, d, J = 5.6 Hz), 8.37 (1H, d, J = 2.8 Hz), 8.33 (1H, d, J = 8.8 Hz), 7.84 (1H, dd, J = 9.2, 2.8 Hz), 7.75 (1H, s), 7.58 (1H, brs), 7.52 (1H, s), 7.40 (1H, s), 7.34 (1H, brs), 6.54 (1H, d, J = 5.2 Hz), 4.78 (2H, s), 4.09 (2H, q, J = 7.2 Hz), 3.94 (3H, s), 3.93 (3H, s), 1.38 (3H, t, J = 7.2 Hz); LCMS: 100%, MS (ESI): m/z 493.2 [M + H]+. |
| 36 | 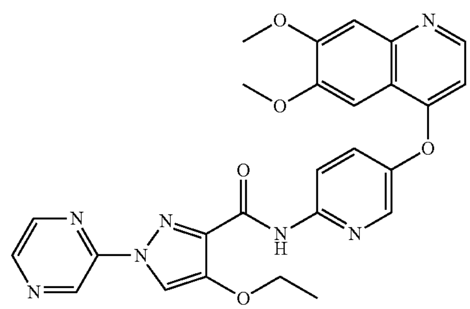 | white powder; ¹H-NMR (DMSO-d6, 400 MHz): δ 10.18 (1H, brs), 9.45 (1H, s), 8.69 (1H, d, J = 2.4 Hz), 8.59-8.61 (2H, m), 8.51 (1H, d, J = 5.2 Hz), 8.44 (1H, d, J = 2.8 Hz), 8.37 (1H, d, J = 8.8 Hz), 7.89 (1H, dd, J = 8.8, 2.8 Hz), 7.55 (1H, s), 7.42 (1H, s), 6.58 (1H, d, J = 5.2 Hz), 4.24 (2H, q, J = 6.8 Hz), 3.96 (3H, s), 3.95 (3H, s), 1.43 (3H, t, J = 6.8 Hz); LCMS: 100% (the sample was dissolved in DMSO, diluted with CH3CN), MS (ESI): m/z 514.1 [M + H]+. |
| 37 | 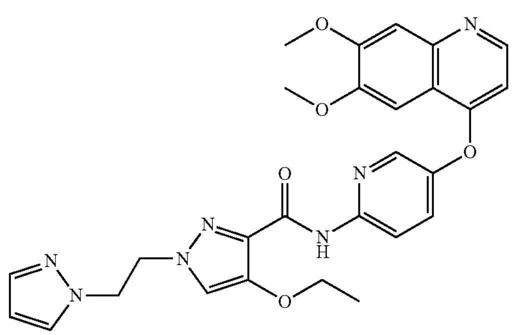 [SMILES: CCOc1cn(CCn2cccn2)nc1C(=O)Nc1ccc(Oc2ccnc3cc(OC)c(OC)cc23)cn1] | white powder; ¹H-NMR (DMSO-d6, 400 MHz): δ 9.57 (1H, brs), 8.50 (1H, d, J = 5.2 Hz), 8.39 (1H, d, J = 2.4 Hz), 8.34 (1H, d, J = 8.8 Hz), 7.86 (1H, dd, J = 8.8, 2.8 Hz), 7.52-7.56 (2H, m), 7.48 (1H, d, J = 1.2 Hz), 7.46 (1H, s), 7.41 (1H, s), 6.54 (1H, d, J = 5.2 Hz), 6.19 (1H, t, J = 2.0 Hz), 4.50-4.64 (4H, m), 3.92-4.02 (8H, m), 1.34 (3H, t, J = 6.8 Hz); LCMS: 98.3%, MS (ESI): m/z 530.1 [M + H]+. |
| 38 | 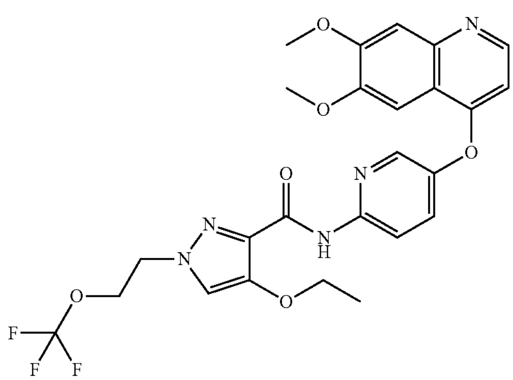 [SMILES: CCOc1cn(CCOC(F)(F)F)nc1C(=O)Nc1ccc(Oc2ccnc3cc(OC)c(OC)cc23)cn1] | white powder; ¹H-NMR (DMSO-d6, 400 MHz): δ 9.61 (1H, brs), 8.49 (1H, d, J = 5.2 Hz), 8.39 (1H, d, J = 2.8 Hz), 8.35 (1H, d, J = 9.2 Hz), 7.83-7.90 (2H, m), 7.54 (1H, s), 7.41 (1H, s), 6.55 (1H, d, J = 5.2 Hz), 4.45-4.56 (4H, m), 4.10 (2H, q, J = 6.8 Hz), 3.95 (3H, s), 3.94 (3H, s), 1.39 (3H, t, J = 6.8 Hz); LCMS: 100%, MS (ESI): m/z 548.0 [M + H]+. |

TABLE 4-continued

Summarizes compounds 1-280 in terms of their structures and corresponding characteristics.

| # cpd | Structure | Characterization Data |
|---|---|---|
| 39 | 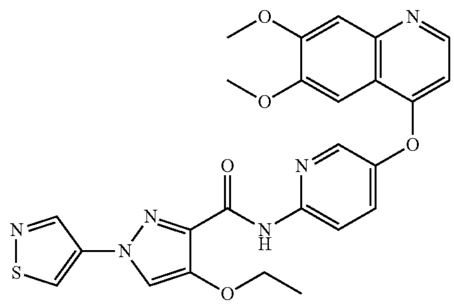 [SMILES: CCOc1cn(-c2cnsc2)nc1C(=O)Nc1ccc(Oc2ccnc3cc(OC)c(OC)cc23)cn1] | white powder; ¹H-NMR (DMSO-d6, 400 MHz): δ 9.90 (1H, brs), 9.34 (1H, s), 9.14 (1H, s), 8.57 (1H, s), 8.51 (1H, d, J = 5.2 Hz), 8.43 (1H, d, J = 2.8 Hz), 8.37 (1H, d, J = 8.8 Hz), 7.90 (1H, dd, J = 8.8, 2.8 Hz), 7.55 (1H, s), 7.42 (1H, s), 6.57 (1H, d, J = 5.2 Hz), 4.19 (2H, q, J = 6.8 Hz), 3.96 (3H, s), 3.95 (3H, s), 1.45 (3H, t, J = 6.8 Hz); LCMS: 97.4%, MS (ESI): m/z 519.1 [M + H]+. |
| 40 | 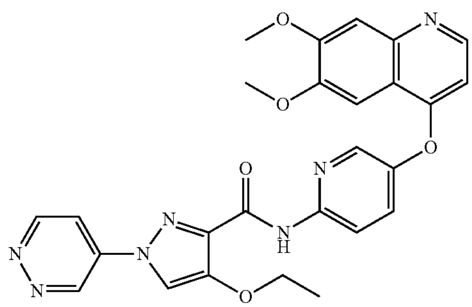 [SMILES: CCOc1cn(-c2ccnnc2)nc1C(=O)Nc1ccc(Oc2ccnc3cc(OC)c(OC)cc23)cn1] | white powder; ¹H-NMR (DMSO-d6, 400 MHz): δ 10.25 (1H, brs), 9.97 (1H, d, J = 2.0 Hz), 9.36 (1H, d, J = 6.0 Hz), 8.83 (1H, s), 8.51 (1H, d, J = 5.2 Hz), 8.45 (1H, d, J = 2.8 Hz), 8.36 (1H, d, J = 8.8 Hz), 8.21 (1H, dd, J = 5.6, 2.8 Hz), 7.90 (1H, dd, J = 8.8, 2.8 Hz), 7.55 (1H, s), 7.42 (1H, s), 6.58 (1H, d, J = 5.2 Hz), 4.20 (2H, q, J = 7.2 Hz), 3.96 (3H, s), 3.95 (3H, s), 1.45 (3H, t, J = 7.2 Hz); LCMS: 97.9%, MS (ESI): m/z 513.2 [M + H]+. |
| 41 | 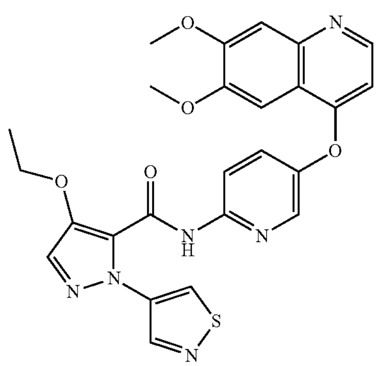 | white powder; ¹H-NMR (DMSO-d6, 400 MHz): δ 9.92 (1H, brs), 9.20 (1H, s), 8.77 (1H, s), 8.50 (1H, d, J = 5.2 Hz), 8.43 (1H, d, J = 2.8 Hz), 8.23 (1H, d, J = 8.8 Hz), 8.01 (1H, s), 7.83 (1H, dd, J = 8.8, 2.8 Hz), 7.53 (1H, s), 7.42 (1H, s), 6.54 (1H, d, J = 5.2 Hz), 4.36 (2H, q, J = 6.8 Hz), 3.95 (3H, s), 3.94 (3H, s), 1.46 (3H, t, J = 6.8 Hz); LCMS: 90.3%, MS (ESI): m/z 530.1 [M + H]+. |
| 42 | 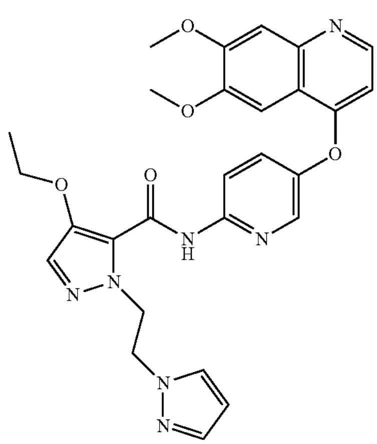 [SMILES: CCOc1cnn(CCn2cccn2)c1C(=O)Nc1ccc(Oc2ccnc3cc(OC)c(OC)cc23)cn1] | white powder; ¹H-NMR (DMSO-d6, 400 MHz): δ 9.69 (1H, brs), 8.50 (1H, d, J = 5.2 Hz), 8.43 (1H, d, J = 2.4 Hz), 8.33 (1H, d, J = 9.2 Hz), 7.88 (1H, dd, J = 9.2, 2.8 Hz), 7.53-7.61 (2H, m), 7.48-7.52 (1H, m), 7.42 (1H, s), 7.38 (1H, s), 6.55 (1H, d, J = 5.2 Hz), 6.15 (1H, m), 4.89 (2H, t, J = 5.6 Hz), 4.54 (2H, t, J = 5.6 Hz), 4.27 (2H, q, J = 6.8 Hz), 3.96 (3H, s), 3.95 (3H, s), 1.43 (3H, t, J = 6.8 Hz); LCMS: 100%, MS (ESI): m/z 530.1 [M + H]+. |

TABLE 4-continued

Summarizes compounds 1-280 in terms of their structures and corresponding characteristics.

| # cpd | Structure | Characterization Data |
|---|---|---|
| 43 | 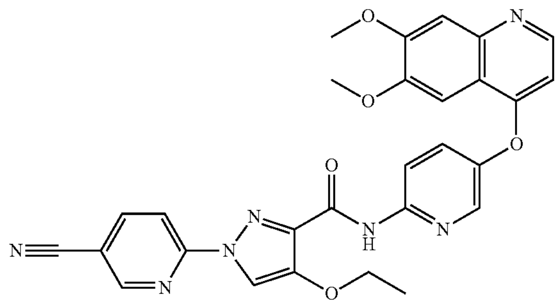 [SMILES: CCOc1cn(-c2ccc(C#N)cn2)nc1C(=O)Nc1ccc(Oc2ccnc3cc(OC)c(OC)cc23)cn1] | white powder; ¹H-NMR (DMSO-d6, 400 MHz): δ 10.21 (1H, s), 9.00 (1H, s), 8.60 (1H, s), 8.49-8.55 (2H, m), 8.43 (1H, d, J = 2.4 Hz), 8.30-8.40 (2H, m), 7.89 (1H, dd, J = 8.8, 2.8 Hz), 7.53 (1H, s), 7.41 (1H, s), 6.56 (1H, d, J = 5.6 Hz), 4.22 (2H, q, J = 6.8 Hz), 3.94 (3H, s), 3.94 (3H, s), 1.41 (3H, t, J = 6.8 Hz); LCMS: 98.7%, MS (ESI): mz 538.1 [M + H]+. |
| 44 | 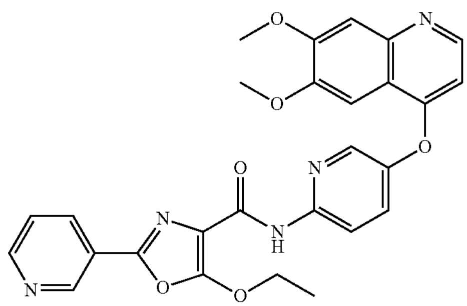 [SMILES: CCOc1oc(-c2cccnc2)nc1C(=O)Nc1ccc(Oc2ccnc3cc(OC)c(OC)cc23)cn1] | white powder; ¹H-NMR (DMSO-d6, 400 MHz): δ 9.56 (1H, brs), 9.19 (1H, s), 8.73 (1H, d, J = 4.4 Hz), 8.51 (1H, d, J = 5.2 Hz), 8.42 (1H, d, J = 2.8 Hz), 8.36 (1H, d, J = 8.0 Hz), 8.32 (1H, d, J = 8.8 Hz), 7.88 (1H, dd, J = 9.2, 2.8 Hz), 7.59 (1H, dd, J = 8.0, 4.8 Hz), 7.55 (1H, s), 7.42 (1H, s), 6.57 (1H, d, J = 5.6 Hz), 4.72 (2H, q, J = 7.2), 3.96 (3H, s), 3.95 (3H, s), 1.47 (3H, t, J = 7.2 Hz); LCMS: 100%, MS (ESI): m/z 514.0 [M + H]+. |
| 45 | 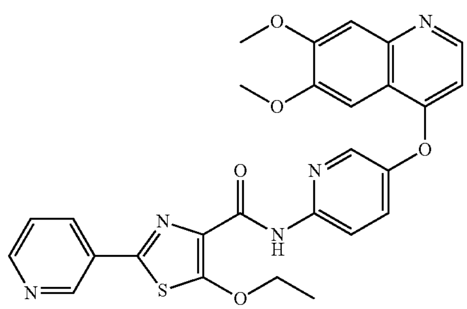 [SMILES: CCOc1sc(-c2cccnc2)nc1C(=O)Nc1ccc(Oc2ccnc3cc(OC)c(OC)cc23)cn1] | white powder; ¹H-NMR (CDCl3, 400 MHz): δ 9.74 (1H, brs), 9.07 (1H, d, J = 1.6 Hz), 8.69 (1H, dd, J = 5.2, 1.6 Hz), 8.54-8.62 (2H, m), 8.30 (1H, d, J = 2.4 Hz), 8.25 (1H, td, J = 8.0, 2.0 Hz), 7.61 (1H, dd, J = 9.2, 3.2 Hz), 7.54-7.58 (2H, m), 7.40-7.45 (2H, m), 6.51 (1H, d, J = 5.6 Hz), 4.44 (2H, q, J = 7.2 Hz), 4.07 (6H, s), 1.65 (3H, t, J = 6.8 Hz); LCMS: 96.7%, MS (ESI): m/z 530.0 [M + H]+. |
| 46 | 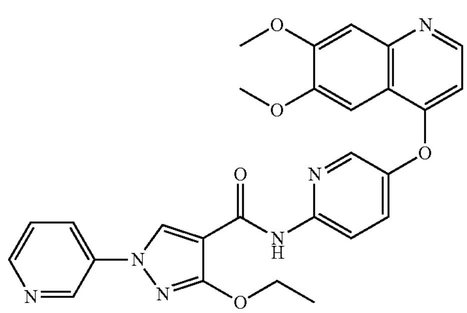 [SMILES: CCOc1nn(-c2cccnc2)cc1C(=O)Nc1ccc(Oc2ccnc3cc(OC)c(OC)cc23)cn1] | off-white solid; ¹H-NMR (DMSO-d6, 400 MHz): δ 9.58 (1H, brs), 9.21 (1H, s), 9.14 (1H, s), 8.56 (1H, d, J = 4.0 Hz), 8.50 (1H, d, J = 5.2 Hz), 8.43 (1H, d, J = 2.8 Hz), 8.38 (1H, d, J = 9.6 Hz), 8.28 (1H, d, J = 7.2 Hz), 7.89 (1H, d, J = 8.8 Hz), 7.52-7.60 (2H, m), 7.43 (1H, s), 6.56 (1H, d, J = 5.2 Hz), 4.56 (2H, q, J = 7.2 Hz), 3.96 (6H, s), 1.51 (3H, t, J = 7.2 Hz); LCMS: 100%, MS (ESI): m/z 513.1 [M + H]+. |
| 47 | 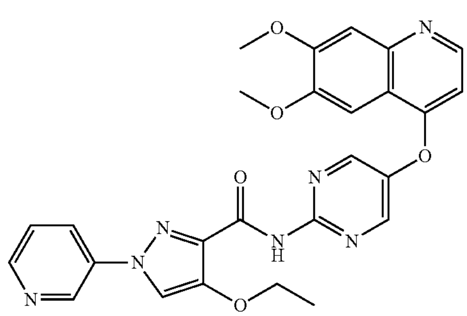 [SMILES: CCOc1cn(-c2cccnc2)nc1C(=O)Nc1ncc(Oc2ccnc3cc(OC)c(OC)cc23)cn1] | white power; ¹H-NMR (DMSO-d6, 400 MHz): δ 10.35 (1H, brs), 9.22 (1H, d, J = 2.4 Hz), 8.85 (2H, s), 8.67 (1H, s), 8.60 (1H, dd, J = 4.8, 1.2 Hz), 8.53 (1H, d, J = 5.2 Hz), 8.34-8.42 (1H, m), 7.56-7.65 (1H, m), 7.57 (1H, s), 7.44 (1H, s), 6.71 (1H, d, J = 5.6 Hz), 4.18 (2H, q, J = 6.8 Hz), 3.97 (3H, s), 3.96 (3H, s), 1.42 (3H, t, J = 7.2 Hz); LCMS: 100.0%, MS (ESI): m/z 514.1 [M + H]+. |

TABLE 4-continued

Summarizes compounds 1-280 in terms of their structures and corresponding characteristics.

| # cpd | Structure | Characterization Data |
|---|---|---|
| 48 | 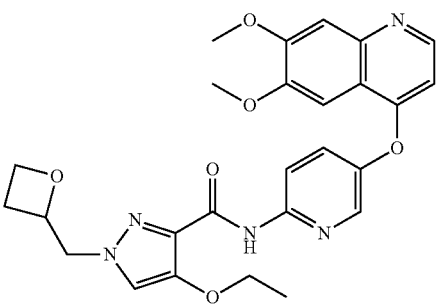 [SMILES: CCOc1cn(CC2CCO2)nc1C(=O)Nc1ccc(Oc2ccnc3cc(OC)c(OC)cc23)cn1] | white powder; ¹H-NMR (DMSO-d6, 400 MHz): δ 9.58 (1H, brs), 8.49 (1H, d, J = 5.2 Hz), 8.38 (1H, d, J = 2.8 Hz), 8.34 (1H, d, J = 9.2 Hz), 7.85 (1H, dd, J = 9.2, 3.2 Hz), 7.79 (1H, s), 7.54 (1H, s), 7.41 (1H, s), 6.55 (1H, d, J = 5.2 Hz), 5.00-5.10 (1H, m), 4.50-4.60 (1H, m), 4.30-4.45 (3H, m), 4.10 (2H, q, J = 7.2 Hz), 3.95 (1H, s), 3.94 (1H, s), 2.60-2.75 (1H, m), 2.30-2.45 (1H, m), 1.39 (3H, t, J = 6.8 Hz); LCMS: 100%, MS (ESI): m/z 506.1 [M + H]+. |
| 49 | 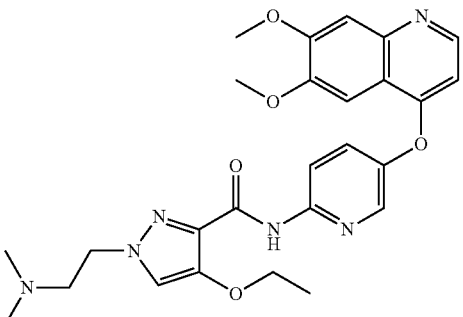 | white powder; ¹H-NMR (DMSO-d6, 400 MHz): δ 9.62 (1H, brs), 8.50 (1H, d, J = 5.2 Hz), 8.40 (1H, d, J = 2.8 Hz), 8.35 (1H, d, J = 9.2 Hz), 7.80-7.95 (2H, m), 7.53 (1H, s), 7.42 (1H, s), 6.54 (1H, d, J = 5.2 Hz), 4.25-4.40 (2H, m), 4.09 (2H, q, J = 6.8 Hz), 3.96 (1H, s), 3.95 (1H, s), 2.90-3.10 (2H, m), 2.39 (6H, s), 1.39 (3H, t, J = 6.8 Hz); LCMS: 97.9%, MS (ESI): m/z 507.0 [M + H]+. |
| 50 | 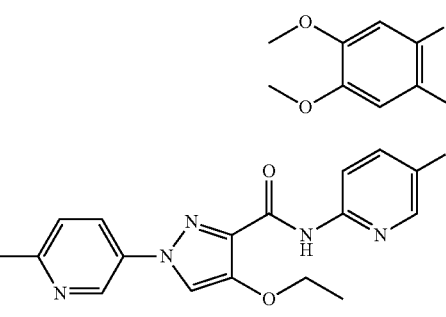 | white; ¹H-NMR (DMSO-d6, 400 MHz): δ 10.23 (1H, brs), 9.44 (1H, d, J = 2.4 Hz), 8.79 (1H, s), 8.63 (1H, dd, J = 8.8, 2.8 Hz), 8.51 (1H, d, J = 5.2 Hz), 8.45 (1H, d, J = 2.8 Hz), 8.37 (1H, d, J = 8.8 Hz), 8.28 (1H, d, J = 8.4 Hz), 7.90 (1H, dd, J = 8.8, 2.8 Hz), 7.55 (1H, s), 7.43 (1H, s), 6.58 (1H, d, J = 5.6 Hz), 4.20 (2H, q, J = 6.8 Hz), 3.96 (1H, s), 3.95 (1H, s), 1.45 (3H, t, J = 6.8 Hz); LCMS: 100%, MS (EIS): m/z 538.0 [M + H]+. |
| 51 | 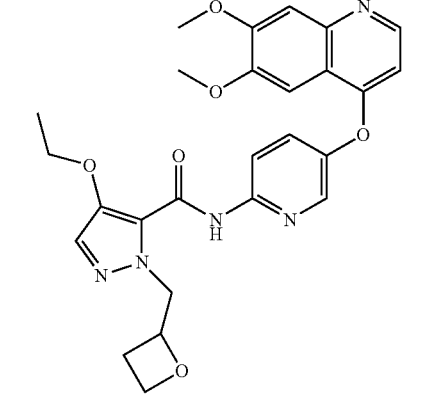 [SMILES: CCOc1cnn(CC2CCO2)c1C(=O)Nc1ccc(Oc2ccnc3cc(OC)c(OC)cc23)cn1] | white powder; ¹H-NMR (DMSO-d6, 400 MHz): δ 9.76 (1H, brs), 8.49 (1H, d, J = 5.2 Hz), 8.42 (1H, d, J = 2.8 Hz), 8.32 (1H, d, J = 9.2 Hz), 7.85 (1H, dd, J = 9.2, 2.8 Hz), 7.66 (1H, s), 7.54 (1H, s), 7.42 (1H, s), 6.55 (1H, d, J = 5.2 Hz), 4.95-5.05 (1H, m), 4.82-4.93 (1H, m), 4.70-4.80 (1H, m), 4.42-4.52 (1H, m), 4.31-4.40 (1H, m), 4.28 (2H, q, J = 7.2 Hz), 3.95 (1H, s), 3.94 (1H, s), 2.60-2.75 (1H, m), 2.35-2.48 (1H, m), 1.43 (3H, t, J = 6.8 Hz); LCMS: 100%, MS (ESI): m/z 506.1 [M + H]+. |

TABLE 4-continued

Summarizes compounds 1-280 in terms of their structures and corresponding characteristics.

| # cpd | Structure | Characterization Data |
|---|---|---|
| 52 | 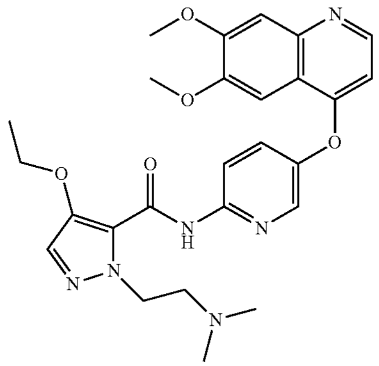 [SMILES: CCOc1cnn(CCN(C)C)c1C(=O)Nc1ccc(Oc2ccnc3cc(OC)c(OC)cc23)cn1] | white powder; $^1$H-NMR (DMSO-d6, 400 MHz): δ 9.76 (1H, brs), 8.50 (1H, d, J = 5.2 Hz), 8.44 (1H, d, J = 2.8 Hz), 8.33 (1H, d, J = 9.2 Hz), 7.89 (1H, dd, J = 8.8, 2.8 Hz), 7.72 (1H, s), 7.53 (1H, s), 7.42 (1H, s), 6.54 (1H, d, J = 5.2 Hz), 4.60-4.75 (2H, m), 4.30 (2H, q, J = 7.2 Hz), 3.95 (1H, s), 3.94 (1H, s), 3.10-3.30 (2H, m), 2.55 (6H, s), 1.44 (3H, t, J = 7.2 Hz); LCMS: 100%, MS (ESI): m/z 507.0 [M + H]+. |
| 53 | 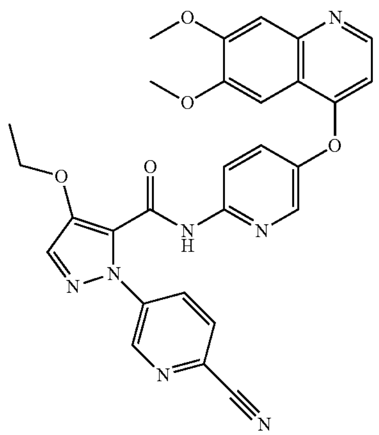 [SMILES: CCOc1cnn(-c2ccc(C#N)nc2)c1C(=O)Nc1ccc(Oc2ccnc3cc(OC)c(OC)cc23)cn1] | white powder; $^1$H-NMR (DMSO-d6, 400 MHz): δ 9.93 (1H, brs), 8.96 (1H, s), 8.50 (1H, d, J = 5.2 Hz), 8.45 (1H, d, J = 2.8 Hz), 8.21-8.30 (2H, m), 8.22 (1H, d, J = 8.8 Hz), 8.17 (1H, s), 7.85 (1H, dd, J = 8.8, 2.8 Hz), 7.53 (1H, s), 7.42 (1H, s), 6.54 (1H, d, J = 5.2 Hz), 4.40 (2H, q, J = 7.2 Hz), 3.96 (1H, s), 3.95 (1H, s), 1.47 (3H, t, J = 7.2 Hz); LCMS: 97.2%, MS (ESI): m/z 538.1 [M + H]+. |
| 54 | 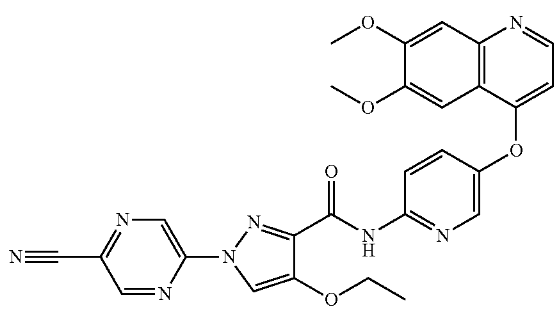 [SMILES: CCOc1cn(-c2cnc(C#N)cn2)nc1C(=O)Nc1ccc(Oc2ccnc3cc(OC)c(OC)cc23)cn1] | white powder; $^1$H-NMR (DMSO-d6, 400 MHz): δ 10.41 (1H, brs), 9.62 (1H, d, J = 1.2 Hz), 9.18 (1H, d, J = 1.2 Hz), 8.63 (1H, s), 8.52 (1H, d, J = 5.6 Hz), 8.47 (1H, d, J = 2.8 Hz), 8.37 (1H, d, J = 8.8 Hz), 7.91 (1H, dd, J = 8.8, 2.8 Hz), 7.55 (1H, s), 7.43 (1H, s), 6.58 (1H, d, J = 5.2 Hz), 4.24 (2H, q, J = 6.8 Hz), 3.96 (3H, s), 3.95 (3H, s), 1.42 (3H, t, J = 6.8 Hz); LCMS: 100%, MS (ESI): m/z 539.0 [M + H]+. |
| 55 | 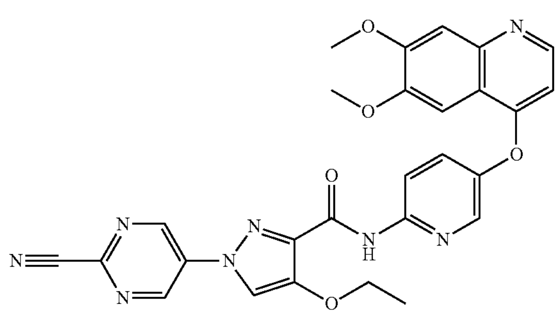 [SMILES: CCOc1cn(-c2cnc(C#N)nc2)nc1C(=O)Nc1ccc(Oc2ccnc3cc(OC)c(OC)cc23)cn1] | white solid; $^1$H-NMR (CDCl3, 400 MHz): δ 9.50 (1H, brs), 9.30 (2H, s), 8.50-8.60 (2H, m), 8.31 (1H, d, J = 2.8 Hz), 7.77 (1H, s), 7.64 (1H, dd, J = 8.8, 2.8 Hz), 7.56 (1H, s), 7.45 (1H, s), 6.48 (1H, d, J = 5.2 Hz), 4.27 (2H, q, J = 7.6 Hz), 4.08 (6H, s), 1.64 (3H, t, J = 6.8 Hz); LCMS: 97.3%, MS (ESI): m/z 539.2 [M + H]+. |

TABLE 4-continued

Summarizes compounds 1-280 in terms of their structures and corresponding characteristics.

| # cpd | Structure | Characterization Data |
|---|---|---|
| 56 | 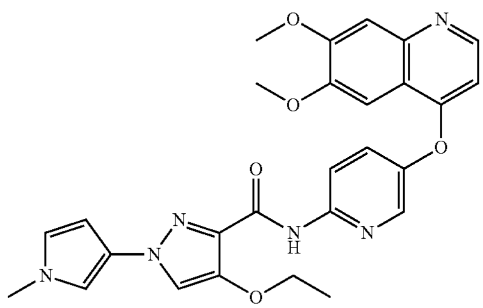 [SMILES: CCOc1cn(-c2ccn(C)c2)nc1C(=O)Nc1ccc(Oc2ccnc3cc(OC)c(OC)cc23)cn1] | white powder; ¹H-NMR (DMSO-d6, 400 MHz): δ 9.63 (1H, brs), 8.50 (1H, d, J = 5.2 Hz), 8.40 (1H, d, J = 3.2 Hz), 8.37 (1H, d, J = 8.8 Hz), 8.17 (1H, s), 7.88 (1H, dd, J = 8.8 Hz, 2.8 Hz), 7.54 (1H, s), 7.42 (1H, s), 7.24 (1H, t, J = 2.0 Hz), 6.78 (1H, t, J = 2.8 Hz), 6.55 (1H, d, J = 5.2 Hz), 6.41-6.44 (1H, m), 4.16 (2H, q, J = 6.8 Hz), 3.96 (3H, s), 3.95 (3H, s), 3.66 (3H, s), 1.42 (3H, t, J = 6.8 Hz); LCMS: 98.8%, MS (ESI): m/z 515.2 [M + H]+. |
| 57 | 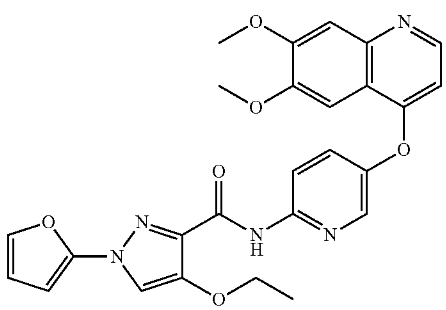 | amorphous; ¹H-NMR (DMSO-d6, 400 MHz): δ 9.80 (1H, brs), 8.50 (1H, d, J = 5.2 Hz), 8.43 (1H, d, J = 3.2 Hz), 8.36 (1H, d, J = 8.8 Hz), 8.33 (1H, s), 7.88 (1H, dd, J = 8.8, 2.8 Hz), 7.72 (1H, d, J = 1.2 Hz), 7.54 (1H, s), 7.42 (1H, s), 6.69 (1H, dd, J = 3.2, 2.0 Hz), 6.64 (1H, d, J = 3.2 Hz), 6.56 (1H, d, J = 5.2 Hz), 4.20 (2H, q, J = 6.8 Hz), 3.96 (3H, s), 3.95 (3H, s), 1.43 (3H, t, J = 7.2 Hz); LCMS: 98%, MS (ESI): m/z 502.1 [M + H]+. |
| 58 | 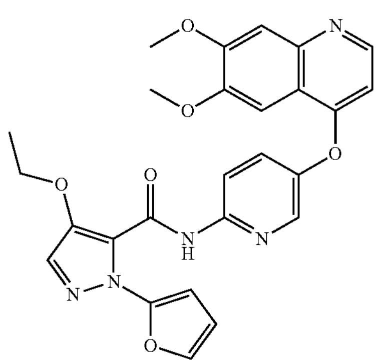 [SMILES: CCOc1cnn(-c2ccco2)c1C(=O)Nc1ccc(Oc2ccnc3cc(OC)c(OC)cc23)cn1] | amorphous; ¹H-NMR (DMSO-d6, 400 MHz): δ 9.83 (1H, brs), 8.49 (1H, d, J = 5.2 Hz), 8.42 (1H, d, J = 2.8 Hz), 8.19 (1H, d, J = 9.2 Hz), 8.04 (1H, s), 7.80 (1H, dd, J = 9.2, 3.2 Hz), 7.67 (1H, d, J = 1.2 Hz), 7.52 (1H, s), 7.41 (1H, s), 6.62 (1H, dd, J = 3.2, 2.0 Hz), 6.57 (1H, d, J = 3.2 Hz), 6.54 (1H, d, J = 5.2 Hz), 4.36 (2H, q, J = 7.2 Hz), 3.95 (3H, s), 3.94 (3H, s), 1.45 (3H, t, J = 6.8 Hz); LCMS: 100%, MS (ESI): m/z 502.1 [M + H]+. |
| 59 | 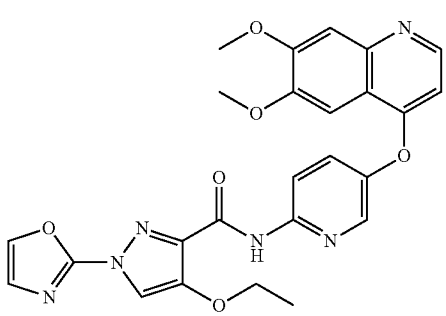 | pale yellow powder; ¹H-NMR (DMSO-d6, 400 MHz): δ 9.96 (1H, brs), 8.45-8.56 (2H, m), 8.44 (1H, d, J = 3.2 Hz), 8.36 (1H, d, J = 9.2 Hz), 8.25 (1H, s), 7.90 (1H, dd, J = 9.2, 2.8 Hz), 7.55 (1H, s), 7.40-7.43 (2H, m), 6.57 (1H, d, J = 5.2 Hz), 4.23 (2H, q, J = 6.8 Hz), 3.96 (3H, s), 3.96 (3H, s), 1.43 (3H, d, J = 6.8 Hz); LCMS: 95.5%, MS (ESI): m/z 503.2 [M + H]+. |

TABLE 4-continued

Summarizes compounds 1-280 in terms of their structures and corresponding characteristics.

| # cpd | Structure | Characterization Data |
|---|---|---|
| 60 | 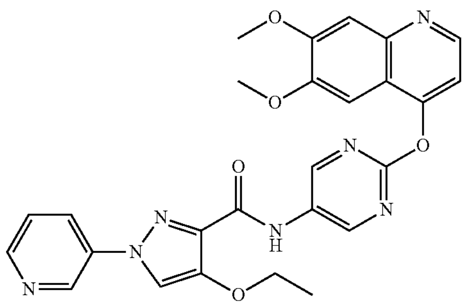 [SMILES: CCOc1cn(-c2cccnc2)nc1C(=O)Nc1cnc(Oc2ccnc3cc(OC)c(OC)cc23)nc1] | white powder; ¹H-NMR (DMSO-d6, 400 MHz): δ 10.73 (1H, brs), 9.45 (2H, s), 9.32 (1H, s), 8.67 (1H, s), 8.63 (1H, d, J = 4.0 Hz), 8.44 (1H, d, J = 8.4 Hz), 8.40 (1H, d, J = 7.6 Hz), 7.68 (1H, dd, J = 8.0, 4.8 Hz), 7.59 (1H, s), 7.47 (1H, s), 6.31 (1H, d, J = 8.0 Hz), 4.12 (2H, q, J = 6.8 Hz), 3.89 (3H, s), 3.79 (3H, s), 1.41 (3H, t, J = 6.8 Hz); LCMS: 100.0%, MS (ESI): m/z 514.1 [M + H]+. |
| 61 | 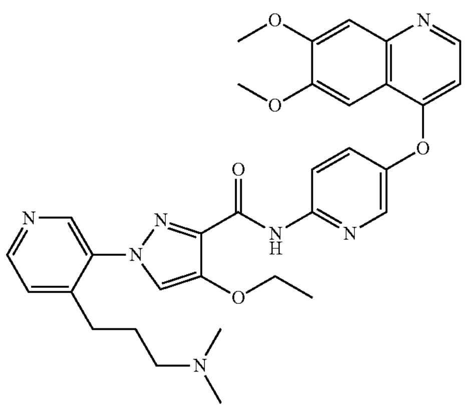 [SMILES: CCOc1cn(-c2cnccc2CCCN(C)C)nc1C(=O)Nc1ccc(Oc2ccnc3cc(OC)c(OC)cc23)cn1] | off-white powder; ¹H-NMR (CDCl3, 400 MHz): δ 9.56 (1H, brs), 8.52-8.64 (4H, m), 8.28 (1H, d, J = 2.8 Hz), 7.62 (1H, dd, J = 8.8, 2.8 Hz), 7.57 (1H, s), 7.50 (1H, s), 7.46 (1H, s), 7.37 (1H, d, J = 5.2 Hz), 6.48 (1H, d, J = 5.2 Hz), 4.23 (2H, q, J = 7.2 Hz), 4.01-4.12 (6H, m), 2.74 (2H, t, J = 7.6 Hz), 2.49-2.60 (2H, m), 2.39 (6H, s), 1.38-1.46 (2H, m), 1.62 (3H, t, J = 7.2 Hz); LCMS: 99.4%, MS (ESI): m/z 598.3 [M + H]+. |
| 62 | 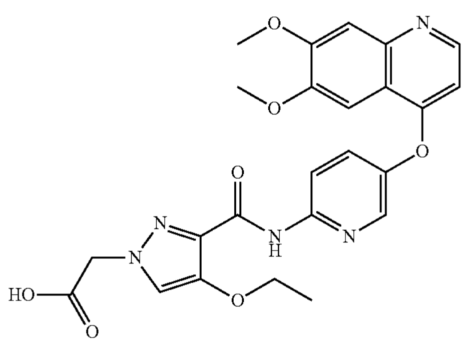 [SMILES: CCOc1cn(CC(=O)O)nc1C(=O)Nc1ccc(Oc2ccnc3cc(OC)c(OC)cc23)cn1] | white powder; ¹H-NMR (DMSO-d6, 400 MHz): δ 9.58 (1H, brs), 8.49 (1H, d, J = 4.8 Hz), 8.40 (1H, d, J = 1.6 Hz), 8.35 (1H, d, J = 9.6 Hz), 7.86 (1H, dd, J = 9.2, 2.0 Hz), 7.80 (1H, s), 7.54 (1H, s), 7.43 (1H, s), 6.56 (1H, d, J = 5.2 Hz), 5.01 (2H, s), 4.10 (2H, q, J = 6.8 Hz), 3.96 (3H, s), 3.95 (3H, s), 1.41 (3H, t, J = 6.8 Hz); LCMS: 100%, MS (ESI): m/z 494.2 [M + H]+. |
| 63 | 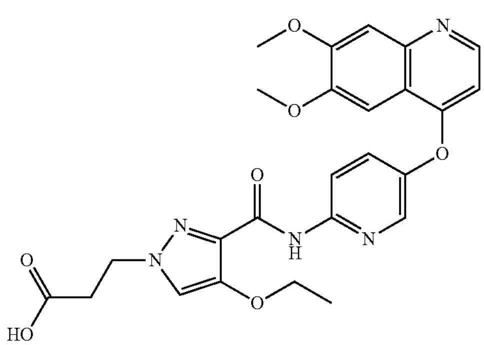 [SMILES: CCOc1cn(CCC(=O)O)nc1C(=O)Nc1ccc(Oc2ccnc3cc(OC)c(OC)cc23)cn1] | white powder; ¹H-NMR (DMSO-d6, 400 MHz): δ 9.65 (1H, brs), 8.84 (1H, d, J = 6.8 Hz), 8.51 (1H, s), 8.42 (1H, d, J = 9.2 Hz), 8.00 (1H, dd, J = 8.8 Hz, 2.4 Hz), 7.83 (1H, s), 7.78 (1H, s), 7.57-7.67 (1H, m), 7.04 (1H, d, J = 6.4 Hz), 4.33 (2H, t, J = 6.8 Hz), 4.01-4.11 (8H, m), 2.88 (2H, t, J= 6.8 Hz), 1.39 (3H, t, J = 6.8 Hz); LCMS: 100%, MS (ESI): m/z 508.2 [M + H]+. |

TABLE 4-continued

Summarizes compounds 1-280 in terms of their structures and corresponding characteristics.

| # cpd | Structure | Characterization Data |
|---|---|---|
| 64 | 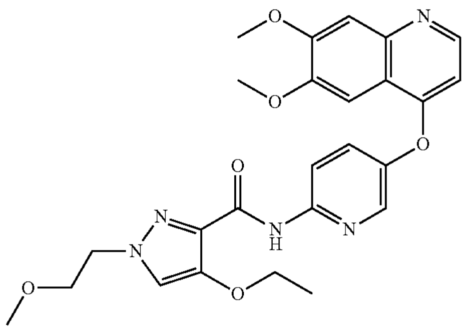 [SMILES: CCOc1cn(CCOC)nc1C(=O)Nc1ccc(Oc2ccnc3cc(OC)c(OC)cc23)cn1] | white powder (amorphous):; ¹H-NMR (DMSO-d6, 400 MHz): δ 9.57 (1H, brs), 8.52 (1H, d, J = 5.6 Hz), 8.39 (1H, d, J = 2.4 Hz), 8.35 (1H, d, J = 8.8 Hz), 7.87 (1H, dd, J = 8.8, 2.8 Hz), 7.80 (1H, s), 7.55 (1H, s), 7.42 (1H, s), 6.58 (1H, d, J = 5.2 Hz), 4.25 (1H, t, J = 5.6 Hz), 4.08 (2H, q, J = 6.8 Hz), 3.96 (3H, s), 3.95 (3H, s), 3.73 (1H, t, J = 5.6 Hz), 3.26 (3H, s), 1.39 (3H, t, J = 7.2 Hz); LCMS: 99.8%, MS (ESI): m/z 494.2 [M + H]+. |
| 65 | 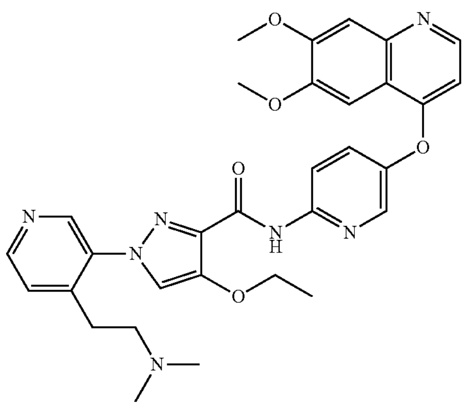 [SMILES: CCOc1cn(-c2cnccc2CCN(C)C)nc1C(=O)Nc1ccc(Oc2ccnc3cc(OC)c(OC)cc23)cn1] | off-white powder; ¹H-NMR (CDCl3, 400 MHz): δ 9.58 (1H, brs), 8.56-8.65 (3H, m), 8.54 (1H, d, J = 5.2 Hz), 8.28 (1H, d, J = 2.8 Hz), 7.62 (1H, dd, J = 8.8, 2.8 Hz), 7.58 (1H, s), 7.43-7.48 (2H, m), 7.39 (1H, d, J = 5.2 Hz), 6.49 (1H, d, J = 5.2 Hz), 4.21 (2H, q, J = 7.2 Hz), 4.05-4.13 (6H, m), 2.89 (2H, t, J = 7.2 Hz), 2.52 (2H, t, J = 7.6 Hz), 2.23 (6H, s), 1.57-1.61 (3H, m, overlapped with H2O signal); LCMS: 97.1%, MS (ESI): m/z 584.1 [M + H]+. |
| 66 | 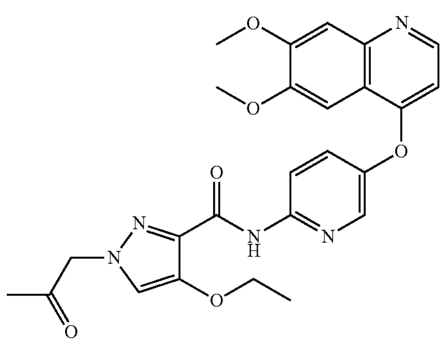 [SMILES: CCOc1cn(CC(C)=O)nc1C(=O)Nc1ccc(Oc2ccnc3cc(OC)c(OC)cc23)cn1] | white powder; ¹H-NMR (DMSO-d6, 400 MHz): δ 9.57 (1H, brs), 8.49 (1H, d, J = 5.2 Hz), 8.39 (1H, d, J = 2.8 Hz), 8.34 (1H, d, J = 9.2 Hz), 7.86 (1H, dd, J = 9.2, 2.8 Hz), 7.70 (1H, s), 7.54 (1H, s), 7.41 (1H, s), 6.55 (1H, d, J = 5.2 Hz), 5.19 (2H, s), 4.10 (2H, q, J = 6.8 Hz), 3.95 (3H, s), 3.94 (3H, s), 2.16 (3H, s), 1.40 (3H, t, J = 6.8 Hz); LCMS: 100%, MS (ESI): m/z 492.2 [M + H]+. |
| 67 | 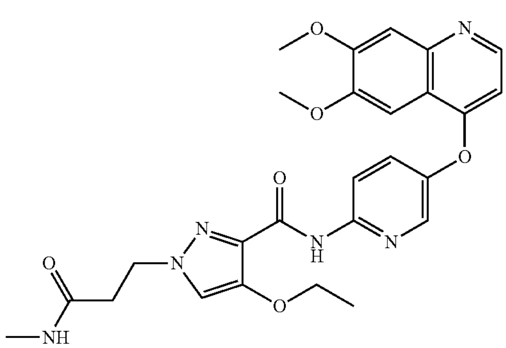 [SMILES: CCOc1cn(CCC(=O)NC)nc1C(=O)Nc1ccc(Oc2ccnc3cc(OC)c(OC)cc23)cn1] | white powder; ¹H-NMR (DMSO-d6, 400 MHz): δ 9.56 (1H, brs), 8.49 (1H, d, J = 5.2 Hz), 8.39 (1H, d, J = 2.8 Hz), 8.34 (1H, d, J = 8.8 Hz), 7.93 (1H, q, J = 4.0 Hz), 7.86 (1H, dd, J = 8.8, 2.8 Hz), 7.74 (1H, s), 7.54 (1H, s), 7.42 (1H, s), 6.55 (1H, d, J = 5.2 Hz), 4.33 (2, t, J = 6.8 Hz), 4.07 (2H, q, J = 6.8 Hz), 3.95 (3H, s), 3.94 (3H, s), 2.68 (2H, t, J = 6.8 Hz), 2.57 (3H, d, J = 4.0 Hz), 1.38 (3H, t, J = 6.8 Hz); LCMS: 100%, MS (ESI): m/z 521.1 [M + H]+. |

TABLE 4-continued

Summarizes compounds 1-280 in terms of their structures and corresponding characteristics.

| # cpd | Structure | Characterization Data |
|---|---|---|
| 68 | 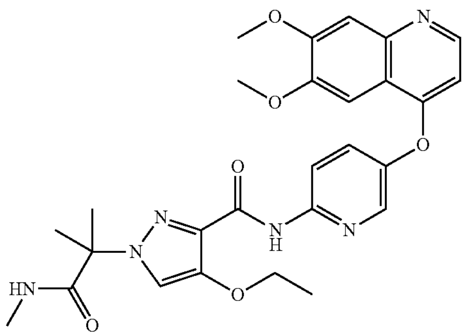 [SMILES: CCOc1cn(C(C)(C)C(=O)NC)nc1C(=O)Nc1ccc(Oc2ccnc3cc(OC)c(OC)cc23)cn1] | white powder (amorphous);; ¹H-NMR (DMSO-d6, 400 MHz): δ 9.71 (1H, brs), 8.51 (1H, d, J = 5.2 Hz), 8.41 (1H, d, J = 2.8 Hz), 8.36 (1H, d, J = 8.8 Hz), 7.91 (1H, s), 7.88 (1H, dd, J = 8.8, 2.8 Hz), 7.55 (1H, s), 7.44-7.47 (1H, m), 7.43 (1H, s), 6.56 (1H, d, J = 5.2 Hz), 4.13 (2H, q, J = 7.2 Hz), 3.96 (3H, s), 3.95 (3H, s), 2.59 (3H, d, J = 4.4 Hz), 1.75 (6H, s), 1.40 (3H ,t, J = 7.2 Hz); LCMS: 99.8%, MS (ESI): m/z 535.2 [M + H]+. |
| 69 | 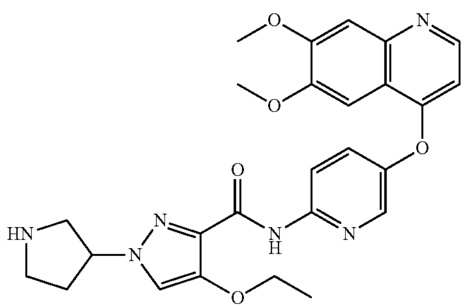 [SMILES: CCOc1cn(C2CCNC2)nc1C(=O)Nc1ccc(Oc2ccnc3cc(OC)c(OC)cc23)cn1] | off-white powder; ¹H-NMR (DMSO-d6, 400 MHz): δ 10.25 (1H, brs), 10.14 (1H, brs), 9.55 (1H, brs), 8.87 (1H, d, J = 6.4 Hz), 8.55 (1H, d, J = 2.8 Hz), 8.42 (1H, d, J = 8.8 Hz), 8.03 (1H, dd, J = 9.2, 2.8 Hz), 7.99 (1H, s), 7.80 (1H, s), 7.79 (1H, s), 7.05 (1H, d, J = 6.8 Hz), 5.14-5.28 (1H, m), 4.00-4.17 (8H, m, overlap with H2O signal), 3.56-3.71 (2H, m), 3.31-3.44 (2H, m), 2.40-2.48 (1H, m), 2.20-2.30 (1H, m), 1.37 (3H, t, J = 7.2 Hz); LCMS: 96.5%, MS (ESI): m/z 505.1 [M + H]+. |
| 70 | 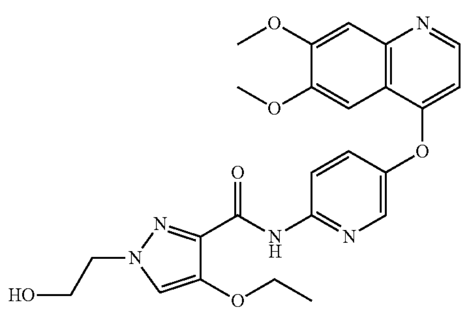 [SMILES: CCOc1cn(CCO)nc1C(=O)Nc1ccc(Oc2ccnc3cc(OC)c(OC)cc23)cn1] | white powder; ¹H-NMR (DMSO-d6, 400 MHz): δ 9.59 (1H, brs), 8.49 (1H, d, J = 5.2 Hz), 8.39 (1H, d, J = 3.2 Hz), 8.35 (1H, d, J = 9.2 Hz), 7.86 (1H, dd, J = 9.2, 3.2 Hz), 7.79 (1H, s0, 7.54 (1H, s), 7.42 (1H, s), 6.55 (1H, d, J = 4.8 Hz), 4.99 (1H, t, J = 5.2 Hz), 4.16 (2H, t, J = 5.2 Hz), 4.09 (2H, q, J = 6.8 Hz), 3.95 (3H, s), 3.94 (3H, s), 3.79 (2H, q, J = 5.2 Hz), 1.39 (3H, t, J = 6.8 Hz); LCMS: 100%, MS (ESI): m/z 480.2 [M + H]+. |
| 71 | 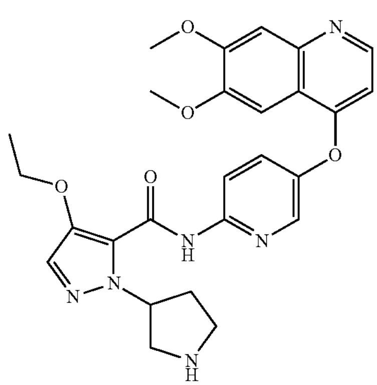 [SMILES: CCOc1cnn(C2CCNC2)c1C(=O)Nc1ccc(Oc2ccnc3cc(OC)c(OC)cc23)cn1] | white powder; ¹H-NMR (DMSO-d6, 400 MHz): δ 9.72-9.90 (2H, m), 9.38 (1H, brs), 8.84 (1H, d, J = 6.0 Hz), 8.56 (1H, s), 8.41 (1H, d, J = 9.2 Hz), 8.05 (1H, d, J = 8.4 Hz), 7.70-7.89 (3H, m), 7.01 (1H, d, J = 6.0 Hz), 5.96-6.10 (1H, m), 4.32 (2H, q, J = 6.8 Hz), 3.98-4.10 (6H, m), 3.60-3.70 (2H, m, overlapped with H2O signal), 3.21-3.38 (2H, m, overlapped with H2O signal), 2.27-2.45 (2H, m), 1.45 (3H, t, J = 6.8 Hz); LCMS: 98.4%, MS (ESI): m/z 505.2 [M + H]+. |

TABLE 4-continued

Summarizes compounds 1-280 in terms of their structures and corresponding characteristics.

| # cpd | Structure | Characterization Data |
|---|---|---|
| 72 | 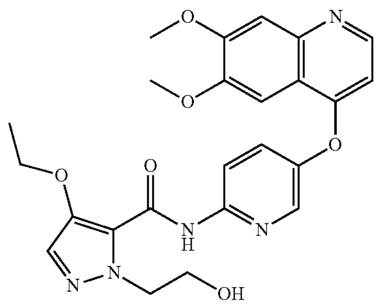 [SMILES: CCOc1cnn(CCO)c1C(=O)Nc1ccc(Oc2ccnc3cc(OC)c(OC)cc23)cn1] | white powder; ¹H-NMR (DMSO-d6, 400 MHz): δ 9.77 (1H, brs), 8.50 (1H, d, J = 5.2 Hz), 8.42 (1H, d, J = 2.8 Hz), 8.34 (1H, d, J = 9.2 Hz), 7.87 (1H, dd, J = 9.2, 2.8 Hz), 7.64 (1H, s), 7.54 (1H, s), 7.42 (1H, s), 6.56 (1H, d, J = 5.2 Hz), 4.86 (1H, m), 4.59 (2H, t, J = 6.4 Hz), 4.28 (2H, q, J = 6.8 Hz), 3.96 (3H, s), 3.95 (3H, s), 3.72 (2H, J = 6.0 Hz), 1.44 (3H, t, J = 6.8 Hz); LCMS: 100%, MS (ESI): m/z 480.1 [M + H]. |
| 73 | 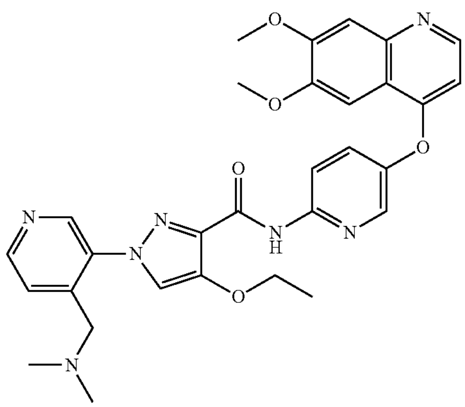 [SMILES: CCOc1cn(-c2cnccc2CN(C)C)nc1C(=O)Nc1ccc(Oc2ccnc3cc(OC)c(OC)cc23)cn1] | pale-yellow powder; ¹H-NMR (CDCl3, 400 mHz): δ 9.54 (1H, s), 8.77 (1H, s), 8.64 (1H, d, J = 4.8 Hz), 8.59 (1H, d, J = 9.2 Hz), 8.53 (1H, d, J = 5.6 Hz), 8.27 (1H, d, J = 2.8 Hz), 7.88 (1H, s), 7.61 (1H, dd, J = 8.8, 2.8 Hz), 7.57 (1H, s), 7.46 (1H, s), 7.27 (1H, s), 6.48 (1H, d, J = 5.2 Hz), 4.20 (2H, q, J = 6.8 Hz), 4.08 (3H, s), 4.07 (3H, s), 3.44 (1H, s), 2.27 (6H, s), 1.50-1.60 (3H, m, overlapped with H2O peak); LCMS: 98.0%, MS (ESI): m/z 570.1 [M + H]+. |
| 74 | 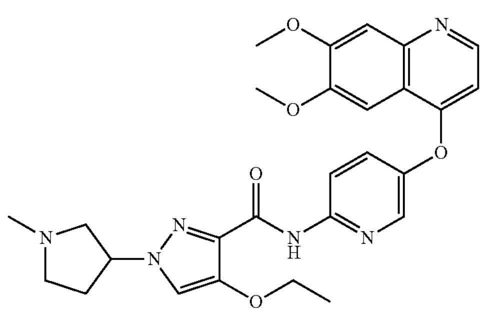 [SMILES: CCOc1cn(C2CCN(C)C2)nc1C(=O)Nc1ccc(Oc2ccnc3cc(OC)c(OC)cc23)cn1] | white powder; ¹H-NMR (CDCl3, 400 MHz): δ 9.51 (1H, brs), 8.58 (1H, d, J = 9.2 Hz), 8.53 (1H, d, J = 5.2 Hz), 8.27 (1H, d, J = 2.8 Hz), 7.54-7.62 (2H, m), 7.46 (1H, s), 7.43 (1H, s), 6.48 (1H, d, J = 5.6 Hz), 4.90-4.99 (1H, m), 4.15 (2H, q, J = 7.2 Hz), 4.09 (3H, s), 4.08 (3H, s), 2.96-3.07 (2H, m), 2.75-2.83 (1H, m), 2.49-2.60 (1H, m), 2.40-2.47 (4H, m), 2.11-2.22 (1H, m), 1.56 (3H, t, J = 7.2 Hz); LCMS: 98.7%, MS (ESI): m/z 519.2 [M + H]+. |
| 75 | 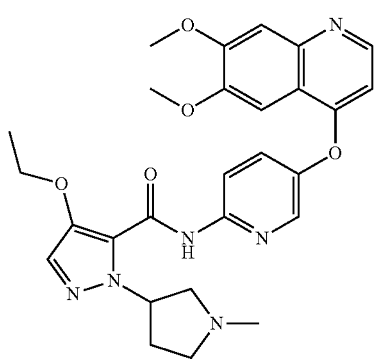 [SMILES: CCOc1cnn(C2CCN(C)C2)c1C(=O)Nc1ccc(Oc2ccnc3cc(OC)c(OC)cc23)cn1] | white powder; ¹H-NMR (CDCl3, 400 MHz): δ 9.80 (1H, brs), 8.51 (1H, d, J = 5.2 Hz), 8.41 (1H, d, J = 8.8 Hz), 8.27 (1H, s), 7.56-7.59 (2H, m), 7.45 (1H, s), 7.38 (1H, s), 6.45 (1H, d, J = 5.2 Hz), 6.00-6.10 (1H, m), 4.27-4.29 (2H, m), 4.07 (6H, s), 2.88-3.02 (3H, m), 2.41-2.54 (6H, m), 1.57-1.62 (3H, m); LCMS: 100%, MS (ESI): m/z 519.1 [M + H]+. |

TABLE 4-continued

Summarizes compounds 1-280 in terms of their structures and corresponding characteristics.

| # cpd | Structure | Characterization Data |
|---|---|---|
| 76 | 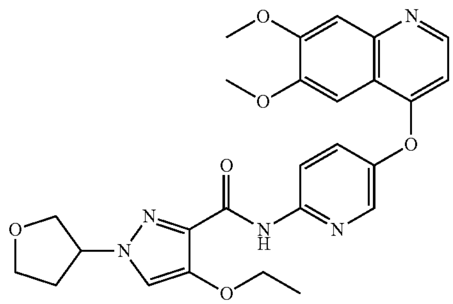 [SMILES: CCOc1cn(C2CCOC2)nc1C(=O)Nc1ccc(Oc2ccnc3cc(OC)c(OC)cc23)cn1] | white powder; ¹H-NMR (DMSO-d6, 400 MHz): δ 9.60 (1H, brs), 8.49 (1H, d, J = 5.2 Hz), 8.39 (1H, d, J = 2.8 Hz), 8.34 (1H, d, J = 8.8 Hz), 7.84-7.90 (2H, m), 7.54 (1H, s), 7.42 (1H, s), 6.55 (1H, d, J = 4.8 Hz), 5.00-5.07 (1H, m), 4.11 (2H, q, J = 6.8 Hz), 3.96-4.05 (3H, m), 3.95 (3H, s), 3.94 (3H, s), 3.78-3.86 (1H, m), 2.35-2.45 (2H, m), 1.39 (3H, t, J = 6.8 Hz); LCMS: 100%, MS (ESI): m/z 506.2 [M + H]+. |
| 77 | 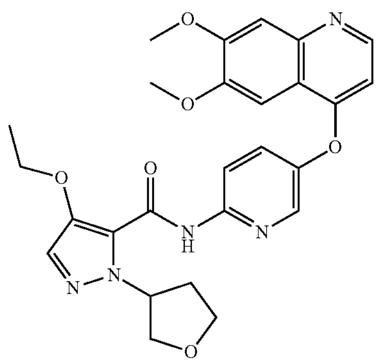 [SMILES: CCOc1cnn(C2CCOC2)c1C(=O)Nc1ccc(Oc2ccnc3cc(OC)c(OC)cc23)cn1] | white powder; ¹H-NMR (DMSO-d6, 400 MHz): δ 9.80 (1H, brs), 8.50 (1H, d, J = 5.2 Hz), 8.42 (1H, d, J = 2.8 Hz), 8.33 (1H, d, J = 8.8 Hz), 7.86 (1H, dd, J = 8.8, 2.8 Hz), 7.67 (1H, s), 7.53 (1H, s), 7.42 (1H, s), 6.55 (1H, d, J = 5.2 Hz), 5.85-5.95 (1H, m), 4.29 (2H, q, J = 6.8 Hz), 3.92-4.05 (8H, m), 3.81-3.88 (2H, m), 2.42-2.47 (1H, m), 2.30-2.36 (1H, m), 1.43 (3H, t, J = 7.2 Hz); LCMS: 98.6%, MS (ESI): m/z 506.2 [M + H]+. |
| 78 | 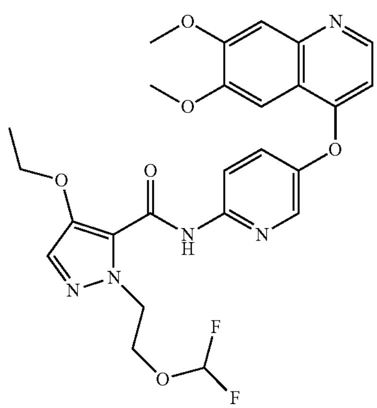 [SMILES: CCOc1cnn(CCOC(F)F)c1C(=O)Nc1ccc(Oc2ccnc3cc(OC)c(OC)cc23)cn1] | white powder; ¹H-NMR (DMSO-d6, 400 MHz): δ 9.75 (1H, brs), 8.50 (1H, d, J = 5.6 Hz), 8.43 (1H, d, J = 2.8 Hz), 8.33 (1H, d, J = 8.8 Hz), 7.87 (1H, dd, J = 8.8, 2.8 Hz), 7.69 (1H, s), 7.54 (1H, s), 7.42 (1H, s), 6.62 (1H, t, J = 75.2 Hz), 6.55 (1H, d, J = 5.2 Hz), 4.79 (2H, t, J = 5.2 Hz), 4.30 (2H, q, J = 6.8 Hz), 4.22 (2H, t, J = 5.2 Hz), 3.95 (3H, s), 3.94 (3H, s), 1.44 (3H, t, J = 6.8 Hz); LCMS: 98.8%, MS (ESI): m/z 530.2 [M + H]+. |
| 79 | 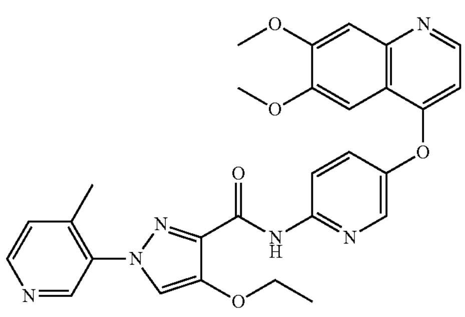 [SMILES: CCOc1cn(-c2cnccc2C)nc1C(=O)Nc1ccc(Oc2ccnc3cc(OC)c(OC)cc23)cn1] | white powder (amorphous); ¹H-NMR (DMSO-d6, 400 MHz): δ 9.81 (1H, brs), 8.67 (1H, s), 8.56 (1H, d, J = 4.8 Hz), 8.50 (1H, d, J = 5.2 Hz), 8.41 (1H, d, J = 2.8 Hz), 8.36 (1H, d, J = 8.8 Hz), 8.26 (1H, s), 7.87 (1H, dd, J = 8.8, 2.4 Hz), 7.54 (1H, s), 7.51 (1H, d, J = 4.8 Hz), 7.42 (1H, s), 6.56 (1H, d, J = 5.2 Hz), 4.18 (2H, q, J = 6.8 Hz), 3.95 (3H, s), 3.94 (3H, s), 2.37 (3H, s), 1.44 (3H, t, J = 6.8 Hz); LCMS: 99%, MS (ESI): m/z 527.1 [M + H]+. |

TABLE 4-continued

Summarizes compounds 1-280 in terms of their structures and corresponding characteristics.

| # cpd | Structure | Characterization Data |
|---|---|---|
| 80 | 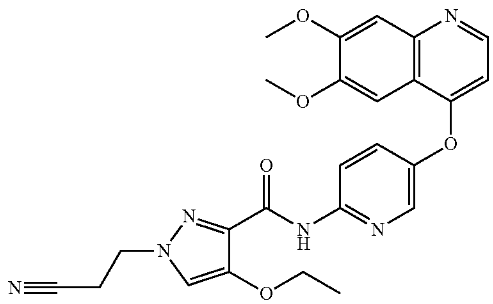 [SMILES: CCOc1cn(CCC#N)nc1C(=O)Nc1ccc(Oc2ccnc3cc(OC)c(OC)cc23)cn1] | white powder; ¹H-NMR (CDCl3, 400 MHz): δ 9.50 (1H, brs), 8.50-8.60 (2H, m), 8.28 (1H, d, J = 2.8 Hz), 7.61 (1H, dd, J = 8.8, 2.8 Hz), 7.58 (1H, s), 7.46 (1H, s), 7.33 (1H, s), 7.28 (1H, s), 6.48 (1H, d, J = 5.2 Hz), 4.43 (2H, t, J = 6.4 Hz), 4.17 (2H, q, J = 6.8 Hz), 4.03-4.11 (6H, m), 3.04 (2H, t, J = 6.4 Hz0, 1.58 (3H, t, J = 7.2 Hz); LCMS: 98.5%, MS (ESI): m/z 489.1 [M + H]+. |
| 81 | 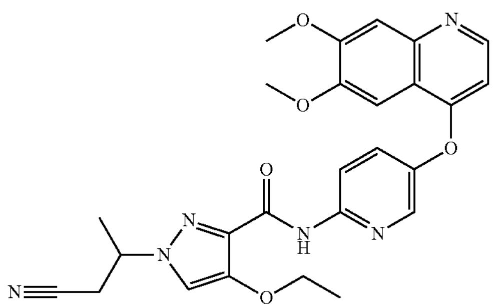 [SMILES: CCOc1cn(C(C)CC#N)nc1C(=O)Nc1ccc(Oc2ccnc3cc(OC)c(OC)cc23)cn1] | white powder; ¹H-NMR (CDCl3, 400 MHz): δ 9.49 (1H, brs), 8.56 (1H, d, J = 9.2 Hz), 8.52 (1H, d, J = 5.6 Hz), 8.26 (1H, d, J = 2.8 Hz), 7.60 (1H, dd, J = 8.8, 2.8 Hz), 7.57 (1H, s), 7.52 (1H, s), 7.30 (1H, s), 7.27 (1H, s), 6.50 (1H, d, J = 5.6 Hz), 4.62-4.73 (1H, m), 4.14 (2H, q, J = 6.8 Hz), 4.02-4.10 (6H, m), 2.91-3.07 (2H, m), 1.74 (3H, d, J = 6.8 Hz), 1.55 (3H, t, J = 7.2 Hz); LCMS: 98.4%, MS (ESI): m/z 503.3 [M + H]+. |
| 82 | 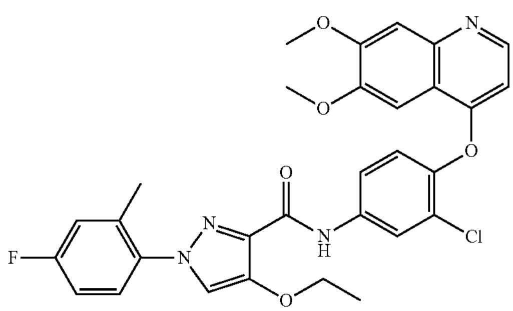 [SMILES: CCOc1cn(-c2ccc(F)cc2C)nc1C(=O)Nc1ccc(Oc2ccnc3cc(OC)c(OC)cc23)c(Cl)c1] | white powder; ¹H-NMR (DMSO-d6, 400 MHz): δ 10.17 (1H, brs), 8.47 (1H, d, J = 4.8 Hz), 8.24 (1H, d, J = 2.8 Hz), 8.04 (1H, s), 7.87 (1H, dd, J = 8.8, 2.4 Hz), 7.50-7.55 (2H, m), 7.44 (1H, d, J = 8.8 Hz), 7.47 (1H, s), 7.33 (1H, dd, J = 9.6, 2.4 Hz), 7.23 (1H, td, J = 8.4, 2.8 Hz), 6.36 (1H, d, J = 5.2 Hz), 4.06 (2H, q, J = 6.8 Hz), 3.95 (6H, s), 2.26 (3H, s), 1.37 (3H, t, J = 6.8 Hz); LCMS: 99.7%, MS (ESI): m/z 577.2 [M + H]+. |
| 83 | 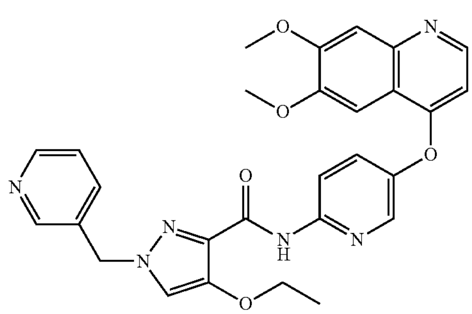 [SMILES: CCOc1cn(Cc2cccnc2)nc1C(=O)Nc1ccc(Oc2ccnc3cc(OC)c(OC)cc23)cn1] | pale yellow powder; ¹H-NMR (DMSO-d6, 400 MHz): δ 9.60 (1H, brs), 8.61 (1H, d, J = 2.0 Hz), 8.55 (1H, dd, J = 4.8, 2.0 Hz), 8.50 (1H, d, J = 5.2 Hz), 8.39 (1H, d, J = 3.2 Hz), 8.34 (1H, d, J = 9.2 Hz), 7.96 (1H, s), 7.86 (1H, dd, J = 8.8, 2.8 Hz), 7.75 (1H, dt, J = 8.0, 2.0 Hz), 7.54 (1H, s), 7.38-7.46 (2H, m), 6.55 (1H, d, J = 5.2 Hz), 5.42 (2H, s), 4.10 (2H, q, J = 6.8 Hz), 3.95 (6H, d, J = 3.6 Hz), 1.39 (3H, t, J = 6.8 Hz); LCMS: 99.0%, MS (ESI): m/z 527.3 [M + H]+. |

TABLE 4-continued

Summarizes compounds 1-280 in terms of their structures and corresponding characteristics.

| # cpd | Structure | Characterization Data |
|---|---|---|
| 84 | 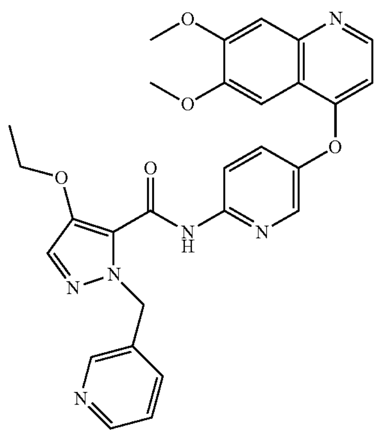 [SMILES: CCOc1cnn(Cc2cccnc2)c1C(=O)Nc1ccc(Oc2ccnc3cc(OC)c(OC)cc23)cn1] | off white powder; $^1$H-NMR (DMSO-d6, 400 MHz): δ 9.76 (1H, brs), 8.45-8.52 (3H, m), 8.42 (1H, d, J = 2.8 Hz), 8.31 (1H, d, J = 9.2 Hz), 7.86 (1H, dd, J = 9.2, 3.2 Hz), 7.75 (1H, s), 7.55-7.61 (1H, m), 7.54 (1H, s), 7.42 (1H, s), 7.36 (1H, dd, J = 8.0, 4.8 Hz), 6.54 (1H, d, J = 5.6 Hz), 5.81 (2H, s), 4.31 (2H, q, J = 7.2 Hz), 3.95 (6H, d, J = 3.6 Hz), 1.44 (3H, t, J = 6.8 Hz); LCMS: 96.5%, MS (ESI): m/z 527.1 [M + H]+. |
| 85 | 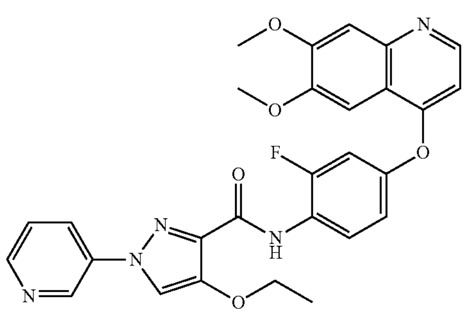 [SMILES: CCOc1cn(-c2cccnc2)nc1C(=O)Nc1ccc(Oc2ccnc3cc(OC)c(OC)cc23)cc1F] | white powder (amorphous); $^1$H-NMR (DMSO-d6, 400 MHz): δ 9.69 (1H, brs), 9.19 (1H, d, J = 2.4 Hz), 8.67 (1H, s), 8.59 (1H, dd, J = 4.8, 1.2 Hz), 8.52 (1H, d, J = 5.2 Hz), 8.33 (1H, d, J = 9.6 Hz), 8.20 (1H, t, J = 8.8 Hz), 7.62 (1H, dd, J = 8.4, 4.4 Hz), 7.49 (1H, s), 7.45 (1H, d, J = 11.2, 2.4 Hz), 7.42 (1H, s), 7.18 (1H, d, J = 8.8 Hz), 6.60 (1H, d, J = 5.2 Hz), 4.18 (2H, q, J = 6.8 Hz), 3.95 (3H, s), 3.94 (3H, s), 1.44 (3H, t, J = 6.8 Hz); LCMS: 97.5%, MS (ESI): m/z 530.1 [M + H]+. |
| 86 | 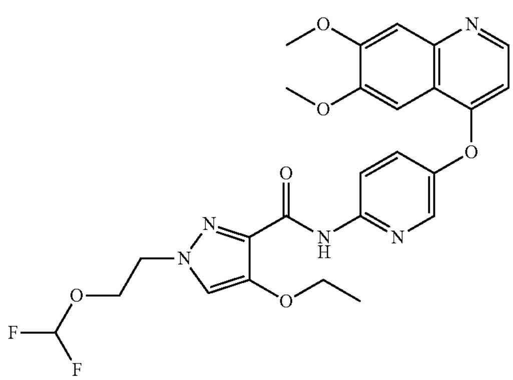 [SMILES: CCOc1cn(CCOC(F)F)nc1C(=O)Nc1ccc(Oc2ccnc3cc(OC)c(OC)cc23)cn1] | white powder; $^1$H-NMR (DMSO-d6, 400 MHz): δ 9.60 (1H, brs), 8.49 (1H, d, J = 4.8 Hz), 8.25-8.45 (2H, m), 7.65-7.90 (2H, m), 7.54 (1H, s), 7.41 (1H, s), 6.68 (1H, t, J = 75.0 Hz), 6.54 (1H, d, J = 5.2 Hz), 4.30-4.40 (2H, m), 4.20-4.28 (2H, m), 4.09 (2H, q, J = 6.8 Hz), 3.95 (3H, s), 3.94 (3H, s), 1.39 (3H, t, J = 6.8 Hz); LCMS: 99.2%, MS (ESI): m/z 530.1 [M + H]+. |
| 87 | 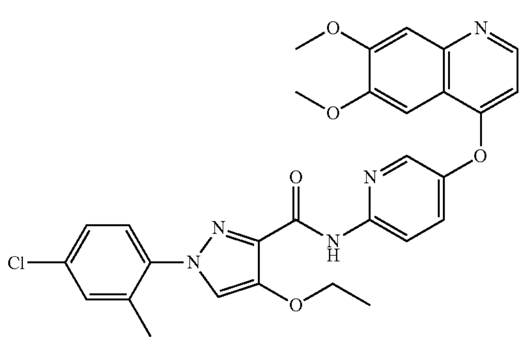 [SMILES: CCOc1cn(-c2ccc(Cl)cc2C)nc1C(=O)Nc1ccc(Oc2ccnc3cc(OC)c(OC)cc23)cn1] | white powder (amorphous); $^1$H-NMR (DMSO-d6, 400 MHz): δ 9.76 (1H, brs), 8.50 (1H, d, J = 5.2 Hz), 8.41 (1H, d, J = 2.8 Hz), 8.36 (1H, d, J = 8.8 Hz), 8.17 (1H, s), 7.85 (1H, dd, J = 9.2, 2.8 Hz), 7.57 (1H, d, J = 2.0 Hz), 7.50-7.55 (2H, m), 7.48 (1H, dd, J = 9.2, 2.4 Hz), 7.42 (1H, s), 6.55 (1H, d, J = 5.2 Hz), 4.17 (2H, q, J = 6.8 Hz), 3.95 (3H, s), 3.94 (3H, s), 2.30 (3H, s), 2.36 (3H, s), 1.43 (3H, t, J = 7.2 Hz); LCMS: 97%, MS (ESI): m/z 560.1 [M + H]+. |

TABLE 4-continued

Summarizes compounds 1-280 in terms of their structures and corresponding characteristics.

| # cpd | Structure | Characterization Data |
|---|---|---|
| 88 | 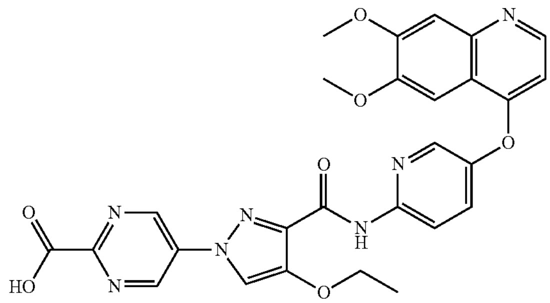 [SMILES: CCOc1cn(-c2cnc(C(=O)O)nc2)nc1C(=O)Nc1ccc(Oc2ccnc3cc(OC)c(OC)cc23)cn1] | off-white solid; ¹H-NMR (DMSO-d6, 400 MHz): δ 10.22 (1H, brs), 9.54 (2H, s), 8.79 (1H, s), 8.55 (1H, d, J = 5.6 Hz), 8.46 (1H, d, J = 2.8 Hz), 8.37 (1H, d, J = 9.2 Hz), 7.91 (1H, dd, J = 8.8, 2.4 Hz), 7.58 (1H, s), 7.43 (1H, s), 6.64 (1H, d, J = 5.2 Hz), 4.19 (2H, q, J = 7.2 Hz), 3.96 (3H, s), 3.95 (3H, s), 1.44 (3H, t, J = 7.2 Hz); LCMS: 100%, MS (ESI): m/z 558.1 [M + H]+. |
| 89 | 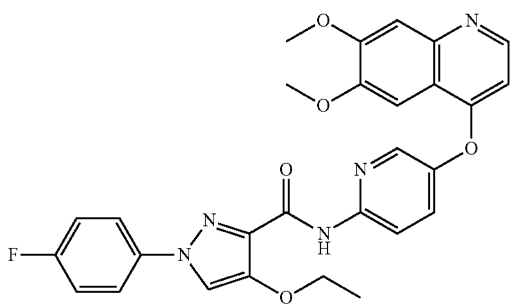 [SMILES: CCOc1cn(-c2ccc(F)cc2)nc1C(=O)Nc1ccc(Oc2ccnc3cc(OC)c(OC)cc23)cn1] | white powder; ¹H-NMR (DMSO-d6, 400 MHz): δ 9.92 (1H, brs), 8.58 (1H, s), 8.50 (1H, d, J = 5.6 Hz), 8.42 (1H, d, J = 2.8 H), 8.37 (1H, d, J = 8.8 Hz), 7.97-8.02 (2H, m), 7.89 (1H, dd, J = 8.8, 2.8 Hz), 7.55 (1H, s), 7.35-7.45 (3H, m), 6.56 (1H, d, J = 5.2 Hz), 4.19 (2H, q, J = 6.8 Hz), 3.96 (3H, s), 3.95 (3H, s), 1.44 (3H, t, J = 6.8 Hz); LCMS: 100%, MS (ESI): m/z 530.2 [M + H]+. |
| 90 | 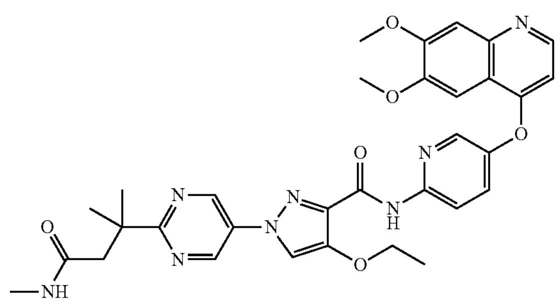 | white powder; ¹H-NMR (CDCl3, 400 MHz): δ 9.53 (1H, s), 8.51-8.57 (2H, m), 8.26 (1H, d, J = 2.8 Hz), 7.60 (1H, dd, J = 9.2, 3.2 Hz), 7.56 (1H, s), 7.44 (1H, s), 7.30 (1H, s), 7.27 (1H, s), 6.46 (1H, d, J = 5.6 Hz), 5.73 (1H, brs), 4.12 (2H, q, J = 6.8 Hz), 4.07 (3H, s), 4.06 (3H, s), 2.86 (2H, s), 2.62 (3H, d, J = 5.2 Hz), 1.74 (6H, s), 1.54 (3H, t, J = 6.8 Hz); LCMS: 98.0%, MS (ESI): m/z 549.1 [M + H]+. |
| 91 | 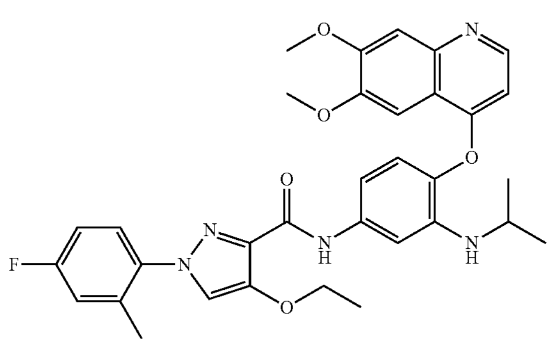 [SMILES: CCOc1cn(-c2ccc(F)cc2C)nc1C(=O)Nc1ccc(Oc2ccnc3cc(OC)c(OC)cc23)c(NC(C)C)c1] | white powder; ¹H-NMR (DMSO-d6, 400 MHz): δ 9.68 (1H, brs), 8.45 (1H, d, J = 5.2 Hz), 8.03 (1H, s), 7.60 (1H, s), 7.49-7.56 (1H, m), 7.38-7.44 (2H, m), 7.30-7.40 (1H, m), 7.20-7.30 (1H, m), 7.10 (1H, dd, J = 8.8, 2.4 Hz), 6.94 (1H, d, J = 8.4 Hz), 6.39 (1H, d, J = 5.2 Hz), 4.66 (1H, d, J = 8.0 Hz), 4.07 (2H, q, J = 6.8 Hz), 3.96 (3H, s), 3.95 (3H, s), 3.53-3.65 (1H, m), 2.28 (3H, s), 1.39 (3H, t, J = 6.8 Hz), 1.12 (6H, d, J = 6.4 Hz); LCMS: 100%, MS (ESI): m/z 600.1 [M + H]+. |

TABLE 4-continued

Summarizes compounds 1-280 in terms of their structures and corresponding characteristics.

| # cpd | Structure | Characterization Data |
|---|---|---|
| 92 | 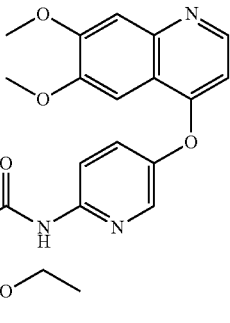 | white powder; ¹H-NMR (DMSO-d6, 400 MHz): δ 9.69 (1H, s), 8.50 (1H, d, J = 5.2 Hz), 8.40 (1H, d, J = 2.8 Hz), 8.35 (1H, d, J = 8.8 Hz), 7.95 (1H, s), 7.87 (1H, dd, J = 9.2, 3.2 Hz), 7.54 (1H, s), 7.42 (1H, s), 6.55 (1H, d, J = 5.2 Hz), 4.14 (2H, q, J = 7.2 Hz), 3.95 (3H, s), 3.94 (3H, s), 3.80 (3H, s), 1.99 (6H, s), 1.42 (3H, t, J = 7.2 Hz); LCMS: 98.9%, MS (ESI): m/z 570.1 [M + H]+. |
| 93 | 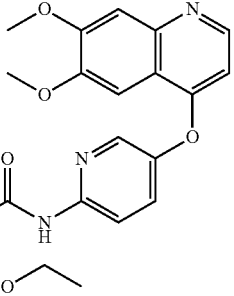 | white powder; ¹H-NMR (DMSO-d6, 400 MHz): δ 9.72 (1H, brs), 8.49 (1H, d, J = 5.2 Hz), 8.30-8.45 (3H, m), 8.18 (2H, s), 7.87 (1H, dd, J = 9.2, 2.8 Hz), 7.53 (1H, s), 7.41 (1H, s), 6.56 (1H, d, J = 4.8 Hz), 5.83 (2H, brs), 4.19 (2H, q, J = 7.2 Hz), 3.94 (3H, s), 3.93 (3H, s), 1.41 (3H, t, J = 7.2 Hz); LCMS: 97.6%, MS (ESI): m/z 529.2 [M + H]+. |
| 94 | 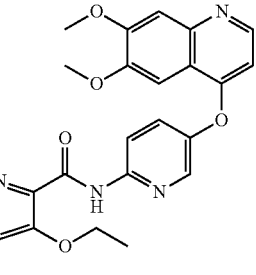 | flesh powder; ¹H-NMR (DMSO-d6, 400 MHz): δ 9.56 (1H, brs), 8.50 (1H, d, J = 5.2 Hz), 8.43 (1H, dd, J = 4.8, 1.6 Hz), 8.38-8.41 (2H, m), 8.35 (1H, d, J = 9.2 Hz), 7.87 (1H, dd, J = 9.2, 3.2 Hz), 7.75 (1H, s), 7.61 (1H, dt, J = 8.0, 2.0 Hz), 7.55 (1H, s), 7.42 (1H, s), 7.32 (1H, dd, J = 8.0, 4.8 Hz0, 7.54 (1H, s), 6.55 (1H, d, j = 5.2 Hz), 4.41 (2H, t, J = 6.8 Hz), 4.04 (2H, q, J = 6.8 Hz), 3.96 (3H, s), 3.95 (3H, s), 3.19 (2H, t, J = 7.2 Hz), 1.36 (3H, t, J = 6.8 Hz); LCMS: 96.8%, MS (ESI): m/z 541.3 [M + H[+. |
| 95 | 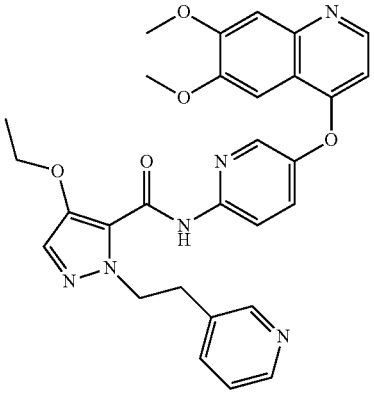 [SMILES: CCOc1cnn(CCc2cccnc2)c1C(=O)Nc1ccc(Oc2ccnc3cc(OC)c(OC)cc23)cn1] | flesh powder; ¹H-NMR (DMSO-d6, 400 MHz): δ 9.72 (1H, brs), 8.50 (1H, d, J = 5.2 Hz), 8.43 (1H, d, J = 2.8 Hz), 8.40 (1H, dd, J = 4.4, 1.2 Hz), 8.30-8.37 (2H, m), 7.88 (1H, dd, J = 8.8, 2.8 Hz), 7.62 (1H, s), 7.59 (1H, dt, J = 8.0, 1.6 Hz), 7.55 (1H, s), 7.42 (1H, s), 7.29 (1H, dd, J = 7.6, 4.8 Hz), 6.55 (1H, d, J = 5.6 Hz), 4.78 (2H, t, J = 7.6 Hz), 4.28 (2H, q, J = 6.8 Hz), 3.96 (3H, s), 3.95 (3H, s), 3.11 (2H, t, J = 6.8 Hz), 1.43 (3H, t, J = 6.8 Hz); LCMS: 96.1%, MS (ESI): m/z 541.2 [M + H]+. |

TABLE 4-continued

Summarizes compounds 1-280 in terms of their structures and corresponding characteristics.

| # cpd | Structure | Characterization Data |
|---|---|---|
| 96 | 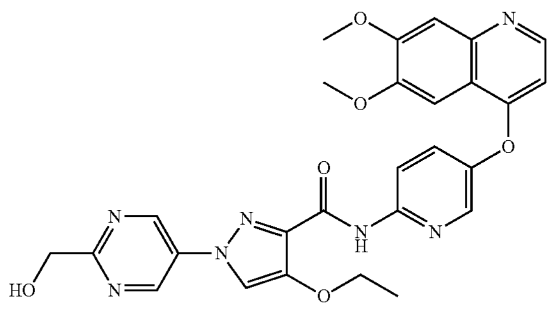 [SMILES: CCOc1cn(-c2cnc(CO)nc2)nc1C(=O)Nc1ccc(Oc2ccnc3cc(OC)c(OC)cc23)cn1] | white powder; ¹H-NMR (DMSO-d6, 400 MHz): δ 10.08 (1H, brs), 9.39 (2H, s), 8.72 (1H, s), 8.51 (1H, d, J = 5.2 Hz), 8.45 (1H, d, J = 3.2 Hz), 8.38 (1H, d, J = 9.2 Hz), 7.90 (1H, dd, J = 8.8, 2.8 Hz), 7.55 (1H, s), 7.43 (1H, s), 6.58 (1H, d, J = 4.8 Hz), 5.49 (1H, brs), 4.69 (2H, s), 4.21 (2H, q, J = 6.8 Hz), 3.97 (3H, s), 3.96 (3H, s), 1.46 (3H, t, J = 7.2 Hz); LCMS: 100%, MS (ESI): m/z 544.2 [M + H]+. |
| 97 | 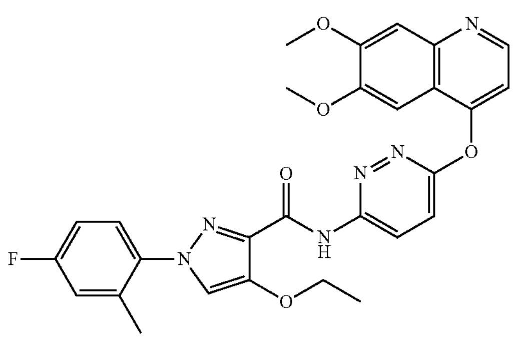 [SMILES: CCOc1cn(-c2ccc(F)cc2C)nc1C(=O)Nc1ccc(Oc2ccnc3cc(OC)c(OC)cc23)nn1] | white powder; ¹H-NMR (CDCl3, 400 MHz): δ 9.88 (1H, s), 8.88 (1H, d, J = 9.6 Hz), 8.64 (1H, d, J = 5.2 Hz), 7.39-7.46 (3H, m), 7.26-7.33 (2H, m), 6.94-7.03 (3H, m), 4.16 (2H, q, J = 6.8 Hz), 4.06 (3H, s), 4.00 (3H, s), 2.27 (3H, s), 1.55 (3tH, t, J = 6.8 Hz); LCMS: 96.9%, MS (ESI): m/z 545.2 [M + H]+. |
| 98 | 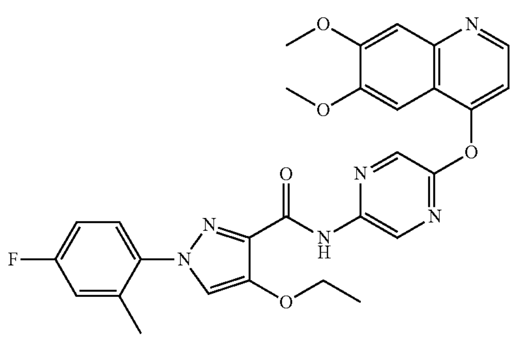 [SMILES: CCOc1cn(-c2ccc(F)cc2C)nc1C(=O)Nc1cnc(Oc2ccnc3cc(OC)c(OC)cc23)cn1] | white powder; ¹H-NMR (DMSO-d6, 400 MHz): δ 9.98 (1H, brs), 9.10 (1H, s), 8.61 (2H, s), 8.14 (1H, s), 7.50-7.60 (1H, m), 7.44 (2H, d, J = 7.6 Hz), 7.34 (1H, d, J = 9.2 Hz), 7.25 (1H, t, J = 7.6 Hz), 7.01 (1H, d, J = 5.2 Hz), 4.14 (2H, q, J = 6.8 Hz), 3.96 (3H, s), 3.91 (3H, s), 2.28 (3H, s), 1.41 (3H, t, J = 6.8 Hz); LCMS: 98.8%, MS (ESI): m/z 545.1 [M + H]+. |
| 99 | 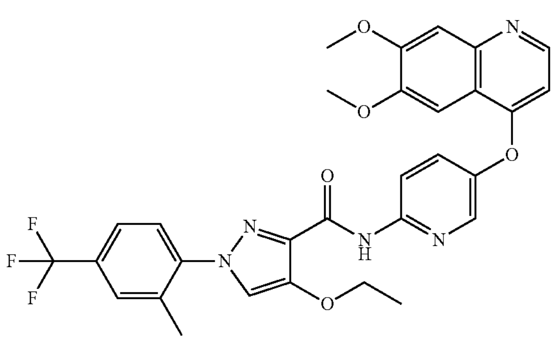 [SMILES: CCOc1cn(-c2ccc(C(F)(F)F)cc2C)nc1C(=O)Nc1ccc(Oc2ccnc3cc(OC)c(OC)cc23)cn1] | white powder; ¹H-NMR (DMSO-d6, 400 MHz): δ 9.82 (1H, brs), 8.50 (1H, d, J = 5.2 Hz), 8.42 (1H, d, J = 2.8 Hz), 8.37 (1H, d, J = 8.8 Hz), 8.27 (1H, s), 7.85-7.92 (2H, m), 7.71-7.82 (2H, m), 7.54 (1H, s), 7.42 (1H, s), 6.56 (1H, d, J = 5.2 Hz), 4.18 (2H, q, J = 6.8 Hz), 3.96 (3H, s), 3.95 (3H, s), 2.44 (3H, s), 1.44 (3H, t, J = 6.8 Hz); LCMS: 98.4%, MS (ESI): m/z 594.1 [M + H]+. |

TABLE 4-continued

Summarizes compounds 1-280 in terms of their structures and corresponding characteristics.

| # cpd | Structure | Characterization Data |
|---|---|---|
| 100 | 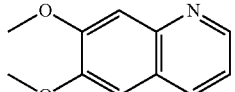 | white powder (amorphous); $^1$H-NMR (DMSO-d6, 400 MHz): δ 9.85 (1H, brs), 8.50 (1H, d, J = 5.2 Hz), 8.42 (1H, d, J = 2.8 Hz), 8.37 (1H, d, J = 9.2 Hz), 8.20 (1H, d, J = 2.4 Hz), 7.87 (1H, dd, J = 9.2, 2.8 Hz), 7.71 (1H, t, J = 8.4 Hz), 7.54 (1H, s), 7.42 (1H, s), 7.36 (1H, d, J = 12.8 Hz), 7.22 (1H, d, J = 8.0 Hz), 6.56 (1H, d, J = 4.8 Hz), 4.18 (2H, q, J = 6.8 Hz), 3.95 (3H, s), 3.94 (3H, s), 2.39 (3H, s), 1.42 (3H, t, J = 6.8 Hz); LCMS: 95.7%, MS (ESI): m/z 544.1 [M + H]+. |
| 101 | 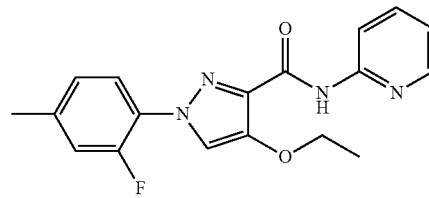 | white powders; $^1$H-NMR (DMSO-d6, 400 MHz): δ 9.68 (1H, brs), 8.50 (1H, d, J = 5.2 Hz), 8.41 (1H, d, J = 2.8 Hz), 8.35 (1H, d, J = 8.8 Hz), 8.20 (1H, s), 8.12 (1H, d, J = 2.0 Hz), 8.02 (1H, dd, J = 8.8, 2.0 Hz), 7.88 (1H, dd, J = 8.8, 2.8 Hz), 7.83 (1H, d, J = 8.8 Hz), 7.54 (1H, s), 7.42 (1H, s), 6.56 (1H, d, J = 5.2 Hz), 4.15 (2H, q, J = 6.8 Hz), 3.96 (3H, s), 3.95 (3H, s), 1.42 (3H, t, J = 6.8 Hz); LCMS: 98.0%, MS (ESI): m/z 614.1 [M + H]+. |
| 102 | 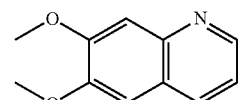 | white powder; $^1$H-NMR (DMSO-d6, 400 MHz): δ 9.75 (1H, brs), 8.48 (1H, d, J = 5.2 Hz), 8.41 (1H, d, J = 2.8 Hz), 8.12 (1H, d, J = 9.2 Hz), 8.01 (1H, s), 7.79 (1H, s), 7.75 (1H, dd, J = 9.2, 2.8 Hz), 7.60-7.68 (1H, m), 7.48-7.53 (2H, m), 7.41 (1H, s), 6.51 (1H, d, J = 5.2 Hz), 4.39 (2H, q, J = 6.8 Hz), 3.95 (3H, s), 3.94 (3H, s), 2.09 (3H, s), 1.49 (3H, t, J = 7.2 Hz); LCMS: 94.6%, MS (ESI): m/z 594.1 [M + H]+. |
| 103 | 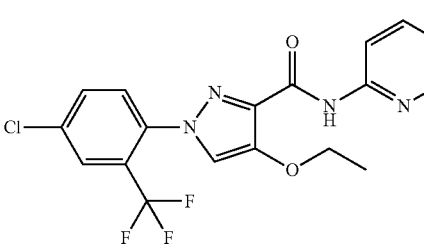 | white powders; $^1$H-NMR (DMSO-d6, 400 MHz): δ 9.62 (1H, brs), 8.48 (1H, d, J = 5.2 Hz), 8.41 (1H, d, J = 2.4 Hz), 8.09 (1H, d, J = 9.2 Hz), 8.01-8.05 (2H, m), 7.92 (1H, d, J = 8.4 Hz), 7.75 (1H, dd, J = 8.8, 2.4 Hz), 7.64 (1H, d, J = 8.4 Hz), 7.51 (1H, s), 7.40 (1H, s), 6.52 (1H, d, J = 5.2 Hz), 4.40 (2H, q, J = 6.8 Hz), 3.96 (3H, s), 3.95 (3H, s), 1.48 (3H, t, J = 6.8 Hz); LCMS: 95.6%, MS (ESI): m/z 614.1 [M + H]+. |

TABLE 4-continued

Summarizes compounds 1-280 in terms of their structures and corresponding characteristics.

| # cpd | Structure | Characterization Data |
|---|---|---|
| 104 | 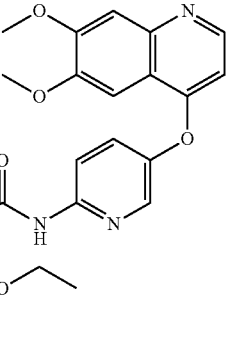 | white powder; ¹H-NMR (DMSO-d6, 400 MHz): δ 9.67 (1H, brs), 8.50 (1H, d, J = 4.8 Hz), 8.41 (1H, d, J = 2.4 Hz), 8.35 (1H, d, J = 9.2 Hz), 8.18 (1H, s), 7.97 (1H, dd, J = 8.4, 2.0 Hz), 7.78-7.93 (3H, m), 7.54 (1H, s), 7.41 (1H, s), 6.56 (1H, d, J = 5.2 Hz), 4.15 (2H, q, J = 7.2 Hz), 3.95 (3H, s), 3.94 (3H, s), 1.42 (3H, t, J = 6.8 Hz); LCMS: 98.1%, MS (ESI): m/z 598.1 [M + H]+. |
| 105 | 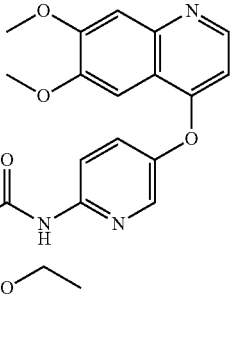 | white powders; ¹H-NMR (DMSO-d6, 400 MHz): δ 9.71 (1H, brs), 8.50 (1H, d, J = 5.2 Hz), 8.42 (1H, d, J = 2.8 Hz), 8.32-8.39 (3H, m), 8.29 (1H, s), 8.06 (1H, d, J = 9.2 Hz), 7.89 (1H, dd, J = 9.2, 3.2 Hz), 7.54 (1H, s), 7.42 (1H, s), 6.56 (1H, d, J = 5.6 Hz), 4.17 (2H, q, J = 6.8 Hz), 3.96 (3H, s), 3.95 (3H, s), 1.43 (3H, t, J = 6.8 Hz); LCMS: 96.7%, MS (ESI): m/z 648.1 [M + H]+. |
| 106 | 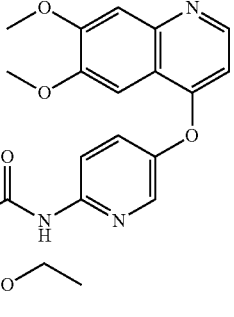 | white powder; ¹H-NMR (DMSO-d6, 400 MHz): δ 9.93 (1H, brs), 8.51 (1H, d, J = 5.2 Hz), 8.42 (1H, d, J = 2.8 Hz), 8.37 (1H, d, J = 8.8 Hz), 8.25 (1H, d, J = 2.4 Hz), 7.98 (1H, t, J = 8.4 Hz), 7.88 (1H, dd, J = 9.2, 2.8 Hz), 7.81 (1H, dd, J = 11.2, 2.4 Hz), 7.55 (1H, s), 7.52 (1H, d, J = 8.8 Hz), 7.43 (1H, s), 6.58 (1H, d, J = 5.2 Hz), 4.18 (2H, q, J = 7.2 Hz), 3.96 (3H, s), 3.95 (3H, s), 1.42 (3H, t, J = 7.2 Hz); LCMS: 100%, MS (ESI): m/z 564.1 [M + H]+. |
| 107 | 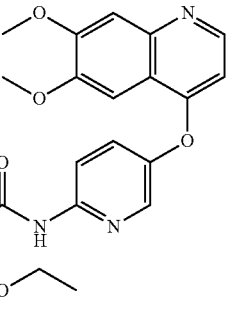 | white powder (amorphous); ¹H-NMR (DMSO-d6, 400 MHz): δ 9.89 (1H, brs), 8.50 (1H, d, J = 5.2 Hz), 8.42 (1H, d, J = 2.8 Hz), 8.37 (1H, d, J = 8.8 Hz), 8.23 (1H, d, J = 2.0 Hz), 7.91-8.01 (1H, m), 7.88 (1H, dd, J = 8.8, 2.8 Hz), 7.60-7.69 (1H, m), 7.54 (1H, s), 7.42 (1H, s), 7.29-7.39 (1H, m), 6.56 (1H, d, J = 5.2 Hz), 4.18 (2H, q, J = 7.2 Hz), 3.95 (3H, s), 3.94 (3H, s), 1.42 (3H, t, J = 6.8 Hz); LCMS: 98.5%, MS (ESI): m/z 548.1 [M + H]+. |

TABLE 4-continued

Summarizes compounds 1-280 in terms of their structures and corresponding characteristics.

| # cpd | Structure | Characterization Data |
|---|---|---|
| 108 | 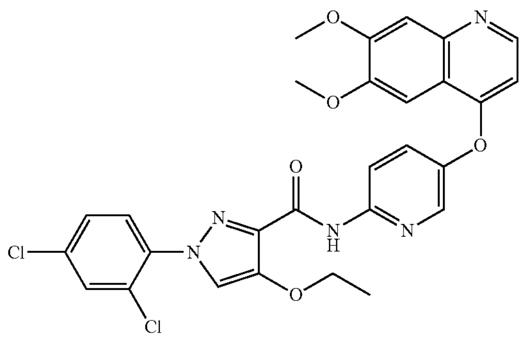 [SMILES: CCOc1cn(-c2ccc(Cl)cc2Cl)nc1C(=O)Nc1ccc(Oc2ccnc3cc(OC)c(OC)cc23)cn1] | white powder (amorphous); ¹H-NMR (DMSO-d6, 400 MHz): δ 9.82 (1H, brs), 8.51 (1H, d, J = 5.2 Hz), 8.42 (1H, d, J = 3.2 Hz), 8.36 (1H, d, J = 8.8 Hz), 8.24 (1H, s), 7.96 (1H, d, J = 2.0 Hz), 7.88 (1H, dd, J = 9.2, 2.8 Hz), 7.77 (1H, d, J = 8.8 Hz), 7.66 (1H, dd, J = 8.8, 2.0 Hz), 7.55 (1H, s), 7.42 (1H, s), 6.57 (1H, d, J = 5.2 Hz), 4.17 (2H, q, J = 6.8 Hz), 3.96 (3H, s), 3.95 (3H, s), 1.42 (3H, t, J = 6.8 Hz); LCMS: 97.5%, MS (ESI): m/z 580.1 [M + H]+. |
| 109 | 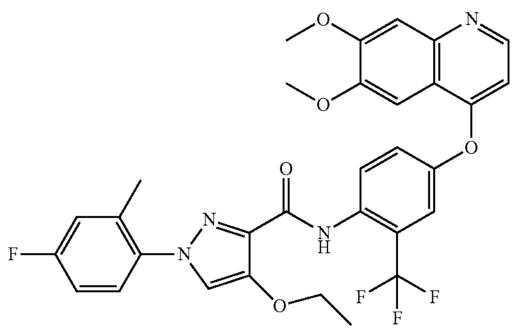 [SMILES: CCOc1cn(-c2ccc(F)cc2C)nc1C(=O)Nc1ccc(Oc2ccnc3cc(OC)c(OC)cc23)cc1C(F)(F)F] | light yellow powder; ¹H-NMR (DMSO-d6, 400 MHz): δ 9.37 (1H, brs), 8.52 (1H, d, J = 5.2 Hz), 8.25 (1H, d, J = 9.2 Hz), 8.13 (1H, s), 7.71 (1H, d, J = 2.4 Hz), 7.64 (1H, dd, J = 8.8, 2.4 Hz), 7.47-7.53 (2H, m), 7.41 (1H, s), 7.33 (1H, dd, J = 9.6, 2.8 Hz), 7.23 (1H, td, J = 8.8, 3.2 Hz), 6.61 (1H, d, J = 5.2 Hz), 4.14 (2H, q, J = 7.2 Hz), 3.94 (3H, s), 3.92 (3H, s), 2.26 (3H, s), 1.38 (3H, t, J = 6.8 Hz); LCMS: 99.0%, MS (ESI): m/z 611.3 [M + H]+. |
| 110 | 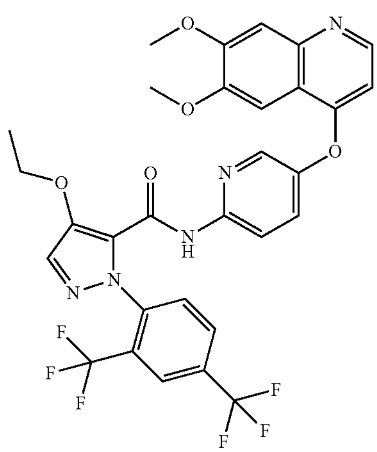 [SMILES: CCOc1cnn(-c2ccc(C(F)(F)F)cc2C(F)(F)F)c1C(=O)Nc1ccc(Oc2ccnc3cc(OC)c(OC)cc23)cn1] | white powders; ¹H-NMR (DMSO-d6, 400 MHz): δ 9.63 (1H, brs), 8.50 (1H, d, J = 5.2 Hz), 8.43 (1H, d, J = 2.0 Hz), 8.23-8.31 (2H, m), 8.06-8.12 (2H, m), 7.89 (1H, d, J = 8.4 Hz), 7.76 (1H, dd, J = 8.8, 2.4 Hz), 7.53 (1H, s), 7.41 (1H, s), 6.55 (1H, d, J = 4.0 Hz), 4.42 (2H, q, J = 6.8 Hz), 3.95 (3H, s), 3.94 (3H, s), 1.49 (3H, t, J = 6.8 Hz); LCMS: 94.8%, MS (ESI): m/z 648.3 [M + H]+. |
| 111 | 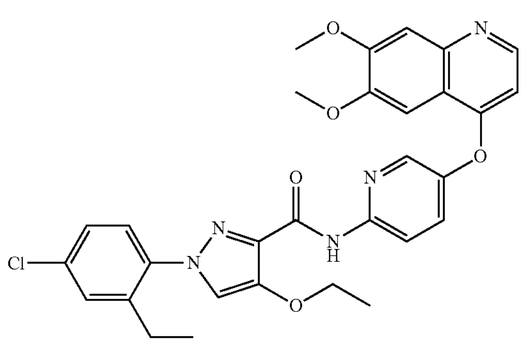 [SMILES: CCOc1cn(-c2ccc(Cl)cc2CC)nc1C(=O)Nc1ccc(Oc2ccnc3cc(OC)c(OC)cc23)cn1] | off-white powder; ¹H-NMR (DMSO-d6, 400 MHz): δ 9.72 (1H, brs), 8.51 (1H, d, J = 4.8 Hz), 8.41 (1H, d, J = 2.8 Hz), 8.36 (1H, d, J = 8.8 Hz), 8.15 (1H, s), 7.88 (1H, dd, J = 8.8, 2.8 Hz), 7.51-7.62 (2H, m), 7.46-7.50 (2H, m), 7.42 (1H, s), 6.56 (1H, d, J = 5.2 Hz), 4.17 (2H, q, J = 6.8 Hz), 3.96 (3H, s), 3.95 (3H, s), 2.62 (2H, q, J = 7.6 Hz), 1.43 (3H, t, J = 6.8 Hz), 1.07 (3H, t, J = 7.6 Hz); LCMS: 98.9%, MS (ESI): m/z 574.3 [M + H]+. |

TABLE 4-continued

Summarizes compounds 1-280 in terms of their structures and corresponding characteristics.

| # cpd | Structure | Characterization Data |
|---|---|---|
| 112 | 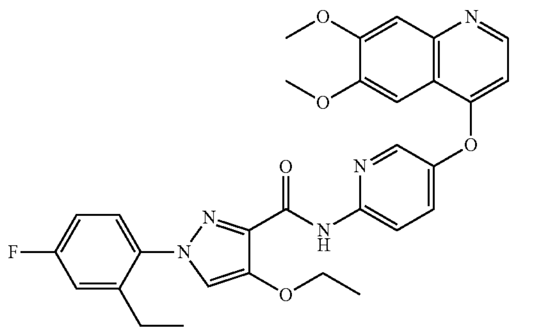 [SMILES: CCOc1cn(-c2ccc(F)cc2CC)nc1C(=O)Nc1ccc(Oc2ccnc3cc(OC)c(OC)cc23)cn1] | white powder; ¹H-NMR (DMSO-d6, 400 MHz): δ 9.70 (1H, brs), 8.51 (1H, d, J = 5.2 Hz), 8.40 (1H, d, J = 3.2 Hz), 8.36 (1H, d, J = 8.8 Hz), 8.11 (1H, s), 7.87 (1H, dd, J = 8.8, 2.8 Hz), 7.54 (1H, s), 7.50 (1H, dd, J = 8.8, 5.2 Hz), 7.41 (1H, s), 7.34 (1H, dd, J = 9.6, 2.8 Hz), 7.24 (1H, td, J = 8.4, 2.8 Hz), 6.57 (1H, d, J = 5.2 Hz), 4.16 (2H, q, J = 6.8 Hz), 3.95 (3H, s), 3.94 (3H, s), 2.56 (2H, q, J = 7.2 Hz), 1.42 (3H, t, J = 6.8 Hz), 1.07 (3H, t, J = 7.6 Hz); LCMS: 97.7%, MS (ESI): m/z 558.2 [M + H]+. |
| 113 | 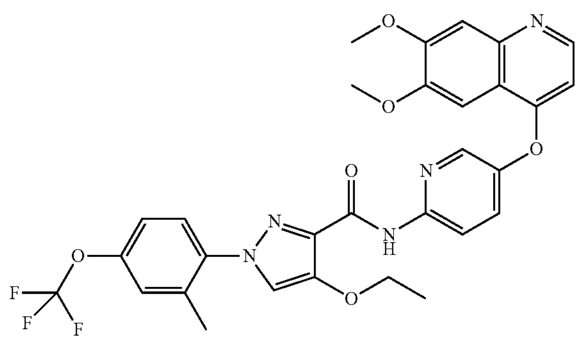 [SMILES: CCOc1cn(-c2ccc(OC(F)(F)F)cc2C)nc1C(=O)Nc1ccc(Oc2ccnc3cc(OC)c(OC)cc23)cn1] | white powder; ¹H-NMR (DMSO-d6, 400 MHz): δ 9.78 (1H, brs), 8.51 (1H, d, J = 5.6 Hz), 8.42 (1H, d, J = 2.8 Hz), 8.37 (1H, d, J = 9.2 Hz), 8.21 (1H, s), 7.87 (1H, dd, J = 8.8, 2.8 Hz), 7.64 (1H, d, J = 8.8 Hz), 7.55 (1H, s), 7.52 (1H, s), 7.35-7.46 (2H, m), 6.56 (1H, d, J = 5.2 Hz), 4.17 (2H, q, J = 7.2 Hz), 3.96 (3H, s), 3.95 (3H, s), 2.34 (3H, s), 1.44 (3H, t, J = 6.8 Hz); LCMS: 100%, MS (ESI): m/z 610.2 [M + H]+. |
| 114 | 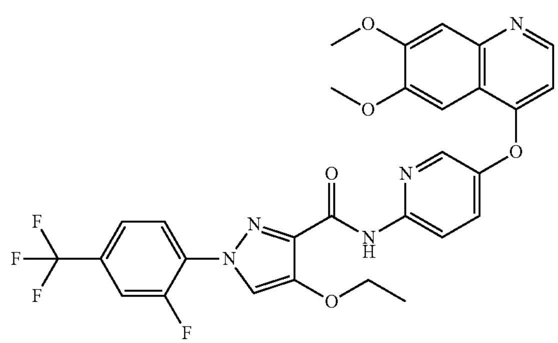 [SMILES: CCOc1cn(-c2ccc(C(F)(F)F)cc2F)nc1C(=O)Nc1ccc(Oc2ccnc3cc(OC)c(OC)cc23)cn1] | white powder; ¹H-NMR (DMSO-d6, 400 MHz): δ 10.02 (1H, brs), 8.50 (1H, d, J = 5.2 Hz), 8.43 (1H, d, J = 2.8 Hz), 8.37 (1H, d, J = 8.8 Hz), 8.32 (1H, d, J = 2.8 Hz), 8.24 (1H, t, J = 8.0 Hz), 8.07 (1H, d, J = 11.6 Hz), 7.89 (1H, dd, J = 9.2, 2.8 Hz), 7.81 (1H, d, J = 8.8 Hz), 7.54 (1H, s), 7.41 (1H, s), 6.56 (1H, d, J = 5.6 Hz), 4.20 (2H, q, J = 6.8 Hz), 3.95 (3H, s), 3.94 (3H, s), 1.43 (3H, t, J = 6.8 Hz); LCMS: 98.5%, MS (ESI): m/z 598.1 [M + H]+. |
| 115 | 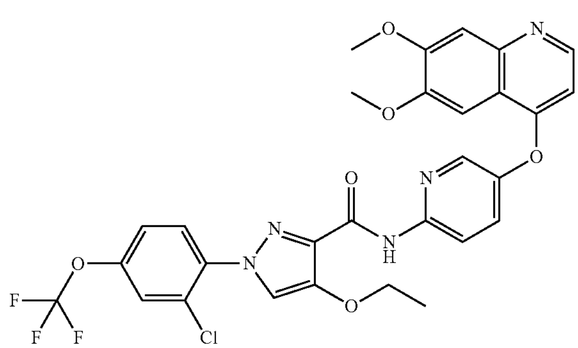 [SMILES: CCOc1cn(-c2ccc(OC(F)(F)F)cc2Cl)nc1C(=O)Nc1ccc(Oc2ccnc3cc(OC)c(OC)cc23)cn1] | white powder (amorphous); ¹H-NMR (DMSO-d6, 400 MHz): δ 9.83 (1H, brs), 8.51 (1H, d, J = 4.8 Hz), 8.42 (1H, d, J = 2.4 Hz), 8.37 (1H, d, J = 9.2 Hz), 8.28 (1H, s), 7.65-7.95 (3H, m), 7.62 (1H, d, J = 8.8 Hz), 7.55 (1H, s), 7.43 (1H, s), 6.57 (1H, d, J = 5.6 Hz), 4.17 (2H, q, J = 6.8 Hz), 3.96 (3H, s), 3.95 (3H, s), 1.44 (3H, t, J = 7.2 Hz); LCMS: 100%, MS (ESI): m/z 630.1 [M + H]+. |

TABLE 4-continued

Summarizes compounds 1-280 in terms of their structures and corresponding characteristics.

| # cpd | Structure | Characterization Data |
|---|---|---|
| 116 | 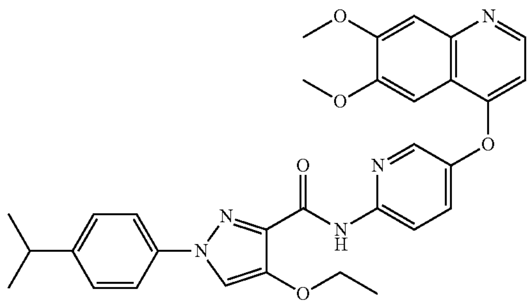 [SMILES: CCOc1cn(-c2ccc(C(C)C)cc2)nc1C(=O)Nc1ccc(Oc2ccnc3cc(OC)c(OC)cc23)cn1] | white powder; ¹H-NMR (DMSO-d6, 400 MHz): δ 9.84 (1H, brs), 8.54 (1H, s), 8.50 (1H, d, J = 5.2 Hz), 8.42 (1H, d, J = 2.8 Hz), 8.38 (1H, d, J = 8.8 Hz), 7.88 (1H, dd, J = 9.2, 2.8 Hz), 7.85 (2H, d, J = 8.8 Hz), 7.55 (1H, s), 7.39-7.46 (3H, m), 6.56 (1H, d, J = 5.2 Hz), 4.21 (2H, q, J = 7.2 Hz), 3.96 (3H, s), 3.95 (3H, s), 2.91-3.05 (1H, m), 1.45 (3H, t, J = 6.8 Hz), 1.24 (6H, d, J = 6.8 Hz); LCMS: 99.5%, MS (ESI): m/z 554.4 [M + H]+. |
| 117 | 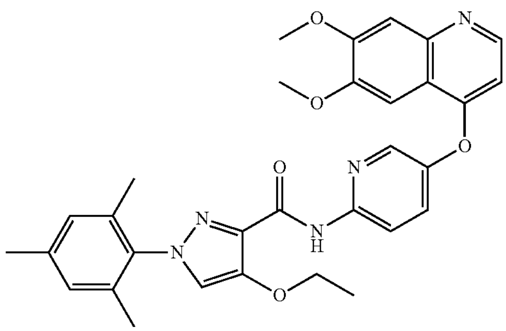 [SMILES: CCOc1cn(-c2c(C)cc(C)cc2C)nc1C(=O)Nc1ccc(Oc2ccnc3cc(OC)c(OC)cc23)cn1] | white powder; ¹H-NMR (DMSO-d6, 400 MHz): δ 9.69 (1H, brs), 8.50 (1H, d, J = 5.2 Hz), 8.40 (1H, d, J = 3.2 Hz), 8.36 (1H, d, J = 8.8 Hz), 7.96 (1H, s), 7.87 (1H, dd, J = 8.8, 2.8 Hz), 7.54 (1H, s), 7.42 (1H, s), 7.06 (2H, s), 6.55 (1H, d, J = 5.2 Hz), 4.14 (2H, q, J = 7.2 Hz), 3.95 (3H, s), 3.94 (3H, s), 2.32 (3H, s), 1.99 (6H, s), 1.42 (3H, t, J = 6.8 Hz); LCMS: 100%, MS (ESI): m/z 554.3 [M + H]+. |
| 118 | 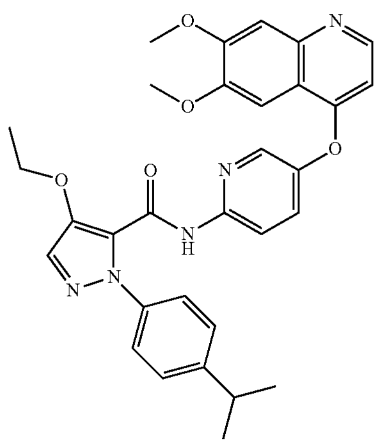 [SMILES: CCOc1cnn(-c2ccc(C(C)C)cc2)c1C(=O)Nc1ccc(Oc2ccnc3cc(OC)c(OC)cc23)cn1] | white powder; ¹H-NMR (DMSO-d6, 400 MHz): δ 10.06 (1H, brs), 8.50 (1H, d, J = 5.2 Hz), 8.42 (1H, d, J = 2.8 Hz), 8.20 (1H, d, J = 9.2 Hz), 7.89 (1H, s), 7.81 (1H, dd, J = 9.2, 2.8 Hz), 7.54 (1H, s), 7.42 (1H, s), 7.31-7.41 (4H, m), 6.54 (1H, d, J = 5.2 Hz), 4.32 (2H, q, J = 6.8 Hz), 3.96 (3H, s), 3.95 (3H, s), 1.45 (3H, t, J = 7.2 Hz), 1.26 (6H, d, J = 7.2 Hz); LCMS: 93.4%, MS (ESI): m/z 554.3 [M + H]+. |
| 119 | 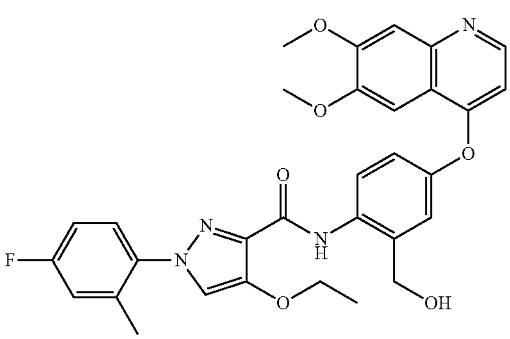 [SMILES: CCOc1cn(-c2ccc(F)cc2C)nc1C(=O)Nc1ccc(Oc2ccnc3cc(OC)c(OC)cc23)cc1CO] | off-white amorphous; ¹H-NMR (DMSO-d6, 400 MHz): δ 9.94 (1H, s), 8.49 (1H, d, J = 5.2 Hz), 8.20 (1H, d, J = 8.4 Hz), 8.07 (1H, s), 7.47-7.53 (2H, m), 7.40 (1H, s), 7.33 (1H, dd, J = 9.6, 2.8 Hz), 7.19-7.28 (3H, m), 6.50 (1H, d, J = 5.6 Hz), 5.63 (1H, brs), 4.59 (2H, s), 4.10 (2H, q, J = 6.8 Hz), 3.95 (3H, s), 3.94 (3H, s), 2.29 (3H, s), 1.40 (3H, t, J = 6.8 Hz); LCMS: 98.2%, MS (ESI): m/z 573.2 [M + H]+. |

TABLE 4-continued

Summarizes compounds 1-280 in terms of their structures and corresponding characteristics.

| # cpd | Structure | Characterization Data |
|---|---|---|
| 120 | 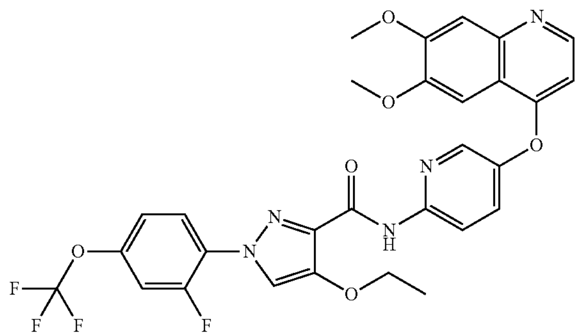 | white powder; ¹H-NMR (DMSO-d6, 400 MHz): δ 9.94 (1H, brs), 8.50 (1H, d, J = 5.2 Hz), 8.41 (1H, d, J = 2.8 Hz), 8.36 (1H, d, J = 8.8 Hz), 8.27 (1H, d, J = 2.4 Hz), 8.09 (1H, t, J = 8.8 Hz), 7.88 (1H, dd, J = 8.8, 2.8 Hz), 7.80 (1H, d, J = 11.6 Hz), 7.54 (1H, s), 7.48 (1H, d, J = 9.2 Hz), 7.42 (1H, s), 6.56 (1H, d, J = 5.2 Hz), 4.19 (2H, q, J = 6.8 Hz), 3.95 (3H, s), 3.94 (3H, s), 1.42 (3H, t, J = 6.8 Hz); LCMS: 99.7%, MS (ESI): m/z 614.1 [M + H]+. |
| 121 | 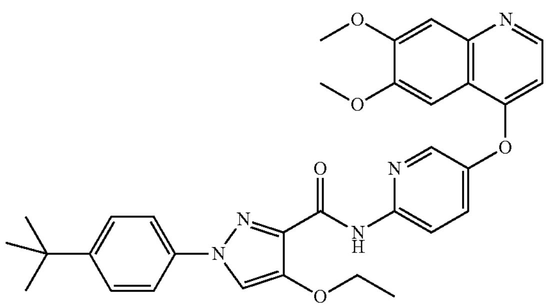 [SMILES: CCOc1cn(-c2ccc(C(C)(C)C)cc2)nc1C(=O)Nc1ccc(Oc2ccnc3cc(OC)c(OC)cc23)cn1] | white powder; ¹H-NMR (DMSO-d6, 400 MHz): δ 9.85 (1H, brs), 8.56 (1H, s), 8.53 (1H, d, J = 5.6 Hz), 8.44 (1H, d, J = 2.8 Hz), 8.39 (1H, d, J = 8.8 Hz), 7.91 (1H, dd, J = 8.8, 2.4 Hz), 7.86 (2H, d, J = 8.8 Hz), 7.52-7.61 (3H, m), 7.44 (1H, s), 6.60 (1H, d, J = 5.2 Hz), 4.22 (2H, q, J = 6.8 Hz), 3.97 (3H, s), 3.96 (3H, s), 1.45 (3H, t, J = 6.8 Hz), 1.34 (9H, s); LCMS: 100%, MS (ESI): m/z 568.3 [M + H]+. |
| 122 | 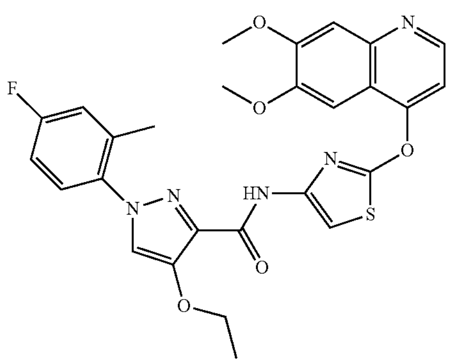 [SMILES: CCOc1cn(-c2ccc(F)cc2C)nc1C(=O)Nc1csc(Oc2ccnc3cc(OC)c(OC)cc23)n1] | off-white powder; ¹H-NMR (CDCl3, 400 MHz): δ 9.36 (1H, brs), 8.69 (1H, d, J = 5.2 Hz), 7.51 (1H, s), 7.48 (1H, s), 7.41 (1H, s), 7.29-7.35 (2H, m), 7.24 (2H, d, J = 5.2 Hz), 6.97-7.08 (2H, m), 4.15 (2H, q, J = 7.2 Hz), 4.08 (3H, s), 4.05 (3H, s), 2.26 (3H, s), 1.53 (3H, t, J = 6.8 Hz); LCMS: 98.7%, MS (ESI): m/z 550.1 [M + H]+. |
| 123 | 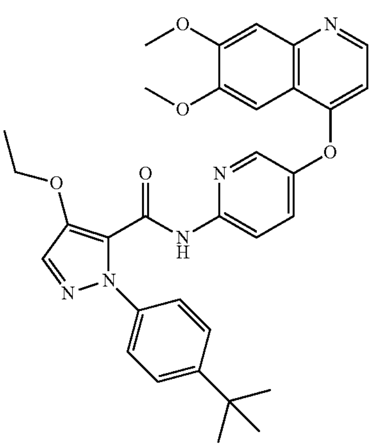 [SMILES: CCOc1cnn(-c2ccc(C(C)(C)C)cc2)c1C(=O)Nc1ccc(Oc2ccnc3cc(OC)c(OC)cc23)cn1] | white powder; ¹H-NMR (DMSO-d6, 400 MHz): δ 10.07 (1H, brs), 8.50 (1H, d, J = 5.6 Hz), 8.42 (1H, d, J = 2.8 Hz), 8.20 (1H, d, J = 8.8 Hz), 7.89 (1H, s), 7.81 (1H, dd, J = 9.2, 3.2 Hz), 7.54 (1H, s), 7.49 (2H, d, J = 8.8 Hz), 7.42 (1H, s), 7.38 (2H, d, J = 8.8 Hz), 6.54 (1H, d, J = 5.6 Hz), 4.32 (2H, q, J = 6.8 Hz), 3.96 (3H, s), 3.95 (3H, s), 1.45 (3H, t, J = 6.8 Hz), 1.34 (9H, s); LCMS: 100%, MS (ESI): m/z 568.3 [M + H]+. |

TABLE 4-continued

Summarizes compounds 1-280 in terms of their structures and corresponding characteristics.

| # cpd | Structure | Characterization Data |
|---|---|---|
| 124 | 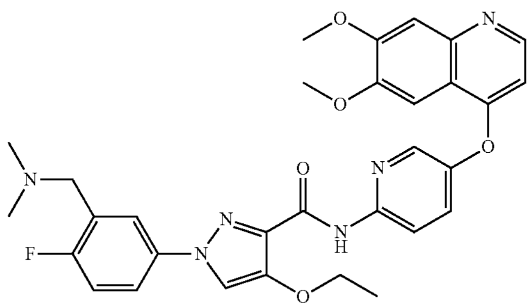 [SMILES: CCOc1cn(-c2ccc(F)c(CN(C)C)c2)nc1C(=O)Nc1ccc(Oc2ccnc3cc(OC)c(OC)cc23)cn1] | white powder; ¹H-NMR (DMSO-d6, 400 MHz): δ 9.89 (1H, brs), 8.58 (1H, s), 8.51 (1H, d, J = 5.6 Hz), 8.43 (1H, d, J = 2.8 Hz), 8.38 (1H, d, J = 8.8 Hz), 7.94-8.03 (1H, m), 7.83-7.93 (2H, m), 7.55 (1H, s), 7.42 (1H, s), 7.39 (1H, t, J = 9.2 Hz), 6.57 (1H, d, J = 5.2 Hz), 4.22 (2H, q, J = 6.8 Hz), 3.96 (3H, s), 3.95 (3H, s), 3.53 (2H, s), 2.21 (6H, s), 1.45 (3H, t, J = 6.8 Hz); LCMS: 100% MS (ESI): m/z 587.2 [M + H]+. |
| 125 | 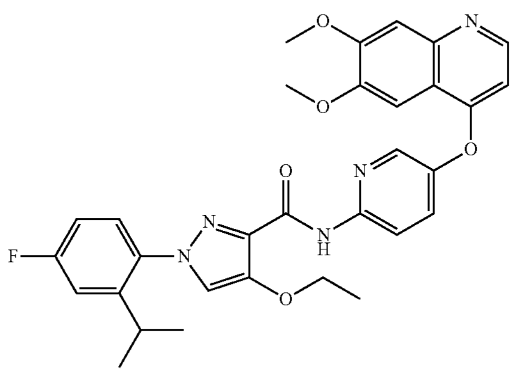 [SMILES: CCOc1cn(-c2ccc(F)cc2C(C)C)nc1C(=O)Nc1ccc(Oc2ccnc3cc(OC)c(OC)cc23)cn1] | white powder; ¹H-NMR (DMSO-d6, 400 MHz): δ 9.68 (1H, brs), 8.50 (1H, d, J = 5.2 Hz), 8.40 (1H, d, J = 2.8 Hz), 8.35 (1H, d, J = 8.8 Hz), 8.11 (1H, s), 7.87 (1H, dd, J = 8.8, 2.8 Hz), 7.54 (1H, s), 7.47 (1H, dd, J = 8.8, 5.2 Hz), 7.39-7.44 (2H, m), 7.23 (1H, td, J = 8.4, 2.8 Hz), 6.55 (1H, d, J = 5.6 Hz), 4.15 (2H, q, J = 6.8 Hz), 3.95 (3H, s), 3.94 (3H, s), 2.77-2.85 (1H, m), 1.42 (3H, t, J = 6.8 Hz), 1.16 (6H, d, J = 8.0 Hz); LCMS: 95.6%, MS (ESI): m/z 572.2 [M + H]+. |
| 126 | 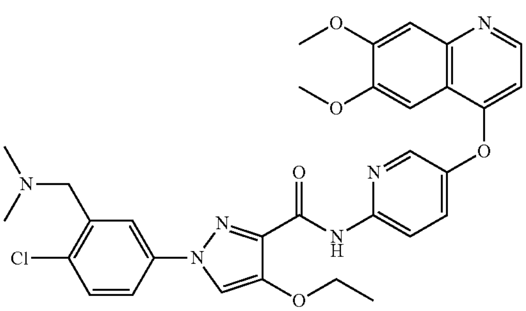 [SMILES: CCOc1cn(-c2ccc(Cl)c(CN(C)C)c2)nc1C(=O)Nc1ccc(Oc2ccnc3cc(OC)c(OC)cc23)cn1] | white powder; ¹H-NMR (DMSO-d6, 400 MHz): δ 9.91 (1H, brs), 8.64 (1H, s), 8.51 (1H, d, J = 5.2 Hz), 8.44 (1H, d, J = 2.8 Hz), 8.38 (1H, d, J = 8.8 Hz), 8.06 (1H, d, J = 2.8 Hz), 7.89 (2H, dt, J = 8.8, 2.8 Hz), 7.63 (1H, d, J = 8.8 Hz), 7.56 (1H, s), 7.43 (1H, s), 6.57 (1H, d, J = 5.2 Hz), 4.23 (2H, q, J = 6.8 Hz), 3.97 (3H, s), 3.96 (3H, s), 3.57 (2H, s), 2.25 (6H, s), 1.46 (3H, t, J = 6.8 Hz); LCMS: 100%, MS (ESI): m/z 603.3 [M + H]+. |
| 127 | 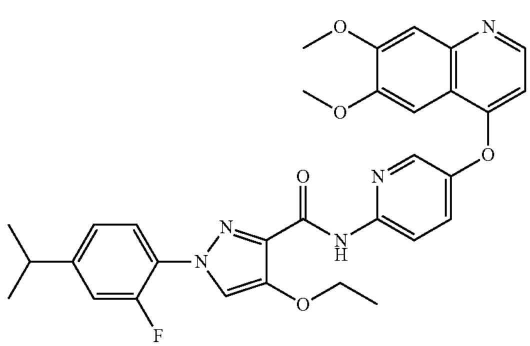 [SMILES: CCOc1cn(-c2ccc(C(C)C)cc2F)nc1C(=O)Nc1ccc(Oc2ccnc3cc(OC)c(OC)cc23)cn1] | white powder; ¹H-NMR (DMSO-d6, 400 MHz): δ 9.84 (1H, brs), 8.51 (1H, d, J = 5.2 Hz), 8.42 (1H, d, J = 2.8 Hz), 8.37 (1H, d, J = 8.8 Hz), 8.20 (1H, d, J = 2.4 Hz), 7.88 (1H, dd, J = 9.2, 2.8 Hz), 7.79 (1H, t, J = 8.4 Hz), 7.54 (1H, s), 7.38-7.45 (2H, m), 7.29 (1H, dd, J = 8.4, 2.0 Hz0, 6.56 (1H, d, J = 5.2 Hz), 4.18 (2H, q, J = 6.8 Hz), 3.95 (3H, s), 3.94 (3H, s), 2.95-3.04 (1H, m), 1.42 (3H, t, J = 6.8 Hz), 1.25 (6H, d, J = 6.8 Hz); LCMS: 100%, MS (ESI): m/z 572.4 [M + H]+. |

TABLE 4-continued

Summarizes compounds 1-280 in terms of their structures and corresponding characteristics.

| # cpd | Structure | Characterization Data |
|---|---|---|
| 128 | 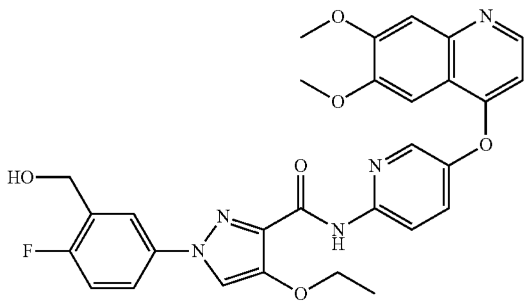 [SMILES: CCOc1cn(-c2ccc(F)c(CO)c2)nc1C(=O)Nc1ccc(Oc2ccnc3cc(OC)c(OC)cc23)cn1] | white powder; ¹H-NMR (DMSO-d6, 400 MHz): δ 9.84 (1H, brs), 8.57 (1H, s), 8.49 (1H, d, J = 5.2 Hz), 8.41 (1H, d, J = 2.8 Hz), 8.36 (1H, d, J = 9.2 Hz), 8.04 (1H, dd, J = 6.0, 2.8 Hz), 7.88 (1H, dd, J = 9.2, 2.8 Hz), 7.80-7.87 (1H, m), 7.53 (1H, s), 7.41 (1H, s), 7.35 (1H, t, J = 9.2 Hz), 6.55 (1H, d, J = 5.2 Hz), 5.50 (1H, t, J = 5.6 Hz), 4.62 (2H, d, J = 5.2 Hz), 4.20 (2H, q, J = 7.2 Hz), 3.94 (3H, s), 3.93 (3H, s), 1.43 (3H, t, J = 6.8 Hz); LCMS: 98.8%, MS (ESI): m/z 560.5 [M + H]+. |
| 129 | 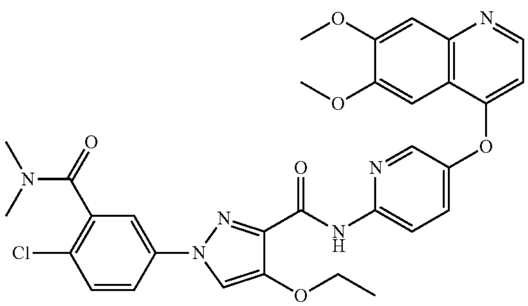 [SMILES: CCOc1cn(-c2ccc(Cl)c(C(=O)N(C)C)c2)nc1C(=O)Nc1ccc(Oc2ccnc3cc(OC)c(OC)cc23)cn1] | off-white powder; ¹H-NMR (DMSO-d6, 400 MHz): δ 10.05 (1H, brs), 8.66 (1H, s), 8.49 (1H, d, J = 5.2 Hz), 8.41 (1H, d, J = 2.4 Hz), 8.35 (1H, d, J = 9.2 Hz), 8.01-8.07 (2H, m), 7.87 (1H, dd, J = 9.2, 3.2 Hz), 7.70 (1H, d, J = 8.0 Hz), 7.53 (1H, s), 7.41 (1H, s), 6.55 (1H, d, J = 5.2 Hz), 4.17 (2H, q, J = 6.8 Hz), 3.94 (3H, s), 3.94 (3H, s), 3.04 (3H, s), 2.83 (3H, s), 1.42 (3H, t, J = 6.8 Hz); LCMS: 100%, MS (ESI): m/z 617.3 [M + H]+. |
| 130 | 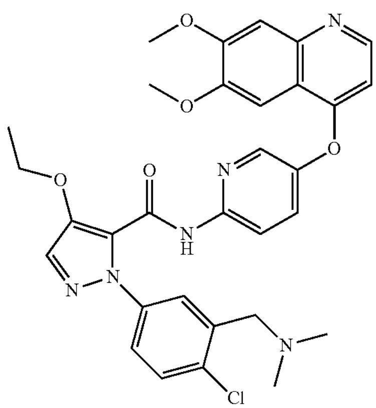 [SMILES: CCOc1cnn(-c2ccc(Cl)c(CN(C)C)c2)c1C(=O)Nc1ccc(Oc2ccnc3cc(OC)c(OC)cc23)cn1] | white powder; ¹H-NMR (DMSO-d6, 400 MHz): δ 10.14 (1H, brs), 8.50 (1H, d, J = 5.6 Hz), 8.42 (1H, d, J = 2.8 Hz), 8.18 (1H, d, J = 8.8 Hz), 7.93 (1H, s), 7.82 (1H, dd, J = 9.2, 3.2 Hz), 7.51-7.58 (3H, m), 7.36-7.44 (2H, m), 6.53 (1H, d, J = 5.2 Hz), 4.32 (2H, q, J = 6.8 Hz), 3.96 (3H, s), 3.95 (3H, s), 3.51 (2H, s), 2.20 (6H, s), 1.44 (3H, t, J = 6.8 Hz); LCMS: 94.5%, MS (ESI): m/z 603.2 [M + H]+. |
| 131 | 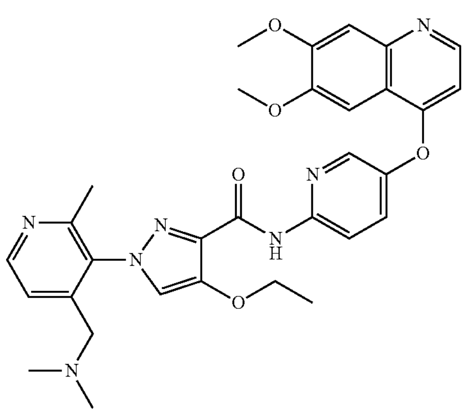 [SMILES: CCOc1cn(-c2c(CN(C)C)ccnc2C)nc1C(=O)Nc1ccc(Oc2ccnc3cc(OC)c(OC)cc23)cn1] | off-white powder; ¹H-NMR (CDCl3, 400 MHz): δ 9.58 (1H, brs), 8.60 (1H, d, J = 9.2 Hz), 8.53 (1H, d, J = 5.2 Hz), 8.38 (1H, s), 8.28 (1H, d, J = 2.8 Hz), 7.88 (1H, d, J = 8.4 Hz), 7.62 (1H, dd, J = 8.8, 2.8 Hz), 7.58 (1H, s), 7.46 (1H, s), 7.26 (1H, d, J = 8.4 Hz), 6.49 (1H, d, J = 5.2 Hz), 4.21 (2H, q, J = 6.8 Hz), 4.04-4.11 (6H, m), 3.50 (2H, s), 2.66 (3H, s), 2.33 (6H, s), 1.60 (3H, t, J = 6.8 Hz); LCMS: 98.3%, MS (ESI): m/z 584.4 [M + H]+. |

TABLE 4-continued

Summarizes compounds 1-280 in terms of their structures and corresponding characteristics.

| # cpd | Structure | Characterization Data |
|---|---|---|
| 132 | 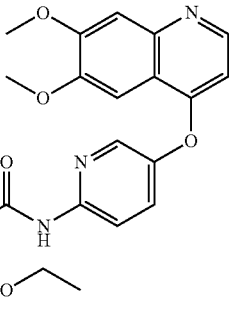 | white powder; $^1$H-NMR (DMSO-d6, 400 MHz): δ 9.77 (1H, brs), 8.47-8.52 (2H, m), 8.41 (1H, d, J = 2.8 Hz), 8.36 (1H, d, J = 8.8 Hz), 8.10 (1H, s), 7.88 (1H, dd, J = 8.8, 2.8 Hz), 7.54 (1H, s), 7.42 (1H, s), 7.35 (1H, d, J = 5.2 Hz), 6.55 (1H, d, J = 5.6 Hz), 4.15 (2H, q, J = 6.8 Hz), 3.95 (3H, s), 3.94 (3H, s), 2.23 (3H, s), 2.09 (3H, s), 1.43 (3H, t, J = 6.8 Hz); LCMS: 100%, MS (ESI): mz 541.4 [M + H]+. |
| 133 | 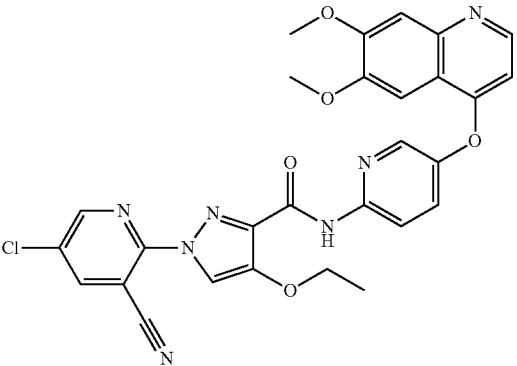 [SMILES: CCOc1cn(-c2ncc(Cl)cc2C#N)nc1C(=O)Nc1ccc(Oc2ccnc3cc(OC)c(OC)cc23)cn1] | white powder; $^1$H-NMR (DMSO-d6, 400 MHz): δ 9.68 (1H, brs), 8.88 (1H, d, J = 2.4 Hz), 8.85 (1H, d, J = 2.4 Hz), 8.55 (1H, s), 8.50 (1H, d, J = 5.2 Hz), 8.43 (1H, d, J = 2.8 Hz), 8.37 (1H, d, J = 8.8 Hz), 7.90 (1H, dd, J = 9.2, 2.8 Hz), 7.54 (1H, s), 7.42 (1H, s), 6.57 (1H, d, J = 4.4 Hz), 4.22 (2H, q, J = 6.8 Hz), 3.96 (3H, s), 3.95 (3H, s), 1.42 (3H, t, J = 6.8 Hz); LCMS: 100%, MS (ESI): m/z 572.3 [M + H]+. |
| 134 | 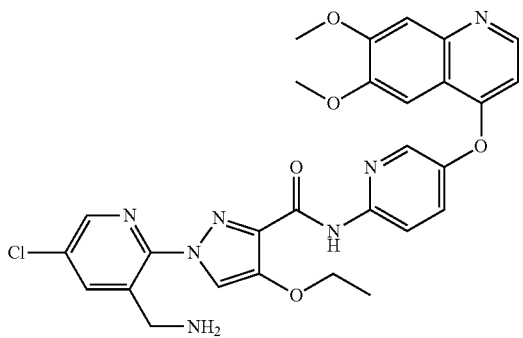 [SMILES: CCOc1cn(-c2ncc(Cl)cc2CN)nc1C(=O)Nc1ccc(Oc2ccnc3cc(OC)c(OC)cc23)cn1] | white powder; $^1$H-NMR (DMSO-d6, 400 MHz): δ 9.86 (1H, brs), 8.48-8.52 (2H, m), 8.43 (1H, d, J = 2.8 Hz), 8.41 (1H, s), 8.37 (1H, d, J = 8.8 Hz), 8.32 (1H, d, J = 2.0 Hz), 7.89 (1H, dd, J = 8.8, 2.8 Hz), 7.54 (1H, s), 7.42 (1H, s), 6.56 (1H, d, J = 5.2 Hz), 4.22 (2H, q, J = 6.8 Hz), 4.01 (2H, s), 3.96 (3H, s), 3.95 (3H, s), 1.43 (3H, t, J = 6.8 Hz); LCMS: 95.4 %, MS (ESI): m/z 576.3 [M + H]+. |
| 135 | 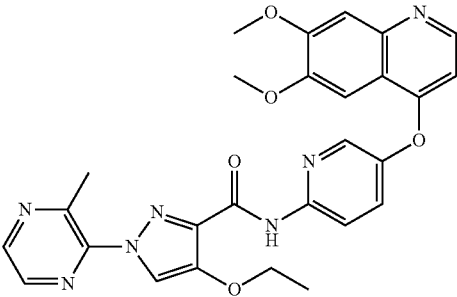 | white powder; $^1$H-NMR (DMSO-d6, 400 MHz): δ 9.88 (1H, brs), 8.65 (1H, d, J = 2.0 Hz), 8.47-8.55 (2H, m), 8.46 (1H, s), 8.43 (1H, d, J = 2.8 Hz), 8.37 (1H, d, J = 8.8 Hz), 7.89 (1H, dd, J = 9.2, 2.8 Hz), 7.54 (1H, s), 7.42 (1H, s), 6.57 (1H, d, J = 5.2 Hz), 4.22 (2H, q, J = 6.8 Hz), 3.96 (3H, s), 3.95 (3H, s), 2.85 (3H, s), 1.44 (3H, t, J = 7.2 Hz); LCMS: 96.8%, MS (ESI): m/z 582.4 [M + H]+. |

TABLE 4-continued

Summarizes compounds 1-280 in terms of their structures and corresponding characteristics.

| # cpd | Structure | Characterization Data |
|---|---|---|
| 136 | 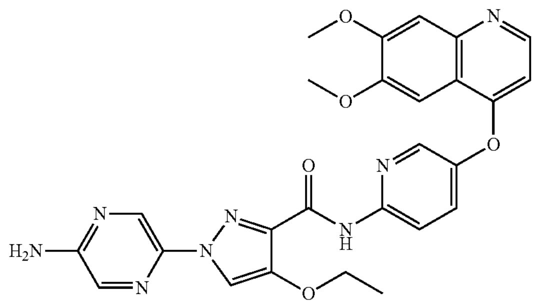 [SMILES: CCOc1cn(-c2cnc(N)cn2)nc1C(=O)Nc1ccc(Oc2ccnc3cc(OC)c(OC)cc23)cn1] | white powder; $^1$H-NMR (DMSO-d6, 400 MHz): δ 9.91 (1H, brs), 8.65 (1H, s), 8.50 (1H, d, J = 5.2 Hz), 8.42 (1H, d, J = 2.8 Hz), 8.37 (1H, d, J = 9.2 Hz), 8.34 (1H, s), 7.88 (1H, dd, J = 9.2, 2.8 Hz), 7.77 (1H, s), 7.55 (1H, s), 7.42 (1H, s), 6.74 (2H, brs), 6.56 (1H, d, J = 5.2 Hz), 4.20 (2H, q, J = 6.8 Hz), 3.96 (3H, s), 3.95 (3H, s), 1.42 (3H, t, J = 6.8 Hz); LCMS: 97.3%, MS (ESI): m/z 529.2 [M + H]+. |
| 137 | 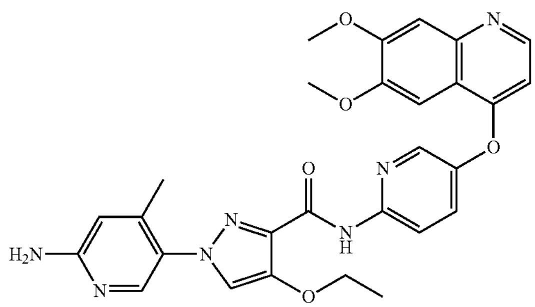 [SMILES: CCOc1cn(-c2cnc(N)cc2C)nc1C(=O)Nc1ccc(Oc2ccnc3cc(OC)c(OC)cc23)cn1] | off-white powder; $^1$H-NMR (DMSO-d6, 400 MHz): δ 9.69 (1H, brs), 8.50 (1H, d, J = 5.6 Hz), 8.40 (1H, d, J = 2.8 Hz), 8.36 (1H, d, J = 9.2 Hz), 8.02 (1H, s), 7.93 (1H, s), 7.87 (1H, dd, J = 9.2, 2.8 Hz), 7.54 (1H, s), 7.42 (1H, s), 6.56 (1H, d, J = 5.2 Hz), 6.40 (1H, s), 6.27 (2H, brs), 4.15 (2H, q, J = 6.8 Hz), 3.95 (3H, s), 3.94 (3H, s), 2.08 (3H, s), 1.42 (3H, t, J = 6.8 Hz); LCMS: 100%, MS (ESI): m/z 542.3 [M + H]+. |
| 138 | 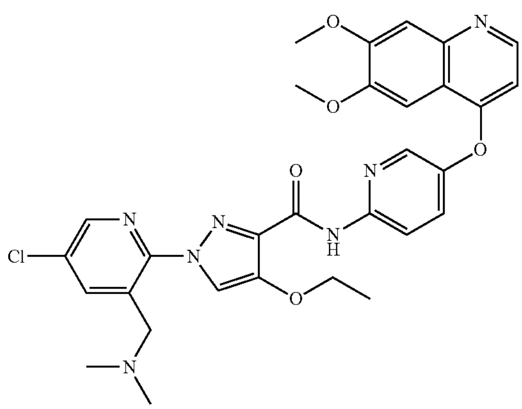 [SMILES: CCOc1cn(-c2ncc(Cl)cc2CN(C)C)nc1C(=O)Nc1ccc(Oc2ccnc3cc(OC)c(OC)cc23)cn1] | white powder; $^1$H-NMR (DMSO-d6, 400 MHz): δ 9.81 (1H, brs), 8.57 (1H, s), 8.50 (1H, d, J = 5.2 Hz), 8.34-8.47 (3H, m), 8.22 (1H, s), 7.89 (1H, dd, J = 8.8, 3.2 Hz), 7.54 (1H, s), 7.42 (1H, s), 6.56 (1H, d, J = 5.6 Hz), 4.17-4.30 (2H, m), 3.96 (3H, s), 3.95 (3H, s), 3.80 (2H, s), 2.16 (6H, s), 1.44 (3H, t, J = 6.8 Hz); LCMS: 95.8%, MS (ESI): m/z 604.5 [M + H]+. |
| 139 | 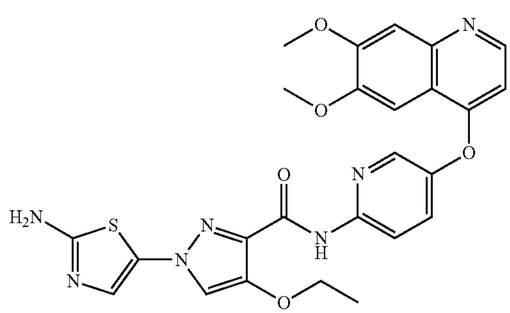 [SMILES: CCOc1cn(-c2cnc(N)s2)nc1C(=O)Nc1ccc(Oc2ccnc3cc(OC)c(OC)cc23)cn1] | white powder; $^1$H-NMR (DMSO-d6, 400 MHz): δ 9.77 (1H, brs), 8.51 (1H, d, J = 5.2 Hz0, 8.42 (1H, d, J = 3.2 Hz), 8.37 (1H, d, J = 9.2 Hz), 8.06 (1H, s), 7.89 (1H, dd, J = 9.2, 3.2 Hz), 7.55 (1H, s), 7.35-7.50 (3H, m), 6.75 (1H, s), 6.57 (1H, d, J = 5.2 Hz), 4.18 (2H, q, J = 7.2 Hz), 3.96 (3H, s), 3.95 (3H, s), 2.12 (3H, s), 1.42 (3H, t, J = 7.2 Hz); LCMS: 98.2%, MS (ESI): m/z 534.4 [M + H]+. |

TABLE 4-continued

Summarizes compounds 1-280 in terms of their structures and corresponding characteristics.

| # cpd | Structure | Characterization Data |
|---|---|---|
| 140 | 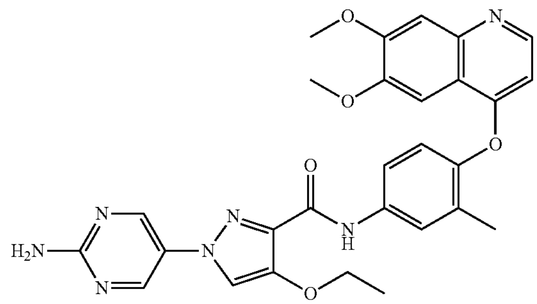 [SMILES: CCOc1cn(-c2cnc(N)nc2)nc1C(=O)Nc1ccc(Oc2ccnc3cc(OC)c(OC)cc23)c(C)c1] | white powder; ¹H-NMR (DMSO-d6, 400 MHz): δ 9.87 (1H, brs), 8.80 (2H, s), 8.45 (1H, d, J = 5.6 Hz), 8.34 (1H, s), 7.84 (1H, s), 7.75 (1H, d, J = 9.2 Hz), 7.58 (1H, s), 7.40 (1H, s), 7.19 (1H, d, J = 8.8 Hz), 7.00 (1H, brs), 6.31 (1H, d, J = 5.6 Hz), 4.09 (2H, q, J = 7.2 Hz), 3.96 (3H, s), 3.95 (3H, s), 2.12 (3H, s), 1.39 (3H, t, J = 6.8 Hz); LCMS: 99.3%, MS (ESI): m/z 542.3 [M + H]+. |
| 141 | 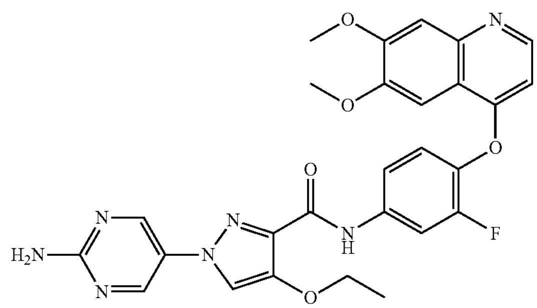 [SMILES: CCOc1cn(-c2cnc(N)nc2)nc1C(=O)Nc1ccc(Oc2ccnc3cc(OC)c(OC)cc23)c(F)c1] | pale white powder; ¹H-NMR (DMSO-d6, 400 MHz): δ 10.15 (1H, brs), 8.79 (2H, s), 8.48 (1H, d, J = 5.2 Hz), 8.34 (1H, s), 8.03 (1H, dd, J = 13.6, 2.8 Hz), 7.71 (1H, d, J = 9.2 Hz), 8.53 (1H, s), 7.46 (1H, t, J = 8.8 Hz), 7.40 (1H, s), 7.02 (2H, brs), 6.47 (1H, d, J = 5.2 Hz), 4.06 (2H, q, J = 6.8 Hz), 3.94 (6H, s), 1.37 (3H, t, J = 6.8 Hz); LCMS: 100%, MS (ESI): m/z 546.3 [M + H]+. |
| 142 | 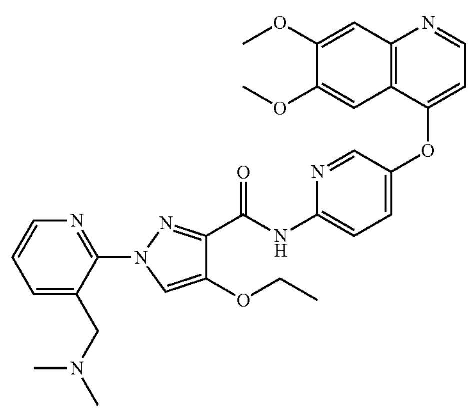 [SMILES: CCOc1cn(-c2ncccc2CN(C)C)nc1C(=O)Nc1ccc(Oc2ccnc3cc(OC)c(OC)cc23)cn1] | white powder; ¹H-NMR (DMSO-d6, 400 MHz): δ 9.78 (1H, brs), 8.46-8.52 (2H, m), 8.42 (1H, d, J = 2.8 Hz), 8.36-8.40 (2H, m), 8.10 (1H, dd, J = 8.0, 2.0 Hz), 7.88 (1H, dd, J = 9.2, 2.8 Hz), 7.51-7.57 (2H, m), 7.42 (1H, s), 6.57 (1H, d, J = 5.2 Hz), 4.22 (2H, q, J = 6.8 Hz), 3.96 (3H, s), 3.95 (3H, s), 3.77 (2H, s), 2.14 (6H, s), 1.44 (3H, t, J = 6.8 Hz); LCMS: 100%, MS (ESI): m/z 570.4 [M + H]+. |
| 143 | 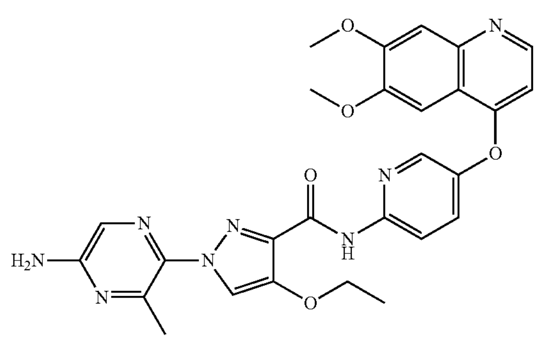 [SMILES: CCOc1cn(-c2ncc(N)nc2C)nc1C(=O)Nc1ccc(Oc2ccnc3cc(OC)c(OC)cc23)cn1] | white powder; ¹H-NMR (DMSO-d6, 400 MHz): δ 9.72 (1H, brs), 8.50 (1H, d, J = 5.2 Hz), 8.40 (1H, d, J = 2.8 Hz), 8.37 (1H, d, J = 9.2 Hz), 8.13 (1H, s), 7.87 (1H, dd, J = 9.2, 2.8 Hz), 7.63 (1H, s), 7.54 (1H, s), 7.42 (1H, s), 6.82 (2H, s), 6.56 (1H, d, J = 5.2 Hz), 4.17 (2H, q, J = 6.,8 Hz), 3.95 (3H, s), 3.94 (3H, s), 2.35 (3H, s), 1.42 (3H, t, J = 6.8 Hz); LCMS: 100%, MS (ESI): m/z 543.4 [M + H]+. |

TABLE 4-continued

Summarizes compounds 1-280 in terms of their structures and corresponding characteristics.

| # cpd | Structure | Characterization Data |
|---|---|---|
| 144 | 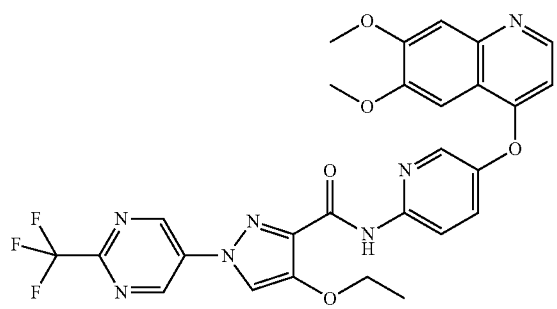 [SMILES: CCOc1cn(-c2cnc(C(F)(F)F)nc2)nc1C(=O)Nc1ccc(Oc2ccnc3cc(OC)c(OC)cc23)cn1] | white powder; ¹H-NMR (DMSO-d6, 400 MHz): δ 10.25 (1H, brs), 9.66 (2H, s), 8.80 (1H, s), 8.51 (1H, d, J = 5.2 Hz), 8.45 (1H, d, J = 3.2 Hz), 8.37 (1H, d, J = 8.8 Hz), 7.90 (1H, dd, J = 9.2, 3.2 Hz), 7.55 (1H, s), 7.42 (1H, s), 6.57 (1H, d, J = 5.2 Hz), 4.20 (2H, q, J = 6.8 Hz), 3.95 (3H, s), 3.96 (3H, s), 1.46 (3H, t, J = 7.2 Hz); LCMS: 99.0%, MS (ESI): m/z 582.3 [M + H]+. |
| 145 | 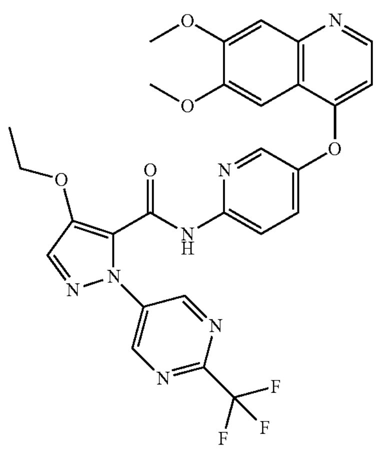 [SMILES: CCOc1cnn(-c2cnc(C(F)(F)F)nc2)c1C(=O)Nc1ccc(Oc2ccnc3cc(OC)c(OC)cc23)cn1] | pale yellow powder; ¹H-NMR (DMSO-d6, 400 MHz): δ 9.82 (1H, brs), 9.35 (2H, s), 8.50 (1H, d, J = 5.2 Hz), 8.46 (1H, d, J = 2.8 Hz), 8.26 (1H, s), 8.22 (1H, d, J = 8.8 Hz), 7.85 (1H, dd, J = 9.2, 3.2 Hz), 7.54 (1H, s), 7.42 (1H, s), 6.54 (1H, d, J = 2.8 Hz), 4.45 (2H, q, J = 7.2 Hz), 3.96 (3H, s), 3.95 (3H, s), 1.50 (3H, t, J = 6.8 Hz); LCMS: 97.6%, MS (ESI): m/z 582.4 [M + H]+. |
| 146 | 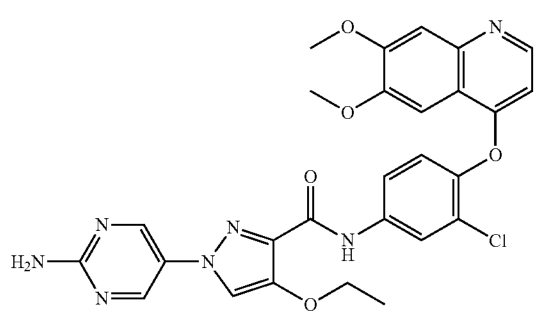 [SMILES: CCOc1cn(-c2cnc(N)nc2)nc1C(=O)Nc1ccc(Oc2ccnc3cc(OC)c(OC)cc23)c(Cl)c1] | white powder.; ¹H-NMR (DMSO-d6, 400 MHz): δ 10.14 (1H, brs), 8.81 (2H, s), 8.48 (1H, d, J = 4.8 Hz), 8.35 (1H, s), 8.23 (1H, d, J = 2.4 Hz), 7.88 (1H, dd, J = 9.2, 2.4 Hz), 7.54 (1H, s), 7.46 (1H, d, J = 8.8 Hz), 7.41 (1H, s), 7.02 (2H, brs), 6.38 (1H, d, J = 5.2 Hz), 4.07 (2H, q, J = 6.8 Hz), 3.95 (6H, s), 1.38 (3H, t, J = 6.8 Hz); LCMS: 98.6%, MS (ESI): m/z 562.4 [M + H]+. |
| 147 | 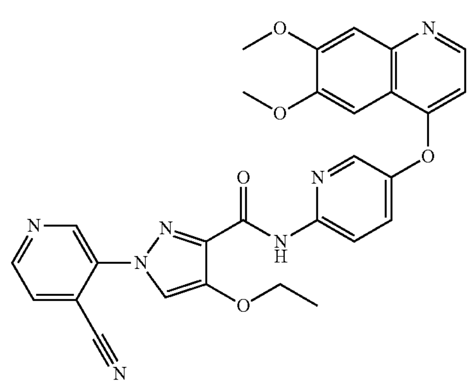 [SMILES: CCOc1cn(-c2cnccc2C#N)nc1C(=O)Nc1ccc(Oc2ccnc3cc(OC)c(OC)cc23)cn1] | white powder; ¹H-NMR (DMSO-d6, 400 MHz): δ 9.83 (1H, brs), 9.29 (1H, s), 8.86 (1H, d, J = 4.8 Hz), 8.55-8.70 (2H, m), 8.48 (1H, d, J = 2.8 Hz), 8.40 (1H, d, J = 8.8 Hz), 8.13 (1H, d, J = 4.8 Hz) 7.90-8.00 (1H, m), 7.63 (1H, s), 7.48 (1H, s), 7.40 (1H, s), 6.74 (1H, d, J = 5.6 Hz), 4.20 (2H, q, J = 6.8 Hz), 3.99 (3H, s), 3.98 (3H, s), 1.46 (3H, t, J = 6.8 Hz); LCMS: 100%, MS (ESI): m/z 538.3 [M + H]+. |

TABLE 4-continued

Summarizes compounds 1-280 in terms of their structures and corresponding characteristics.

| # cpd | Structure | Characterization Data |
|---|---|---|
| 148 | 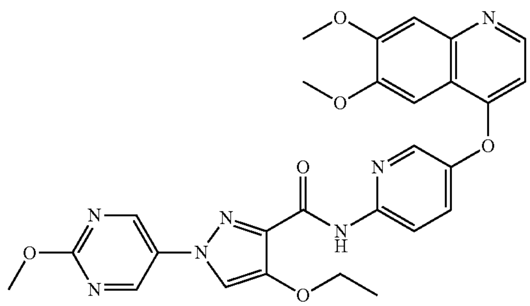 [SMILES: CCOc1cn(-c2cnc(OC)nc2)nc1C(=O)Nc1ccc(Oc2ccnc3cc(OC)c(OC)cc23)cn1] | white powder; ¹H-NMR (DMSO-d6, 400 MHz): δ 10.00 (1H, brs), 9.18 (2H, s), 8.57 (1H, s), 8.50 (1H, d, J = 5.2 Hz), 8.43 (1H, d, J = 2.8 Hz), 8.37 (1H, d, J = 8.8 Hz), 7.89 (1H, dd, J = 8.8, 2.8 Hz), 7.54 (1H, s), 7.42 (1H, s), 6.56 (1H, d, J = 5.2 Hz), 4.18 (2H, q, J = 7.2 Hz), 3.99 (3H, s), 3.95 (3H, s), 3.94 (3H, s), 1.44 (3H, t, J = 7.2 Hz); LCMS: 100%, MS (ESI): m/z 544.4 [M + H]+. |
| 149 | 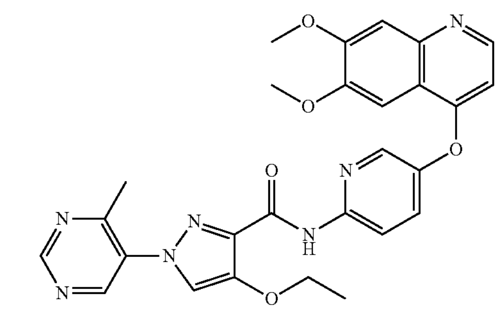 [SMILES: CCOc1cn(-c2cncnc2C)nc1C(=O)Nc1ccc(Oc2ccnc3cc(OC)c(OC)cc23)cn1] | white powder; ¹H-NMR (DMSO-d6, 400 MHz): δ 9.95 (1H, brs), 9.16 (1H, s), 8.97 (1H, s), 8.73 (1H, d, J = 6.0 Hz), 8.50 (1H, d, J = 2.8 Hz), 8.41 (1H, d, J = 8.8 Hz), 8.34 (1H, s), 7.97 (1H, dd, J = 8.8, 2.8 Hz), 7.70 (1H, s), 7.51 (1H, s), 6.88 (1H, d, J = 5.6 Hz), 4.18 (2H, q, J = 6.8 Hz), 4.02 (3H, s), 4.01 (3H, s), 2.60 (3H, s), 1.44 (3H, t, J = 7.2 Hz); LCMS: 99.2%, MS (ESI): m/z 528.4 [M + H]+. |
| 150 | 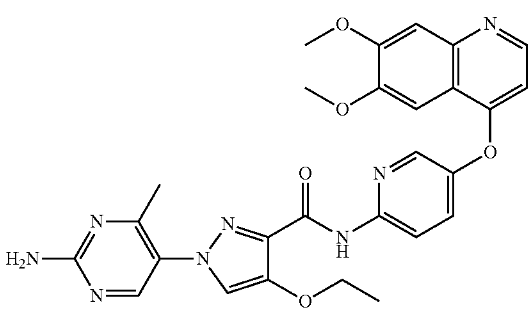 [SMILES: CCOc1cn(-c2cnc(N)nc2C)nc1C(=O)Nc1ccc(Oc2ccnc3cc(OC)c(OC)cc23)cn1] | white powder; ¹H-NMR (DMSO-d6, 400 MHz): δ 9.74 (1H, brs), 8.50 (1H, d, J = 5.2 Hz), 8.41 (1H, d, J = 2.8 Hz), 8.36 (1H, d, J = 8.8 Hz), 8.27 (1H, s), 8.08 (1H, s), 7.87 (1H, dd, J = 9.2, 3.2 Hz), 7.54 (1H, s), 7.42 (1H, s), 7.05 (2H, brs), 6.56 (1H, d, J = 5.6 Hz), 4.15 (2H, q, J = 7.2 Hz), 3.95 (3H, s), 3.94 (3H, s), 2.20 (3H, s), 1.42 (3H, t, J = 7.2 Hz); LCMS: 100%, MS (ESI): m/z 543.4 [M + H]+. |
| 151 | 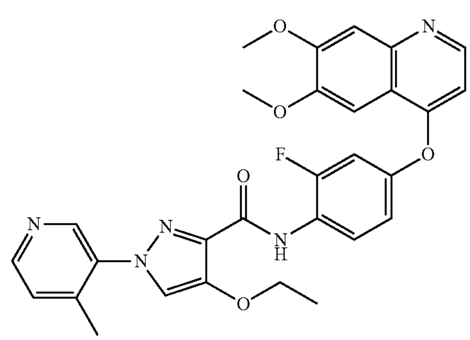 [SMILES: CCOc1cn(-c2cnccc2C)nc1C(=O)Nc1ccc(Oc2ccnc3cc(OC)c(OC)cc23)cc1F] | off-white powder; ¹H-NMR (DMSO-d6, 400 MHz): δ 9.58 (1H, brs), 8.65 (1H, s), 8.56 (1H, d, J = 5.2 Hz), 8.52 (1H, d, J = 5.2 Hz), 8.18-8.27 (2H, m), 7.48-7.53 (2H, m), 7.40-7.46 (2H, m), 7.17 (1H, d, J = 8.8 Hz), 6.59 (1H, d, J = 5.2 Hz), 4.15 (2H, q, J = 6.8 Hz), 3.95 (3H, s), 3.93 (3H, s), 2.36 (3H, s), 1.42 (3H, t, J = 6.8 Hz); LCMS: 100%, MS (ESI): m/z 544.3 [M + H]+. |
| 152 | 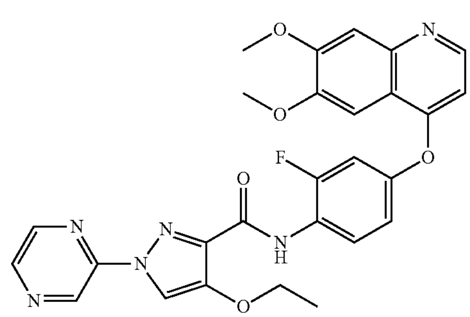 [SMILES: CCOc1cn(-c2cnccn2)nc1C(=O)Nc1ccc(Oc2ccnc3cc(OC)c(OC)cc23)cc1F] | off-white powder; ¹H-NMR (CDCl3, 400 MHz): δ 9.52 (1H, brs), 9.40 (1H, d, J = 3.2 Hz), 8.75 (1H, t, J = 8.8 Hz), 8.58-8.51 (2H, m), 8.38 (1H, s), 8.27 (1H, s), 7.53 (1H, s), 7.47 (1H, s), 7.00-7.10 (2H, m), 6.56 (1H, d, J = 5.2 Hz), 4.25 (2H, q, J = 6.8 Hz), 4.06 (6H, s), 1.58-0-1.58 (3H, m, overlapped with H2O peak); LCMS: 100%, MS (ESI): m/z 531.2 [M + H]+. |

TABLE 4-continued

Summarizes compounds 1-280 in terms of their structures and corresponding characteristics.

| # cpd | Structure | Characterization Data |
|---|---|---|
| 153 | 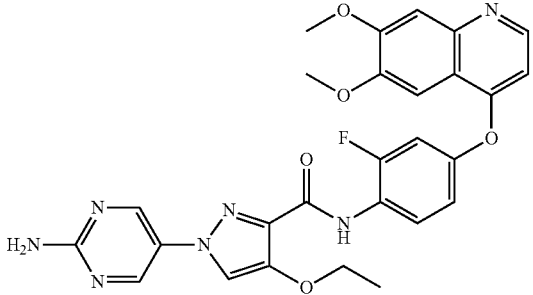 [SMILES: CCOc1cn(-c2cnc(N)nc2)nc1C(=O)Nc1ccc(Oc2ccnc3cc(OC)c(OC)cc23)cc1F] | brown powder; ¹H-NMR (DMSO-d6, 400 MHz): δ 9.59 (1H, brs), 8.74 (2H, s), 8.52 (1H, d, J = 5.2 Hz), 8.40 (1H, s), 8.21 (1H, t, J = 8.4 Hz), 7.49 (1H, s), 7.40-7.46 (2H, m), 7.15-7.20 (1H, m), 7.03 (2H, brs), 6.59 (1H, d, J = 5.2 Hz), 4.14 (2H, q, J = 6.8 Hz), 3.95 (3H, s), 3.93 (3H, s), 1.42 (3H, t, J = 6.8 Hz); LCMS: 95.7%, MS (ESI): m/z 546.2 [M + H]+. |
| 154 | 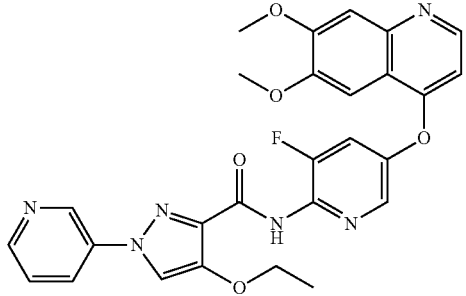 [SMILES: CCOc1cn(-c2cccnc2)nc1C(=O)Nc1ncc(Oc2ccnc3cc(OC)c(OC)cc23)cc1F] | white powder; ¹H-NMR (DMSO-d6, 400 MHz): δ 10.31 (1H, brs), 9.25 (1H, d, J = 2.4 Hz), 8.62 (1H, s), 8.55-8.60 (2H, m), 8.35-8.41 (2H, m), 8.06 (1H, dd, J = 10.0, 2.8 Hz), 7.61 (1H, dd, J = 8.4, 5.2 Hz), 7.52 (1H, s), 7.44 (1H, s), 6.70 (1H, d, J = 5.2 Hz), 4.12 (2H, q, J = 6.8 Hz), 3.96 (3H, s), 3.94 (3H, s), 1.39 (3H, t, J = 6.8 Hz); LCMS: 100%, MS (ESI): m/z 531.4 [M + H]+. |
| 155 | 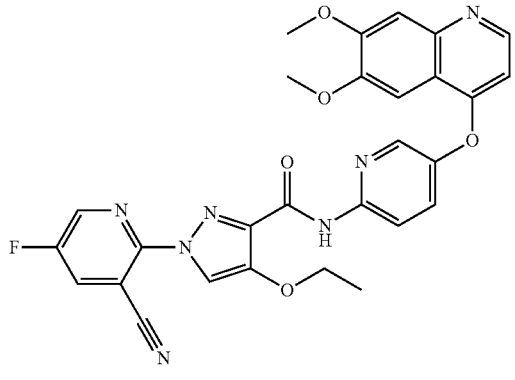 [SMILES: CCOc1cn(-c2ncc(F)cc2C#N)nc1C(=O)Nc1ccc(Oc2ccnc3cc(OC)c(OC)cc23)cn1] | white powder; ¹H-NMR (DMSO-d6, 400 MHz): δ 9.69 (1H, brs), 8.89 (1H, d, J = 2.8 Hz), 8.75 (1H, dd, J = 8.4, 2.8 Hz), 8.58 (1H, d, J = 5.6 Hz), 8.53 (1H, s), 6.46 (1H, d, J = 2.8 Hz), 8.39 (1H, d, J = 9.2 Hz), 7.93 (1H, dd, J = 9.6, 3.2 Hz), 7.60 (1H, s), 7.44 (1H, s), 6.69 (1H, d, J = 5.2 Hz), 4.21 (2H, q, J = 6.8 Hz), 3.98 (3H, s), 3.97 (3H, s), 1.42 (3H, t, J = 7.2 Hz); LCMS: 97.4%, MS (ESI): m/z 556.2 [M + H]+. |
| 156 | 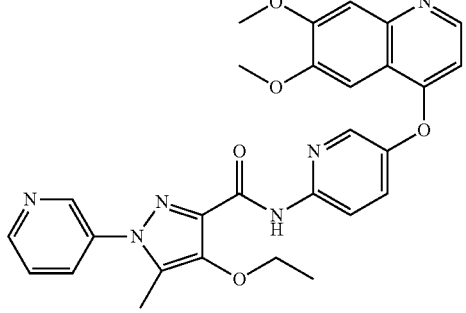 | off-white powder; ¹H-NMR (DMSO-d6, 400 MHz): δ 10.04 (1H, brs), 8.96 (1H, d, J = 2.4 Hz), 8.70 (1H, d, J = 4.8 Hz), 8.50 (1H, d, J = 5.2 Hz), 8.42 (1H, d, J = 2.8 Hz), 8.36 (1H, d, J = 9.2 Hz), 8.19 (1H, d, J = 8.4 Hz), 7.87 (1H, dd, J = 8.8, 2.8 Hz), 7.64 (1H, dd, J = 8.4, 5.2 Hz), 7.54 (1H, s), 7.42 (1H, s), 6.57 (1H, d, J = 5.2 Hz), 4.17 (2H, q, J = 6.8 Hz), 3.95 (3H, s), 3.94 (3H, s), 2.35 (3H, s), 1.35 (3H, t, J = 6.8 Hz); LCMS: 100%, MS (ESI): m/z 527.3 [M + H]+. |

TABLE 4-continued

Summarizes compounds 1-280 in terms of their structures and corresponding characteristics.

| # cpd | Structure | Characterization Data |
|---|---|---|
| 157 | 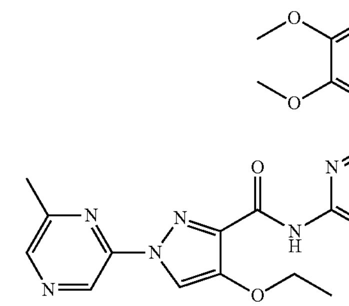 | white powder; ¹H-NMR (CDCl3, 400 MHz): δ 9.57 (1H, brs), 9.27 (1H, s), 8.59 (1H, d, J = 9.2 Hz), 8.54 (1H, d, J = 5.2 Hz), 8.42 (1H, s), 8.29 (1H, d, J = 2.8 Hz), 8.27 (1H, s), 7.62 (1H, dd, J = 8.8, 2.4 Hz), 7.57 (1H, s), 7.48 (1H, s), 6.50 (1H, d, J = 5.2 Hz), 4.25 (2H, q, J = 6.8 Hz), 4.07 (6H, s), 2.61 (3H, s), 1.60 (3H, t, J = 7.2 Hz); LCMS: 99.3%, MS (ESI): m/z 528.3 [M + H]+. |
| 158 | 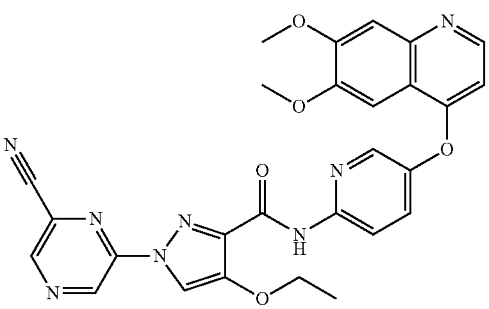 [SMILES: CCOc1cn(-c2cncc(C#N)n2)nc1C(=O)Nc1ccc(Oc2ccnc3cc(OC)c(OC)cc23)cn1] | white solid; ¹H-NMR (CDCl3, 400 MHz): δ 9.70 (1H, brs), 9.56 (1H, s), 8.84 (1H, s), 8.57 (1H, d, J = 8.8 Hz), 8.53 (1H, d, J = 5.2 Hz), 8.30 (1H, d, J = 2.8 Hz), 8.23 (1H, s), 7.63 (1H, dd, J = 9.2, 2.8 Hz), 7.55 (1H, s), 7.46 (1H, s), 6.48 (1H, d, J = 5.2 Hz), 4.28 (2H, q, J = 6.8 Hz), 4.07 (6H, s), 1.63 (3H, t, J = 6.8 Hz); LCMS: 100%, MS (ESI): m/z 539.2 [M + H]+. |
| 159 | 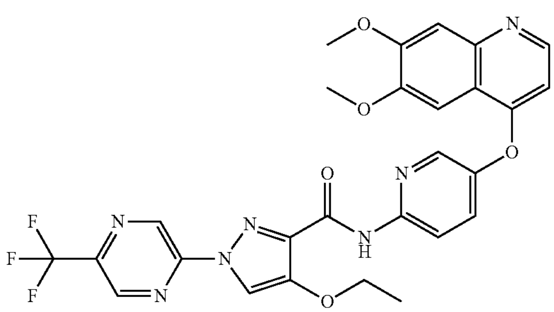 [SMILES: CCOc1cn(-c2cnc(C(F)(F)F)cn2)nc1C(=O)Nc1ccc(Oc2ccnc3cc(OC)c(OC)cc23)cn1] | pale yellow powder; ¹H-NMR (DMSO-d6, 400 MHz): δ 10.32 (1H, brs), 9.60 (1H, s), 9.10 (1 H, s), 8.62 (1H, s), 8.51 (1H, d, J = 5.2 Hz), 8.46 (1H, d, J = 2.8 Hz), 8.70 (1H, d, J = 8.8 Hz), 7.91 (1H, dd, J = 8.8, 2.8 Hz), 7.55 (1H, s), 7.42 (1H, s), 6.58 (1H, d, J = 5.6 Hz), 4.25 (2H, q, J = 7.2 Hz), 3.96 (3H, s), 3.95 (3H, s), 1.42 (3H, t, J = 7.2 Hz); LCMS: 98.4%, MS (ESI): m/z 582.2 [M + H]+. |
| 160 | 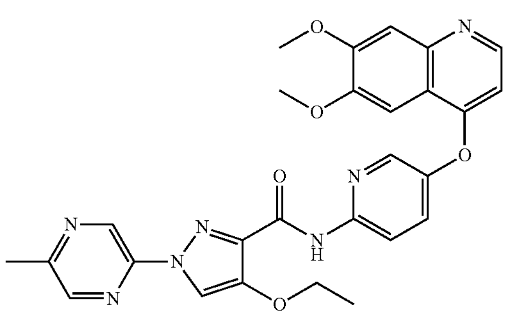 [SMILES: CCOc1cn(-c2cnc(C)cn2)nc1C(=O)Nc1ccc(Oc2ccnc3cc(OC)c(OC)cc23)cn1] | white powder; ¹H-NMR (CDCl3, 400 MHz): δ 9.59 (1H, brs), 9.36 (1H, s), 8.60 (1H, d, J = 9.2 Hz), 8.53 (1H, d, J = 5.2 Hz), 8.30 (1H, d, J = 2.8 Hz), 8.21-8.26 (2H, m), 7.63 (1H, dd, J = 9.2, 2.8 Hz), 7.57 (1H, s), 7.49 (1H, s), 6.50 (1H, d, J = 5.2 Hz), 4.25 (2H, q, J = 6.8 Hz), 4.08 (6H, s), 2.64 (3H, s), 1.58 (3H, t, J = 6.8 Hz); LCMS: 98.4%, MS (ESI): m/z 528.1 [M + H]+. |
| 161 | 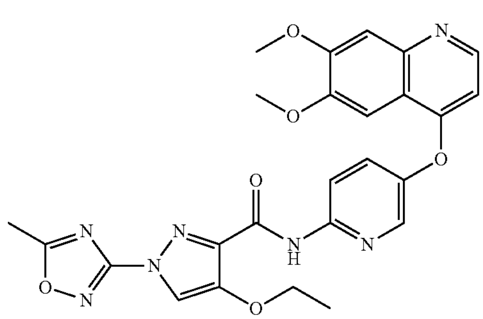 [SMILES: CCOc1cn(-c2noc(C)n2)nc1C(=O)Nc1ccc(Oc2ccnc3cc(OC)c(OC)cc23)cn1] | pale-yellow powder; ¹H-NMR (DMSO-d6, 400 MHz): δ 9.98 (1H, brs), 8.50 (1H, d, J = 5.2 Hz), 8.41-8.46 (2H,m), 8.35 (1H, d, J = 9.2 Hz), 7.89 (1H, dd, J = 9.2, 2.8 Hz), 7.54 (1H, s), 7.42 (1H, s), 6.57 (1H, d, J = 5.2 Hz), 4.22 (2H, q, J = 6.8 Hz), 3.96 (3H, s), 3.95 (3H, s), 2.71 (3H, s), 1.42 (3H, t, J = 6.8 Hz); LCMS: 100%, MS (ESI): m/z 518.1 [M + H]+. |

TABLE 4-continued

Summarizes compounds 1-280 in terms of their structures and corresponding characteristics.

| # cpd | Structure | Characterization Data |
|---|---|---|
| 162 | 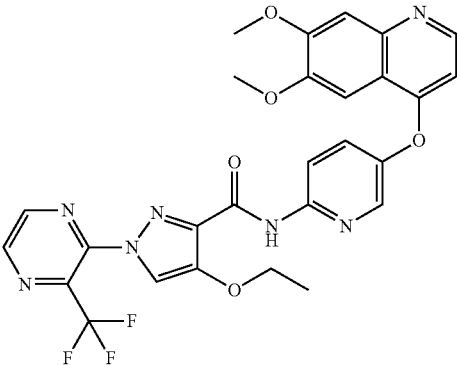 [SMILES: CCOc1cn(-c2nccnc2C(F)(F)F)nc1C(=O)Nc1ccc(Oc2ccnc3cc(OC)c(OC)cc23)cn1] | white powder; ¹H-NMR (CDCl3, 400 MHz): δ 9.41 (1H, brs), 8.73 (1H, d, J = 2.4 Hz), 8.67 (1H, d, J = 2.0 Hz), 8.56 (1H, d, J = 9.2 Hz), 8.52 (1H, d, J = 5.2 Hz), 8.29 (1H, d, J = 2.8 Hz), 8.06 (1H, s), 7.60 (1H, dd, J = 9.2, 2.8 Hz), 7.56 (1H, s), 7.45 (1H, s), 6.48 (1H, d, J = 5.2 Hz), 4.21 (2H, q, J = 6.8 Hz), 4.07 (3H, s), 4.06 (3H, s), 1.58 (3H, t, J = 6.8 Hz); LCMS: 97.8%, MS (ESI): m/z 582.1 [M + H]+. |
| 163 | 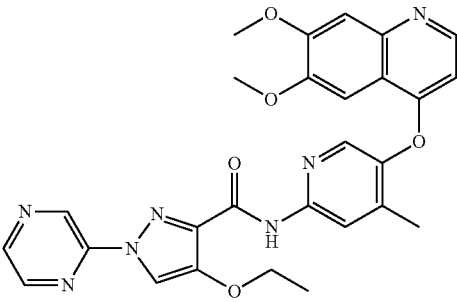 [SMILES: CCOc1cn(-c2cnccn2)nc1C(=O)Nc1cc(C)c(Oc2ccnc3cc(OC)c(OC)cc23)cn1] | white powder; ¹H-NMR (CDCl3, 400 MHz): δ 9.50 (1H, brs), 9.49 (1H, s), 8.56 (1H, d, J = 2.4 Hz), 8.45-8.55 (2H, m), 8.39 (1H, s), 8.25 (1H, s), 8.16 (1H, s), 7.61 (1H, s), 7.49 (1H, s), 6.33 (1H, d, J = 5.2 Hz), 4.24 (2H, q, J = 6.8 Hz), 4.09 (3H, s), 4.07 (3H, s), 2.26 (3H, s), 1.60 (3H, t, J = 6.8 Hz); LCMS: 100%, MS (ESI): m/z 528.3 [M + H]+. |
| 164 | 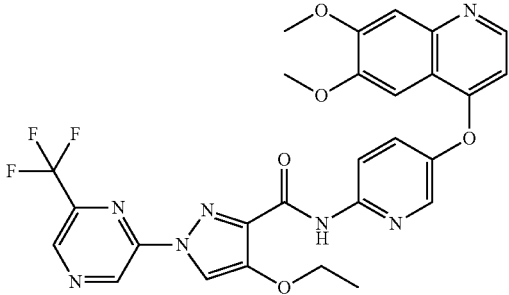 [SMILES: CCOc1cn(-c2cncc(C(F)(F)F)n2)nc1C(=O)Nc1ccc(Oc2ccnc3cc(OC)c(OC)cc23)cn1] | white powder; ¹H-NMR (CDCl3, 400 MHz): δ 9.71 (1H, brs), 9.58 (1H, s), 8.89 (1 H, s), 8.58 (1H, d, J = 8.8 Hz), 8.53 (1H, d, J = 5.2 Hz), 8.30 (1H, d, J = 2.4 Hz), 8.26 (1H, s), 7.63 (1H, dd, J = 9.2, 2.8 Hz), 7.56 (1H, s), 7.46 (1H, s), 6.49 (1H, d, J = 5.2 Hz), 4.29 (2H, q, J = 7.2 Hz), 4.07 (6H, s0, 1.62 (3H, t, J = 7.2 Hz); LCMS: 100%, MS (ESI): m/z 582.1 [M + H]+. |
| 165 | 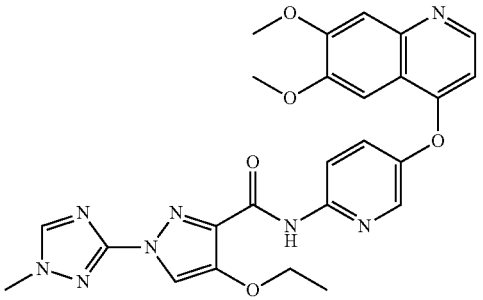 [SMILES: CCOc1cn(-c2ncn(C)n2)nc1C(=O)Nc1ccc(Oc2ccnc3cc(OC)c(OC)cc23)cn1] | white powder; ¹H-NMR (CDCl3, 400 MHz): δ 9.54 (1H, brs), 8.56 (1H, d, J = 9.2 Hz), 8.52 (1H, d, J = 5.2 Hz), 8.25 (1H, d, J = 2.8 Hz), 8.02 (1H, s), 7.93 (1H, s), 7.57 (1H, dd, J = 8.8, 3.2 Hz), 7.56 (1H, s), 7.44 (1H, s), 6.48 (1H, d, J = 5.2 Hz), 4.17 (2H, q, J = 7.2 Hz), 4.06 (6H, s), 4.00 (3H, s), 1.55 (3H, t, J = 6.8 Hz); LCMS: 96.7%, MS (ESI): m/z 517.3 [M + H]+. |

TABLE 4-continued

Summarizes compounds 1-280 in terms of their structures and corresponding characteristics.

| # cpd | Structure | Characterization Data |
|---|---|---|
| 166 | 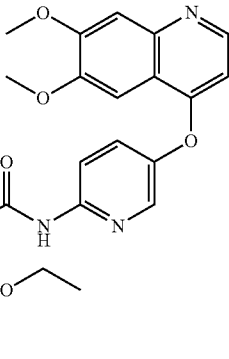 | pale-yellow powder; ¹H-NMR (CDCl3, 400 MHz): δ 9.48 (1H, brs), 9.24 (1H, s), 8.69 (1H, s), 8.57 (1H, d, J = 9.2 Hz), 8.52 (1H, d, J = 5.6 Hz), 8.26 (1H, d, J = 2.8 Hz), 7.60 (1H, dd, J = 8.8, 2.8 Hz), 7.55 (1H, s), 7.44 (1H, s), 7.39 (1H, s), 6.47 (1H, d, J = 5.2 Hz), 4.20 (2H, q, J = 6.8 Hz), 4.07 (3H, s), 4.06 (3H, s), 3.17-3.27 (1H, m), 1.60 (3H, t, J = 6.8 Hz), 1.30 (6H, d, J = 6.8 Hz); LCMS: 97.3%, MS (ESI): m/z 556.4 [M + H]+. |
| 167 | 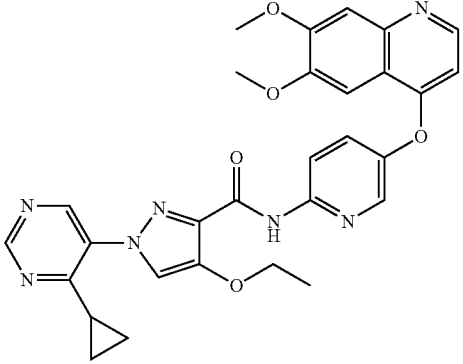 [SMILES: CCOc1cn(-c2cncnc2C2CC2)nc1C(=O)Nc1ccc(Oc2ccnc3cc(OC)c(OC)cc23)cn1] | pale-yellow powder; ¹H-NMR (DMSO-d6, 400 MHz): δ 9.87 (1H, brs), 9.10 (1H, s), 8.85 (1H, s), 8.50 (1H, d, J = 5.2 Hz), 8.42 (1H, d, J = 2.8 Hz), 8.36 (1H, d, J = 9.2 Hz), 8.32 (1H, s), 7.88 (1H, dd, J = 9.2, 2.8 Hz), 7.54 (1H, s), 7.42 (1H, s), 6.56 (1H, d, J = 5.2 Hz), 4.19 (2H, q, J = 6.8 Hz), 3.95 (3H, s), 3.94 (3H, s), 2.19-2.28 (1H, m), 1.44 (3H, t, J = 6.8 Hz), 1.14-1.21 (4H, m); LCMS: 97.6%, MS (ESI): m/z 554.3 [M + H]+. |
| 168 | 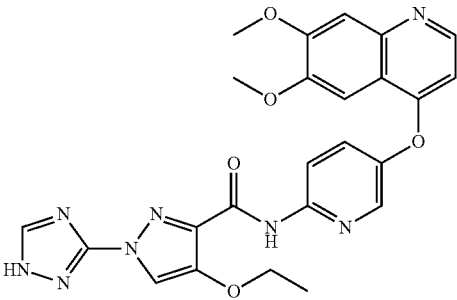 | white powder; ¹H-NMR (DMSO-d6, 400 MHz): δ 9.78 (1H, brs), 8.65 (1H, brs), 8.49 (1H, d, J = 5.6 Hz), 8.41 (1H, d, J = 3.2 Hz), 8.36 (1H, d, J = 8.8 Hz), 8.33 (1H, s), 7.88 (1H, dd, J = 8.8, 2.8 Hz), 7.53 (1H, s), 7.41 (1H, s), 6.55 (1H, d, J = 5.2 Hz), 4.21 (2H, q, J = 6.8 Hz), 3.94 (3H, s), 3.93 (3H, s), 1.41 (3H, t, J = 6.8 Hz); LCMS: 92.3%, MS (ESI): m/z 503.4 [M + H]+. |
| 169 | 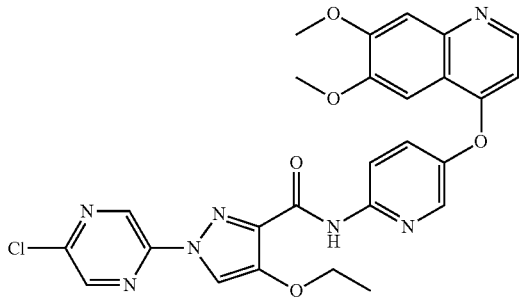 [SMILES: CCOc1cn(-c2cnc(Cl)cn2)nc1C(=O)Nc1ccc(Oc2ccnc3cc(OC)c(OC)cc23)cn1] | off-white solid; ¹H-NMR (CDCl3, 400 MHz): δ 9.55 (1H, brs), 9.25 (1H, d, J = 1.2 Hz), 8.57 (1H, d, J = 8.8 Hz), 8.53 (1H, d, J = 5.2 Hz), 8.38 (1H, d, J = 1.6 Hz), 8.29 (1H, d, J = 2.8 Hz), 8.19 (1H, s), 7.62 (1H, dd, J = 9.2, 2.8 Hz), 7.56 (1H, s), 7.44 (1H, s), 6.48 (1H, d, J = 5.2 Hz), 4.25 (2H, q, J = 6.8 Hz), 4.07 (3H, s), 4.06 (3H, s), 1.60 (3H, t, J = 6.8 Hz); LCMS: 99.0%, MS (ESI): m/z 548.3 [M + H]+. |

TABLE 4-continued

Summarizes compounds 1-280 in terms of their structures and corresponding characteristics.

| # cpd | Structure | Characterization Data |
|---|---|---|
| 170 | 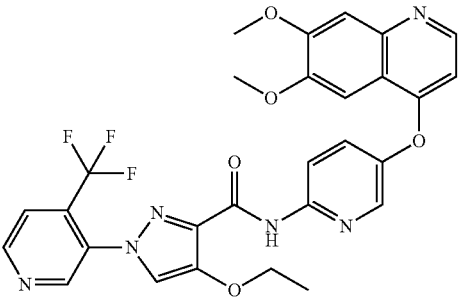 [SMILES: CCOc1cn(-c2cnccc2C(F)(F)F)nc1C(=O)Nc1ccc(Oc2ccnc3cc(OC)c(OC)cc23)cn1] | white powder; ¹H-NMR (CDCl3, 400 MHz): δ 9.49 (1H, brs), 8.95 (1H, s), 8.92 (1H, d, J = 5.2 Hz), 8.57 (1H, d, J = 9.2 Hz), 8.52 (1H, d, J = 5.2 Hz), 8.26 (1H, d, J = 2.8 Hz), 7.73 (1H, d, J = 4.8 Hz), 7.60 (1H, dd, J = 9.2, 2.8 Hz), 7.56 (1H, s), 7.49 (1H, s), 7.44 (1H, s), 6.47 (1H, d, J = 5.2 Hz), 4.19 (2H, q, J = 6.8 Hz), 4.07 (3H, s), 4.06 (3H, s), 1.58 (3H, t, J = 6.8 Hz); LCMS: 94.9%, MS (ESI): m/z 581.3 [M + H]+. |
| 171 | 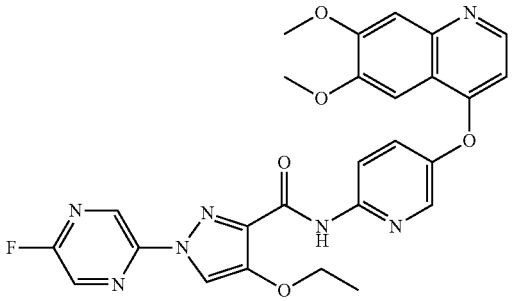 [SMILES: CCOc1cn(-c2cnc(F)cn2)nc1C(=O)Nc1ccc(Oc2ccnc3cc(OC)c(OC)cc23)cn1] | white powder; ¹H-NMR (CDCl3, 400 MHz): δ 9.57 (1H, brs), 9.08 (1H, s), 8.60 (1H, d, J = 8.8 Hz), 8.54 (1H, d, J = 5.2 Hz), 8.30 (1H, d, J = 2.4 Hz), 8.23 (1H, d, J = 8.0 Hz), 8.18 (1H, s), 7.63 (1H, dd, J = 9.2, 2.8 Hz), 7.58 (2H, s), 6.53 (1H, d, J = 5.6 Hz), 4.25 (2H, q, J = 6.8 Hz), 4.09 (3H, s), 4.08 (3H, s), 1.61 (3H, t, J = 6.8 Hz); LCMS: 92.8%, MS (ESI): m/z 532.3 [M + H]+. |
| 172 | 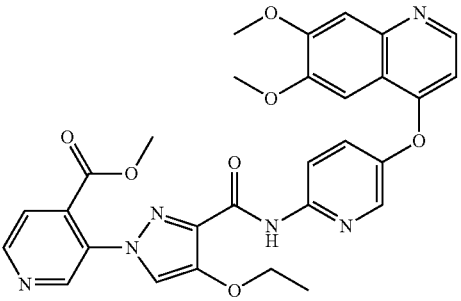 [SMILES: CCOc1cn(-c2cnccc2C(=O)OC)nc1C(=O)Nc1ccc(Oc2ccnc3cc(OC)c(OC)cc23)cn1] | white powder; ¹H-NMR (DMSO-d6, 400 MHz): δ 9.63 (1H, brs), 9.10 (1H, s), 8.79 (1H, d, J = 4.8 Hz), 8.53 (1H, s), 8.50 (1H, d, J = 5.2 Hz), 8.42 (1H, d, J = 3.2 Hz), 8.36 (1H, d, J = 8.8 Hz), 7.88 (1H, dd, J = 8.8, 2.8 H), 7.70 (1H, d, J = 4.8 Hz), 7.54 (1H, s), 7.42 (1H, s), 6.56 (1H, d, J = 4.8 Hz), 4.21 (2H, q, J = 6.8 Hz), 3.95 (3H, s), 3.94 (3H, s), 3.81 (3H, s), 1.45 (3H, t, J = 6.8 Hz); LCMS: 99.1%, MS (ESI): m/z 571.4 [M + H]+. |
| 173 | 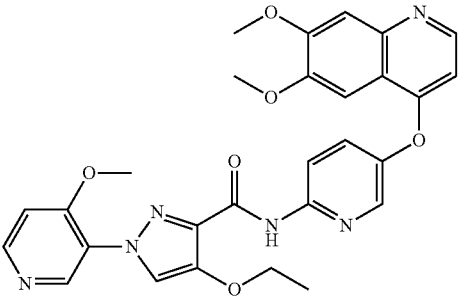 [SMILES: CCOc1cn(-c2cnccc2OC)nc1C(=O)Nc1ccc(Oc2ccnc3cc(OC)c(OC)cc23)cn1] | white powder; ¹H-NMR (DMSO-d6, 400 MHz): δ 9.88 (1H, s), 8.77 (1H, s), 8.54 (1H, d, J = 5.6 Hz), 8.50 (1H, d, J = 5.2 Hz), 8.41 (1H, d, J = 3.2 Hz), 8.36 (1H, d, J = 8.8 Hz), 8.17 (1H, s), 7.89 (1H, dd, J = 9.2, 2.8 Hz), 7.54 (1H, s), 7.42 (1H, s), 7.36 (1H, d, J = 6.0 Hz), 6.56 (1H, d, J = 5.2 Hz), 4.16 (2H, q, J = 7.2 Hz), 3.98 (3H, s), 3.95 (3H, s), 3.94 (3H, s), 1.42 (3H, t, J = 7.2 Hz); LCMS: 100%, MS (ESI): m/z 543.4 [M + H]+. |

TABLE 4-continued

Summarizes compounds 1-280 in terms of their structures and corresponding characteristics.

| # cpd | Structure | Characterization Data |
|---|---|---|
| 174 | 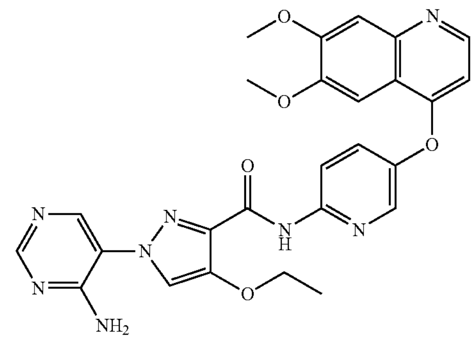 | yellow powder; ¹H-NMR (CDCl3, 400 MHz): δ 10.56 (1H, brs), 8.51 (1H, d, J = 5.2 Hz), 8.45 (1H, s), 8.40-8.45 (2H, m), 8.36 (1H, d, J = 9.2 Hz0, 8.29 (1H, s), 7.87 (1H, dd, J = 8.8, 2.8 Hz), 7.66 (2H, brs), 7.55 (1H, s), 7.42 (1H, s), 6.57 (1H, d, J = 5.2 Hz), 4.13 (2H, q, J = 6.8 Hz), 3.96 (3H, s), 3.95 (3H, s), 1.41 (3H, t, J = 7.2 Hz); LCMS: 98.9%, MS (ESI): m/z 592.3 [M + H]+. |
| 175 | 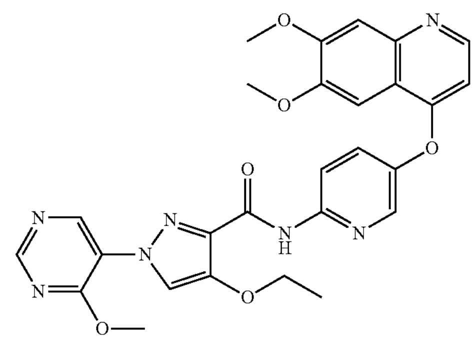 | white powder; ¹H-NMR (DMSO-d6, 400 MHz): δ 10.00 (1H, brs), 9.06 (1H, s), 8.86 (1H, s), 8.50 (1H, d, J = 5.2 Hz), 8.43 (1H, d, J= 2.8 Hz), 8.36 (1H, d, J = 9.2 Hz), 8.26 (1H, s), 7.89 (1H, dd, J = 9.2, 3.2 Hz), 7.54 (1H, s), 7.42 (1H, s), 6.57 (1H, d, J = 5.2 Hz), 4.17 (2H, q, J = 7.2 Hz), 4.11 (3H, s), 3.95 (3H, s), 3.94 (3H, s), 1.42 (3H, t, J = 7.2 Hz); LCMS: 93.8%, MS (ESI): m/z 544.4 [M + H]+. |
| 176 | 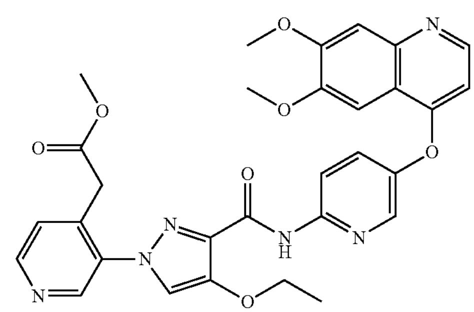 [SMILES: CCOc1cn(-c2cnccc2CC(=O)OC)nc1C(=O)Nc1ccc(Oc2ccnc3cc(OC)c(OC)cc23)cn1] | white powder; ¹H-NMR (DMSO-d6, 400 MHz): δ 9.66 (1H, brs), 8.82 (1H, s), 8.64 (1H, d, J = 5.2 Hz), 8.50 (1H, d, J = 5.2 Hz), 8.42 (1H, d, J = 2.4 Hz), 8.30-8.40 (2H, m), 7.88 (1H, dd, J = 9.2, 3.2 Hz), 7.58 (1H, d, J = 4.8 Hz), 7.54 (1H, s), 7.42 (1H, s), 6.57 (1H, d, J = 5.2 Hz), 4.16 (2H, q, J = 6.8 Hz), 3.99 (2H, s), 3.95 (3H, s), 3.94 (3H, s), 3.59 (3H, s) 1.42 (3H, t, J = 7.2 Hz); LCMS: 98.7%, MS (ESI): m/z 585.4 [M + H]+. |
| 177 | 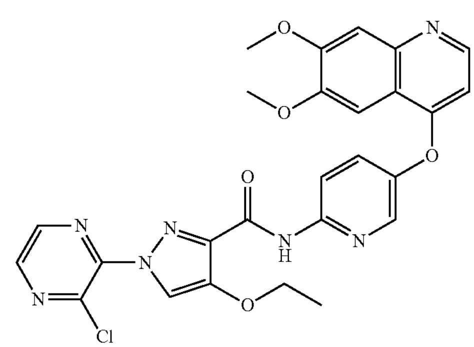 [SMILES: CCOc1cn(-c2nccnc2Cl)nc1C(=O)Nc1ccc(Oc2ccnc3cc(OC)c(OC)cc23)cn1] | white powder; ¹H-NMR (CDCl3, 400 MHz): δ 9.51 (1H, brs), 8.58 (1H, d, J = 9.2 Hz), 8.52 (1H, d, J = 5.2 Hz), 8.43-8.47 (2H, m), 8.28 (1H, d, J = 2.8 Hz), 8.00 (1H, s), 7.60 (1H, dd, J = 9.2, 2.8 Hz), 7.56 (1H, s), 7.45 (1H, s), 6.48 (1H, d, J = 5.6 Hz), 4.22 (2H, q, J = 7.2 Hz), 4.07 (3H, s), 4.06 (3H, s), 1.59 (3H, t, J = 6.8 Hz); LCMS: 98.9%, MS (ESI): m/z 548.2 [M + H]+. |

TABLE 4-continued

Summarizes compounds 1-280 in terms of their structures and corresponding characteristics.

| # cpd | Structure | Characterization Data |
|---|---|---|
| 178 | 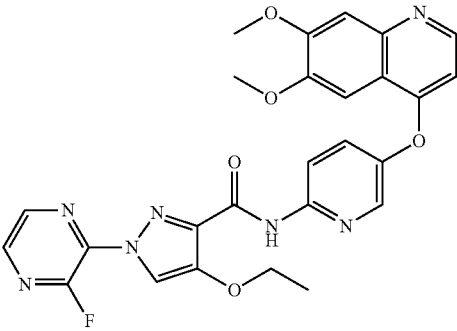 [SMILES: CCOc1cn(-c2nccnc2F)nc1C(=O)Nc1ccc(Oc2ccnc3cc(OC)c(OC)cc23)cn1] | white powder; ¹H-NMR (CDCl3, 400 MHz): δ 9.53 (1H, brs), 8.58 (1H, d, J = 8.8 Hz), 8.53 (1H, d, J = 5.2 Hz), 8.39 (1H, t, J = 2.8 Hz), 8.29 (1H, d, J = 2.8 Hz), 8.21 (1H, t, J = 2.0 Hz), 8.15 (1H, s), 7.61 (1H, dd, J = 9.2, 2.8 Hz), 7.57 (1H, s), 7.49 (1H, s0, 6.50 (1H, d, J = 5.2 Hz), 4.23 (2H, q, J = 7.2 Hz), 4.07 (6H, s), 1.59 (3H, t, J = 7.2 Hz); LCMS: 98.9%, MS (ESI): m/z 532.2 [M + H]+. |
| 179 | 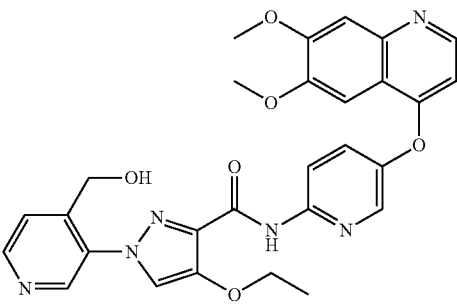 [SMILES: CCOc1cn(-c2cnccc2CO)nc1C(=O)Nc1ccc(Oc2ccnc3cc(OC)c(OC)cc23)cn1] | white powder; ¹H-NMR (DMSO-d6, 400 MHz): δ 9.84 (1H, brs), 8.73 (1H, s), 8.68 (1H, d, J = 4.8 Hz), 8.50 (1H, d, J = 5.2 Hz), 8.42 (1H, d, J = 3.2 Hz), 8.36 (1H, d, J = 8.8 Hz), 8.31 (1H, s), 7.88 (1H, dd, J = 8.8, 2.8 Hz), 7.74 (1H, d, J = 4.8 Hz), 7.54 (1H, s), 7.42 (1H, s), 6.56 (1H, d, J = 5.2 Hz), 5.61 (1H, t, J = 5.6 Hz), 4.68 (2H, d, J = 5.6 Hz), 4.18 (2H, q, J = 6.8 Hz), 3.96 (3H, s), 3.95 (3H, s), 1.44 (3H, t, J = 6.8 Hz); LCMS: 100%, MS (ESI): m/z 543.1 [M + H]+. |
| 180 | 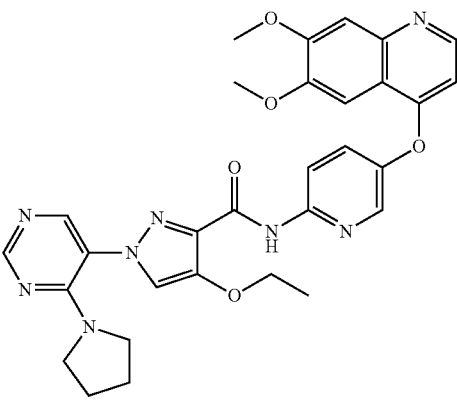 [SMILES: CCOc1cn(-c2cncnc2N2CCCC2)nc1C(=O)Nc1ccc(Oc2ccnc3cc(OC)c(OC)cc23)cn1] | pale-yellow powder; ¹H-NMR (CDCl3, 400 MHz): δ 8.62-8.69 (2H, m), 8.59 (1H, d, J = 4.8 Hz), 8.15 (1H, s), 7.62 (1H, dd, J = 10.4, 2.8 Hz), 7.56 (1H, d, J = 2.4 Hz0, 7.45 (1H, s), 7.44 (1H, s), 7.30 (1H, s), 6.55 (1H, d, J = 5.2 Hz), 4.01-4.12 (8H, m), 3.29-3.55 (4H, m), 1.85-1.95 (4H,m), 1.39 (3H, t, J = 6.8 Hz); LCMS: 95.2%, MS (EIS): m/z 583.1 [M + H]+. |
| 181 | 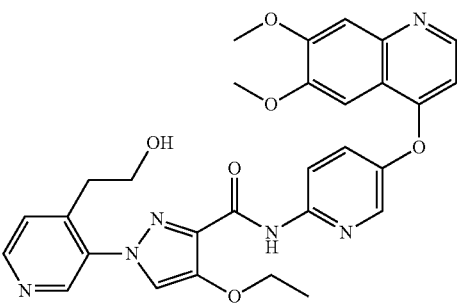 [SMILES: CCOc1cn(-c2cnccc2CCO)nc1C(=O)Nc1ccc(Oc2ccnc3cc(OC)c(OC)cc23)cn1] | white powder; ¹H-NMR (DMSO-d6, 400 MHz): δ 9.78 (1H, s), 8.66 (1H, s), 8.61 (1H, d, J = 5.2 Hz), 8.50 (1H, d, J = 5.2 Hz), 8.42 (1H, d, J = 2.4 Hz0, 8.37 (1H, d, J = 8.8 Hz), 8.27 (1H, s), 7.89 (1H, dd, J = 8.8, 2.8 Hz), 7.56 (1H, d, J = 5.6 Hz), 7.54 (1H, s), 7.42 (1H, s), 6.56 (1H, d, J = 5.6 Hz), 4.81 (1H, t, J = 5.2 Hz), 4.17 (2H, q, J = 7.2 Hz), 3.953 (3H, s), 3.946 (3H, s), 3.50-3.60 (2H, m), 2.82 (2H, t, J = 6.4 Hz), 1.43 (3H, t, J = 7.2 Hz); LCMS: 100%, MS (ESI): m/z 557.3 [M + H]+. |

TABLE 4-continued

Summarizes compounds 1-280 in terms of their structures and corresponding characteristics.

| # cpd | Structure | Characterization Data |
|---|---|---|
| 182 | 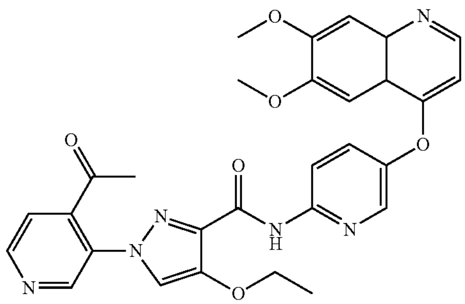 [SMILES: CCOc1cn(-c2cnccc2C(C)=O)nc1C(=O)Nc1ccc(OC2=CC=NC3C=C(OC)C(OC)=CC23)cn1] | white powder; ¹H-NMR (DMSO-d6, 400 MHz): δ 9.65 (1H, s), 9.06 (1H, s), 8.77 (1H, d, J = 4.8 Hz0, 8.57 (1H, s), 8.53 (1H, d, J = 5.2 Hz), 8.44 (1H, d, J = 2.8 Hz), 8.36 (1H, d, J = 9.2 Hz0, 7.90 (1H, dd, J = 9.2, 2.8 Hz), 7.64 (1H, d, J = 5.2 Hz0, 7.56 (1H, s), 7.43 (1H, s), 6.61 (1H, d, J = 5.2 Hz), 4.22 (2H, q, J = 6.8 Hz), 3.963 (3H, s), 3.956 (3H, s), 2.34 (3H, s) 1.45 (3H, t, J = 6.8 Hz); LCMS: 100%, MS (ESI): m/z 555.1 [M + H]+. |
| 183 | 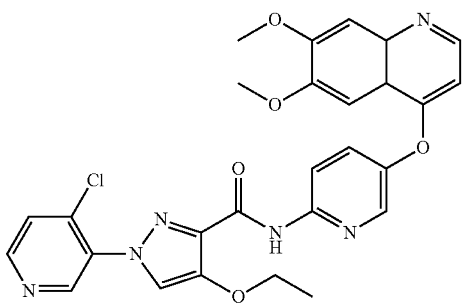 [SMILES: CCOc1cn(-c2cnccc2Cl)nc1C(=O)Nc1ccc(OC2=CC=NC3C=C(OC)C(OC)=CC23)cn1] | white powder; ¹H-NMR (DMSO-d6, 400 MHz): δ 9.88 (1H, brs), 8.91 (1H, s), 8.69 (1H, d, J = 5.2 Hz), 8.50 (1H, d, J = 5.2 Hz), 8.42 (1H, d, J = 2.8 Hz), 8.36 (1H, d, J = 9.2 Hz), 8.32 (1H, s), 7.85-7.91 (2H, m), 7.54 (1H, s), 7.42 (1H, s), 9.56 (1H, d, J = 5.2 Hz), 4.18 (2H, q, J = 6.8 Hz), 3.95 (3H, s0, 3.94 (3H, s), 1.43 (3H, t, J = 6.8 Hz); LCMS: 99.3%, MS (ESI): m/z 547.0 [M + H]+. |
| 184 | 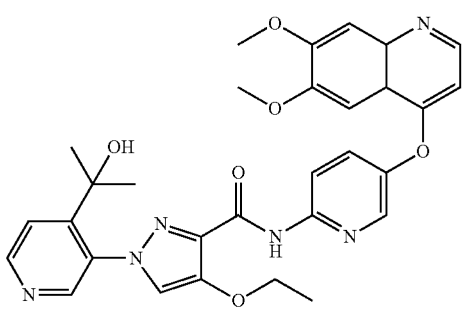 [SMILES: CCOc1cn(-c2cnccc2C(C)(C)O)nc1C(=O)Nc1ccc(OC2=CC=NC3C=C(OC)C(OC)=CC23)cn1] | white powder; ¹H-NMR (DMSO-d6, 400 MHz): δ 9.68 (1H, s), 8.71 (1H, d, J = 5.2 Hz0, 8.48-8.60 (2H, m), 8.41 (1H, d, J = 2.8 Hz), 8.36 (1H, d, J = 9.2 Hz), 8.19 (1H, s), 7.65-7.80 (2H, m), 7.54 (1H, s), 7.42 (1H, s), 6.55 (1H, d, J = 5.2 Hz), 5.47 (1H, s), 4.16 (2H, q, J = 6.8 Hz), 3.95 (3H, s), 3.94 (3H, s), 1.42 (3H, t, J = 6.8 Hz), 1.28 (6H, s); LCMS: 97.9%, MS (ESI): m/z 571.2 [M + H]+. |
| 185 | 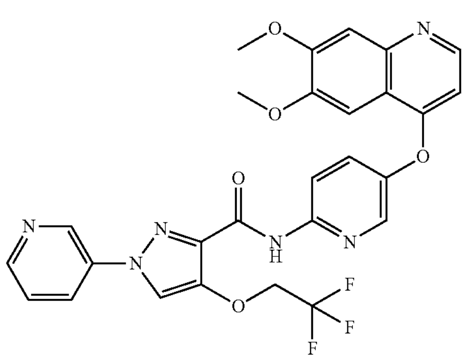 [SMILES: COc1cc2nccc(Oc3ccc(NC(=O)c4nn(-c5cccnc5)cc4OCC(F)(F)F)nc3)c2cc1OC] | white powder; ¹H-NMR (DMSO-d6, 400 MHz): δ 10.27 (1H, s), 9.24 (1H, d, J = 2.4 Hz), 8.85 (1H, s), 8.62 (1H, d, J = 4.0 Hz), 8.51 (1H, d, J = 5.2 Hz), 8.45 (1H, d, J = 2.8 Hz), 8.41 (1H, d, J = 8.8 Hz), 8.35 (1H, d, J = 8.8 Hz), 7.89 (1H, dd, J = 9.2, 2.8 Hz), 7.63 (1H, dd, J = 8.4, 4.8 Hz), 7.55 (1H, s), 7.42 (1H, s), 6.58 (1H, d, J = 5.2 Hz), 4.86 (2H, q, J = 4.8 Hz), 3.96 (3H, s), 3.95 (3H, s); LCMS: 100%, MS (ESI): m/z 567.2 [M + H]+. |

TABLE 4-continued

Summarizes compounds 1-280 in terms of their structures and corresponding characteristics.

| # cpd | Structure | Characterization Data |
|---|---|---|
| 186 | 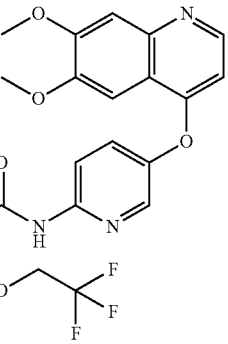 | white powder; ¹H-NMR (DMSO-d6, 400 MHz): δ 9.97 (1H, brs), 8.52 (1H, d, J= 5.2 Hz), 8.44 (1H, s), 8.42 (1H, d, J = 2.8 Hz), 8.33 (1H, d, J = 8.8 Hz), 7.93-7.98 (2H, m), 7.89 (1H, dd, J = 8.8, 2.8 Hz), 7.66 (1H, d, J = 8.8 Hz), 7.55 (1H, s), 7.43 (1H, s), 6.59 (1H, d, J = 5.2 Hz), 4.86 (2H, q, J = 8.8 Hz), 3.96 (3H, s), 3.95 (3H, s); LCMS: 98.6%, MS (ESI): m/z 684.1 [M + H]+. |
| 187 | 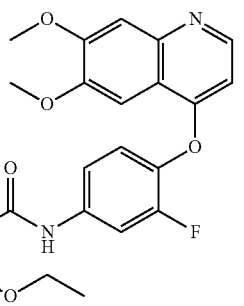 | white solid; ¹H-NMR (DMSO-d6, 400 MHz): δ 10.38 (1H, brs), 8.70-8.80 (2H, m), 8.49 (1H, d, J = 5.6 Hz), 8.31 (1H, s), 8.03 (1H, dd, J = 13.2, 2.4 Hz), 7.70 (1H, d, J = 9.2 Hz), 7.54 (1H, s), 7.47 (1H, t, J = 8.8 Hz), 7.41 (1H, s), 6.47 (1H, d, J = 5.2 Hz), 4.19 (2H, q, J = 7.2 Hz), 3.95 (6H, s), 1.39 (3H, t, J = 7.2 Hz); LCMS: 99.65%, MS (ESI): m/z 454.1 [M + H]+. |
| 188 | 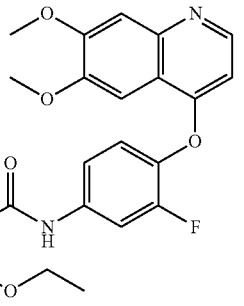 | white powder; ¹H-NMR (DMSO-d6, 400 MHz): δ 10.19 (1H, brs), 8.40-8.50 (2H, m), 8.00-8.10 (2H, m), 7.74 (1H, d, J = 9.2 Hz), 7.54 (1H, s), 7.40-7.50 (2H, m), 7.35 (1H, d, J = 4.8 Hz), 6.47 (1H, d, J = 5.2 Hz), 4.05 (2H, q, J = 7.2 Hz), 3.95 (6H, s), 2.25 (3H, s), 2.10 (3H, s), 1.38 (3H, t, J = 7.2 Hz); LCMS: 100%, MS (ESI): m/z 558.1 [M + H]+. |
| 189 | 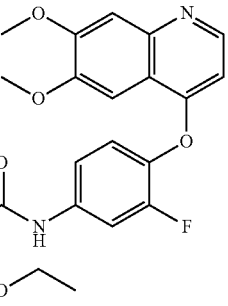 | white solid; ¹H-NMR (DMSO-d6, 400 MHz): δ 10.28 (1H, brs), 8.49 (1H, d, J = 5.2 Hz), 8.19 (1H, s), 8.04 (1H, dd, J = 10.8, 2.0 Hz), 7.93 (1H, d, J = 2.4 Hz), 7.88 (1H, d, J = 8.8 Hz), 7.72 (1H, d, J = 10.00 Hz), 7.63 (1H, dd, J = 8.8, 2.4 Hz), 7.54 (1H, s), 7.35-7.50 (2H, m), 6.47 (1H, d, J = 5.2 Hz), 4.06 (2H, q, J = 7.2 Hz), 3.95 (6H, s), 1.37 (3H, t, J = 7.2 Hz); LCMS: 98.4%, MS (ESI): m/z 647.1 [M + H]+. |

TABLE 4-continued

Summarizes compounds 1-280 in terms of their structures and corresponding characteristics.

| # cpd | Structure | Characterization Data |
|---|---|---|
| 190 | 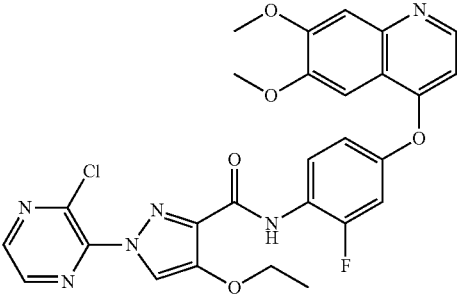 [SMILES: CCOc1cn(-c2nccnc2Cl)nc1C(=O)Nc1ccc(Oc2ccnc3cc(OC)c(OC)cc23)cc1F] | white powder; $^1$H-NMR (DMSO-d6, 400 MHz): δ 9.65 (1H, brs), 8.74 (1H, d, J = 2.0 Hz), 8.70 (1H, d, J = 2.4 Hz), 8.53 (1H, d, J = 5.6 Hz), 8.39 (1H, s), 8.20-8.27 (1H, m), 7.50 (1H, s), 7.45 (1H, dd, J = 11.6, 2.4 Hz), 7.42 (1H, s), 7.19 (1H, d, J = 8.8 Hz), 6.61 (1H, d, J = 5.2 Hz), 4.18 (2H, q, J = 6.8 Hz), 3.95 (3H, s), 3.94 (3H, s), 1.43 (3H, t, J = 7.2 Hz); LCMS: 97.2%, MS (ESI): m/z 565.0 [M + H]+. |
| 191 | 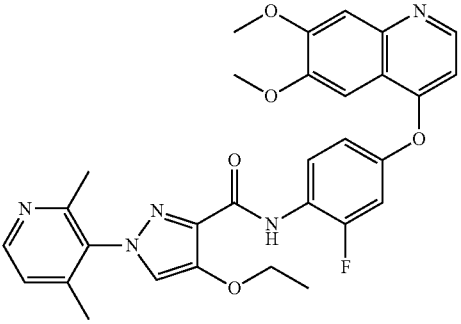 [SMILES: CCOc1cn(-c2c(C)ccnc2C)nc1C(=O)Nc1ccc(Oc2ccnc3cc(OC)c(OC)cc23)cc1F] | white powder; $^1$H-NMR (DMSO-d6, 400 MHz): δ 9.57 (1H, brs), 8.52 (1H, d, J = 5.2 Hz), 8.48 (1H, d, J = 4.8 Hz), 8.21 (1H, t, J = 8.8 Hz), 8.09 (1H, s), 7.49 (1H, s), 7.40-7.46 (2H, m), 7.35 (1H, d, J = 4.8 Hz), 7.16 (1H, d, J = 8.8 Hz), 6.59 (1H, d, J = 4.8 Hz), 4.13 (2H, q, J = 6.8 Hz), 3.95 (3H, s), 3.93 (3H, s), 2.23 (3H, s), 2.09 (3H, s), 1.42 (3H, t, J = 6.8 Hz); LCMS: 99.1%, MS (ESI): m/z 558.0 [M + H]+. |
| 192 | 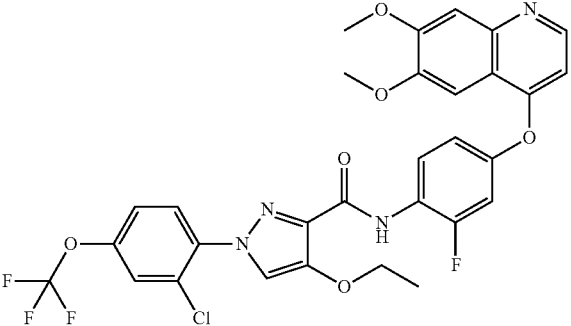 [SMILES: CCOc1cn(-c2ccc(OC(F)(F)F)cc2Cl)nc1C(=O)Nc1ccc(Oc2ccnc3cc(OC)c(OC)cc23)cc1F] | white powder; $^1$H-NMR (DMSO-d6, 400 MHz): δ 9.61 (1H, brs), 8.54 (1H, d, J = 5.2 Hz), 8.17-8.27 (2H, m), 7.93 (1H, d, J = 2.0 Hz), 7.86 (1H, d, J = 8.8 Hz), 7.63 (1H, d, J = 9.2 Hz), 7.51 (1H, s), 7.41-7.47 (2H, m), 7.18 (1H, dd, J = 8.4, 2.0 Hz), 6.63 (1H, d, J = 5.2 Hz), 4.14 (2H, q, J = 6.8 Hz), 3.95 (3H, s), 3.94 (3H, s), 1.42 (3H, t, J = 6.8 Hz); LCMS: 99.3%, MS (ESI): m/z 646.9 [M + H]+. |
| 193 | 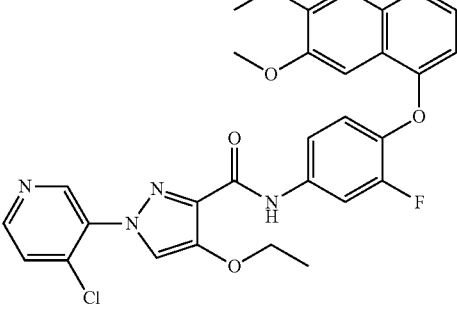 | white solid; $^1$H-NMR (DMSO-d6, 400 MHz): δ 10.33 (1H, brs), 8.92 (1H, s), 8.69 (1H, d, J = 5.6 Hz), 8.49 (1H, d, J = 5.6 Hz), 8.24 (1H, s), 8.04 (1H, dd, J = 13.2, 2.4 Hz), 7.88 (1H, d, J = 5.6 Hz), 7.72 (1H, d, J = 8.8 Hz), 7.54 (1H, s), 7.35-7.50 (2H, m), 6.48 (1H, d, J = 5.2 Hz), 4.09 (2H, q, J = 7.2 Hz), 3.96 (6H, s), 1.39 (3H, t, J = 7.2 Hz); LCMS: 99.1%, MS (ESI): m/z 564.1 [M + H]+. |

TABLE 4-continued

Summarizes compounds 1-280 in terms of their structures and corresponding characteristics.

| # cpd | Structure | Characterization Data |
|---|---|---|
| 194 | 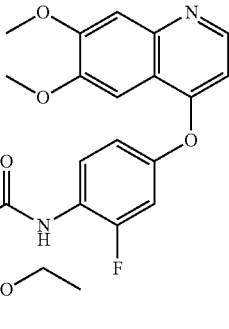 | white powder; $^1$H-NMR (DMSO-d6, 400 MHz): δ 9.65 (1H, brs), 8.88 (1H, s), 8.69 (1H, d, J = 5.2 Hz), 8.52 (1H, d, J = 5.2 Hz), 8.29 (1H, s), 8.19 (1H, t, J = 8.8 Hz), 7.88 (1H, d, J = 5.2 Hz), 7.49 (1H, s), 7.41-7.46 (2H, m), 7.17 (1H, d, J = 8.8 Hz), 6.59 (1H, d, J = 5.2 Hz), 4.14 (2H, q, J = 6.8 Hz), 3.95 (3H, s), 3.93 (3H, s), 1.42 (3H, t, J = 6.8 Hz); LCMS: 99.6%, MS (ESI): m/z 564.0 [M + H]+. |
| 195 | 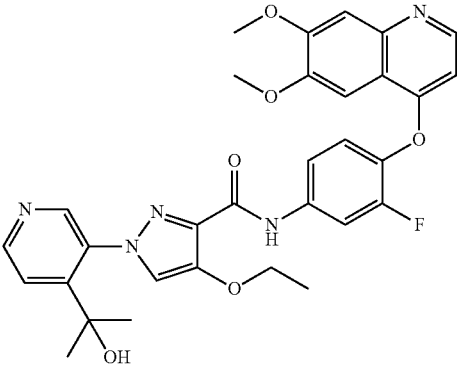 [SMILES: CCOc1cn(-c2cnccc2C(C)(C)O)nc1C(=O)Nc1ccc(Oc2ccnc3cc(OC)c(OC)cc23)c(F)c1] | white solid; $^1$H-NMR (DMSO-d6, 400 MHz): δ 10.16 (1H, s), 8.70 (1H, d, J = 5.6 Hz), 8.45-8.55 (2H, m), 8.11 (1H, s), 8.04 (1H, dd, J = 13.2, 2.0 Hz), 7.88 (1H, d, J = 5.6 Hz), 7.72 (1H, d, J = 9.6 Hz), 7.53 (1H, s), 7.35-7.50 (2H, m), 6.46 (1H, d, J = 5.2 Hz), 5.48 (1H, brs), 4.05 (2H, q, J = 7.2 Hz), 3.95 (6H, s), 1.37 (3H, t, J = 7.2 Hz), 1.27 (6H, s); LCMS: 99.5%, MS (ESI): m/z 588.2 [M + H]+. |
| 196 | 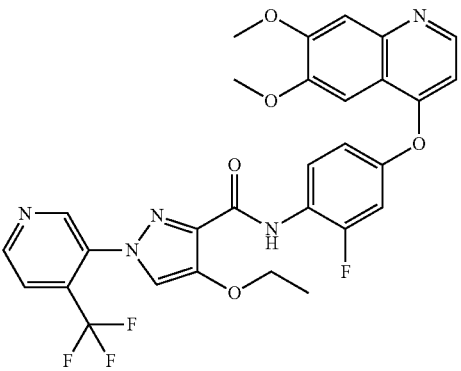 [SMILES: CCOc1cn(-c2cnccc2C(F)(F)F)nc1C(=O)Nc1ccc(Oc2ccnc3cc(OC)c(OC)cc23)cc1F] | white powder; $^1$H-NMR (DMSO-d6, 400 MHz): δ 9.53 (1H, brs), 9.01-9.07 (2H, m), 8.52 (1H, d, J = 5.2 Hz), 8.29 (1H, s), 8.24 (1H, t, J = 8.4 Hz), 8.06 (1H, d, J = 4.8 Hz), 7.49 (1H, s), 7.44 (1H, dd, J = 11.2, 2.4 Hz), 7.41 (1H, s), 7.18 (1H, d, J = 8.8 Hz), 6.59 (1H, d, J = 5.2 Hz), 4.14 (2H, q, J = 6.8 Hz), 3.95 (3H, s), 3.93 (3H, s), 1.42 (3H, t, J = 6.8 Hz); LCMS: 100%, MS (ESI): m/z 598.0 [M + H]+. |
| 197 | 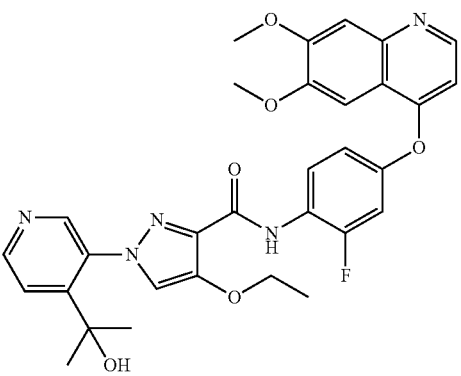 [SMILES: CCOc1cn(-c2cnccc2C(C)(C)O)nc1C(=O)Nc1ccc(Oc2ccnc3cc(OC)c(OC)cc23)cc1F] | white powder; $^1$H-NMR (DMSO-d6, 400 MHz): δ 9.50 (1H, brs), 8.71 (1H, d, J = 5.2 Hz0, 8.51 (1H, d, J = 5.2 Hz), 8.47 (1H, s), 8.26 (1H, t, J = 8.8 Hz), 8.17 (1H, s), 7.88 (1H, d, J = 5.2 Hz), 7.49 (1H, s), 7.39-7.47 (2H, m), 7.17 (1H, d, J = 9.2 Hz), 6.58 (1H, d, J = 5.2 Hz), 5.49 (1H, s), 4.13 (2H, q, J = 6.8 Hz), 3.95 (3H, s), 3.93 (3H, s), 1.41 (3H, t, J = 6.8 Hz), 1.27 (6H, s); LCMS: 97.2%, MS (ESI): m/z 588.0 [M + H]+. |

TABLE 4-continued

Summarizes compounds 1-280 in terms of their structures and corresponding characteristics.

| # cpd | Structure | Characterization Data |
|---|---|---|
| 198 | 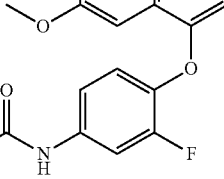 | white powder; ¹H-NMR (DMSO-d6, 400 MHz): δ 10.25 (1H, brs), 9.07 (1H, s), 9.03 (1H, d, J = 5.6 Hz), 8.48 (1H, d, J = 5.2 Hz), 8.19 (1H, s), 8.00-8.15 (2H, m), 7.65-7.75 (1H, m), 7.54 (1H, s), 7.35-7.50 (2H, m), 6.47 (1H, d, J = 5.2 Hz), 4.06 (2H, q, J = 6.8 Hz), 3.95 (6H, s), 1.38 (3H, t, J = 6.8 Hz); LCMS: 100%, MS (ESI): m/z 598.1 [M + H]+ |
| 199 | 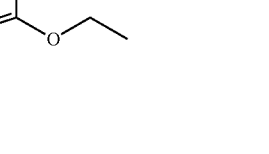 | pale yellow powder; ¹H-NMR (DMSO-d6, 400 MHz): δ 10.03 (1H, brs), 9.22 (1H, d, J = 2.8 Hz), 8.71 (1H, d, J = 5.6 Hz), 8.68 (1H, s), 8.60 (1H, d, J = 4.0 Hz), 8.48 (1H, d, J = 2.8 Hz), 8.34-8.44 (2 H, m), 8.21 (1H, s), 7.95 (1H, dd, J = 8.8, 2.8 Hz0, 7.70 (1H, s), 7.61 (1H, dd, J = 8.0, 4.4 Hz0, 6.67 (1H, d, J = 5.2 Hz), 4.21 (2H, q, J = 6.8 Hz), 4.06 (3H, s), 1.45 (3H, t, J = 6.8 Hz); LCMS: 100%, MS (ESI): m/z 567.1 [M + H]+. |
| 200 | 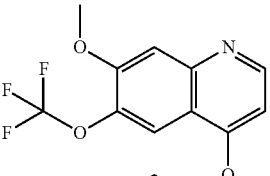 | white powder; ¹H-NMR (CDCl3, 400 MHz): δ 9.49 (1H, brs), 8.60 (1H, d, J = 2.4 Hz), 8.57 (1H, d, J = 9.2 Hz), 8.52 (1H, d, J = 5.2 Hz), 8.37 (1H, d, J = 2.4 Hz), 8.27 (1H, d, J = 2.8 Hz), 8.14 (1H, s), 7.60 (1H, dd, J = 9.2, 2.8 Hz), 7.56 (1H, s), 7.44 (1H, s), 6.46 (1H, d, J = 5.2 Hz), 5.99 (1H, s), 4.28 (2H, q, J = 7.2 Hz), 4.07 (3H, s), 4.06 (3H, s), 1.67 (6H, s), 1.62 (3H, t, J = 7.2 Hz); LCMS: 100%, MS (ESI): m/z 572.0 [M + H]+. |
| 201 | 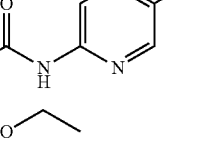 | white powder; ¹H-NMR (DMSO, 400 MHz): δ 9.84 (1H, brs), 8.71 (1H, d, J = 5.2 Hz), 8.46 (1H, d, J = 2.4 Hz), 8.37 (1H, d, J = 8.8 Hz), 8.28 (1H, s), 8.20 (1H, s), 7.80-8.05 (3H, m), 7.70 (1H, s), 7.63 (1H, d, J = 8.4 Hz), 6.66 (2H, d, J = 5.2 Hz), 4.17 (2H, q, J = 6.8 Hz), 4.05 (3H, s), 1.43 (3H, t, J = 7.2 Hz); LCMS: 97.4%, MS (ESI): m/z 683.9 [M + H]+. |

TABLE 4-continued

Summarizes compounds 1-280 in terms of their structures and corresponding characteristics.

| # cpd | Structure | Characterization Data |
|---|---|---|
| 202 | 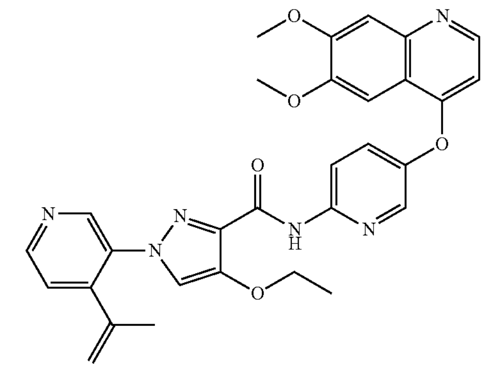 [SMILES: C=C(C)c1ccncc1-n1cc(OCC)c(C(=O)Nc2ccc(Oc3ccnc4cc(OC)c(OC)cc34)cn2)n1] | white powder; $^1$H-NMR (DMSO-d6, 400 MHz): δ 9.75 (1H, brs), 8.76 (1H, s), 8.68 (1H, d, J = 4.8 Hz), 8.50 (1H, d, J = 5.2 Hz), 8.41 (1H, d, J = 2.4 Hz), 8.36 (1H, d, J = 9.2 Hz), 8.11 (1H, s), 7.88 (1H, d, J = 9.2 Hz), 7.54 (1H, s), 7.51 (1H, d, J = 4.8 Hz), 7.42 (1H, s), 6.55 (1H, d, J = 5.2 Hz), 5.27 (1H, s), 5.05 (1H, s), 4.14 (2H, q, J = 6.8 Hz), 3.95 (3H, s), 3.94 (3H, s), 1.76 (3H, s), 1.41 (3H, t, J = 7.2 Hz); LCMS: 100%, MS (ESI): m/z 553.0 [M + H]+. |
| 203 | 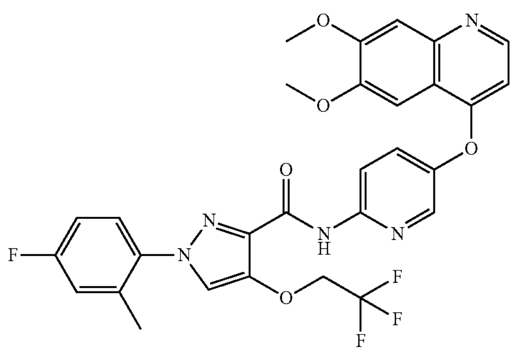 [SMILES: COc1cc2nccc(Oc3ccc(NC(=O)c4nn(-c5ccc(F)cc5C)cc4OCC(F)(F)F)nc3)c2cc1OC] | white powder; $^1$H-NMR (DMSO-d6, 400 MHz): δ 9.83 (1H, s), 8.50 (1H, d, J = 5.2 Hz), 8.41 (1H, d, J = 2.8 Hz), 8.32 (1H, d, J = 9.2 Hz), 8.28 (1H, s), 7.88 (1H, dd, J = 8.8, 2.8 Hz), 7.45-7.65 (2 H, m), 7.42 (1H, s), 7.36 (1H, dd, J = 9.2, 2.4 Hz), 7.20-7.30 (1 H, m), 6.56 (1H, d, J = 5.2 Hz), 4.85 (2H, q, J = 8.8 Hz), 3.95 (3H, s), 3.94 (3H, s), 2.29 (3H, s); LCMS: 98.49%, MS (ESI): m/z 597.9 [M + H]+. |
| 204 | 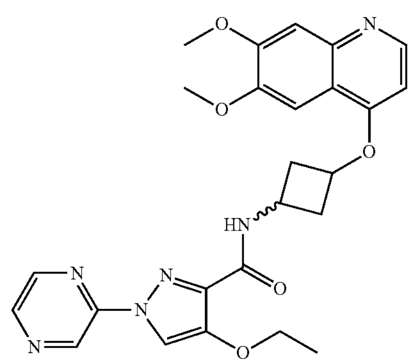 [SMILES: CCOc1cn(-c2cnccn2)nc1C(=O)NC1CC(Oc2ccnc3cc(OC)c(OC)cc23)C1] | white powder; $^1$H-NMR (DMSO-d6, 400 MHz): δ 9.39 (1H, brs), 8.66 (1H, d, J = 2.8 Hz), 8.55-8.65 (2H, m), 8.51 (1H, d, J = 5.6 Hz), 8.43 (1H, s), 7.42 (1H, s), 7.32 (1H, s), 6.68 (1H, d, J = 5.2 Hz), 5.10-5.30 (1H, m), 4.50-4.70 (1H, m), 4.10 (2H, q, J = 7.2 Hz), 3.94 (3H, s), 3.92 (3H, s), 2.69-2.80 (2H, m), 2.60-2.68 (2H, m), 1.36 (3H, t, J = 7.2 Hz); LCMS: 98.6%, MS (ESI): m/z 491.0 [M + H]+. From H NMR it contains ~20% Cis QWAX0248-01A. |
| 205 | 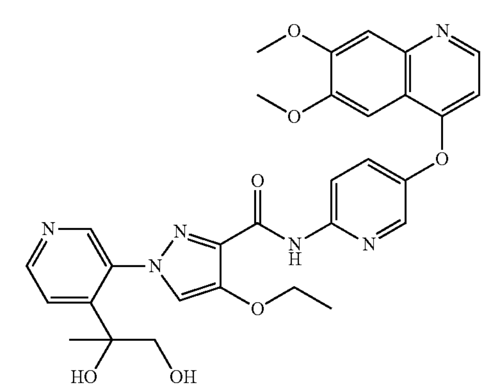 [SMILES: CCOc1cn(-c2cnccc2C(C)(O)CO)nc1C(=O)Nc1ccc(Oc2ccnc3cc(OC)c(OC)cc23)cn1] | white powder; $^1$H-NMR (DMSO-d6, 400 MHz): δ 9.69 (1H, brs), 8.69 (1H, d, J = 5.2 Hz), 8.50 (1H, d, J = 5.2 Hz), 8.46 (1H, s), 8.41 (1H, d, J = 2.4 Hz), 8.36 (1H, d, J = 9.2 Hz), 8.12 (1H, s), 7.88 (1H, dd, J = 9.2, 2.8 Hz), 7.84 (1H, d, J = 5.6 Hz), 7.54 (1H, s), 7.42 (1H, s), 6.55 (1H, d, J = 5.2 Hz), 5.32 (1H, s), 4.83 (1H, t, J = 6.0 Hz), 4.16 (2H, q, J = 6.8 Hz), 3.95 (3H, s), 3.94 (3H, s), 3.40-3.50 (2H, m), 1.43 (3H, t, J = 6.8 Hz), 1.16 (3H, s); LCMS: 95.7%, MS (ESI): m/z 609.0 [M + Na]+. |

TABLE 4-continued

Summarizes compounds 1-280 in terms of their structures and corresponding characteristics.

| # cpd | Structure | Characterization Data |
|---|---|---|
| 206 | 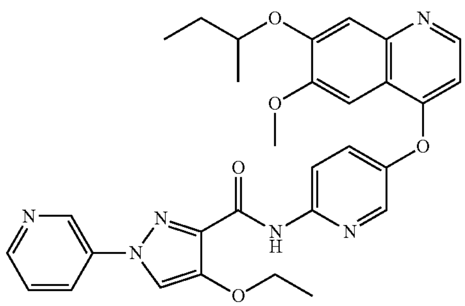 [SMILES: CCOc1cn(-c2cccnc2)nc1C(=O)Nc1ccc(Oc2ccnc3cc(OC(C)CC)c(OC)cc23)cn1] | white powder; ¹H-NMR (DMSO-d6, 400 MHz): δ 10.01 (1H, brs), 9.22 (1H, d, J = 2.0 Hz), 8.68 (1H, s), 8.59 (1H, d, J = 3.6 Hz), 8.49 (1H, d, J = 5.2 Hz), 8.43 (1H, d, J = 2.8 Hz), 8.37 (2H, d, J = 8.8 Hz), 7.88 (1H, dd, J = 8.8, 2.4 Hz), 7.58-7.65 (1H, m), 7.54 (1H, s), 7.41 (1H, s), 6.55 (1H, d, J = 5.2 Hz), 4.59-4.71 (1H, m), 4.20 (2H, q, J = 6.8 Hz), 3.94 (3H, s), 1.61-1.85 (2H, m), 1.45 (3H, t, J = 7.2 Hz), 1.34 (3H, d, J = 6.0 Hz), 0.97 (3H, t, J = 7.2 Hz); LCMS: 100%, MS (ESI): m/z 577.0 [M + Na]+. |
| 207 | 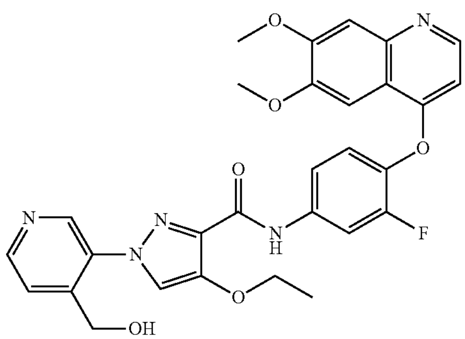 [SMILES: CCOc1cn(-c2cnccc2CO)nc1C(=O)Nc1ccc(Oc2ccnc3cc(OC)c(OC)cc23)c(F)c1] | white powder; ¹H-NMR (DMSO-d6, 400 MHz): δ 10.22 (1H, s), 8.73 (1H, brs), 8.68 (1H, d, J = 4.8 Hz), 8.48 (1H, d, J = 5.2 Hz), 8.23 (1H, s), 8.04 (1H, dd, J = 13.2, 1.6 Hz), 7.50-7.90 (2H, m), 7.54 (1H, s), 7.46 (1H, t, J = 9.2 Hz), 7.41 (1H, s), 6.48 (1H, d, J = 4.8 Hz), 5.60 (1H, t, J = 5.6 Hz), 4.68 (2H, d, J = 5.2 Hz), 4.08 (2H, q, J = 7.2 Hz), 3.95 (6H, s), 1.39 (3H, t, J = 7.2 Hz); LCMS: 99.2%, MS (ESI): m/z 581.9 [M + Na]+. |
| 208 | 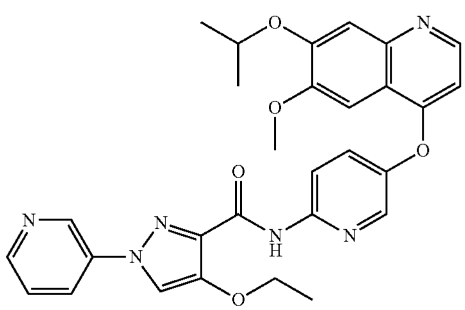 [SMILES: CCOc1cn(-c2cccnc2)nc1C(=O)Nc1ccc(Oc2ccnc3cc(OC(C)C)c(OC)cc23)cn1] | ff-white powder; ¹H-NMR (DMSO-d5, 400 MHz): δ 10.01 (1H, brs), 9.21 (1H, d, J = 2.0 Hz), 8.69 (1H, s), 8.59 (1H, d, J = 4.4 Hz), 8.49 (1H, d, J = 5.2 Hz), 8.43 (1H, d, J = 2.4 Hz), 8.37 (2H, d, J = 8.8 Hz), 7.89 (1H, dd, J = 8.8, 2.4 Hz), 7.58-7.64 (1H, m), 7.54 (1H, s), 7.41 (1H, s), 6.56 (1H, d, J = 5.2 Hz), 4.83-4.89 (1H, m), 4.20 (2H, q, J = 6.8 Hz), 3.94 (3H, s), 1.45 (3H, t, J = 7.2 Hz), 1.37 (6H, d, J = 5.6 Hz); LCMS: 100%, MS (ESI): m/z 563.1 [M + Na]+. |
| 209 | 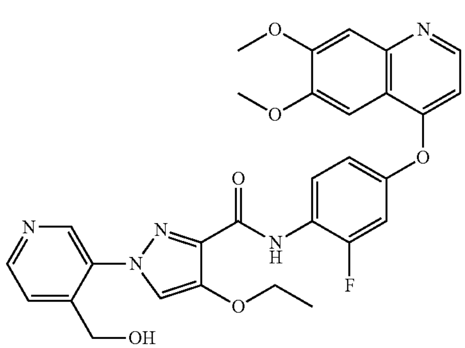 [SMILES: CCOc1cn(-c2cnccc2CO)nc1C(=O)Nc1ccc(Oc2ccnc3cc(OC)c(OC)cc23)cc1F] | white powder; ¹H-NMR (DMSO-d6, 400 MHz): δ 9.60 (1H, brs), 8.71 (1H, s), 8.68 (1H, d, J = 4.8 Hz), 8.52 (1H, d, J = 5.2 Hz), 8.30 (1H, s), 8.20 (1H, t, J = 8.8 Hz), 7.74 (1H, d, J = 4.8 Hz), 7.49 (1H, s), 7.40-7.47 (2H, m), 7.18 (1H, d, J = 9.2 Hz), 6.59 (1H, d, J = 5.2 Hz), 5.60 (1H, t, J = 5.6 Hz), 4.67 (2H, d, J = 5.6 Hz), 4.15 (2H, q, J = 6.8 Hz), 3.95 (3H, s), 3.93 (3H, s), 1.42 (3H, t, J = 6.8 Hz); LCMS: 100%, MS (ESI): m/z 582.0 [M + Na]+. |

TABLE 4-continued

Summarizes compounds 1-280 in terms of their structures and corresponding characteristics.

| # cpd | Structure | Characterization Data |
|---|---|---|
| 210 | 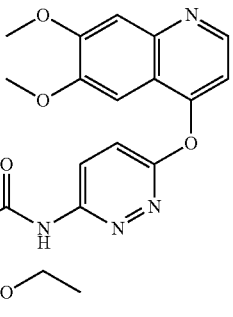 | pale yellow powder; ¹H-NMR (DMSO-d6, 400 MHz): δ 10.29 (1H, brs), 8.68 (1H, s), 8.60-8.65 (2H, m), 8.56 (1H, d, J = 4.8 Hz), 8.26 (1H, s), 7.83 (1H, d, J = 9.6 Hz), 7.51 (1H, d, J = 4.8 Hz), 7.45 (1H, s), 7.39 (1H, s), 7.04 (1H, d, J = 5.2 Hz), 4.15 (2H, q, J = 7.2 Hz), 3.96 (3H, s), 3.89 (3H, s), 2.37 (3H, s), 1.41 (3H, t, J = 6.8 Hz); LCMS: 100.0%, MS (ESI): m/z 528.0 [M + H]+. |
| 211 | 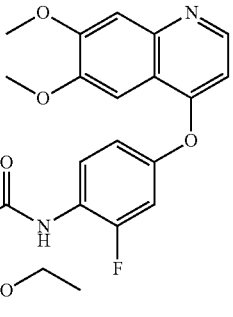 | white powder; ¹H-NMR (DMSO-d6, 400 MHz): δ 9.38 (1H, s), 8.51 (1H, d, J = 5.2 Hz), 8.32 (1H, t, J = 8.8 Hz), 7.82 (1H, s), 7.49 (1H, s), 7.39-7.46 (2H, m), 7.16 (1H, d, J = 8.8 Hz), 6.57 (1H, d, J = 5.2 Hz), 4.14-4.22 (1H, m), 4.07 (2H, q, J = 6.8 Hz), 3.97-4.03 (1H, m), 3.95 (3H, s), 3.93 (3H, s), 2.90-3.00 (1H, m), 2.60-2.65 (1H, m), 2.23 (3H, s), 2.14-2.20 (1H, m), 1.70-1.82 (1H, m), 1.50-1.68 (3H, m), 1.38 (3H, t, J = 6.8 Hz); LCMS: 100.0%, MS (ESI): m/z 572.0 [M + Na]+. |
| 212 | 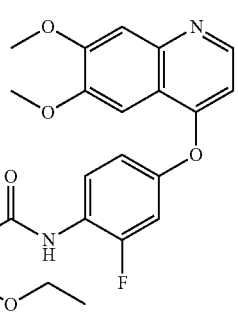 | white powder; ¹H-NMR (DMSO-d6, 400 MHz): δ 9.39 (1H, d, J = 2.4 Hz), 8.50 (1H, d, J = 5.2 Hz), 8.32 (1H, t, J = 9.2 Hz), 7.82 (1H, s), 7.49 (1H, s), 7.39-7.44 (2H, m), 7.16 (1H, d, J = 9.2), 6.58 (1H, d, J = 5.2 Hz), 4.84-4.93 (1H, m), 4.08 (2H, q, J = 7.2 Hz), 3.95 (3H, s), 3.93 (3H, s), 2.76-2.85 (3H, m), 2.31-2.47 (2H, m), 2.30 (3H, s), 2.06-2.15 (1H, m), 1.38 (3H, t, J = 6.8 Hz); LCMS: 95.0%, MS (ESI): m/z 536.2 [M + H]+. |
| 213 | 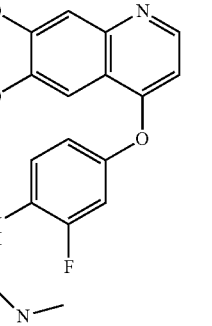 | white powder; ¹H-NMR (DMSO-d6, 400 MHz): δ 9.56 (1H, d, J = 2.4 Hz), 8.50 (1H, d, J = 5.6 Hz), 8.40 (1H, t, J = 8.8 Hz), 7.61 (1H, s), 7.43-7.51 (2H, m), 7.41 (1H, s), 7.19 (1H, d, J = 8.8 Hz), 6.57 (1H, d, J = 5.2 Hz), 4.64-4.71 (1H, m), 4.20-4.35 (3H, m), 3.95 (3H, s), 3.93 (3H, s), 2.88-2.99 (1H, m), 2.59-2.64 (1H, m), 2.24 (3H, s), 2.03-2.20 (1H, m), 1.55-1.68 (4H, m), 1.42 (3H, t, J = 6.8 Hz); LCMS: 99.0%, MS (ESI): m/z 550.0 [M + H]+. |

TABLE 4-continued

Summarizes compounds 1-280 in terms of their structures and corresponding characteristics.

| # cpd | Structure | Characterization Data |
|---|---|---|
| 214 | 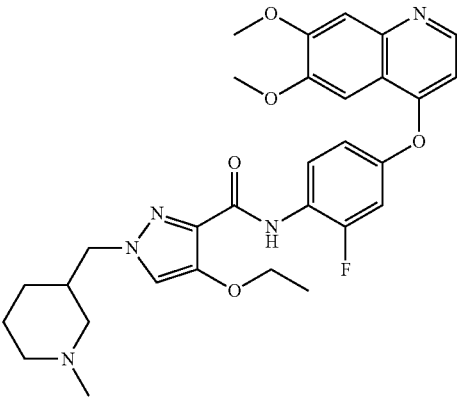 [SMILES: CCOc1cn(CC2CCCN(C)C2)nc1C(=O)Nc1ccc(Oc2ccnc3cc(OC)c(OC)cc23)cc1F] | white powder; $^1$H-NMR (CDCl3, 400 MHz): δ 9.24 (1H, brs), 8.72 (1H, t, J = 8.8 Hz), 8.51 (1H, d, J = 4.8 Hz), 7.52 (1H, s), 7.43 (1H, s), 7.14 (1H, s), 6.94-7.07 (2H, m), 6.52 (1H, d, J = 5.2 Hz), 3.99-4.16 (10H, m), 2.52-2.76 (2H, m), 2.16-2.35 (4H, m), 1.95-2.07 (1H, m), 1.72-1.86 (2H, m), 1.56-1.64 (2H, m), 1.52 (3H, t, J = 6.8 Hz), 1.00-1.14 (1H, m); LCMS: 98.8%, MS (ESI): m/z 564.1 [M + H]+. |
| 215 | 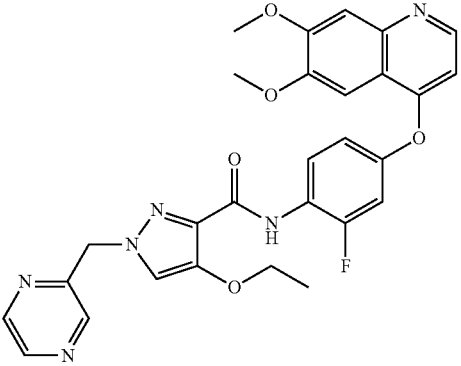 [SMILES: CCOc1cn(Cc2cnccn2)nc1C(=O)Nc1ccc(Oc2ccnc3cc(OC)c(OC)cc23)cc1F] | white powder; $^1$H-NMR (DMSO-d6, 400 MHz): δ 9.39 (1H, d, J = 2.0 Hz), 8.60-8.65 (2H, m), 8.48 (1H, d, J = 5.2 Hz), 8.27 (1H, t, J = 8.8 Hz), 7.93 (1H, s), 7.46 (1H, s), 7.35-7.38 (2H, m), 7.13 (1H, d, J = 8.8 Hz), 6.55 (1H, d, J = 5.2 Hz), 5.54 (2H, s), 4.07 (2H, q, J = 6.8 Hz), 3.93 (3H, s), 3.91 (3H, s), 1.37 (3H, t, J = 6.8 Hz); LCMS: 100.0%, MS (ESI): m/z 545.0 [M + H]+. |
| 216 | 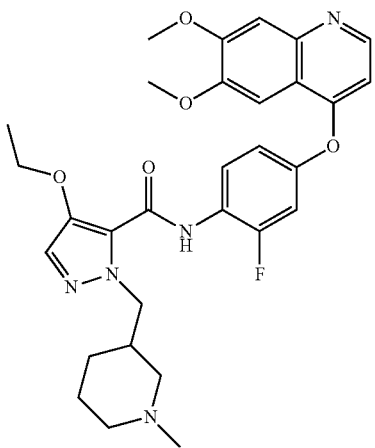 [SMILES: CCOc1cnn(CC2CCCN(C)C2)c1C(=O)Nc1ccc(Oc2ccnc3cc(OC)c(OC)cc23)cc1F] | white powder; $^1$H-NMR (CDCl3, 400 MHz): δ 9.51 (1H, brs), 8.47-8.63 (2H, m), 7.52 (1H, s), 7.43 (1H, s), 7.30 (1H, s), 6.95-7.09 (2H, m), 6.52 (1H, d, J = 4.8 Hz), 4.55-4.66 (1H, m), 4.38-4.50 (1H, m), 4.23 (2H, q, J = 6.8 Hz), 4.05 (6H, s), 2.57-2.82 (2H, m), 2.19-2.36 (4H, m), 1.87-2.00 (1H, m), 1.74-1.86 (3H, m), 1.58-1.65 (1H, m), 1.54 (3H, t, J = 6.8 Hz), 0.95-1.10 (1H, m); LCMS: 96.7%, MS (ESI): m/z 564.1 [M + H]+. |

TABLE 4-continued

Summarizes compounds 1-280 in terms of their structures and corresponding characteristics.

| # cpd | Structure | Characterization Data |
|---|---|---|
| 217 | 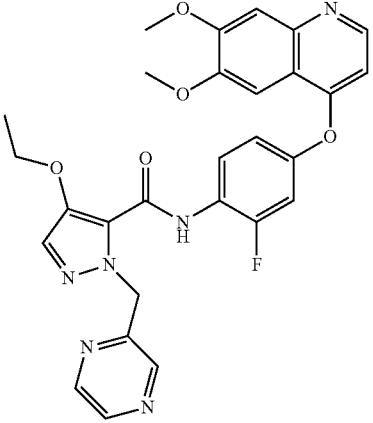 [SMILES: CCOc1cnn(Cc2cnccn2)c1C(=O)Nc1ccc(Oc2ccnc3cc(OC)c(OC)cc23)cc1F] | white powder; ¹H-NMR (DMSO-d6, 400 MHz): δ 9.47 (1H, s), 8.52-8.54 (2H, m), 8.47 (1H, d, J = 5.2 Hz), 8.29 (1H, t, J = 8.8 Hz), 7.72 (1H, s), 7.40-7.45 (2H, m), 7.38 (1H, s), 7.10 (1H, d, J = 7.6 Hz), 6.53 (1H, d, J = 6.0 Hz), 5.91 (2H, s), 4.27 (2H, q, J = 6.8 Hz0, 3.92 (3H, s), 3.90 (3H, s), 1.43 (3H, t, J = 6.8 Hz); LCMS: 100.0%, MS (ESI): m/z 567.0 [M + Na]+. |
| 218 | 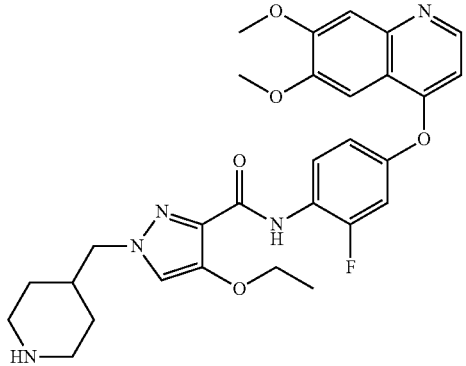 [SMILES: CCOc1cn(CC2CCNCC2)nc1C(=O)Nc1ccc(Oc2ccnc3cc(OC)c(OC)cc23)cc1F] | white powder; ¹H-NMR (DMSO-d6, 400 MHz): δ 9.37 (1H, brs), 8.51 (1H, d, J = 5.6 Hz), 8.33 (1H, t, J = 8.8 Hz), 7.79 (1H, s), 7.49 (1H, s), 7.39-7.46 (2H, m), 7.16 (1H, d, J = 8.0 Hz), 6.57 (1H, d, J = 5.2 Hz), 4.07 (2H, q, J = 6.8 Hz), 3.89-4.00 (8H, m), 2.92 (2H, d, J = 11.6 Hz), 2.37-2.46 (2H, m), 1.84-1.99 (1H, m), 1.33-1.48 (5H, m), 1.00-1.18 (2H, m); LCMS: 98.5%, MS (ESI): m/z 572.0 [M + Na]+. |
| 219 | 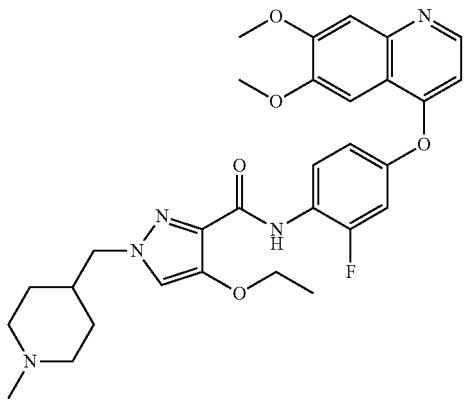 [SMILES: CCOc1cn(CC2CCN(C)CC2)nc1C(=O)Nc1ccc(Oc2ccnc3cc(OC)c(OC)cc23)cc1F] | white powder; ¹H-NMR (DMSO-d6, 400 MHz): δ 9.36 (1H, brs), 8.51 (1H, d, J = 5.2 Hz), 8.33 (1H, t, J = 9.2 Hz), 7.80 (1H, s), 7.49 (1H, s), 7.38-7.46 (2H, m), 7.16 (1H, d, J = 8.0 Hz), 6.57 (1H, d, J = 5.2 Hz), 4.07 (2H, q, J = 6.8 Hz), 3.99 (2H, d, J = 6.8 Hz), 3.95 (3H, s), 3.93 (3, s), 2.74 (2H, d, J = 11.2 Hz), 2.13 (3H, s), 1.74-1.85 (3H, m), 1.42-1.50 (2H, m), 1.38 (3H, t, J = 6.8 Hz), 1.17-1.29 (2H, m); LCMS: 97.9%, MS (ESI): m/z 564.1 [M + H]+. |

TABLE 4-continued

Summarizes compounds 1-280 in terms of their structures and corresponding characteristics.

| # cpd | Structure | Characterization Data |
|---|---|---|
| 220 | 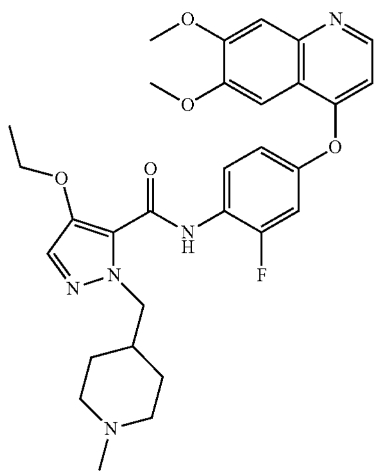 [SMILES: CCOc1cnn(CC2CCN(C)CC2)c1C(=O)Nc1ccc(Oc2ccnc3cc(OC)c(OC)cc23)cc1F] | white powder; $^1$H-NMR (DMSO-d6, 400 MHz): δ 9.52 (1H, brs), 8.51 (1H, d, J = 5.2 Hz), 8.43 (1H, t, J = 8.8 Hz), 7.61 (1H, s), 7.44-7.53 (2H, m), 7.41 (1H, s), 7.17 (1H, d, J = 10.0 Hz), 6.57 (1H, d, J = 5.2 Hz), 4.42 (2H, q, J = 7.2 Hz), 4.24 (2H, d, J = 7.2 Hz), 3.95 (3H, s), 3.93 (3H, s), 2.68-2.76 (2H, m), 2.12 (3H, s), 1.70-1.82 (2H, m), 1.34-1.48 (5H, m), 1.15-1.30 (2H, m). It should be noted that a proton is overlapped with solvent peak (δ 2.50); LCMS: 97.6%, MS (ESI): m/z 564.1 [M + H]+. |
| 221 | 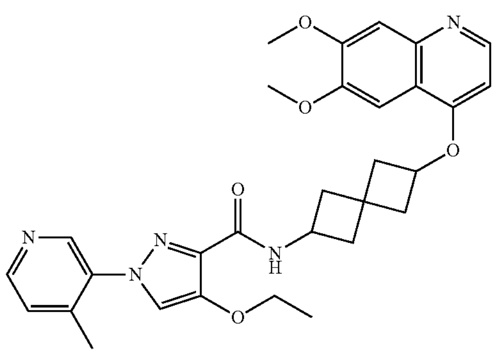 [SMILES: CCOc1cn(-c2cnccc2C)nc1C(=O)NC1CC2(C1)CC(Oc1ccnc3cc(OC)c(OC)cc13)C2] | white powder; $^1$H-NMR (DMSO-d6, 400 MHz): δ 8.60 (1H, s), 8.52 (1H, d, J = 4.8 Hz), 8.47 (1H, d, J = 5.2 Hz), 8.06 (1H, s), 8.03 (1H, d, J = 7.6 Hz), 7.47 (1H, d, J = 4.8 Hz), 7.33 (1H, s), 7.29 (1H, s), 6.73 (1H, d, J = 5.2 Hz), 4.84-4.95 (1H, m), 4.31-4.42 (1H, m), 4.02 (2H, q, J = 6.8 Hz), 3.90 (3H, s), 3.89 (3H, s), 2.77-2.86 (1H, m), 2.56-2.65 (2H, m), 2.16-2.36 (8H, m), 1.34 (3H, t, J = 6.8 Hz); LCMS: 100%, MS (ESI): m/z 566.1 [M + Na]+. |
| 222 | 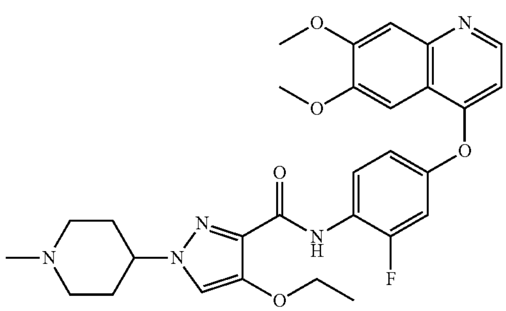 [SMILES: CCOc1cn(C2CCN(C)CC2)nc1C(=O)Nc1ccc(Oc2ccnc3cc(OC)c(OC)cc23)cc1F] | white powder; $^1$H-NMR (DMSO-d6, 400 MHz): δ 9.37 (1H, brs), 8.51 (1H, d, J = 5.2 Hz), 8.33 (1H, t, J = 8.8 Hz), 7.89 (1H, s), 7.49 (1H, s), 7.39-7.46 (2H, m), 7.16 (1H, d, J = 7.6 Hz), 6.58 (1H, d, J = 5.2 Hz), 4.03-4.18 (3H, m), 3.95 (3H, s), 3.93 (3H, s), 2.83-2.91 (2H, m), 2.21 (3H, s), 1.90-2.11 (6H, m), 1.38 (3H, t, J = 6.8 Hz); LCMS: 97.5%, MS (ESI): m/z 572.1 [M + Na]+. |
| 223 | 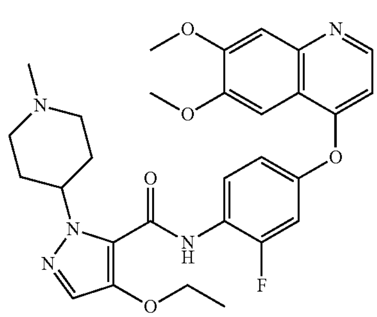 [SMILES: CCOc1cnn(C2CCN(C)CC2)c1C(=O)Nc1ccc(Oc2ccnc3cc(OC)c(OC)cc23)cc1F] | white powder; $^1$H-NMR (DMSO-d6, 400 MHz): δ 9.55 (1H, brs), 8.51 (1H, d, J = 5.2 Hz), 8.42 (1H, t, J = 8.8 Hz), 7.63 (1H, s), 7.43-7.51 (2H, m), 7.41 (1H, s), 7.16 (1H, d, J = 9.6 Hz), 6.57 (1H, d, J = 5.2 Hz), 5.10-5.23 (1H, m), 4.24 (2H, q, J = 7.2 Hz), 3.95 (3H, s), 3.93 (3H, s), 2.83-2.93 (2H, m), 2.20 (3H, s), 1.95-2.05 (4H, m), 1.83-1.91 (2H, m), 1.43 (3H, t, J = 6.8 Hz); LCMS: 94.6%, MS (ESI): m/z 550.3 [M + H]+, m/z 572.1 [M + Na]+. |

TABLE 4-continued

Summarizes compounds 1-280 in terms of their structures and corresponding characteristics.

| # cpd | Structure | Characterization Data |
|---|---|---|
| 224 | 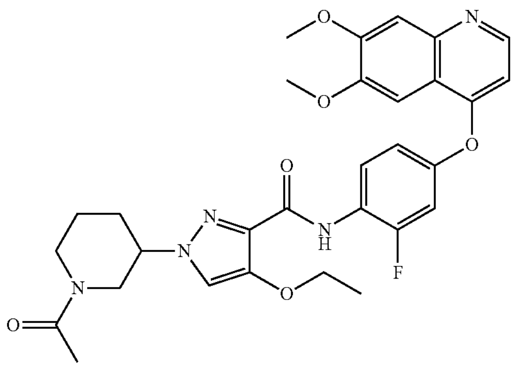 [SMILES: CCOc1cn(C2CCCN(C(C)=O)C2)nc1C(=O)Nc1ccc(Oc2ccnc3cc(OC)c(OC)cc23)cc1F] | white powder; ¹H-NMR (DMSO-d6, 400 MHz): δ 9.39 (1H, brs), 8.51 (1H, d, J = 5.2 Hz), 8.27-8.39 (1H, m), 7.91 (1H, m), 7.49 (1H, s), 7.38-7.46 (2H, m), 7.17 (1H, d, J = 8.8 Hz), 6.58 (1H, d, J = 5.2 Hz), 4.47-4.59 (0.5H, m), 4.27-4.38 (0.5H, m), 4.03-4.20 (3H, m), 3.95 (3H, s), 3.93 (3H, s), 3.73-3.83 (0.5H, m), 3.48-3.60 (0.5H, m), 2.95-3.17 (1H, m), 2.77-2.89 (0.5H, m), 2.09-2.21 (1H, m), 2.05 (3H, s), 1.35-1.90 (5H, m), 0.77-0.89 (1H, m); LCMS: 100%, MS (ESI): m/z 578.1 [M + H]+, m/z 600.0 [M + Na]+. |
| 225 | 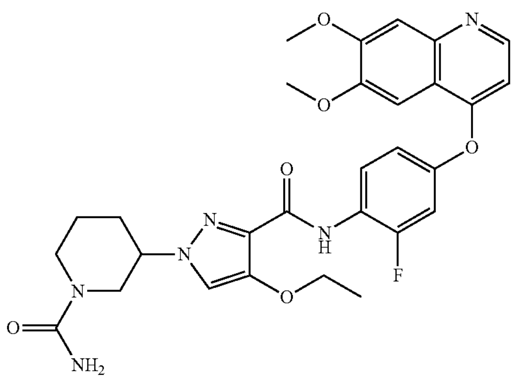 [SMILES: CCOc1cn(C2CCCN(C(N)=O)C2)nc1C(=O)Nc1ccc(Oc2ccnc3cc(OC)c(OC)cc23)cc1F] | white powder; ¹H-NMR (CDCl3, 400 MHz): δ 9.29 (1H, s), 8.69 (1H, t, J = 8.8 Hz), 8.50 (1H, d, J = 5.2 Hz), 7.52 (1H, s), 7.42 (1H, s), 7.30 (1H, s), 6.95-7.05 (2H, m), 6.52 (1H, d, J = 5.2 Hz), 4.73 (2H, brs), 4.20-4.30 (1H, m), 3.95-4.17 (9H, m), 3.60-3.70 (1H, m), 3.50-3.62 (1H, m), 3.25-3.35 (1H, m), 2.25-2.47 (1H, m), 2.15-2.25 (1H, m), 1.74-1.85 (1H, m), 1.65-1.72 (1H, m), 1.53 (3H, t, J = 6.8 Hz); LCMS: 100%, MS (ESI): m/z 579.1 [M + H]+. |
| 226 | 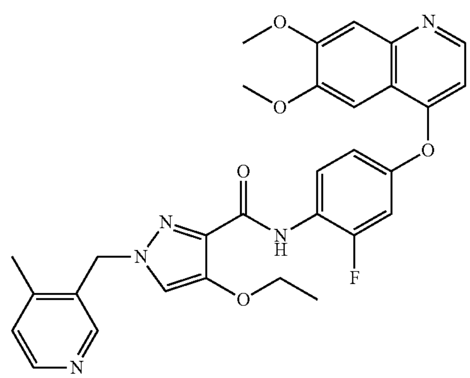 [SMILES: CCOc1cn(Cc2cnccc2C)nc1C(=O)Nc1ccc(Oc2ccnc3cc(OC)c(OC)cc23)cc1F] | white powder; ¹H-NMR (DMSO-d6, 400 MHz): δ 9.36 (1H, brs), 8.49 (1H, d, J = 5.2 Hz), 8.40 (1H, d, J = 5.2 Hz), 8.23-8.34 (2H, m), 7.83 (1H, s), 7.47 (1H, s), 7.35-7.46 (2H, m), 7.25 (1H, d, J = 4.4 Hz), 7.14 (1H, d, J = 8.8 Hz), 6.55 (1H, d, J = 4.8 Hz), 5.41 (2H, s), 4.05 (2H, q, J = 6.8 Hz), 3.93 (3H, s), 3.91 (3H, s), 2.31 (3H, s), 1.36 (3H, t, J = 7.2 Hz); LCMS: 100.0%, MS (ESI): m/z 558.1 [M + H]+. |
| 227 | 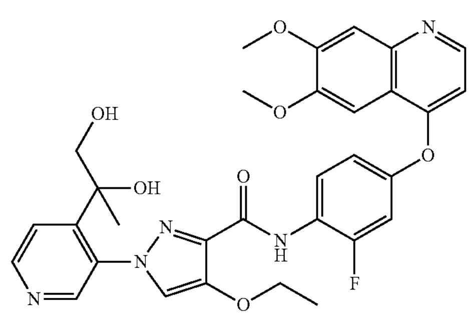 [SMILES: CCOc1cn(-c2cnccc2C(C)(O)CO)nc1C(=O)Nc1ccc(Oc2ccnc3cc(OC)c(OC)cc23)cc1F] | white powder; ¹H-NMR (DMSO-d6, 400 MHz): δ 9.47 (1H, brs), 8.67 (1H, d, J = 5.2 Hz), 8.50 (1H, d, J = 5.2 Hz), 8.44 (1H, s), 8.25 (1H, t, J = 9.2 Hz), 8.08 (1H, s), 7.83 (1H, d, J = 5.2 Hz), 7.38-7.51 (3H, m), 7.15 (1H, d, J = 8.4 Hz), 6.57 (1H, d, J = 5.2 Hz), 5.30 (1H, s), 4.79 (1H, t, J = 5.6 Hz), 4.11 (2H, q, J = 6.8 Hz), 3.93 (3H, s), 3.92 (3H, s), 3.36-3.47 (2H, m), 1.40 (3H, t, J = 7.2 Hz), 1.14 (3H, s); LCMS: 96.7%, MS (ESI): m/z 604.1 [M + H]+. |

TABLE 4-continued

Summarizes compounds 1-280 in terms of their structures and corresponding characteristics.

| # cpd | Structure | Characterization Data |
|---|---|---|
| 228 | 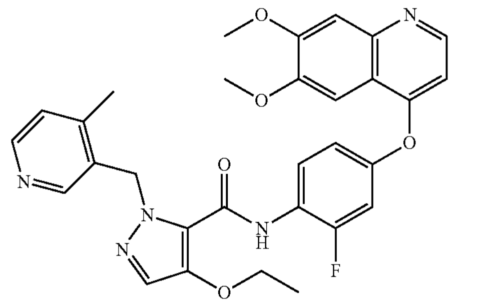 [SMILES: CCOc1cnn(Cc2cnccc2C)c1C(=O)Nc1ccc(Oc2ccnc3cc(OC)c(OC)cc23)cc1F] | white powder; ¹H-NMR (DMSO-d6, 400 MHz): δ 9.53 (1H, brs), 8.49 (1H, d, J = 5.2 Hz), 8.28-8.40 (2H, m), 7.89 (1H, s), 7.73 (1H, s), 7.41-7.51 (2H, m), 7.41 (1H, s), 7.22 (1H, d, J = 4.8 Hz), 7.15 (1H, d, J = 8.4 Hz), 6.56 (1H, d, J = 5.2 Hz), 5.82 (2H, s), 4.28 (2H, q, J = 7.2 Hz), 3.95 (3H, s), 3.93 (3H, s), 2.35 (3H, s), 1.44 (3H, t, J = 6.8 Hz); LCMS: 100.0%, MS (ESI): m/z 580.1 [M + Na]+. |
| 229 | 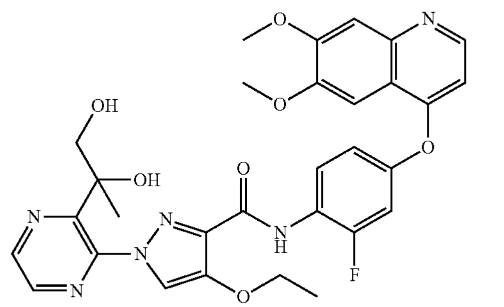 [SMILES: CCOc1cn(-c2nccnc2C(C)(O)CO)nc1C(=O)Nc1ccc(Oc2ccnc3cc(OC)c(OC)cc23)cc1F] | pale yellow powder; ¹H-NMR (DMSO-d6, 400 MHz): δ 9.50 (1H, d, J = 1.2 Hz), 8.81 (1H, d, J = 2.0 Hz), 8.59 (1H, d, J = 2.0 Hz), 8.50 (1H, d, J = 4.8 Hz), 8.25-8.35 (2H, m), 7.47 (1H, s), 7.43 (1H, dd, J = 11.6, 2.8 Hz), 7.40 (1H, s), 7.16 (1 H, d, J = 8.8 Hz), 6.57 (1H, d, J = 5.2 Hz), 5.31 (1H, s), 4.70 (1H, t, J = 6.0 Hz), 4.17 (2H, q, J = 6.8 Hz), 3.93 (3H, s), 3.92 (3H, s), 3.60-3.70 (1H, m), 3.50-3.60 (1H, m), 1.30-1.40 (6H, m); LCMS: 100%, MS (ESI): m/z 605.1 [M + H]+. |
| 230 | 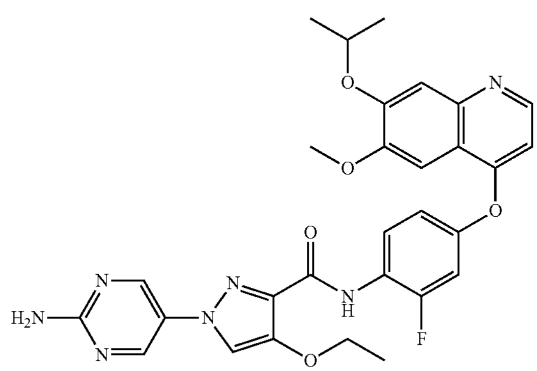 [SMILES: CCOc1cn(-c2cnc(N)nc2)nc1C(=O)Nc1ccc(Oc2ccnc3cc(OC(C)C)c(OC)cc23)cc1F] | white powder; ¹H-NMR (DMSO-d6, 400 MHz): δ 9.59 (1H, brs), 8.74 (2H, s), 8.50 (1H, d, J = 5.6 Hz), 8.40 (1H, s), 8.21 (1H, t, J = 8.8 Hz), 7.48 (1H, s), 7.39-7.46 (2H, m), 7.17 (1H, d, J = 8.8 Hz), 7.04 (2 H, brs), 6.57 (1H, d, J = 5.2 Hz), 4.80-4.91 (1H, m), 4.14 (2H, q, J = 6.8 Hz), 3.92 (3H, s), 1.42 (3H, t, J = 6.8 Hz), 1.37 (6H, d, J = 6.0 Hz); LCMS: 100%, MS (ESI): m/z 574.1 [M + H]+. |
| 231 | 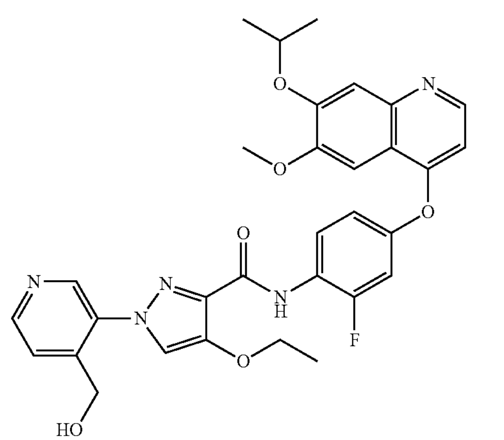 [SMILES: CCOc1cn(-c2cnccc2CO)nc1C(=O)Nc1ccc(Oc2ccnc3cc(OC(C)C)c(OC)cc23)cc1F] | white powder; ¹H-NMR (DMSO-d6, 400 MHz): δ 9.60 (1H, brs), 8.71 (1H, s), 8.68 (1H, d, J = 4.8 Hz), 8.50 (1H, d, J = 5.2 Hz), 8.29 (1H, s), 8.20 (1H, t, J = 8.8 Hz), 7.74 (1H, d, J = 5.2 Hz), 7.48 (1H, s), 7.39-7.46 (2H, m), 7.17 (1H, d, J = 8.4 Hz), 6.58 (1H, d, J = 5.2 Hz), 4.80-4.91 (1H, m), 4.67 (2H, s), 4.15 (2H, q, J = 6.4 Hz), 3.92 (3H, s), 1.42 (3H, t, J = 6.8 Hz), 1.37 (6H, d, J = 6.0 Hz); LCMS: 100%, MS (ESI): m/z 588.1 [M + H]+. |

TABLE 4-continued

Summarizes compounds 1-280 in terms of their structures and corresponding characteristics.

| # cpd | Structure | Characterization Data |
|---|---|---|
| 232 | 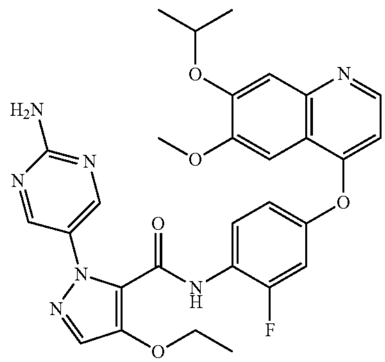 [SMILES: CCOc1cnn(-c2cnc(N)nc2)c1C(=O)Nc1ccc(Oc2ccnc3cc(OC(C)C)c(OC)cc23)cc1F] | white powder; $^1$H-NMR (DMSO-d6, 400 MHz): δ 9.51 (1H, brs), 8.48 (1H, d, J = 5.2 Hz), 8.23-8.33 (3H, m), 7.93 (1H, s), 7.42-7.49 (2H, m), 7.40 (1H, s), 7.10 (1H, d, J = 8.8 Hz), 7.02 (2H, brs), 6.54 (1H, d, J = 4.8 Hz), 4.80-4.91 (1H, m), 4.32 (2H, q, J = 6.8 Hz), 3.91 (3H, s), 1.46 (3H, t, J = 6.8 Hz), 1.36 (6H, d, J = 6.0 Hz); LCMS: 100%, MS (ESI): m/z 574.1 [M + H]+. |
| 233 | 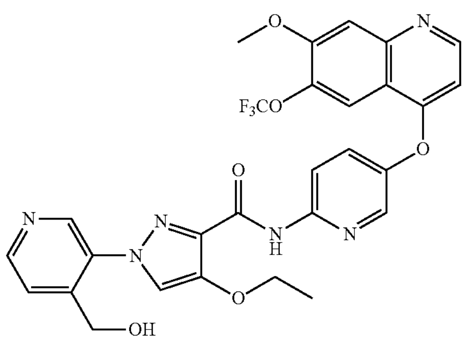 [SMILES: CCOc1cn(-c2cnccc2CO)nc1C(=O)Nc1ccc(Oc2ccnc3cc(OC)c(OC(F)(F)F)cc23)cn1] | white powder; $^1$H-NMR (DMSO-d6, 400 MHz): δ 9.86 (1H, brs), 8.74 (1H, s), 8.71 (1H, d, J = 5.6 Hz), 8.68 (1H, d, J = 4.8 Hz), 8.46 (1H, d, J = 2.4 Hz), 8.37 (1H, d, J = 8.8 Hz), 8.32 (1H, s), 8.20 (1H, s), 7.94 (1H, dd, J = 9.2, 2.8 Hz), 7.74 (1H, d, J= 4.8 Hz), 7.70 (1H, s), 6.66 (1H, d, J = 5.6 Hz), 5.60 (1H, t, J = 5.6 Hz0, 4.68 (2H, d, J = 5.6 Hz), 4.18 (2H, q, J = 7.2 Hz), 4.05 (3H, s), 1.44 (3H, t, J = 6.8 Hz); LCMS: 100%, MS (ESI): m/z 597.5 [M + H]+. |
| 234 | 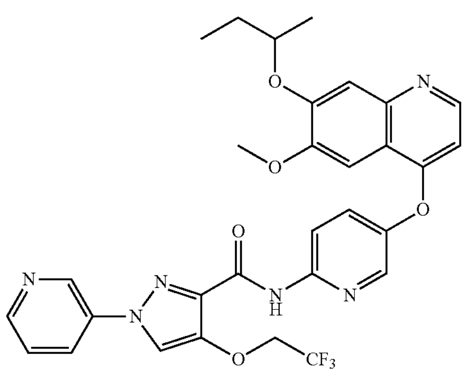 [SMILES: CCC(C)Oc1cc2nccc(Oc3ccc(NC(=O)c4nn(-c5cccnc5)cc4OCC(F)(F)F)nc3)c2cc1OC] | white powder; $^1$H-NMR (DMSO-d6, 400 MHz): δ 10.25 (1H, brs), 9.24 (1H, d, J = 2.0 Hz), 8.84 (1H, s), 8.62 (1H, d, J = 4.8 Hz), 8.49 (1H, d, J = 4.8 Hz), 8.44 (1H, d, J = 2.8 Hz), 8.40 (1H, d, J = 8.4 Hz), 8.35 (1H, d, J = 8.8 Hz), 7.88 (1H, dd, J = 9.2, 2.8 Hz), 7.63 (1H, dd, J = 8.4, 4.8 Hz), 7.54 (1H, s0, 7.41 (1H, s), 6.56 (1H, d, J = 5.2 Hz), 4.86 (2H, q, J = 8.8 Hz), 4.59-4.70 (1H, m), 3.94 (3H, s), 1.61-1.85 (2H, m), 1.34 (3H, d, J = 6.0 Hz), 0.97 (3H, t, J = 7.2 Hz); LCMS: 100%, MS (ESI): m/z 609.6 [M + H]+. |
| 235 | 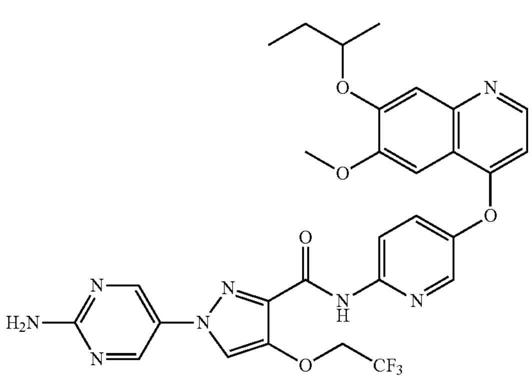 [SMILES: CCC(C)Oc1cc2nccc(Oc3ccc(NC(=O)c4nn(-c5cnc(N)nc5)cc4OCC(F)(F)F)nc3)c2cc1OC] | white powder; $^1$H-NMR (DMSO-d6, 400 MHz): δ 10.06 (1H, brs), 8.80 (2H, s), 8.56 (1H, s), 8.50 (1H, d, J = 5.6 Hz), 8.42 (1H, d, J = 2.8 Hz), 8.34 (1H, d, J = 8.8 Hz), 7.87 (1H, dd, J = 9.2, 2.8 Hz), 7.54 (1H, s), 7.41 (1H, s), 7.08 (2H, brs), 6.57 (1H, d, J = 4.8 Hz0, 4.82 (2H, q, J = 8.4 Hz), 4.60-4.71 (1H, m), 3.94 (3H, s), 1.59-1.87 (2H, m), 1.34 (3H, d, J = 6.0 Hz), 0.97 (3H, t, J = 6.8 Hz); LCMS: 100%, MS (ESI): m/z 625.6 [M + H]+. |

TABLE 4-continued

Summarizes compounds 1-280 in terms of their structures and corresponding characteristics.

| # cpd | Structure | Characterization Data |
|---|---|---|
| 236 | 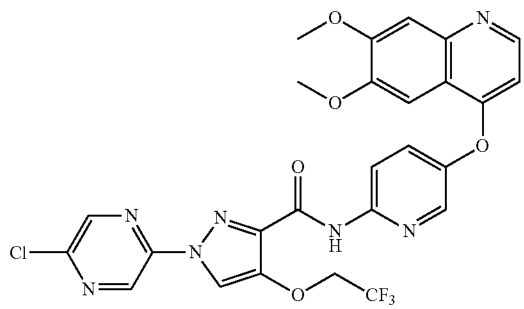 [SMILES: COc1cc2nccc(Oc3ccc(NC(=O)c4nn(-c5cnc(Cl)cn5)cc4OCC(F)(F)F)nc3)c2cc1OC] | white powder; ¹H-NMR (DMSO-d6, 400 MHz): δ 10.47 (1H, brs), 9.40 (1H, s), 8.75-8.80 (2H, m), 8.51 (1H, d, J = 5.2 Hz), 8.46 (1H, d, J = 2.4 Hz), 8.35 (1H, d, J = 9.2 Hz), 7.89 (1H, dd, J 8.8, 2.4 Hz), 7.55 (1H, s), 7.42 (1H, s), 6.58 (1H, d, J = 5.2 Hz), 4.95 (2H, q, J = 6.4 Hz), 3.96 (3H, s), 3.95 (3H, s); LCMS: 99.2%, MS (ESI): m/z 602.6 [M + H]+ |
| 237 | 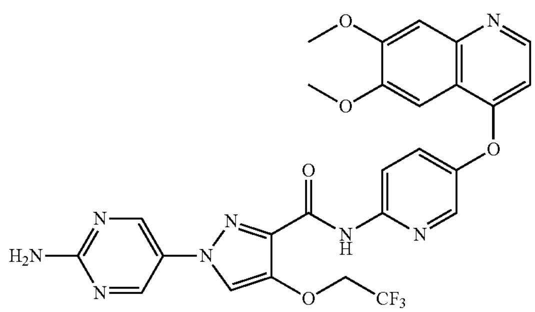 [SMILES: COc1cc2nccc(Oc3ccc(NC(=O)c4nn(-c5cnc(N)nc5)cc4OCC(F)(F)F)nc3)c2cc1OC] | white powder; ¹H-NMR (DMSO-d6, 400 MHz): δ 10.06 (1H, s), 8.80 (2H, s), 8.56 (1H, s), 8.45-8.55 (1H, m), 8.43 (1H, s), 8.34 (1H, d, J = 8.8 Hz), 7.88 (1H, d, J = 6.8 Hz), 7.55 (1H, s), 7.42 (1H, s), 7.08 (1H, s), 6.58 (1H, d, J = 4.8 Hz), 4.80-4.85 (2H, m), 3.96 (3H, s), 3.95 (3H, s); LCMS: 96.5%, MS (ESI): m/z 583.5 [M + H]+ |
| 238 | 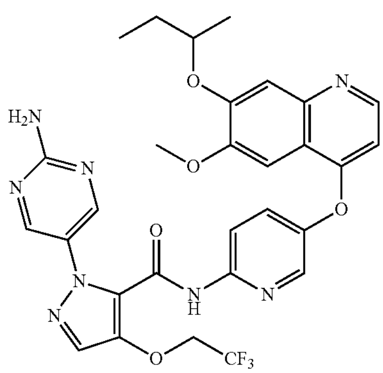 [SMILES: CCC(C)Oc1cc2nccc(Oc3ccc(NC(=O)c4c(OCC(F)(F)F)cnn4-c4cnc(N)nc4)nc3)c2cc1OC] | white powder; ¹H-NMR (DMSO-d6, 400 MHz): δ 9.84 (1H, brs), 8.47 (1H, d, J = 5.2 Hz), 8.41 (1H, d, J = 2.4 Hz0, 8.32 (2H, s), 8.19 (1H, d, J = 9.2 Hz), 8.03 (1H, s), 7.66-7.84 (1H, m), 7.51 (1H, s), 7.39 (1H, s), 7.06 (2H, brs), 6.53 (1H, d, J = 5.2 Hz), 5.06 (2H, q, J = 9.2 Hz), 4.60-4.67 (1H, m), 3.93 (3H, s), 1.63-1.80 (2H, m), 1.33 (3H, d, J = 6.0 Hz), 0.97 (3H, t, J = 7.6 Hz); LCMS: 100%, MS (ESI): m/z 625.6 [M + H]+. |
| 239 | 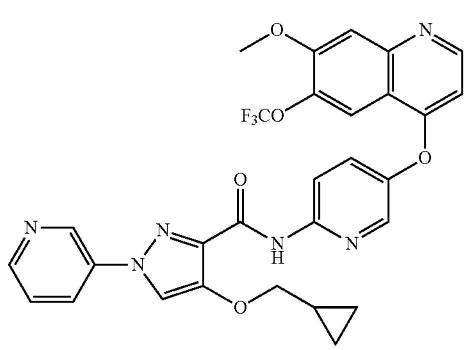 [SMILES: COc1cc2nccc(Oc3ccc(NC(=O)c4nn(-c5cccnc5)cc4OCC4CC4)nc3)c2cc1OC(F)(F)F] | white solid; ¹H-NMR (400 MHz, DMSO-d6): δ 10.05 (1H, brs), 9.20 (1H, d, J = 2.8 Hz), 8.71 (1H, d, J = 5.2 Hz), 8.67 (2H, brs), 8.59 (1H, dd, J = 4.8, 1.6 Hz), 8.47 (1H, d, J = 2.8 Hz), 8.39 (1H, d, J = 8.8 Hz), 8.34-8.38 (1H, m), 8.20 (1H, d, J = 1.2 Hz), 7.95 (1H, dd, J = 9.2, 2.8 Hz), 7.70 (1H, s), 7.61 (1H, dd, J = 8.0, 4.4 Hz), 6.67 (1H, d, J = 5.2 Hz), 4.05 (3H, s), 4.00 (2H, d, J = 7.2 Hz), 1.32-1.44 (1H, m), 0.61-0.67 (2H, m), 0.40-0.45 (2H, m); LCMS: 100%, MS (ESI): m/z 615.1 [M + Na]+. |

TABLE 4-continued

Summarizes compounds 1-280 in terms of their structures and corresponding characteristics.

| # cpd | Structure | Characterization Data |
|---|---|---|
| 240 | 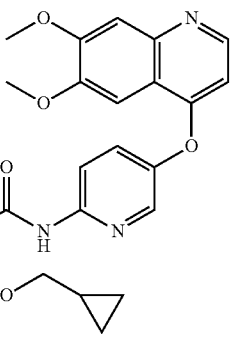 | white powder; ¹H-NMR (400 MHz, DMSO-d6) δ 9.91 (1H, s), 8.76 (2H, s), 8.50 (1H, d, J = 4.8 Hz), 8.40-8.42 (2H, m), 8.38 (1H, d, J = 9.2 Hz), 7.88 (1H, d, J = 7.6 Hz), 7.54 (1H, s0, 7.42 (1H, s), 7.04 (2H, brs), 6.57 (1H, d, J = 4.8 Hz), 3.99-3.92 (8H, m), 1.34-1.37 (1H, m), 0.60-0.65 (2H, m), 0.38-0.42 (2H, m); LCMS: 98.5%, MS (ESI): m/z 555.1 [M + H]+. |
| 241 | 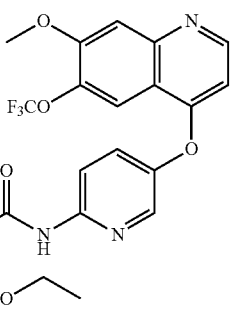 | white powder; ¹H-NMR (DMSO-d6, 400 MHz): δ 9.89 (1H, brs), 8.77 (2H, s), 8.70 (1H, d, J = 5.2 Hz), 8.46 (1H, d, J = 2.4 Hz), 8.42 (1H, s), 8.37 (1H, d, J = 8.8 Hz), 8.20 (1H, s), 7.94 (1H, dd, J = 9.2, 2.8 Hz), 7.69 (1H, s), 7.05 (2H, brs), 6.65 (1H, d, J = 5.2 Hz), 4.16 (2H, q, J = 7.2 Hz), 4.05 (3H, s), 1.43 (3H, t, J = 7.2 Hz); LCMS: 100%, MS (ESI): m/z 583.1 [M + H]+. |
| 242 | 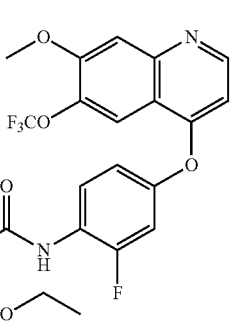 | off-white powder; ¹H-NMR (DMSO-d6, 400 MHz): δ 9.59 (1H, brs), 8.67-8.78 (3H, m), 8.40 (1H, s), 8.24 (1H, t, J = 8.4 Hz), 8.16 (1H, s), 7.69 (1H, s), 7.46-7.55 (1H, m), 7.24 (1H, d, J = 9.2 Hz), 7.03 (2H, brs), 6.67 (1H, d, J = 5.6 Hz), 4.15 (2H, q, J = 6.4 Hz), 4.05 (3H, s), 1.42 (3H, t, J = 6.8 Hz); LCMS: 100%, MS (ESI): m/z 600.0 [M + H]+. |
| 243 | 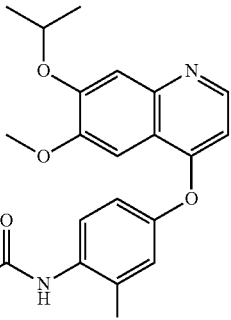 | white solid; ¹H-NMR (DMSO-d6, 400 MHz): δ 9.75 (1H, brs), 8.75 (2H, s), 8.55 (1H, s), 8.51 (1H, d, J = 4.8 Hz), 7.94 (1H, t, J = 8.8 Hz), 7.48 (1H, s), 7.37-7.43 (2H, m), 7.15 (1H, d, J = 9.2 Hz), 7.09 (2H, brs), 6.59 (1H, d, J = 5.2 Hz), 4.73-4.93 (3H, m), 3.92 (3H, s), 1.37 (6H, d, J = 6.0 Hz); LCMS: 100%, MS (ESI): m/z 628.1 [M + H]+. |

TABLE 4-continued

Summarizes compounds 1-280 in terms of their structures and corresponding characteristics.

| # cpd | Structure | Characterization Data |
|---|---|---|
| 244 | 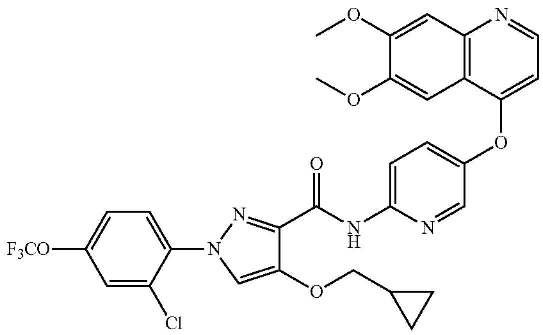 [SMILES: COc1cc2nccc(Oc3ccc(NC(=O)c4nn(-c5ccc(OC(F)(F)F)cc5Cl)cc4OCC4CC4)nc3)c2cc1OC] | white solid; $^1$H NMR (400 MHz, DMSO-d6): δ 9.87 (1H, s), 8.50 (1H, d, J = 5.2 Hz), 8.41 (1H, d, J = 2.4 Hz), 8.37 (1H, d, J = 9.2 Hz), 8.26 (1H, s) 7.85-7.95 (3H, m), 7.63 (1H, d, J = 8.4 Hz), 7.54 (1H, s), 7.42 (1 H, s), 6.57 (1H, d, J = 4.8 Hz), 3.90-4.00 (8H, m), 1.30-1.35 (1H, m), 0.60-0.65 (2H, m), 0.40-0.45 (2H, m); LCMS: 100%, MS (ESI): m/z 656.1 [M + H]+. |
| 245 | 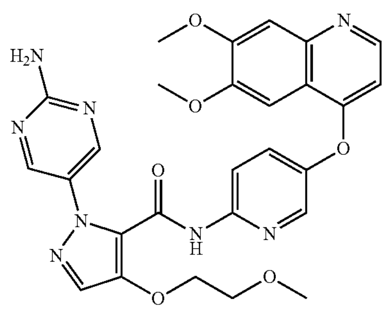 [SMILES: COCCOc1cnn(-c2cnc(N)nc2)c1C(=O)Nc1ccc(Oc2ccnc3cc(OC)c(OC)cc23)cn1] | white powder; $^1$H NMR (400 MHz, DMSO-d6) δ 9.85 (1H, s), 8.49 (1H, d, J = 5.2 Hz), 8.41 (1H, d, J = 2.4 Hz), 8.32 (2H, s), 8.21 (1H, d, J = 8.8 Hz), 7.96 (1H, s), 7.80 (1H, dd, J = 8.8, 2.4 Hz), 7.53 (1H, s), 7.41 (1H, s), 7.03 (2H, brs), 6.54 (1H, d, J = 5.2 Hz), 4.40-4.45 (2H, m), 3.95 (3H, s), 3.94 (3H, s), 3.73-3.75 (2 H, m), 3.35 (3H, s); LCMS: 97.4%, MS (ESI): m/z 581.1 [M + Na]+. |
| 246 | 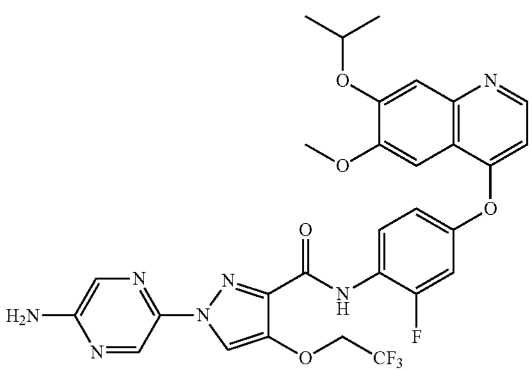 [SMILES: COc1cc2c(Oc3ccc(NC(=O)c4nn(-c5cnc(N)cn5)cc4OCC(F)(F)F)c(F)c3)ccnc2cc1OC(C)C] | pale-yellow solid; $^1$H-NMR (DMSO-d6, 400 MHz): δ 9.73 (1H, brs), 8.67 (1H, s), 8.46-8.55 (2H, m), 7.98 (1H, t, J = 9.2 Hz), 7.77 (1H, s), 7.48 (1H, s), 7.38-7.45 (2H, m), 7.16 (1H, d, J = 8.8 Hz), 6.78 (2H, brs), 6.59 (1H, d, J = 5.2 Hz), 4.82-4.94 (3H, m), 3.92 (3H, s), 1.37 (6H, d, J = 6.4 Hz); LCMS: 100%, MS (ESI): m/z 628.1 [M + H]+. |
| 247 | 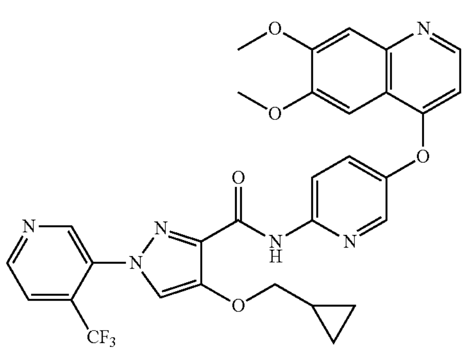 [SMILES: COc1cc2nccc(Oc3ccc(NC(=O)c4nn(-c5cnccc5C(F)(F)F)cc4OCC4CC4)nc3)c2cc1OC] | white powder; $^1$H-NMR (DMSO-d6, 400 MHz): δ 9.77 (1H, brs), 9.06 (1H, s), 9.02 (1H, d, J = 5.2 Hz), 8.50 (1H, d, J = 5.6 Hz), 8.41 (1H, d, J = 2.4 Hz), 8.36 (1H, d, J = 9.2 Hz), 8.30 (1H, s), 8.05 (1H, d, J = 5.2 Hz), 7.89 (1H, dd, J = 8.8, 2.4 Hz), 7.54 (1H, s), 7.42 (1H, s), 6.57 (1H, d, J = 5.2 Hz), 3.94-4.00 (8H, m), 1.30-1.40 (1H, m), 0.60-0.65 (2H, m), 0.40-0.43 (2H, m); LCMS: 100%, MS (ESI): m/z 629.0 [M + Na]+. |

TABLE 4-continued

Summarizes compounds 1-280 in terms of their structures and corresponding characteristics.

| # cpd | Structure | Characterization Data |
|---|---|---|
| 248 | 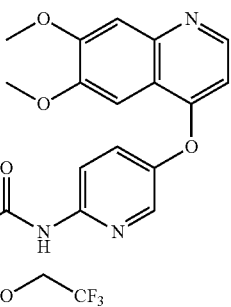 | white powder; ¹H-NMR (DMSO-d6, 400 MHz): δ 10.07 (1H, br), 8.75 (1H, s), 8.54 (1H, s), 8.51 (1H, d, J = 4.8 Hz), 8.43 (1H, d, J = 2.4 Hz), 8.35 (1H, d, J = 9.2 Hz), 7.88 (1H, dd, J = 9.2, 2.4 Hz), 7.77 (1H, s), 7.55 (1H, s), 7.42 (1H, s), 6.78 (2H, br), 6.58 (1H, d, J = 5.2 Hz), 4.90 (2H, q, J = 8.8 Hz), 3.80-4.05 (6H, m); LCMS: 100%, MS (ESI): m/z 583.1.0 [M + H]+. |
| 249 | 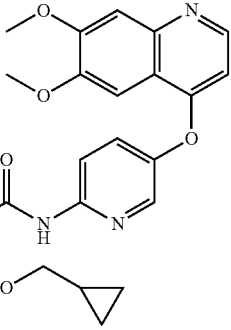 | white powder; ¹H-NMR (DMSO-d6, 400 MHz): δ 9.96 (1H, brs), 8.65 (1H, s), 8.50 (1H, d, J = 5.2 Hz), 8.42 (1H, d, J = 2.4 Hz), 8.38 (1H, d, J = 9.2 Hz), 8.33 (1H, s), 7.89 (1H, dd, J = 8.8, 2.8 Hz), 7.76 (1H, s), 7.55 (1H, s), 7.42 (1H, s), 6.74 (2H, s), 6.57 (1H, d, J = 5.6 Hz), 4.01 (2H, d, J = 7.2 Hz), 3.85-3.98 (6H, m), 1.25-1.43 (1H, m), 0.55-0.73 (2H, m), 0.35-0.49 (2H, m); LCMS: 95.2%, MS (ESI): m/z 555.1 [M + H]+. |
| 250 | 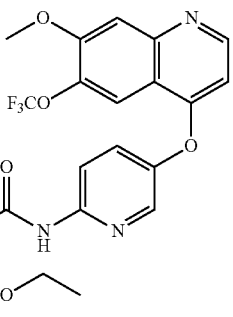 | off-white powder; ¹H-NMR (DMSO-d6, 400 MHz): δ 9.61 (1H, s), 8.70-8.80 (2H, m), 8.68 (1H, d, J = 4.8 Hz), 8.30 (1H, s), 8.23 (1H, t, J = 8.8 Hz), 8.16 (1H, s), 7.74 (1H, d, J = 4.8 Hz), 7.69 (1H, s), 7.52 (1H, dd, J = 11.2, 2.4 Hz), 7.24 (1H, d, J = 8.4 Hz), 6.67 (1H, d, J = 4.8 Hz), 5.60 (1H, t, J = 5.2 Hz), 4.67 (2H, d, J = 5.2 Hz), 4.16 (2H, q, J = 7.2 Hz), 4.05 (3H, s), 1.43 (3H, t, J = 6.8 Hz); LCMS: 100%, MS (ESI): m/z 636.1 [M + Na]+. |
| 251 | 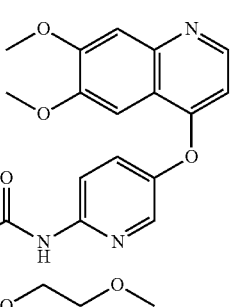 | white powder; ¹H NMR (400 MHz, DMSO-d6): δ 9.91 (1H, brs), 8.77 (2H, s), 8.51 (1H, s), 8.40-8.45 (1H, m), 8.39-8.43 (1H, m), 8.36 (1H, d, J = 8.8 Hz), 7.88 (1H, d, J = 6.8 Hz), 7.55 (1H, s), 7.42 (1H, s), 7.05 (2H, brs), 6.58 (1H, s), 4.20-4.25 (2H, m), 3.95 (6H, s), 3.70-3.75 (2H, m), 3.33 (3H, s); LCMS: 100%, MS (ESI): m/z 681.1 [M + Na]+. |

TABLE 4-continued

Summarizes compounds 1-280 in terms of their structures and corresponding characteristics.

| # cpd | Structure | Characterization Data |
|---|---|---|
| 252 | 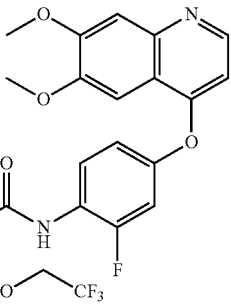 | white powder; ¹H-NMR (DMSO-d6, 400 MHz): δ 9.73 (1H, s), 8.67 (1H, s), 8.50-8.60 (2H, m), 7.99 (1H, t, J = 8.8 Hz), 7.77 (1H, s), 7.49 (1H, s), 7.35-7.48 (2H, m), 7.17 (1H, d, J = 8.8 Hz), 6.78 (2H, brs), 6.60 (1H, d, J = 5.2 Hz), 4.88 (2H, q, J = 8.8 Hz), 3.95 (3H, s), 3.94 (3H, s); LCMS: 100%, MS (ESI): m/z 622.1 [M + Na]+. |
| 253 | 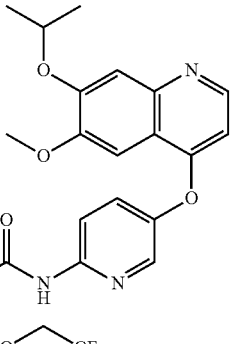 | pale-yellow powder; ¹H-NMR (DMSO-d6, 400 Mhz): δ 10.08 (1H, brs), 8.75 (1H, s), 8.54 (1H, s), 8.51 (1H, d, J = 5.2 Hz), 8.43 (1H, d, J = 2.4 Hz), 8.35 (1H, d, J = 9.2 Hz), 7.88 (1H, dd, J = 8.8, 2.4 Hz), 7.77 (1H, s), 7.55 (1H, s), 7.42 (1H, s), 6.79 (2H, brs), 6.58 (1H, d, J = 5.2 Hz), 4.85-4.94 (3H, m), 3.94 (3H, s), 1.38 (6H, d, J = 6.0 Hz); LCMS: 100%, MS (ESI): m/z 611.1 [M + H]+. |
| 254 | 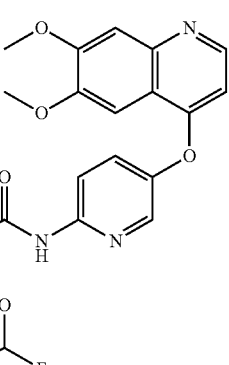 | white powder; ¹H-NMR (DMSO-d6, 400 MHz): δ 10.39 (1H, brs), 8.86 (2H, s), 8.68 (1H, s), 8.57 (1H, d, J = 5.2 Hz), 8.46 (1H, d, J = 2.4 Hz), 8.33 (1H, d, J = 8.8 Hz), 7.91 (1H, dd, J = 8.8, 2.4 Hz), 7.59 (1H, s), 7.44 (1H, s), 7.18 (1H, t, J = 74.0, Hz), 7.11 (2H, brs), 6.65 (1H, d, J = 5.2 Hz), 3.97 (3H, s), 3.96 (3H, s); LCMS: 100%, MS (ESI): m/z 573.1 [M + Na]+. |
| 255 | 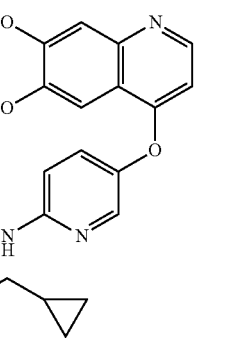 | white solid; ¹H NMR (400 MHz, DMSO-d6): δ 10.03 (1H, s), 9.20 (1H, s), 8.67 (1H, s), 8.58 (1H, d, J = 4.0 Hz), 8.50 (1H, d, J = 4.8 Hz), 8.43 (1H, s), 8.30-8.38 (2H, m), 7.89 (1H, d, J = 7.2 Hz), 7.55-7.65 (1H, m), 7.54 (1H, s), 7.41 (1H, s), 6.57 (1H, d, J = 4.4 Hz), 4.00 (2H, d, J = 7.2 Hz), 3.95 (6H, s), 1.35-1.40 (1H, m), 0.60-0.65 (2H, m), 0.40-0.45 (2H, m); LCMS: 100%, MS (ESI): m/z 539.1 [M + H]+. |

TABLE 4-continued

Summarizes compounds 1-280 in terms of their structures and corresponding characteristics.

| # cpd | Structure | Characterization Data |
|---|---|---|
| 256 | 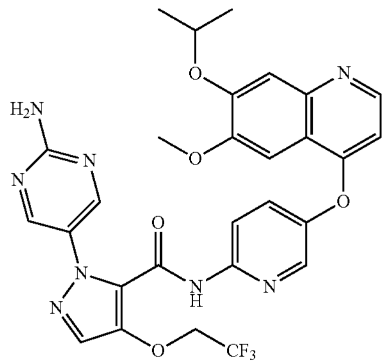 [SMILES: COc1cc2c(Oc3ccc(NC(=O)c4c(OCC(F)(F)F)cnn4-c4cnc(N)nc4)nc3)ccnc2cc1OC(C)C] | off-white powder; $^1$H-NMR (DMSO-d6, 400 MHz): δ 9.83 (1H, brs), 8.47 (1H, d, J = 4.8 Hz), 8.38-8.43 (1H, m), 8.32 (2H, s), 8.19 (1H, d, J = 8.8 Hz), 8.02 (1H, s), 7.75-7.83 (1H, m), 7.51 (1H, s), 7.40 (1H, s), 7.06 (2H, brs), 6.53 (1H, d, J = 4.8 Hz), 5.06 (2H, q, J = 8.4 Hz), 4.80-4.91 (1H, m), 3.92 (3H, s), 1.37 (6H, d, J = 5.6 Hz); LCMS: 100%, MS (ESI): m/z 611.1 [M + H]+. |
| 257 | 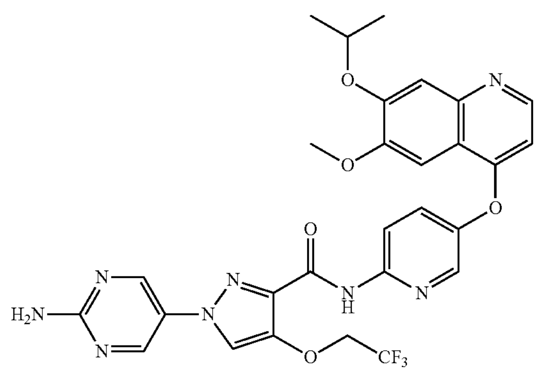 [SMILES: COc1cc2c(Oc3ccc(NC(=O)c4nn(-c5cnc(N)nc5)cc4OCC(F)(F)F)nc3)ccnc2cc1OC(C)C] | off-white solid; $^1$H-NMR (DMSO-d6, 400 MHz): δ 10.10 (1H, brs), 8.80 (2H, s), 8.53-8.60 (2H, m), 8.45 (1H, d, J = 2.0 Hz), 8.36 (1H, d, J = 9.2 Hz), 7.90 (1H, dd, J = 9.6, 2.8 Hz), 7.59 (1H, s), 7.45 (1H, s), 7.09 (2H, brs), 6.66 (1H, d, J = 4.4 Hz), 4.76-4.92 (3H, m), 3.95 (3H, s), 1.39 (6H, d, J = 6.0 Hz); LCMS: 100%, MS (ESI): m/z 611.1 [M + H]+. |
| 258 | 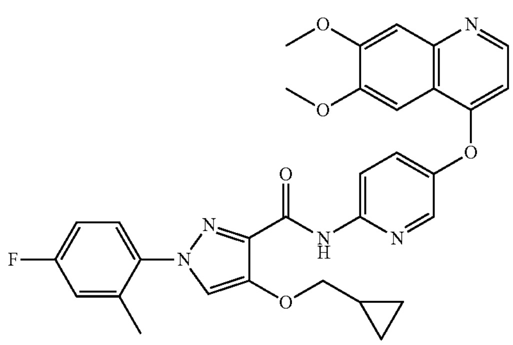 [SMILES: COc1cc2nccc(Oc3ccc(NC(=O)c4nn(-c5ccc(F)cc5C)cc4OCC4CC4)nc3)c2cc1OC] | white powder; $^1$H-NMR (DMSO-d6, 400 MHz): δ 9.80 (1H, brs), 8.51 (1H, d, J = 5.2 Hz), 8.41 (1H, d, J = 2.8 Hz), 8.37 (1H, d, J = 9.2 Hz), 8.13 (1H, s), 7.85-7.90 (1H, m), 7.54 (1H, s), 7.49-7.53 (1H, m), 7.42 (1H, s), 7.34 (1H, dd, J = 9.2, 2.4 Hz), 7.20-7.28 (1H, m), 6.57 (1H, d, J = 4.8 Hz), 3.85-4.05 (8H, m), 2.27 (3H, s), 1.30-1.40 (1H, m), 0.59-0.66 (2H, m), 0.37-0.44 (2H, m); LCMS: 100%, MS (ESI): m/z 570.1 [M + H]+. |
| 249 | 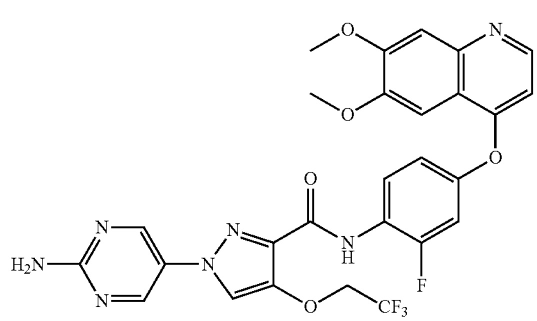 [SMILES: COc1cc2nccc(Oc3ccc(NC(=O)c4nn(-c5cnc(N)nc5)cc4OCC(F)(F)F)c(F)c3)c2cc1OC] | white powder; $^1$H-NMR (DMSO-d6, 400 MHz): δ 9.76 (1H, brs), 8.75 (2H, s), 8.55 (1H, s), 8.53 (1H, d, J = 5.2 Hz0, 7.94 (1H, t, J = 8.8 Hz), 7.49 (1H, s), 7.35-7.45 (2H, m), 7.17 (1H, d, J = 9.2 Hz), 7.09 (2H, brs), 6.60 (1H, d, J = 5.2 Hz), 4.88 (2H, q, J = 8.8 Hz), 3.95 (3H, s), 3.93 (3H, s); LCMS: 100%, MS (ESI): m/z 622.1 [M + Na]+. |

TABLE 4-continued

Summarizes compounds 1-280 in terms of their structures and corresponding characteristics.

| # cpd | Structure | Characterization Data |
|---|---|---|
| 260 | 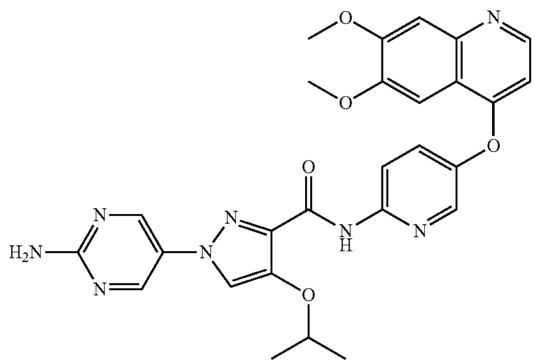 [SMILES: COc1cc2nccc(Oc3ccc(NC(=O)c4nn(-c5cnc(N)nc5)cc4OC(C)C)nc3)c2cc1OC] | white powder; $^1$H-NMR (DMSO-d6, 400 MHz): δ 9.90 (1H, brs), 8.76 (2H, s), 8.50 (1H, d, J = 5.2 Hz), 8.40-8.44 (2H, m), 8.37 (1H, d, J = 9.0 Hz), 7.88 (1H, dd, J = 8.8, 2.4 Hz), 7.54 (1H, s), 7.42 (1H, s), 7.05 (2H, brs), 6.56 (1H, d, J = 4.8 Hz), 4.43-4.54 (1H, m), 3.96 (3H, s0, 3.95 (3H, s), 1.41 (6H, d, J = 6.0 Hz); LCMS: 100%, MS (ESI): m/z 565.1 [M + Na]+. |
| 261 | 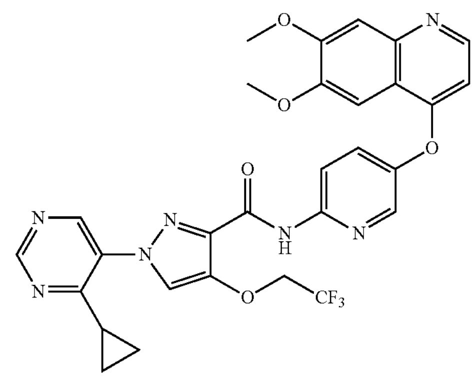 [SMILES: COc1cc2nccc(Oc3ccc(NC(=O)c4nn(-c5cncnc5C5CC5)cc4OCC(F)(F)F)nc3)c2cc1OC] | white powder; $^1$H-NMR (DMSO-d6, 400 MHz): δ 10.03 (1H, brs), 9.11 (1H, s), 8.87 (1H, s), 8.50 (1H, d, J = 4.8 Hz), 8.40-8.50 (2H, m), 8.33 (1H, d, J = 8.8 Hz), 7.88 (1H, d, J = 8.8 Hz), 7.54 (1H, s), 7.41 (1H, s), 6.56 (1H, d, J = 4.8 Hz), 4.80-4.90 (2H, m), 3.95 (6H, s), 2.50-2.70 (1H, m), 1.15-1.25 (4H, m); LCMS: 100%, MS (ESI): m/z 608.1 [M + H]+. |
| 262 | 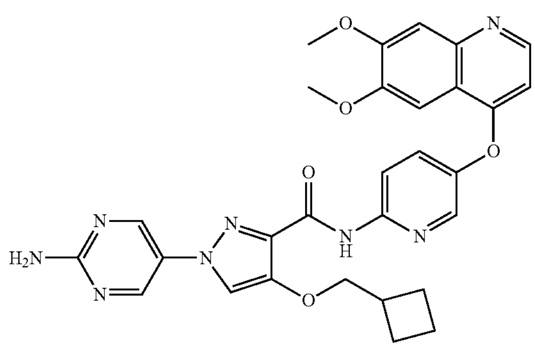 [SMILES: COc1cc2nccc(Oc3ccc(NC(=O)c4nn(-c5cnc(N)nc5)cc4OCC4CCC4)nc3)c2cc1OC] | white powder; $^1$H-NMR (DMSO-d6, 400 MHz): δ 9.87 (1H, brs), 8.76 (2H, s0, 8.50 (1H, d, J = 4.8 Hz), 8.43 (1H, s), 8.41 (1H, d, J = 2.8 Hz), 8.37 (1H, d, J = 8.8 Hz), 7.88 (1H, dd, J = 9.2, 2.8 Hz), 7.54 (1H, s), 7.42 (1H, s), 7.05 (2H, brs), 6.56 (1H, d, J = 5.6 Hz), 4.10 (2H, d, J = 6.4 Hz), 3.95 (3H, s), 3.94 (3H, s), 2.81-2.86 (1H, m), 2.08-2.15 (2H, m), 1.90-1.98 (4H, m); LCMS: 100%, MS (ESI): m/z 569.1 [M + H]+. |
| 263 | 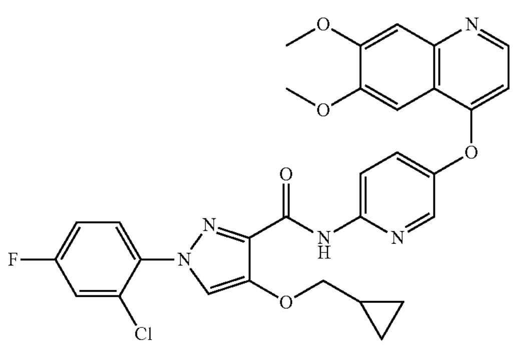 [SMILES: COc1cc2nccc(Oc3ccc(NC(=O)c4nn(-c5ccc(F)cc5Cl)cc4OCC4CC4)nc3)c2cc1OC] | off-white powder; $^1$H-NMR (DMSO-d6, 400 MHz): δ 9.85 (1H, brs), 8.51 (1H, d, J = 4.8 Hz), 8.41 (1H, d, J = 2.4 Hz), 8.37 (1H, d, J = 8.8 Hz), 8.20 (1H, s), 7.89 (1H, dd, J = 8.8, 2.8 Hz), 7.75-7.83 (2H, m), 7.54 (1H, s), 7.47 (1H, td, J = 8.8, 2.8 Hz), 7.42 (1H, s), 6.58 (1H, d, J = 5.2 Hz), 3.92-4.00 (8H, m), 1.29-1.40 (1H, m), 0.58-0.66 (2H, m), 0.37-0.45 (2H, m); LCMS: 100%, MS (EIS): m/z 612.0 [M + Na]+. |

TABLE 4-continued

Summarizes compounds 1-280 in terms of their structures and corresponding characteristics.

| # cpd | Structure | Characterization Data |
|---|---|---|
| 264 | 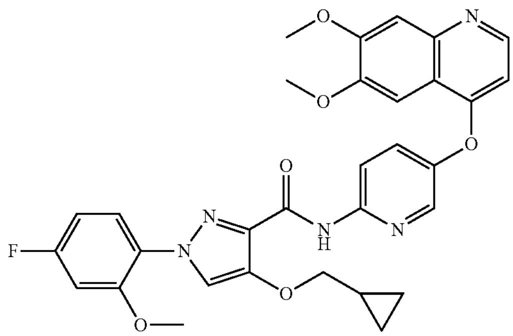 [SMILES: COc1cc2nccc(Oc3ccc(NC(=O)c4nn(-c5ccc(F)cc5OC)cc4OCC4CC4)nc3)c2cc1OC] | off-white powder; ¹H-NMR (DMSO-d6, 400 MHz): δ 9.86 (1H, brs), 8.50 (1H, d, J = 5.2 Hz), 8.41 (1H, d, J = 2.4 Hz), 8.38 (1H, d, J = 8.8 Hz), 8.10 (1H, s), 7.88 (1H, dd, J = 9.2, 2.8 Hz), 7.71 (1H, dd, J = 8.8, 6.4 Hz), 7.55 (1H, s), 7.42 (1H, s), 7.24 (1H, dd, J = 10.8, 6.4 Hz), 6.97 (1H, td, J = 8.4, 2.4 Hz), 6.57 (1H, d, J = 5.2 Hz), 3.93-3.99 (8H, m), 3.90 (3H, s), 1.27-1.40 (1H, m), 0.58-0.69 (2H, m), 0.37-0.45 (2H, m); LCMS: 100%, MS (ESI): m/z 608.1 [M + Na]+. |
| 265 | 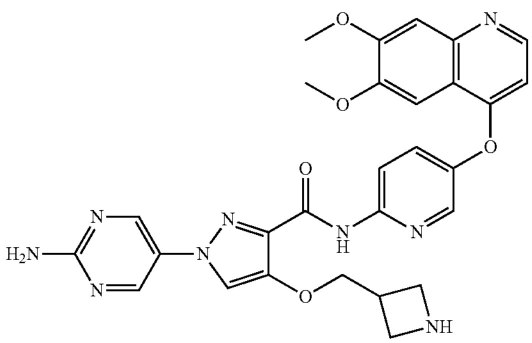 [SMILES: COc1cc2nccc(Oc3ccc(NC(=O)c4nn(-c5cnc(N)nc5)cc4OCC4CNC4)nc3)c2cc1OC] | white powder; ¹H-NMR (DMSO-d6, 400 MHz): δ 9.92 (1H, brs), 8.77 (2H, s), 8.50 (1H, d, J = 5.2 Hz), 8.46 (1H, s), 8.41 (1H, d, J = 2.4 Hz), 8.36 (1H, d, J = 9.2 Hz), 7.87 (1H, dd, J = 8.8, 2.0 Hz), 7.54 (1H, s), 7.41 (1H, s), 7.06 (2H, brs), 6.56 (1H, d, J = 5.2 Hz), 4.25 (2H, d, J = 5.6 Hz), 3.95 (3H, s), 3.94 (3H, s), 3.75-3.60 (2H, m), 3.18-3.05 (1H, m); LCMS: 97%, MS (ESI): m/z 570.1 [M + H]+. |
| 266 | 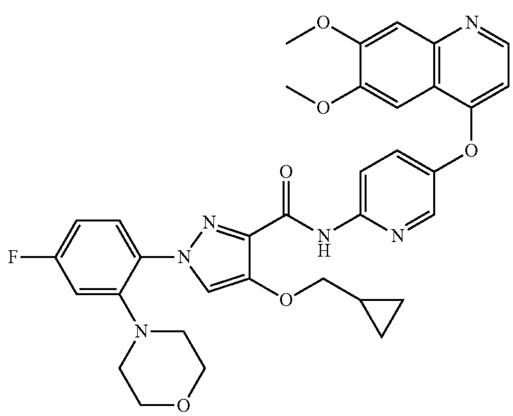 [SMILES: COc1cc2nccc(Oc3ccc(NC(=O)c4nn(-c5ccc(F)cc5N5CCOCC5)cc4OCC4CC4)nc3)c2cc1OC] | off-white powder; ¹H-NMR (DMSO-d6, 400 MHz): δ 9.85 (1H, brs), 8.51 (1H, d, J = 5.2 Hz), 8.41 (1H, d, J = 2.4 Hz), 8.37 (1H, d, J = 9.2 Hz), 8.23 (1H, s), 7.88 (1H, dd, J = 9.2, 2.8 Hz), 7.52-7.60 (2H, m), 7.42 (1H, s), 6.97-7.08 (2H, m), 6.56 (1H, d, J = 5.2 Hz), 3.98 (2H, d, J = 7.2 Hz), 3.96 (3H, s), 3.95 (3H, s), 3.57-3.68 (4H, m), 2.63-2.72 (4H, m), 1.30-1.39 (1H, m), 0.59-0.68 (2H, m), 0.38-0.47 (2H, m); LCMS: 100%, MS (ESI): m/z 663.1 [M + Na]+. |
| 267 | 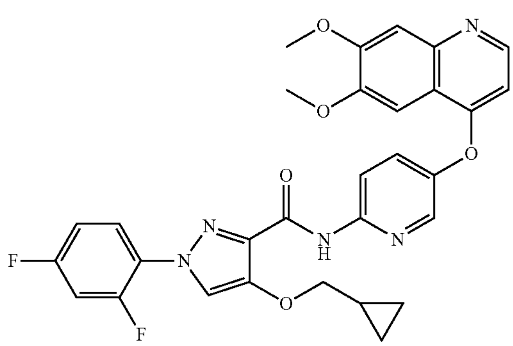 | white powder; ¹H-NMR (DMSO-d6, 400 MHz): δ 9.94 (1H, brs), 8.51 (1H, d, J = 5.6 Hz), 8.42 (1H, d, J = 2.8 Hz0, 8.38 (1H, d, J = 9.2 Hz), 8.23 (1H, d, J = 2.0 Hz), 7.92-8.00 (1H, m), 7.89 (1H, dd, J = 8.8, 2.4 Hz), 7.59-7.69 (1H, m), 7.55 (1H, s), 7.42 (1H, s), 7.33 (1H, t, J = 9.6 Hz), 6.58 (1H, d, J = 4.8 Hz), 3.91-4.04 (8H, m), 1.28-1.38 (1H, m), 0.57-0.69 (2H, m), 0.37-0.46 (2H, m); LCMS: 100%, MS (ESI): m/z 574.1 [M + H]+. |

TABLE 4-continued

Summarizes compounds 1-280 in terms of their structures and corresponding characteristics.

| # cpd | Structure | Characterization Data |
|---|---|---|
| 268 | 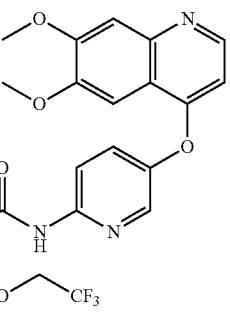 | off-white powder; ¹H-NMR (DMSO-d6, 400 MHz): δ 10.08 (1H, brs), 8.51 (1H, d, J = 5.2 Hz), 8.39-8.45 (2H, m), 8.34 (1H, d, J = 8.8 Hz), 8.02-8.14 (1H, m), 7.88 (1H, dd, J = 8.8, 2.8 Hz), 7.62-7.74 (1H, m), 7.54 (1H, s), 7.42 (1H, s), 7.36 (1H, t, J = 8.0 Hz0, 6.57 (1H, d, J = 4.8 Hz0, 4.88 (2H, q, J = 8.8 Hz), 3.96 (3H, s), 3.95 (3H, s); LCMS: 100%, MS (ESI): m/z 624.0 [M + Na]+. |
| 269 | 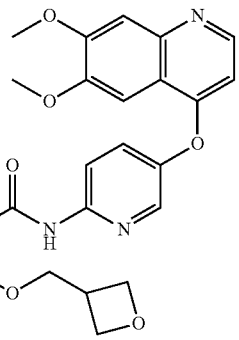 | white powder; ¹H-NMR (DMSO-d6, 400 MHz): δ 9.90 (1H, brs), 8.78 (2H, s), 8.46-8.54 (2H, m), 8.41 (1H, d, J = 2.8 Hz), 8.35 (1H, d, J = 8.8 Hz), 7.87 (1H, d, J = 9.2 Hz), 7.54 (1H, s), 7.42 (1H, s), 7.06 (2H, brs), 6.56 (1H, d, J = 5.2 Hz), 4.75 (2H, t, J = 7.2 Hz), 4.48 (2H, t, J = 6.0 Hz), 4.34 (2H, d, J = 6.8 Hz), 3.96 (3H, s), 3.95 (3H, s), 3.44-3.58 (1H, m); LCMS: 100%, MS (ESI): m/z 571.1 [M + H]+, 593.1 [M + Na]+. |
| 270 | 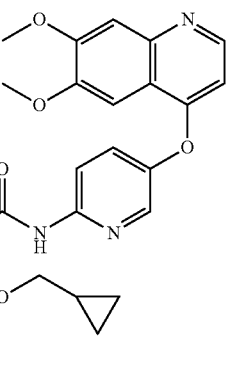 | white powder; ¹H-NMR (DMSO-d6, 400 MHz): δ 9.74 (1H, brs), 8.50 (1H, d, J = 5.2 Hz), 8.40 (1H, d, J = 2.8 Hz), 8.37 (1H, d, J = 8.8 Hz), 8.07 (1H, s), 7.88 (1H, dd, J = 9.2, 2.8 Hz), 7.54 (1H, s), 7.46 (1H, dd, J = 8.8, 6.0 Hz), 7.42 (1H, s), 7.38 (1H, dd, J = 10.4, 2.4 Hz), 7.22 (1H, td, J = 8.0, 2.4 Hz), 6.56 (1H, d, J = 5.2 Hz), 3.89-4.04 (8H, m), 2.80-2.94 (1H, m), 1.81-1.94 (2H, m), 1.69-1.79 (2H, m), 1.48-1.61 (4H, m), 1.27-1.39 (1H, m), 0.57-0.67 (2 H, m), 0.36-0.44 (2 H, m); LCMS: 100%, MS (ESI): m/z 624.1 [M + H]+. |
| 271 | 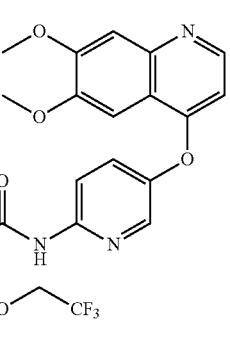 | white powder; ¹H-NMR (DMSO-d6, 400 MHz): δ 9.89 (1H, brs), 8.50 (1H, d, J = 5.2 Hz), 8.41 (1H, d, J = 2.8 Hz), 8.37 (1H, s), 8.32 (1H, d, J = 9.2 Hz), 7.76-7.92 (3H, m), 7.54 (1H, s), 7.49 (1H, td, J = 8.4, 2.8 Hz), 7.42 (1H, s), 6.57 (1H, d, J = 4.8 Hz), 4.86 (2H, q, J = 8.4 Hz), 3.95 (3H, s), 3.94 (3H, s); LCMS: 100%, MS (ESI): m/z 628.0 [M + H]+. |

TABLE 4-continued

Summarizes compounds 1-280 in terms of their structures and corresponding characteristics.

| # cpd | Structure | Characterization Data |
|---|---|---|
| 272 | 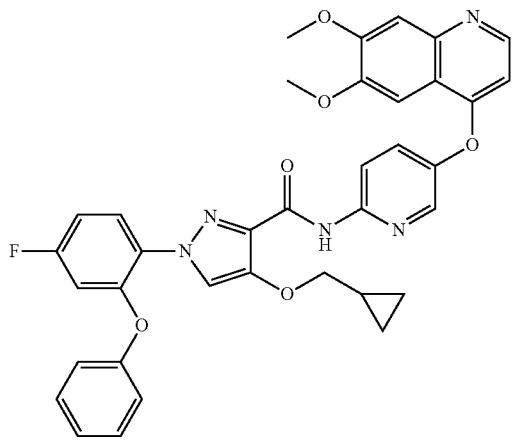 [SMILES: COc1cc2nccc(Oc3ccc(NC(=O)c4nn(-c5ccc(F)cc5Oc5ccccc5)cc4OCC4CC4)nc3)c2cc1OC] | white powder; ¹H NMR (DMSO-d6, 400 MHz): δ 9.85 (1H, s), 8.50 (1H, d, J = 5.2 Hz), 8.41 (1H, d, J = 2.8 Hz0, 8.36 (1H, d, J = 9.2 Hz), 8.18 (1H, s), 7.85-7.94 (2H, m), 7.54 (1H, s), 7.39-7.44 (3H, m), 7.18-7.26 (2H, m), 7.11 (2H, d, J = 7.6 Hz), 6.97 (1H, dd, J = 9.6, 2.0 Hz), 6.56 (1H, d, J = 5.2 Hz), 3.87-3.99 (8H, m), 1.20-1.28 (1H, m), 0.54-0.60 (2H, m) 0.33-0.39 (2H, m); LCMS: 100%, MS (ESI): m/z 670.1 [M + Na]+. |
| 273 | 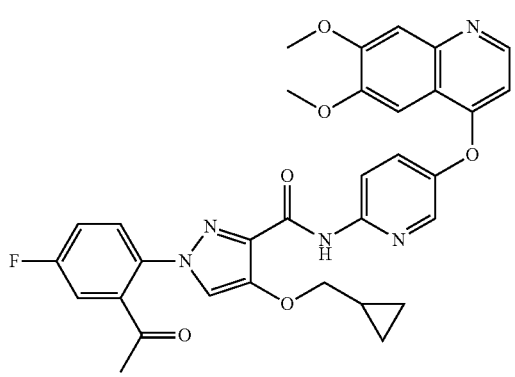 [SMILES: COc1cc2nccc(Oc3ccc(NC(=O)c4nn(-c5ccc(F)cc5C(C)=O)cc4OCC4CC4)nc3)c2cc1OC] | white powder; ¹H-NMR (DMSO-d6, 400 MHz): δ 9.56 (1H, brs), 8.51 (1H, d, J = 5.2 Hz), 8.35-8.45 (2H, m), 7.89 (1H, d, J = 6.4 Hz), 7.69 (1H, dd, J = 8.4, 4.0 Hz), 7.51-7.60 (2H, m), 7.42 (1H, s), 7.35 (1H, t, J = 8.0 Hz), 6.58 (1H, d, J = 5.2 Hz), 6.53 (1H, s0, 4.15-4.35 (2H, m), 3.95 (6H, s), 1.79 (3H, s), 1.32-1.43 (1H, m), 0.580-0.69 (2H, m), 0.40-0.51 (2H, m); LCMS: 100%, MS (ESI): m/z 620.0 [M + Na]+. |
| 274 | 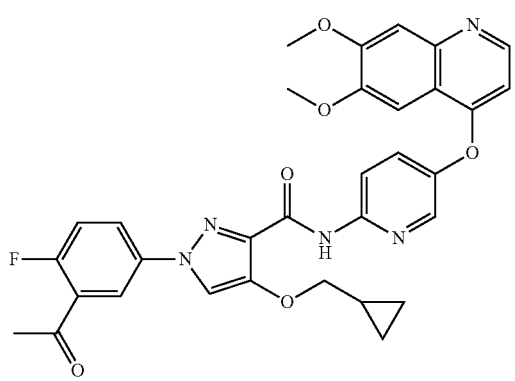 [SMILES: COc1cc2nccc(Oc3ccc(NC(=O)c4nn(-c5ccc(F)c(C(C)=O)c5)cc4OCC4CC4)nc3)c2cc1OC] | white powder; ¹H-NMR (DMSO-d6, 400 MHz): δ 9.66 (1H, brs), 8.50 (1H, d, J = 4.8 Hz), 8.32-8.44 (3H, m), 7.89 (1H, d, J = 8.8 Hz), 7.75-7.80 (1H, m), 7.52-7.63 (3H, m), 7.42 (1H, s), 6.57 (1H, d, J = 4.8 Hz), 3.83-4.09 (8H, m), 2.21 (3H, s), 1.31-1.39 (1H, m), 0.58-0.69 (2H, m), 0.36-0.49 (2H, m); LCMS: 100%, MS (EIS): m/z 620.1 [M + Na]+. |

TABLE 4-continued

Summarizes compounds 1-280 in terms of their structures and corresponding characteristics.

| # cpd | Structure | Characterization Data |
|---|---|---|
| 275 | 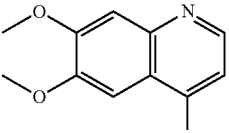 | white powder; ¹H-NMR (DMSO-d6, 400 MHz): δ 9.64 (1H, s), 8.50 (1H, d, J = 5.2 Hz), 8.39 (1H, d, J = 2.4 Hz), 8.33 (1H, d, J = 8.8 Hz), 7.87 (1H, dd, J = 8.8, 2.4 Hz), 7.70-7.76 (1H, m), 7.52-7.59 (2H, m), 7.33-7.49 (6H, m), 7.13-7.19 (2H, m), 6.55 (1H, d, J = 5.6 Hz), 3.95 (3H, s), 3.94 (3H, s), 3.71 (2H, d, J = 7.2 Hz), 1.03-1.10 (1H, m), 0.47-0.53 (2H, m), 0.23-0.30 (2H, m); LCMS: 100%, MS (ESI): m/z 654.1 [M + Na]+. |
| 276 | 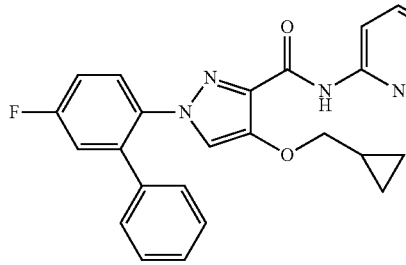 | pink powder; ¹H NMR (400 MHz, DMSO-d6): δ 10.17 (1H, brs), 8.49 (1H, d, J = 5.2 Hz), 8.10 (1H, s), 8.00 (1H, d, J = 13.2 Hz), 7.64-7.74 (1H, m), 7.50-7.56 (2H, m), 7.41-7.51 (1H, m), 7.41 (1H, s), 7.29-7.34 (1H, m), 7.18-7.23 (1H, m), 6.48 (1H, d, J = 5.2 Hz0, 4.12 (2H, t, J = 5.6 Hz0, 3.95 (6H, s), 2.67 (2H, t, J = 5.6 Hz), 2.20-2.29 (9H, m); LCMS: 100%, MS (ESI): m/z 626.0 [M + Na]+. |
| 277 | 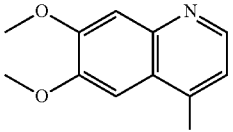 | light yellow solid; ¹H-NMR (DMSO-d6, 400 MHz): δ 9.51 (1H, brs), 8.45-8.50 (2H, m), 7.98 (1H, d, J = 13.2 Hz), 7.51-7.58 (2H, m), 7.43-7.51 (2H, m), 7.41 (1H, s), 7.31 (1H, d, J = 9.2 Hz), 7.20 (1H, t, J = 8.4 Hz), 6.47 (1H, d, J = 4.8 Hz), 4.37 (2H, q, J = 6.8 Hz), 3.95 (6H, s), 2.28 (3H, s), 1.44 (3H, t, J = 6.8 Hz); LCMS: 100%, MS (ESI): m/z 561.0 [M + H]+. |

TABLE 4-continued

Summarizes compounds 1-280 in terms of their structures and corresponding characteristics.

| # cpd | Structure | Characterization Data |
|---|---|---|
| 278 | 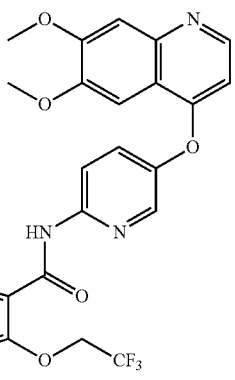 | white powder; ¹H NMR (400 MHz, DMSO-d6): δ 10.35 (1H, brs), 8.79 (1H, s), 8.52 (1H, d, J = 5.2 Hz), 8.44 (1H, d, J = 2.8 Hz), 8.30-8.40 (2H, m), 7.97-8.05 (1H, m), 7.88 (1H, dd, J = 8.8, 2.8 Hz0, 7.66 (1H, t, J = 9.2 Hz), 7.55 (1H, s), 7.42 (1H, s), 6.58 (1H, d, J = 5.2 Hz), 4.83 (2H, q, J = 8.8 Hz), 3.96 (3H, s), 3.95 (3H, s); LCMS: 100%; MS (ESI): m/z 617.9 [M + H]+. |
| 279 | 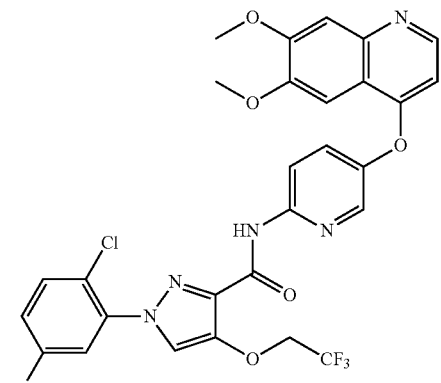 | white solid; ¹H-NMR (DMSO-d6, 400 MHz): δ 8.50 (1H, d, J = 4.8 Hz), 8.39-8.48 (2H, m), 8.33 (1H, d, J = 8.8 Hz), 7.84-7.92 (2H, m), 7.77-7.83 (1H, m), 7.45-7.55 (2H, m), 7.41 (1H, s), 6.57 (1H, d, J = 4.8 Hz), 4.86 (2H, q, J = 8.4 Hz), 3.95 (6H, s); LCMS: 100%, MS (ESI): m/z 617.9 [M + H]+. |
| 280 | 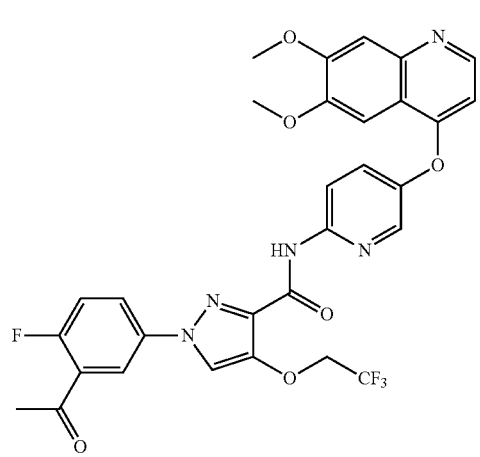 [SMILES: COc1cc2nccc(Oc3ccc(NC(=O)c4nn(-c5ccc(F)c(C(C)=O)c5)cc4OCC(F)(F)F)nc3)c2cc1OC] | white solid; ¹H-NMR (DMSO-d6, 400 MHz): δ 10.23 (1H, brs), 8.86 (1H, s), 8.51 (1H, d, J = 5.2 Hz), 8.44 (1H, s), 8.26-8.38 (3H, m), 7.89 (1H, d, J = 9.2 Hz), 7.62 (1H, t, J = 9.6 Hz), 7.55 (1H, s), 7.42 (1H, s), 6.57 (1H, d, J = 4.8 Hz), 4.85 (2H, q, J = 8.0 Hz), 3.95 (6H, s), 2.67 (3H, s); LCMS: 100%, MS (ESI): m/z 626.0 [M + H]+. |

The invention claimed is:
1. A compound having the general formula I:

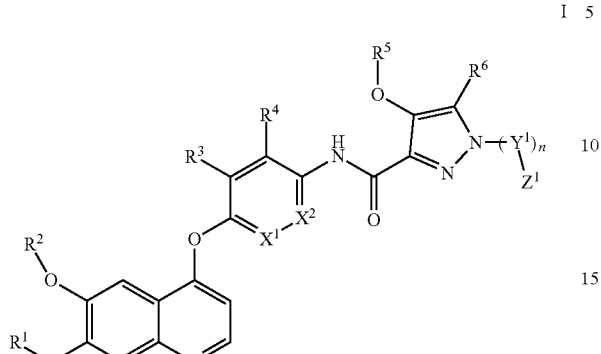

wherein
X¹ is, independently at each occurrence, selected from CH and N;
X² is, independently at each occurrence, selected from CH and N;
wherein one of X¹ and X² is N and the other is not;
Y¹ is, independently at each occurrence, selected from $CH_2$, $CH(CH_3)CH_2$, $C(CH_3)_2$, $C(CH_3)_2CH_2$ and $CH_2CH_2$;
n is, independently at each occurrence, selected from 0 and 1;
$R^1$ is, at each occurrence, independently selected from the group consisting of C1-C6 alkyl and C1-C3 haloalkyl;
$R^2$ is, at each occurrence, independently selected from the group consisting of C1-C6 alkyl and C1-C3 haloalkyl, any of which is optionally substituted;
$R^3$ is, at each occurrence, independently selected from the group consisting of hydrogen, halogen, C1-C3 alkyl, which is optionally substituted, and $NHCH(CH_3)CH_3$;
$R^4$ is, at each occurrence, independently selected from the group consisting of hydrogen, halogen, $NHCH(CH_3)_2$, —$CH_2OH$, C1-C3 alkyl, which is optionally substituted, alkoxy, and —$CF_3$;
$R^5$ is, at each occurrence, independently selected from the group consisting of C1-C6 alkyl; C1-C6 alkyl substituted with C1-C6 cycloalkyl, with heterocyclyl or with O—(C1-C6 alkyl); C1-C3 haloalkyl; N,N-dimethylethane-amino; and N,N-dimethylpropan-1-amino;
$R^6$ is, at each occurrence, independently selected from the group consisting of hydrogen and $CH_3$;
$Z^1$ is, at each occurrence, independently selected from the group consisting of hydrogen, hydroxyl, C1-C6 alkyl, $C(O)R^7$, $C(O)NHR^7$, $C(O)OR^7$, CN, $C(O)R^8$, $C(O)OR^8$, $N(R^7)_2$, $OR^8$, $OCH_3$, $OCH_2F$, $OCHF_2$, $OCF_3$ and any structure of the following group A, any structure of which is optionally substituted;

group A

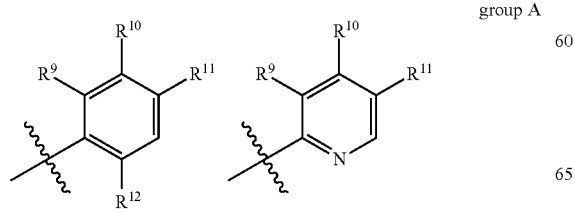

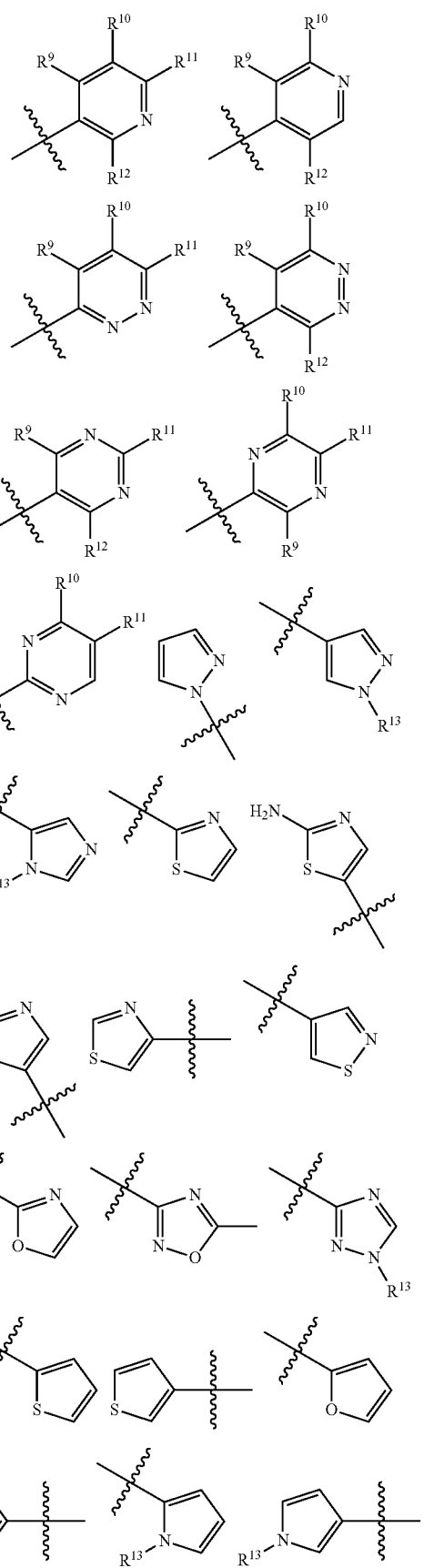

-continued

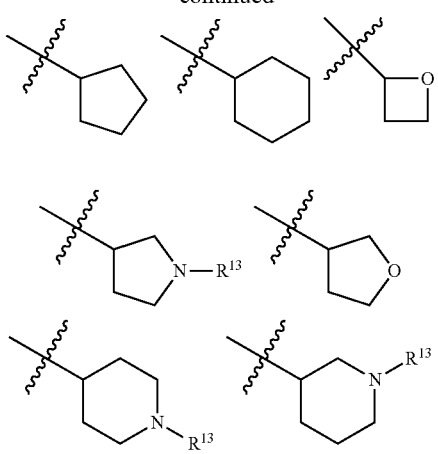

R⁷ is, at each occurrence, independently selected from the group consisting of hydrogen and C1-C6 alkyl, any of which is optionally substituted;

R⁸ is, at each occurrence, independently selected from the group consisting of hydrogen, C1-C6 alkyl, C1-C3 haloalkyl, and phenyl any of which is optionally substituted;

R⁹ is, at each occurrence, independently selected from the group consisting of hydrogen, C2-C6 alkyl; C1-C6 cycloalkyl; C1-C6 alkyl substituted with C1-C6 cycloalkyl; C1-C6 alkenyl; heterocyclyl; C1-C3 haloalkyl; $C(O)OR^7$; $CH_2C(O)OR^7$; $C(O)R^7$; $-(CH_2)_m NR^7R^{13}$; $-(CH_2)_m OR^7$; $OR^8$; alkoxy; haloalkoxy; aryloxy; $C(CH_3)_2OH$; $C(CH_3)(OH)CH_2OH$; N,N-dimethylethane-amino; F; Cl; $NO_2$; $NH_2$; CN; aryl; and pyrrolidinyl, any of which is optionally substituted, m being an integer, independently at each occurrence, selected from 0, 1, 2, and 3;

R¹⁰ is, at each occurrence, independently selected from the group consisting of hydrogen, hydroxyl, halogen, C1-C6 alkyl, C1-C3 haloalkyl, $C(O)R^7$, $CH_2NR^7R^{13}$, $CH_2OH$, $C(O)NR^7R^{13}$, $NO_2$, and CN, any of which is optionally substituted;

R¹¹ is, at each occurrence, independently selected from the group consisting of hydrogen, hydroxyl, C1-C6 alkyl, C1-C3 haloalkyl, $C(O)OR^7$, $C(CH_3)_2(CH_2)_m NR^7R^{13}$, $-(CH_2)_m NR^7R^{13}$, $CH_2OH$, alkoxy, haloalkoxy, halogen, CN, $NO_2$, $NH_2$, $NH_2-(CH_2)_m$ aryl, $-(CH_2)_m$heteroaryl, $-NH(C_1-C_6$ alkyl), and $OR^8$, any of which is optionally substituted; m being an integer, independently at each occurrence, selected from 0, 1, 2 and 3;

R¹² is, at each occurrence, independently selected from the group consisting of hydrogen, halogen, C2-C6 alkyl, C1-C6 alkyl substituted with C1-C6 cycloalkyl; $-(CH_2)_m NR^7R^{13}$, C1-C6 cycloalkyl, and heterocycloalkyl any of which is optionally substituted, m being an integer independently at each occurrence selected from 0, 1, 2 and 3;

R¹³ is, at each occurrence, independently selected from the group consisting of hydrogen, C1-C6 alkyl, COMe, and $CONH_2$, any of which is optionally substituted;

and pharmaceutically acceptable salts thereof.

2. A compound having the general formula II:

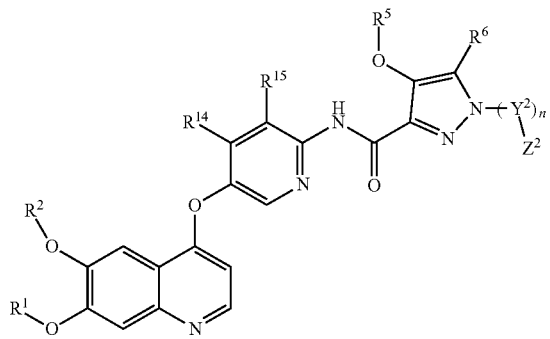

II wherein
$Y^2$ is, independently at each occurrence, selected from $CH_2$ and $CH_2CH_2$;
n is, independently at each occurrence, selected from 0 and 1;
$R^1$ is, at each occurrence, independently selected from the group consisting of C1-C6 alkyl and C1-C3 haloalkyl;
$R^2$ is, at each occurrence, independently selected from the group consisting of C1-C6 alkyl and C1-C3 haloalkyl, any of which is optionally substituted;
$R^5$ is, at each occurrence, independently selected from the group consisting of C1-C6 alkyl; C1-C6 alkyl substituted with C1-C6 cycloalkyl, with heterocyclyl or with O—(C1-C6 alkyl); C1-C3 haloalkyl, N,N-dimethylethane-amino, and N,N-dimethylpropan-1-amino;
$R^6$ is, at each occurrence, independently selected from the group consisting of hydrogen and $CH_3$;
$Z^2$ is, at each occurrence, independently selected from the group consisting of hydrogen, hydroxyl, C1-C6 alkyl, $C(O)R^7$, $C(O)NHR^7$, CN, $C(O)R^8$, $N(R^7)_2$, $OR^8$ and any structure of the following group B, any structure of which is optionally substituted;

group B

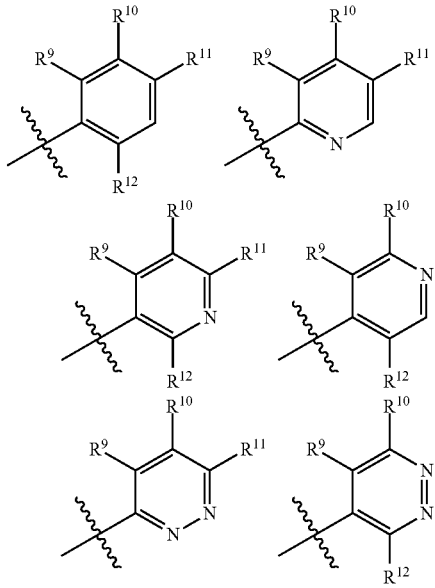

-continued

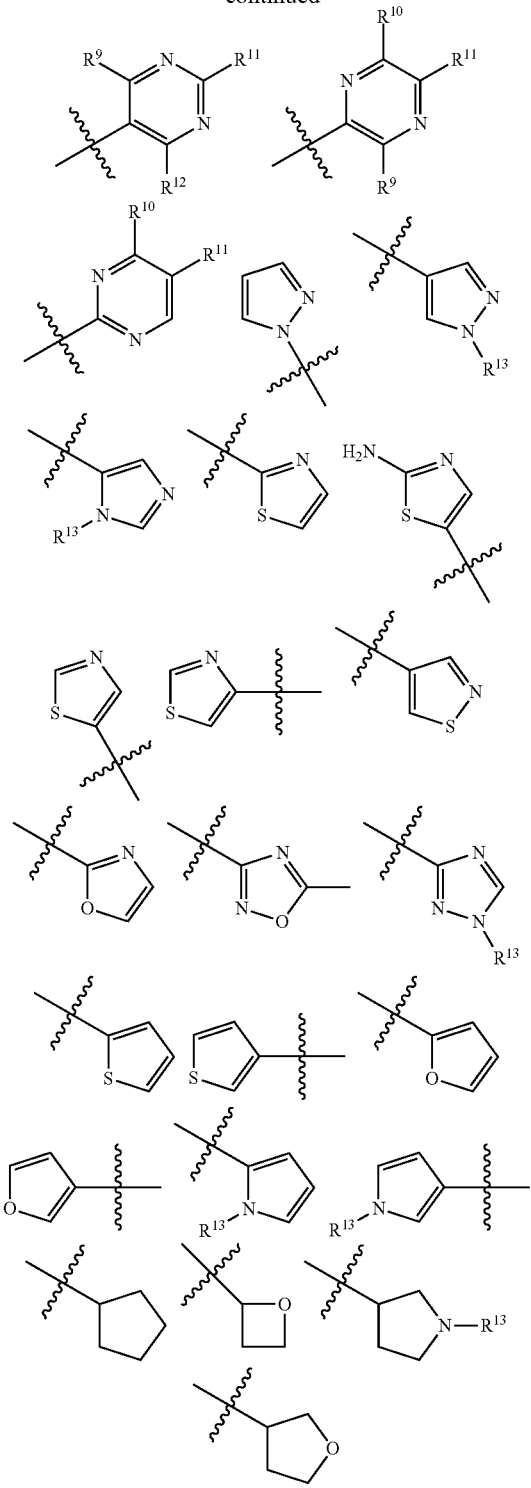

$R^7$ is, at each occurrence, independently selected from the group consisting of hydrogen and C1-C6 alkyl, any of which is optionally substituted;

$R^8$ is, at each occurrence, independently selected from the group consisting of hydrogen, C1-C6 alkyl, C1-C3 haloalkyl, and phenyl, any of which is optionally substituted;

$R^9$ is, at each occurrence, independently selected from the group consisting of hydrogen, C2-C6 alkyl, C1-C6 cycloalkyl, C1-C6 alkyl substituted with C1-C6 cycloalkyl, C1-C6 alkenyl, heterocyclyl, C1-C3 haloalkyl, C(O)OR$^7$, CH$_2$C(O)OR$^7$, C(O)R$^7$, —(CH$_2$)$_m$NR$^7$R$^{13}$, —(CH$_2$)$_m$OR$^7$, OR8, alkoxy, haloalkoxy, aryloxy, C(CH$_3$)$_2$OH, C(CH$_3$)(OH)CH$_2$OH, N,N-dimethylethane-amino, F, Cl, NO$_2$, NH$_2$, CN, aryl, benzyl hydroxyl and pyrrolidinyl, any of which is optionally substituted, m being an integer, independently at each occurrence, selected from 0, 1, 2, and 3;

$R^{10}$ is, at each occurrence, independently selected from the group consisting of hydrogen, hydroxyl, halogen, C1-C6 alkyl, C1-C3 haloalkyl, C(O)R$^7$, CH$_2$NR$^7$R$^{13}$, CH$_2$OH, C(O)NR$^7$R$^{13}$, NO$_2$ and CN, any of which is optionally substituted;

$R^{11}$ is, at each occurrence, independently selected from the group consisting of hydrogen, hydroxyl, C1-C6 alkyl, C1-C3 haloalkyl, C(O)OR$^7$, C(CH$_3$)$_2$(CH$_2$)$_m$NR$^7$R$^{13}$, —(CH$_2$)$_m$NR$^7$R$^{13}$, CH$_2$OH, alkoxy, haloalkoxy, halogen, CN, NO$_2$, NH$_2$, NH$_2$—(CH$_2$)$_m$aryl, —(CH$_2$)$_m$heteroaryl, —NH(C$_1$-C$_6$ alkyl), and OR$^8$, any of which is optionally substituted; m being an integer, independently at each occurrence, selected from 0, 1, 2 and 3;

$R^{12}$ is, at each occurrence, independently selected from the group consisting of hydrogen, halogen, C2-C6 alkyl, C1-C6 alkyl substituted with C1-C6 cycloalkyl, —(CH$_2$)$_m$NR$^7$R$^{13}$, C1-C6 cycloalkyl, and heterocycloalkyl any of which is optionally substituted, m being an integer independently at each occurrence selected from 0, 1, 2 and 3;

$R^{13}$ is, at each occurrence, independently selected from the group consisting of hydrogen and C1-C6 alkyl, COMe, and CONH$_2$, any of which is optionally substituted;

$R^{14}$ and $R^{15}$ are, at each occurrence, independently selected from the group consisting of hydrogen, halogen, and methyl, which is optionally substituted;

and pharmaceutically acceptable salts thereof.

3. A method for inhibiting a TAM family receptor tyrosine kinase and/or a Met receptor tyrosine kinase, wherein said method comprises contacting the TAM family receptor tyrosine kinase and/or a Met receptor tyrosine kinase with a compound of claim 1.

4. The method according to claim 3 for the treatment of a disorder associated with, accompanied by, caused by and/or induced by TAM family receptor tyrosine kinase and/or Met receptor tyrosine kinase.

5. The method according to claim 4, wherein the TAM family receptor tyrosine kinase induced disorder is selected from hyperproliferative disorders.

6. The method according to claim 5, wherein the hyperproliferative disorder is selected from the group consisting of immune-suppressive cancer and primary tumor metastases.

7. The method according to claim 5, wherein the hyperproliferative disorder is selected refractory cancer.

8. The method according to claim 5, wherein the hyperproliferative disorder is selected from adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, breast cancer, Burkitt's lymphoma, corpus cancer, CUP-syndrome, colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear tumors, nose tumors and throat tumors, hematologic neoplasias, hairy cell leukemia, urethral cancer, skin cancer, skin testis cancer, brain tumors, brain metastases, testicle cancer, hypophysis tumor, carcinoids, Kaposi's sarcoma, laryngeal cancer, germ cell tumor, bone cancer, colorectal carcinoma, head and neck tumors, colon carcinoma, craniopharyngiomas, oral cancer, cancer of the central nervous system, liver cancer, liver metastases, leukemia, eyelid tumor, lung cancer, lymph node cancer, lymphomas, stomach cancer, malignant melanoma, malignant neoplasia, malignant tumors of the gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinaliomas, T-cell lymphoma, thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer.

9. The method according to claim 4, wherein the TAM family receptor tyrosine kinase induced disorder is an infectious disease.

10. The method according to claim 4, wherein said method is in combination with an anti-cancer agent.

11. A pharmaceutical composition comprising at least one compound according to claim 1, together with at least one pharmaceutically acceptable carrier, excipient and/or diluent.

12. The pharmaceutical composition according to claim 11, further comprising an anti-cancer agent.

13. The pharmaceutical composition according to claim 12, wherein the anti-cancer agent is an inhibitor of a growth factor receptor.

14. A pharmaceutical composition comprising at least one compound according to claim 2, together with at least one pharmaceutically acceptable carrier, excipient and/or diluent.

15. The pharmaceutical composition according to claim 14, further comprising an anti-cancer agent.

16. The pharmaceutical composition according to claim 15, wherein the anti-cancer agent is an inhibitor of a growth factor receptor.

* * * * *